United States Patent
Lu

(10) Patent No.: US 11,730,823 B2
(45) Date of Patent: Aug. 22, 2023

(54) DELIVERY OF THERAPEUTIC RNAS VIA ARRDC1-MEDIATED MICROVESICLES

(71) Applicant: President and Fellows of Harvard College, Cambridge, MA (US)

(72) Inventor: Quan Lu, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1177 days.

(21) Appl. No.: 16/338,969

(22) PCT Filed: Oct. 3, 2017

(86) PCT No.: PCT/US2017/054912
§ 371 (c)(1),
(2) Date: Apr. 2, 2019

(87) PCT Pub. No.: WO2018/067546
PCT Pub. Date: Apr. 12, 2018

(65) Prior Publication Data
US 2021/0213139 A1  Jul. 15, 2021

Related U.S. Application Data

(60) Provisional application No. 62/403,678, filed on Oct. 3, 2016.

(51) Int. Cl.
| | | |
|---|---|---|
| *A61K 47/69* | (2017.01) | |
| *A61K 47/62* | (2017.01) | |
| *A61K 47/54* | (2017.01) | |
| *A61K 9/50* | (2006.01) | |
| *C12N 15/87* | (2006.01) | |

(52) U.S. Cl.
CPC ........ *A61K 47/6901* (2017.08); *A61K 9/5068* (2013.01); *A61K 47/54* (2017.08); *A61K 47/62* (2017.08); *C12N 15/87* (2013.01); *C12N 2740/16322* (2013.01); *C12N 2795/10222* (2013.01); *C12N 2795/10322* (2013.01); *C12N 2795/18122* (2013.01)

(58) Field of Classification Search
None
See application file for complete search history.

(56) References Cited

U.S. PATENT DOCUMENTS

| | | | |
|---|---|---|---|
| 4,182,449 A | 1/1980 | Kozlow | |
| 4,880,635 A | 11/1989 | Janoff et al. | |
| 4,906,477 A | 3/1990 | Kurono et al. | |
| 4,911,928 A | 3/1990 | Wallach | |
| 4,917,951 A | 4/1990 | Wallach | |
| 4,920,016 A | 4/1990 | Allen et al. | |
| 4,921,757 A | 5/1990 | Wheatley et al. | |
| 5,270,163 A | 12/1993 | Gold et al. | |
| 5,449,639 A | 9/1995 | Wei et al. | |
| 5,475,096 A | 12/1995 | Gold et al. | |
| 5,496,938 A | 3/1996 | Gold et al. | |
| 5,595,887 A | 1/1997 | Coolidge et al. | |
| 5,817,785 A | 10/1998 | Gold et al. | |
| 5,861,254 A | 1/1999 | Schneider et al. | |
| 5,958,691 A | 9/1999 | Pieken et al. | |
| 5,962,219 A | 10/1999 | Gold et al. | |
| 6,013,443 A | 1/2000 | Heilig et al. | |
| 6,030,776 A | 2/2000 | Eaton et al. | |
| 6,083,696 A | 7/2000 | Biesecker et al. | |
| 6,110,900 A | 8/2000 | Gold et al. | |
| 6,127,119 A | 10/2000 | Stephens et al. | |
| 6,147,204 A | 11/2000 | Gold et al. | |
| 6,376,019 B1 | 4/2002 | Leung | |
| 7,314,923 B2 | 1/2008 | Kaneko et al. | |
| 7,335,765 B2 | 2/2008 | Kaneko et al. | |
| 7,399,845 B2 | 7/2008 | Seth et al. | |
| 7,479,573 B2 | 1/2009 | Chu et al. | |
| 7,569,686 B1 | 8/2009 | Bhat et al. | |
| 7,741,457 B2 | 6/2010 | Seth et al. | |
| 7,816,333 B2 | 10/2010 | Seth et al. | |
| 8,022,193 B2 | 9/2011 | Seth et al. | |
| 8,680,069 B2 | 3/2014 | de Fougerolles et al. | |

(Continued)

FOREIGN PATENT DOCUMENTS

| | | |
|---|---|---|
| CN | 111088283 A | 5/2020 |
| EP | 2 604 255 A1 | 6/2013 |

(Continued)

OTHER PUBLICATIONS

Baccile et al., Modular synthesis of photocleavable peptides using click chemistry. Tetrahedron Lett. Apr. 11, 2012;53(15):1933-5.
Buchwald, Long-term, continuous intravenous heparin administration by an implantable infusion pump in ambulatory patients with recurrent venous thrombosis. Surgery. Oct. 1980;88(4):507-16.
Buys et al., Effect of screening on ovarian cancer mortality: the Prostate, Lung, Colorectal and Ovarian (PLCO) Cancer Screening Randomized Controlled Trial. JAMA. Jun. 8, 2011;305(22):2295-303. doi: 10.1001/jama.2011.766.
Cai et al., Solution structure of P22 transcriptional antitermination N peptide-boxB RNA complex. Nat Struct Biol. Mar. 1998;5(3):203-12.
Cochrane et al., The human immunodeficiency virus rev protein is a nuclear phosphoprotein. Virology. Jul. 1989;171(1):264-6.

(Continued)

*Primary Examiner* — Nicole Kinsey White
(74) *Attorney, Agent, or Firm* — Wolf, Greenfield & Sacks, P.C.

(57) ABSTRACT

Methods, systems, compositions and strategies for the delivery of RNA into cells in vivo, ex vivo, or in vitro via ARMMs are provided. In some aspects, ARMMs containing fusion proteins of ARRDC1 fused to an RNA binding protein or an RNA binding protein fused to a WW domain are provided. In some aspects, ARMMs containing binding RNAs associated with cargo RNAs are provided. In other aspects, cargo RNAs associated with a binding RNA, such as a TAR element, are loaded into ARMMs via ARRDC1 fusion proteins containing an RNA binding protein, such as trans-activator of transcription (Tat) protein.

28 Claims, 13 Drawing Sheets

Specification includes a Sequence Listing.

(56) References Cited

U.S. PATENT DOCUMENTS

| | | |
|---|---|---|
| 8,795,965 B2 | 6/2014 | Zhang et al. |
| 9,061,043 B2 | 6/2015 | Sullenger et al. |
| 9,737,480 B2 | 8/2017 | Lu et al. |
| 9,816,080 B2 | 11/2017 | Lu et al. |
| 10,260,055 B2 | 4/2019 | Lu et al. |
| 10,945,954 B2 | 3/2021 | Lu et al. |
| 11,001,817 B2 | 5/2021 | Lu et al. |
| 2003/0083294 A1 | 5/2003 | Sullenger et al. |
| 2003/0175703 A1 | 9/2003 | Sullenger et al. |
| 2006/0024780 A1 | 2/2006 | Aldaz et al. |
| 2006/0188560 A1 | 8/2006 | Cheresh et al. |
| 2011/0009471 A1 | 1/2011 | Kaneko et al. |
| 2011/0046208 A1* | 2/2011 | Rossi ............... C12N 15/1132 435/325 |
| 2011/0053157 A1 | 3/2011 | Skog et al. |
| 2011/0151460 A1 | 6/2011 | Klass et al. |
| 2012/0129759 A1 | 5/2012 | Liu et al. |
| 2013/0202559 A1 | 8/2013 | Skog et al. |
| 2014/0005126 A1 | 1/2014 | Ullman et al. |
| 2014/0273226 A1 | 9/2014 | Wu |
| 2014/0364588 A1 | 12/2014 | Haugwitz et al. |
| 2015/0037421 A1 | 2/2015 | Lu et al. |
| 2015/0050699 A1 | 2/2015 | Siksnys et al. |
| 2015/0071903 A1 | 3/2015 | Liu et al. |
| 2015/0071906 A1 | 3/2015 | Liu et al. |
| 2015/0093433 A1 | 4/2015 | Leonard et al. |
| 2015/0118216 A1 | 4/2015 | Liu et al. |
| 2015/0315252 A1 | 11/2015 | Haugwitz et al. |
| 2016/0200779 A1 | 7/2016 | Liu et al. |
| 2016/0201089 A1 | 7/2016 | Gersbach et al. |
| 2016/0206566 A1 | 7/2016 | Lu et al. |
| 2017/0073382 A1 | 3/2017 | Wong et al. |
| 2017/0130197 A1 | 5/2017 | Haugwitz et al. |
| 2018/0055768 A1 | 3/2018 | Lu et al. |
| 2018/0119118 A1 | 5/2018 | Lu et al. |
| 2019/0241876 A1 | 8/2019 | Lu et al. |
| 2020/0138938 A1 | 5/2020 | Wegmann et al. |
| 2021/0261930 A1 | 8/2021 | Lu et al. |
| 2021/0315814 A1 | 10/2021 | Lu et al. |

FOREIGN PATENT DOCUMENTS

| | | |
|---|---|---|
| WO | WO 2001/038547 A2 | 5/2001 |
| WO | WO 2011/127219 A1 | 10/2011 |
| WO | WO 2013/013105 A2 | 1/2013 |
| WO | WO 2013/119602 A1 | 8/2013 |
| WO | WO 2014/093655 A2 | 6/2014 |
| WO | WO 2014/165825 A2 | 10/2014 |
| WO | WO 2015/002956 A1 | 1/2015 |
| WO | WO 2015/042308 A2 | 3/2015 |
| WO | WO 2018/067546 A1 | 4/2018 |
| WO | WO 2018/208728 A1 | 11/2018 |
| WO | WO 2019/155060 A1 | 8/2019 |
| WO | WO 2020/191361 A2 | 9/2020 |

OTHER PUBLICATIONS

During et al., Controlled release of dopamine from a polymeric brain implant: in vivo characterization. Ann Neurol. Apr. 1989;25(4):351-6.
Fernandes et al., The HIV-1 Rev response element: an RNA scaffold that directs the cooperative assembly of a homo-oligomeric ribonucleoprotein complex. RNA Biol. Jan. 2012;9(1):6-11. doi: 10.4161/rna.9.1.18178. Epub Jan. 1, 2012.
Gatignol et al., Characterization of a human TAR RNA-binding protein that activates the HIV-1 LTR. Science. Mar. 29, 1991;251(5001):1597-600.
Heaphy et al., HIV-1 regulator of virion expression (Rev) protein binds to an RNA stem-loop structure located within the Rev response element region. Cell. Feb. 23, 1990;60(4):685-93.
Howard et al., Intracerebral drug delivery in rats with lesion-induced memory deficits. J Neurosurg. Jul. 1989;71(1):105-12.
Kakiyama et al., A peptide release system using a photo-cleavable linker in a cell array format for cell-toxicity analysis. Polymer Journal. Feb. 27, 2013;45:535-9.
Kalderon et al., A short amino acid sequence able to specify nuclear location. Cell. Dec. 1984;39(3 Pt 2):499-509.
Kamine et al., Mapping of HIV-1 Tat protein sequences required for binding to Tar RNA. Virology. Jun. 1991;182(2):570-7.
Keryer-Bibens et al., Tethering of proteins to RNAs by bacteriophage proteins. Biol Cell. Feb. 2008;100(2):125-38. doi: 10.1042/BC20070067.
Langer et al., Chemical and physical structure of polymers as carriers for controlled release of bioactive agents: A review. J Macromol Sci C. 1983;23(1):61-126. doi: 10.1080/07366578308079439. Epub Dec. 19, 2006.
Langer, New methods of drug delivery. Science. Sep. 28, 1990;249(4976):1527-33.
Levy et al., Inhibition of calcification of bioprosthetic heart valves by local controlled-release diphosphonate. Science. Apr. 12, 1985;228(4696):190-2.
Loh et al., The Oct4 and Nanog transcription network regulates pluripotency in mouse embryonic stem cells. Nat Genet. Apr. 2006;38(4):431-40. Epub Mar. 5, 2006.
Makkerh et al., Comparative mutagenesis of nuclear localization signals reveals the importance of neutral and acidic amino acids. Curr Biol. Aug. 1, 1996;6(8):1025-7.
Marciniak et al., Identification and characterization of a HeLa nuclear protein that specifically binds to the trans-activation-response (TAR) element of human immunodeficiency virus. Proc Natl Acad Sci U S A. May 1990;87(9):3624-8.
McElroy et al., The use of alveolar epithelial type I cell-selective markers to investigate lung injury and repair. Eur Respir J. Oct. 2004;24(4):664-73.
Muesing et al., Regulation of mRNA accumulation by a human immunodeficiency virus trans-activator protein. Cell. Feb. 27, 1987;48(4):691-701.
Nimjee et al., Aptamers: an emerging class of therapeutics. Annu Rev Med. 2005;56:555-83.
Patel, Adaptive recognition in RNA complexes with peptides and protein modules. Curr Opin Struct Biol. Feb. 1999;9(1):74-87.
Potti et al., Regulatable aptamers in medicine: focus on antithrombotic strategies. Expert Opin Biol Ther. Oct. 2004;4(10):1641-7.
Roy et al., Control of the interferon-induced 68-kilodalton protein kinase by the HIV-1 tat gene product. Science. Mar. 9, 1990;247(4947):1216-9.
Saudek et al., A preliminary trial of the programmable implantable medication system for insulin delivery. N Engl J Med. Aug. 31, 1989;321(9):574-9.
Sefton, Implantable pumps. Crit Rev Biomed Eng. 1987;14(3):201-40.
Tuerk et al., Systematic evolution of ligands by exponential enrichment: RNA ligands to bacteriophage T4 DNA polymerase. Science. Aug. 3, 1990;249(4968):505-10.
Ulrich et al., DNA and RNA aptamers: from tools for basic research towards therapeutic applications. Comb Chem High Throughput Screen. Sep. 2006;9(8):619-32.
Weeks et al., Fragments of the HIV-1 Tat protein specifically bind Tar Rna. Science. Sep. 14, 1990;249(4974):1281-5.
Weeks et al., RNA binding assays for Tat-derived peptides: implications for specificity. Biochemistry. Oct. 27, 1992;31(42):10281-7.
Weiss, RNA-mediated signaling in transcription. Nat Struct Biol. May 1998;5(5):329-33.
Witherell et al., Specific interaction between RNA phage coat proteins and RNA. Prog Nucleic Acid Res Mol Biol. 1991;40:185-220.
International Search Report and Written Opinion for PCT/US2013/024839, dated May 28, 2013.
International Preliminary Report on Patentability for PCT/US2013/024839, dated Aug. 21, 2014.
Invitation to Pay Additional Fees for PCT/US2017/54912, dated Dec. 12, 2017.
International Search Report and Written Opinion for PCT/US2017/54912, dated Feb. 13, 2018.

(56) References Cited

OTHER PUBLICATIONS

International Preliminary Report on Patentability for PCT/US2017/54912, dated Apr. 18, 2019.
Extended European Search Report for EP App. No. 17859007.1, dated May 12, 2020.
Genbank Submission; NIH/NCBI, Accession No. NC_015683. Trost et al., Jul. 6, 2013.
Genbank Submission; NIH/NCBI, Accession No. NC_016782. Trost et al., Jun. 11, 2013.
Genbank Submission; NIH/NCBI, Accession No. NC_016786. Trost et al., Aug. 28, 2013.
Genbank Submission; NIH/NCBI, Accession No. NC_017053. Fittipaldi et al., Jul. 6, 2013.
Genbank Submission; NIH/NCBI, Accession No. NC_017317. Trost et al., Jun. 11, 2013.
Genbank Submission; NIH/NCBI, Accession No. NC_017861. Heidelberg et al., Jun. 11, 2013.
Genbank Submission; NIH/NCBI, Accession No. NC_018010. Lucas et al., Jun. 11, 2013.
Genbank Submission; NIH/NCBI, Accession No. NC_018721. Feng et al., Jun. 11, 2013.
Genbank Submission; NIH/NCBI, Accession No. NC_021284. Ku et al., Jul. 12, 2013.
Genbank Submission; NIH/NCBI, Accession No. NC_021314. Zhang et al., Jul. 15, 2013.
Genbank Submission; NIH/NCBI, Accession No. NC_021846. Lo et al., Jul. 22, 2013.
Genbank Submission; NIH/NCBI, Accession No. NM_015277.5. Wilkars et al., Aug. 16, 2014.
Genbank Submission; NIH/NCBI, Accession No. NP_001155957. Skarnes et al., Feb. 26, 2014.
Genbank Submission; NIH/NCBI, Accession No. NP_006283. Rush et al., May 4, 2014.
Genbank Submission; NIH/NCBI, Accession No. NP_056092.2. Wilkars et al., Aug. 16, 2014.
Genbank Submission; NIH/NCBI, Accession No. NP_068684. Gunn et al., Feb. 26, 2014.
Genbank Submission; NIH/NCBI, Accession No. NP_472073. Glaser et al., Jun. 27, 2013.
Genbank Submission; NIH/NCBI, Accession No. NP_689498. Puca et al., Mar. 22, 2014.
Genbank Submission; NIH/NCBI, Accession No. NP_848495. Skarnes et al., Feb. 26, 2014.
Genbank Submission; NIH/NCBI, Accession No. NP_853659. Leithe et al., Aug. 10, 2014.
Genbank Submission; NIH/NCBI, Accession No. YP_002342100. Bernardini et al., Jun. 10, 2013.
Genbank Submission; NIH/NCBI, Accession No. YP_002344900. Gundogdu et al., Jul. 11, 2013.
Genbank Submission; NIH/NCBI, Accession No. YP_820832. Makarova et al., Aug. 27, 2013.
UniProt Submission; UniProt, Accession No. O00308. Last modified Oct. 29, 2014, version 141.
UniProt Submission; UniProt, Accession No. P46934. Last modified Oct. 29, 2014, version 152.
UniProt Submission; UniProt, Accession No. Q76N89. Last modified Oct. 29, 2014, version 95.
UniProt Submission; UniProt, Accession No. Q96J02. Last modified Oct. 29, 2014, version 129.
UniProt Submission; UniProt, Accession No. Q9H0M0. Last modified Oct. 29, 2014, version 136.
UniProt Submission; UniProt, Accession No. Q9HAU4. Last modified Oct. 29, 2014, version 143.
UniProt Submission; UniProt, Accession No. Q9HCE7.Last modified Oct. 29, 2014, version 136.
UniProt Submission; UniProt, Accession No. Q9P2P5. Last modified Oct. 29, 2014, version 105.
[No Author Listed], Invitrogen Lipofectamine™ 2000 product sheets, 2002. 2 pages.
[No Author Listed], Invitrogen Lipofectamine™ 2000 product sheets, 2005. 3 pages.
[No Author Listed], Invitrogen Lipofectamine™ LTX product sheets, 2011. 4 pages.
[No Author Listed], Thermo Fisher Scientific—How Cationic Lipid Mediated Transfection Works, retrieved from the internet Aug. 27, 2015. 2 pages.
Adrian et al., Targeted SAINT-O-Somes for improved intracellular delivery of siRNA and cytotoxic drugs into endothelial cells. J Control Release. Jun. 15, 2010;144(3):341-9. doi: 10.1016/j.jconrel.2010.03.003. Epub Mar. 11, 2010.
Aguilera et al., Systemic in vivo distribution of activatable cell penetrating peptides is superior to that of cell penetrating peptides. Integr Biol (Camb). Jun. 2009;1(5-6):371-81. doi: 10.1039/b904878b. Epub May 11, 2009.
Allen et al., Liposomal drug delivery systems: from concept to clinical applications. Adv Drug Deliv Rev. Jan. 2013;65(1):36-48. doi: 10.1016/j.addr.2012.09.037. Epub Oct. 1, 2012.
Al-Taei et al., Intracellular traffic and fate of protein transduction domains HIV-1 TAT peptide and octaarginine. Implications for their utilization as drug delivery vectors. Bioconjug Chem. Jan.-Feb. 2006;17(1):90-100.
Altschul et al., Basic local alignment search tool. J Mol Biol. Oct. 5, 1990;215(3):403-10.
Alvarez, On the origins of arrestin and rhodopsin. BMC Evol Biol. Jul. 29, 2008;8:222. doi: 10.1186/1471-2148-8-222.
Andriole et al., Mortality results from a randomized prostate-cancer screening trial. N Engl J Med. Mar. 26, 2009;360(13):1310-9. doi: 10.1056/NEJMoa0810696. Epub Mar. 18, 2009. Erratum in: N Engl J Med. Apr. 23, 2009;360(17):1797.
Babst et al., Mammalian tumor susceptibility gene 101 (TSG101) and the yeast homologue, Vps23p, both function in late endosomal trafficking. Traffic. Mar. 2000;1(3):248-58.
Babst, A protein's final ESCRT. Traffic. Jan. 2005;6(1):2-9.
Bache et al., Hrs regulates multivesicular body formation via ESCRT recruitment to endosomes. J Cell Biol. Aug. 4, 2003;162(3):435-42.
Basha et al., Influence of cationic lipid composition on gene silencing properties of lipid nanoparticle formulations of siRNA in antigen-presenting cells. Mol Ther. Dec. 2011;19(12):2186-200. doi: 10.1038/mt.2011.190. Epub Oct. 4, 2011.
Bieniasz, The cell biology of HIV-1 virion genesis. Cell Host Microbe. Jun. 18, 2009;5(6):550-8. doi: 10.1016/j.chom.2009.05.015.
Bork et al., The WW domain: a signaling site in dystrophin? Trends Biochem Sci. Dec. 1994;19(12):531-3.
Brown et al., Serine recombinases as tools for genome engineering. Methods. Apr. 2011;53(4):372-9. doi: 10.1016/j.ymeth.2010.12.031. Epub Dec. 30, 2010.
Carillo et al., The multiple sequence alignment problem in biology. SIAM J Appl Math. 1988;48:1073-1082.
Carroll, Progress and prospects: zinc-finger nucleases as gene therapy agents. Gene Ther. Nov. 2008;15(22):1463-8. doi: 10.1038/gt.2008.145. Epub Sep. 11, 2008.
Chantry, WWP2 ubiquitin ligase and its isoforms: new biological insight and promising disease targets. Cell Cycle. Aug. 1, 2011;10(15):2437-9. Epub Aug. 1, 2011.
Chavez et al., Therapeutic applications of the ΦC31 integrase system. Curr Gene Ther. Oct. 2011;11(5):375-81.
Chen et al., Design of an in vivo cleavable disulfide linker in recombinant fusion proteins. Biotechniques. Jul. 2010;49(1):513-8. doi: 10.2144/000113450.
Chen et al., Fusion protein linkers: property, design and functionality. Adv Drug Deliv Rev. Oct. 2013;65(10):1357-69. doi: 10.1016/j.addr.2012.09.039. Epub Sep. 29, 2012.
Chesnoy et al., Structure and function of lipid-DNA complexes for gene delivery. Annu Rev Biophys Biomol Struct. 2000;29:27-47.
Choi et al., Protease-activated drug development. Theranostics. 2012;2(2):156-78. doi: 10.7150/thno.4068. Epub Feb. 8, 2012.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.

(56) References Cited

OTHER PUBLICATIONS

Cilley et al., Structural mimicry in the phage Φ21 N peptide-boxB RNA complex. RNA. Jun. 2003;9(6):663-76.
Colletier et al., Protein encapsulation in liposomes: efficiency depends on interactions between protein and phospholipid bilayer. BMC Biotechnol. May 10, 2002;2:9.
Cong et al., Multiplex genome engineering using CRISPR/Cas systems. Science. Feb. 15, 2013;339(6121):819-23. doi: 10.1126/science.1231143. Epub Jan. 3, 2013.
Cook et al., Characterization of HIV-1 REV protein: binding stoichiometry and minimal RNA substrate. Nucleic Acids Res. Apr. 11, 1991;19(7):1577-83.
Cordingley et al., Sequence-specific interaction of Tat protein and Tat peptides with the transactivation-responsive sequence element of human immunodeficiency virus type 1 in vitro. Proc Natl Acad Sci U S A. Nov. 1990;87(22):8985-9.
Cramer et al., Ovarian cancer biomarker performance in prostate, lung, colorectal, and ovarian cancer screening trial specimens. Cancer Prev Res (Phila). Mar. 2011;4(3):365-74. doi: 10.1158/1940-6207.CAPR-10-0195.
Cronican et al., A class of human proteins that deliver functional proteins into mammalian cells in vitro and in vivo. Chem Biol. Jul. 29, 2011;18(7):833-8. doi: 10.1016/j.chembiol.2011.07.003.
Cronican et al., Potent delivery of functional proteins into mammalian cells in vitro and in vivo using a supercharged protein. ACS Chem Biol. Aug. 20, 2010;5(8):747-52. doi: 10.1021/cb1001153.
Deltcheva et al., CRISPR RNA maturation by trans-encoded small RNA and host factor RNase III. Nature. Mar. 31, 2011;471(7340):602-7. doi: 10.1038/nature09886.
Demirov et al., Overexpression of the N-terminal domain of TSG101 inhibits HIV-1 budding by blocking late domain function. Proc Natl Acad Sci U S A. Jan. 22, 2002;99(2):955-60.
Demirov et al., Retrovirus budding. Virus Res. Dec. 2004;106(2):87-102.
Denzer et al., Exosome: from internal vesicle of the multivesicular body to intercellular signaling device. J Cell Sci. Oct. 2000;113 Pt 19:3365-74.
Devereux et al., A comprehensive set of sequence analysis programs for the VAX. Nucleic Acids Res. Jan. 11, 1984;12(1 Pt 1):387-95.
DiCarlo et al., Genome engineering in Saccharomyces cerevisiae using CRISPR-Cas systems. Nucleic Acids Res. Apr. 2013;41(7):4336-43. doi: 10.1093/nar/gkt135. Epub Mar. 4, 2013.
Dingwall et al., Human immunodeficiency virus 1 tat protein binds trans-activation-responsive region (TAR) RNA in vitro. Proc Natl Acad Sci U S A. Sep. 1989;86(18):6925-9.
Dingwall et al., The nucleoplasmin nuclear location sequence is larger and more complex than that of SV-40 large T antigen. J Cell Biol. Sep. 1988;107(3):841-9.
Dowdy, Overcoming cellular barriers for RNA therapeutics. Nat Biotechnol. Mar. 2017;35(3):222-229. doi: 10.1038/nbt.3802. Epub Feb. 27, 2017.
Draheim et al., ARRDC3 suppresses breast cancer progression by negatively regulating integrin beta4. Oncogene. Sep. 9, 2010;29(36):5032-47. doi: 10.1038/onc.2010.250. Epub Jul. 5, 2010.
Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.
Esvelt et al., Genome-scale engineering for systems and synthetic biology. Mol Syst Biol. 2013;9:641. doi: 10.1038/msb.2012.66.
Ferretti et al., Complete genome sequence of an M1 strain of *Streptococcus pyogenes*. Proc Natl Acad Sci U S A Apr. 10, 2001;98(8):4658-63.
Freed et al., The cell biology of HIV-1 and other retroviruses. Retrovirology. Nov. 3, 2006;3:77.
Fuchs et al., Polyarginine as a multifunctional fusion tag. Protein Sci. Jun. 2005;14(6):1538-44.
Fujii et al., Beyond Tsg101: the role of Alix in 'ESCRTing' HIV-1. Nat Rev Microbiol. Dec. 2007;5(12):912-6.
Garrus et al., Tsg101 and the vacuolar protein sorting pathway are essential for HIV-1 budding. Cell. Oct. 5, 2001;107(1):55-65.
Gatignol et al., Identification of cellular proteins that bind to the human immunodeficiency virus type 1 trans-activation-responsive TAR element RNA. Proc Natl Acad Sci U S A. Oct. 1989;86(20):7828-32.
Gaynor et al., Specific binding of a HeLa cell nuclear protein to RNA sequences in the human immunodeficiency virus transactivating region. Proc Natl Acad Sci U S A. Jul. 1989;86(13):4858-62.
Gordley et al., Synthesis of programmable integrases. Proc Natl Acad Sci U S A. Mar. 31, 2009;106(13):5053-8. doi: 10.1073/pnas.0812502106. Epub Mar. 12, 2009.
Gottlinger et al., Effect of mutations affecting the p6 gag protein on human immunodeficiency virus particle release. Proc Natl Acad Sci U S A. Apr. 15, 1991;88(8):3195-9.
Grate et al., Role REVersal: understanding how RRE RNA binds its peptide ligand. Structure. Jan. 15, 1997;5(1):7-11.
Groth et al., Phage integrases: biology and applications. J Mol Biol. Jan. 16, 2004;335(3):667-78.
Hammarstedt et al., Passive and active inclusion of host proteins in human immunodeficiency virus type 1 gag particles during budding at the plasma membrane. J Virol. Jun. 2004;78(11):5686-97.
Hartung et al., Correction of metabolic, craniofacial, and neurologic abnormalities in MPS I mice treated at birth with adeno-associated virus vector transducing the human alpha-L-iduronidase gene. Mol Ther. Jun. 2004;9(6):866-75.
Hatahet et al., Disruption of reducing pathways is not essential for efficient disulfide bond formation in the cytoplasm of *E. coli*. Microb Cell Fact. Sep. 13, 2010;9:67. doi: 10.1186/1475-2859-9-67.
Heitz et al., Twenty years of cell-penetrating peptides: from molecular mechanisms to therapeutics. Br J Pharmacol. May 2009;157(2):195-206. doi: 10.1111/j.1476-5381.2009.00057.x. Epub Mar. 20, 2009.
Henne et al., The ESCRT pathway. Dev Cell. Jul. 19, 2011;21(1):77-91. doi: 10.1016/j.devcel.2011.05.015.
Hirano et al., Site-specific recombinases as tools for heterologous gene integration. Appl Microbiol Biotechnol. Oct. 2011;92(2):227-39. doi: 10.1007/s00253-011-3519-5. Epub Aug. 7, 2011.
Hockemeyer et al., Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.
Huang et al., p6Gag is required for particle production from full-length human immunodeficiency virus type 1 molecular clones expressing protease. J Virol. Nov. 1995;69(11):6810-8.
Hurley et al., Membrane budding. Cell. Dec. 10, 2010;143(6):875-87. doi: 10.1016/j.cell.2010.11.030.
Hurley et al., Molecular mechanisms of ubiquitin-dependent membrane traffic. Annu Rev Biophys. 2011;40:119-42. doi: 10.1146/annurev-biophys-042910-155404.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Jiang et al., RNA-guided editing of bacterial genomes using CRISPR-Cas systems. Nat Biotechnol. Mar. 2013;31(3):233-9. doi: 10.1038/nbt.25Q8. Epub Jan. 29, 2013.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Jinek et al., RNA-programmed genome editing in human cells. Elife. Jan. 29, 2013;2:e00471. doi: 10.7554/eLife.00471.
Kandavelou et al., Targeted manipulation of mammalian genomes using designed zinc finger nucleases. Biochem Biophys Res Commun. Oct. 9, 2009;388(1):56-61. doi: 10.1016/j.bbrc.2009.07.112. Epub Jul. 25, 2009.
Karpenshif et al., From yeast to mammals: recent advances in genetic control of homologous recombination. DNA Repair (Amst). Oct. 1, 2012;11(10):781-8. doi: 10.1016/j.dnarep.2012.07.001. Epub Aug. 11, 2012.
Katzmann et al., Receptor downregulation and multivesicular-body sorting. Nat Rev Mol Cell Biol. Dec. 2002;3(12):893-905.
Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.

(56) References Cited

OTHER PUBLICATIONS

Kim et al., Targeted genome editing in human cells with zinc finger nucleases constructed via modular assembly. Genome Res. Jul. 2009;19(7):1279-88. doi: 10.1101/gr.089417.108. Epub May 21, 2009.

Kole et al., RNA therapeutics: beyond RNA interference and antisense oligonucleotides. Nat Rev Drug Discov. Jan. 20, 2012;11(2):125-40. doi: 10.1038/nrd3625.

Komada et al., Hrs, a FYVE finger protein localized to early endosomes, is implicated in vesicular traffic and required for ventral folding morphogenesis. Genes Dev. Jun. 1, 1999;13(11):1475-85.

Kosaka et al., Secretory mechanisms and intercellular transfer of microRNAs in living cells. J Biol Chem. Jun. 4, 2010;285(23):17442-52.

Kosugi et al., Six classes of nuclear localization signals specific to different binding grooves of importin α. J Biol Chem. Jan. 2, 2009;284(1):478-85. doi: 10.1074/jbc.M807017200. Epub Nov. 10, 2008.

Kuo et al., ARRDC1 as a mediator of microvesicle budding. PNAS. Mar. 2012;109(11):4025-4026.

Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.

Lawrence et al., Supercharging proteins can impart unusual resilience. J Am Chem Soc. Aug. 22, 2007;129(33):10110-2. Epub Aug. 1, 2007.

Legault et al., NMR structure of the bacteriophage lambda N peptide/boxB RNA complex: recognition of a GNRA fold by an arginine-rich motif. Cell. Apr. 17, 1998;93(2):289-99.

Levary et al., Protein-protein fusion catalyzed by sortase A. PLoS One. Apr. 6, 2011;6(4):e18342. doi: 10.1371/journal.pone.0018342.

Liu et al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.

Lombardo et al., Gene editing in human stem cells using zinc finger nucleases and integrase-defective lentiviral vector delivery. Nat Biotechnol. Nov. 2007;25(11):1298-306. Epub Oct. 28, 2007.

Lu et al., TSG101 interaction with HRS mediates endosomal trafficking and receptor down-regulation. PNAS. Jun. 24, 2003;100(13):7626-31. Epub Jun. 11, 2003.

Maeder et al., Robust, synergistic regulation of human gene expression using TALE activators. Nat Methods. Mar. 2013;10(3):243-5. doi: 10.1038/nmeth.2366. Epub Feb. 10, 2013.

Maeder et al., Targeted DNA demethylation and activation of endogenous genes using programmable TALE-TET1 fusion proteins. Nat Biotechnol. Dec. 2013;31(12):1137-42. doi: 10.1038/nbt.2726. Epub Oct. 9, 2013.

Mak et al., The crystal structure of TAL effector PthXol bound to its DNA target. Science. Feb. 10, 2012;335(6069):716-9. doi: 10.1126/science.1216211. Epub Jan. 5, 2012.

Mali et al., RNA-guided human genome engineering via Cas9. Science. Feb. 15, 2013;339(6121):823-6. doi: 10.1126/science.1232033. Epub Jan. 3, 2013.

Mani et al., Design, engineering, and characterization of zinc finger nucleases. Biochem Biophys Res Commun. Sep. 23, 2005;335(2):447-57.

Martin-Serrano et al., HIV-1 and Ebola virus encode small peptide motifs that recruit Tsg101 to sites of particle assembly to facilitate egress. Nat Med. Dec. 2001;7(12):1313-9.

Martin-Serrano et al., Host factors involved in retroviral budding and release. Nat Rev Microbiol. Jun. 16, 2011;9(7):519-31. doi: 10.1038/nrmicro2596.

Martin-Serrano et al., Role of ESCRT-I in retroviral budding. J Virol. Apr. 2003;77(8):4794-804.

Mathivanan et al., Proteomics analysis of A33 immunoaffinity-purified exosomes released from the human colon tumor cell line LIM1215 reveals a tissue-specific protein signature. Mol Cell Proteomics. Feb. 2010;9(2):197-208. doi: 10.1074/mcp.M900152-MCP200. Epub Oct. 16, 2009.

McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.

Midoux et al., Chemical vectors for gene delivery: a current review on polymers, peptides and lipids containing histidine or imidazole as nucleic acids carriers. Br J Pharmacol. May 2009; 157(2):166-78. doi: 10.1111/j.1476-5381.2009.00288.x.

Morita et al., Retrovirus budding. Annu Rev Cell Dev Biol. 2004;20:395-425.

Morris et al., A peptide carrier for the delivery of biologically active proteins into mammalian cells. Nat Biotechnol. Dec. 2001; 19(12):1173-6.

Murphy, Phage recombinases and their applications. Adv Virus Res. 2012;83:367-414. doi: 10.1016/B978-0-12-394438-2.00008-6.

Myers et al., Optimal alignments in linear space. Comput Appl Biosci. 1988;4(1):11-17. doi: 10.1093/bioinformatics/4.1.11.

Nabhan et al., Arrestin domain-containing protein 3 recruits the NEDD4 E3 ligase to mediate ubiquitination of the beta2-adrenergic receptor. EMBO Rep. Aug. 2010;11(8):605-11. doi: 10.1038/embor.2010.80. Epub Jun. 18, 2010.

Nabhan et al., Formation and release of arrestin domain-containing protein 1-mediated microvesicles (ARMMs) at plasma membrane by recruitment of TSG101 protein. Proc Natl Acad Sci U S A. Mar. 13, 2012;109(11):4146-51. doi: 10.1073/pnas.1200448109. Epub Feb. 6, 2012.

Nichols et al., Formation of pluripotent stem cells in the mammalian embryo depends on the POU transcription factor Oct. 4. Cell. Oct. 30, 1998;95(3):379-91.

Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.

Olejnik et al., Photocleavable biotin phosphoramidite for 5'-end-labeling, affinity purification and phosphorylation of synthetic oligonucleotides. Nucleic Acids Res. Jan. 15, 1996;24(2):361-6.

Ono et al., Cell-type-dependent targeting of human immunodeficiency virus type 1 assembly to the plasma membrane and the multivesicular body. J Virol. Feb. 2004;78(3):1552-63.

Ono et al., Relationship between human immunodeficiency virus type 1 Gag multimerization and membrane binding. J Virol. Jun. 2000;74(11):5142-50.

Parrott et al., RNA aptamers for the MS2 bacteriophage coat protein and the wild-type RNA operator have similar solution behaviour. Nucleic Acids Res. Jan. 15, 2000;28(2):489-97.

Pennisi, The CRISPR craze. Science. Aug. 23, 2013;341(6148):833-6. doi: 10.1126/science.341.6148.833.

Perez et al., Establishment of HIV-1 resistance in CD4+ T cells by genome editing using zinc-finger nucleases. Nat Biotechnol. Jul. 2008;26(7):808-16. doi: 10.1038/nbt1410. Epub Jun. 29, 2008.

Pisitkun et al., Identification and proteomic profiling of exosomes in human urine. Proc Natl Acad Sci U S A. Sep. 7, 2004;101(36):13368-73. Epub Aug. 23, 2004.

Pornillos et al., HIV Gag mimics the Tsg101-recruiting activity of the human Hrs protein. J Cell Biol. Aug. 4, 2003;162(3):425-34.

Pornillos et al., Structure and functional interactions of the Tsg101 UEV domain. Embo J. May 15, 2002;21(10):2397-406.

Pornillos et al., Structure of the Tsg101 UEV domain in complex with the PTAP motif of the HIV-1 p6 protein. Nat Struct Biol. Nov. 2002;9(11):812-7.

Properzi et al., Exosomes: the future of biomarkers in medicine. Biomark Med. Oct. 2013;7(5):769-78.

Qi et al., Repurposing CRISPR as an RNA-guided platform for sequence-specific control of gene expression. Cell. Feb. 28, 2013;152(5):1173-83. doi: 10.1016/j.cell.2013.02.022.

Rauch et al., Multiple interactions between the ESCRT machinery and arrestin-related proteins: implications for PPXY-dependent budding. J Virol. Apr. 2011;85(7):3546-56. doi: 10.1128/JVI.02045-10. Epub Dec. 29, 2010.

Ray et al., Quantitative tracking of protein trafficking to the nucleus using cytosolic protein delivery by nanoparticle-stabilized nanocapsules. Bioconjug Chem. Jun. 17, 2015;26(6):1004-7. doi: 10.1021/acs.bioconjchem.5b00141. Epub Jun. 2, 2015.

(56) References Cited

OTHER PUBLICATIONS

Razi et al., Distinct roles for Tsg101 and Hrs in multivesicular body formation and inward vesiculation. Mol Biol Cell. Aug. 2006;17(8):3469-83. Epub May 17, 2006.
Rotin et al., Physiological functions of the HECT family of ubiquitin ligases. Nat Rev Mol Cell Biol. Jun. 2009;10(6):398-409. doi: 10.1038/nrm2690. Epub May 13, 2009.
Roy et al., A bulge structure in HIV-1 TAR RNA is required for Tat binding and Tat-mediated trans-activation. Genes Dev. Aug. 1990;4(8):1365-73.
Roy et al., Candidate prognostic markers in breast cancer: focus on extracellular proteases and their inhibitors. Breast Cancer (Dove Med Press). Jul. 3, 2014;6:81-91. doi: 10.2147/BCTT.S46020.
Schorey et al., Exosome function: from tumor immunology to pathogen biology. Traffic. Jun. 2008;9(6):871-81. doi: 10.1111/j.1600-0854.2008.00734.x. Epub Mar. 6, 2008.
Schröder et al., Screening and prostate-cancer mortality in a randomized European study. N Engl J Med. Mar. 2, 20096;360(13):1320-8. doi: 10.1056/NEJMoa0810084. Epub Mar. 18, 2009.
Scott et al., Structural and mechanistic studies of VPS4 proteins. EMBO J. Oct. 19, 2005;24(20):3658-69. Epub Sep. 29, 2005.
Sells et al., Delivery of protein into cells using polycationic liposomes. Biotechniques. Jul. 1995;19(1):72-6, 78.
Sen et al., Cellular unfolded protein response against viruses used in gene therapy. Front Microbiol. May 26, 2014;5:250. doi: 10.3389/fmicb.2014.00250. eCollection 2014.
Shui et al., RNA aptamers that functionally interact with green fluorescent protein and its derivatives. Nucleic Acids Res. Mar. 2012;40(5):e39. doi: 10.1093/nar/gkr1264. Epub Dec. 20, 2011.
Skog et al., Glioblastoma micro vesicles transport RNA and proteins that promote tumour growth and provide diagnostic biomarkers. Nat Cell Biol. Dec. 2008;10(12):1470-6. doi: 10.1038/ncb1800. Epub Nov. 16, 2008.
Srisawat et al., Streptavidin aptamers: affinity tags for the study of RNAs and ribonucleoproteins. RNA. Apr. 2001;7(4):632-41.
Stockley et al., Probing sequence-specific RNA recognition by the bacteriophage MS2 coat protein. Nucleic Acids Res. Jul. 11, 1995;23(13):2512-8.
Sundquist et al., Ubiquitin recognition by the human TSG101 protein. Mol Cell. Mar. 26, 2004;13(6):783-9.
Theile et al., Site-specific N-terminal labeling of proteins using sortase-mediated reactions. Nat Protoc. Sep. 2013;8(9): 1800-7. doi: 10.1038/nprot.2013.102. Epub Aug. 29, 2013.
Thery et al., Exosomes: composition, biogenesis and function. Nat Rev Immunol. Aug. 2002;2(8):569-79.
Thery et al., Membrane vesicles as conveyors of immune responses. Nat Rev Immunol. Aug. 2009;9(8):581-93. doi: 10.1038/nri2567. Epub Jun. 5, 2009.
Turan et al., Site-specific recombinases: from tag-and-target- to tag-and-exchange-based genomic modifications. FASEB J. Dec. 2011;25(12):4088-107. doi: 10.1096/fj.11-186940. Epub Sep. 2, 2011.
Tykodi, PD-1 as an emerging therapeutic target in renal cell carcinoma: current evidence. Onco Targets Ther. Jul. 25, 2014;7:1349-59. doi: 10.2147/OTT.S48443.
Urnov et al., Highly efficient endogenous human gene correction using designed zinc-finger nucleases. Nature. Jun. 2, 2005;435(7042):646-51. Epub Apr. 3, 2005.
Valadi et al., Exosome-mediated transfer of mRNAs and microRNAs is a novel mechanism of genetic exchange between cells. Nat Cell Biol. Jun. 2007;9(6):654-9. Epub May 7, 2007.
Venken et al., Genome-wide manipulations of *Drosophila melanogaster* with transposons, Flp recombinase, and ΦC31 integrase. Methods Mol Biol. 2012;859:203-28. doi: 10.1007/978-1-61779-603-6_12.
Verplank et al., Tsg101, a homologue of ubiquitin-conjugating (E2) enzymes, binds the L domain in HIV type 1 Pr55(Gag). Proc Natl Acad Sci U S A. Jul. 3, 2001;98(14):7724-9. Epub Jun. 26, 2001.
Von Schwedler et al., The protein network of HIV budding. Cell. Sep. 19, 2003;114(6):701-13.

Wang et al., ARMMs as a versatile platform for intracellular delivery of macromolecules. Nat Commun. 2018;9(1):960. Published Mar. 6, 2018.
Wehman et al., The P4-ATPase TAT-5 inhibits the budding of extracellular vesicles in C. elegans embryos. Curr Biol. Dec. 6, 2011;21(23):1951-9. doi: 10.1016/j.cub.2011.10.040. Epub Nov. 17, 2011.
Welton et al., Proteomics analysis of bladder cancer exosomes. Mol Cell Proteomics. Jun. 2010;9(6):1324-38. doi: 10.1074/mcp.M000063-MCP201. Epub Mar. 11, 2010.
Xu et al., Extracellular vesicle isolation and characterization: toward clinical application. J Clin Invest. Apr. 1, 2016;126(4):1152-62. doi: 10.1172/JCI81129. Epub Apr. 1, 2016.
Zelphati et al., Intracellular delivery of proteins with a new lipid-mediated delivery system. J Biol Chem. Sep. 14, 2001;276(37):35103-10. Epub Jul. 10, 2001.
Zhang et al., Conditional gene manipulation: Cre-ating a new biological era. J Zhejiang Univ Sci B. Jul. 2012;13(7):511-24. doi: 10.1631/jzus.B1200042.
Zhang et al., Stabilized plasmid-lipid particles for regional gene therapy: formulation and transfection properties. Gene Ther. Aug. 1999;6(8):1438-47.
U.S. Appl. No. 14/376,967, filed Aug. 6, 2014, Lu et al.
U.S. Appl. No. 15/669,720, filed Aug. 4, 2017, Lu et al.
U.S. Appl. No. 14/929,177, filed Oct. 30, 2015, Lu et al.
U.S. Appl. No. 15/809,470, filed Nov. 10, 2017, Lu et al.
U.S. Appl. No. 16/382,927, filed Apr. 12, 2019, Lu et al.
PCT/US2013/024839, May 28, 2013, International Search Report and Written Opinion.
PCT/US2013/024839, Aug. 21, 2014, International Preliminary Report on Patentability.
PCT/US2017/54912, Dec. 12, 2017, Invitation to Pay Additional Fees.
PCT/US2017/54912, Feb. 13, 2018, International Search Report and Written Opinion.
PCT/US2017/54912, Apr. 18, 2019, International Preliminary Report on Patentability.
EP 17859007.1, May 12, 2020, Extended European Search Report.
U.S. Appl. No. 17/168,988, filed Feb. 5, 2021, Lu et al.
U.S. Appl. No. 17/168,808, filed Feb. 5, 2021, Lu et al.
International Search Report and Written Opinion for PCT/US2020/052784, dated Jan. 27, 2021.
International Preliminary Report on Patentability for PCT/US2020/052784, dated Apr. 7, 2022.
International Search Report and Written Opinion for PCT/US2021/037053, dated Oct. 6, 2021.
Invitation to Pay Additional Fees for PCT/US2021/055203, dated Dec. 29, 2021.
International Search Report and Written Opinion for PCT/US2021/055203, dated Mar. 17, 2022.
Invitation to Pay Additional Fees for PCT/US2021/055158, dated Dec. 8, 2021.
International Search Report and Written Opinion for PCT/US2021/055158, dated Feb. 23, 2022.
Invitation to Pay Additional Fees for PCT/US2021/055154, dated Dec. 23, 2021.
International Search Report and Written Opinion for PCT/US2021/055154, dated Mar. 10, 2022.
Abbas et al., Plasma membrane signaling in HIV-1 infection. Biochim Biophys Acta. Apr. 2014;1838(4):1132-42. doi: 10.1016/j.bbamem.2013.06.020. Epub Jun. 24, 2013.
Beltri, Mechanisms controlling the secretion and composition of exosomes. Doctoral Thesis, Universidad Autónoma de Madrid. Dec. 2016. 208 pages.
Bigbee et al., Tumor markers and immunodiagnosis. Chapter 13. Cancer Medicine. 6th Ed. BC Decker Inc., Eds. 2003. pp. 209-220.
Biomarkers Definitions Working Group, Biomarkers and Surrogate Endpoints: Preferred Definitions and Conceptual Framework. Clin Pharmacol Ther. Mar. 2001;69(3):89-95. doi: 10.1067/mcp.2001.113989.

(56) References Cited

OTHER PUBLICATIONS

Chang et al., Human immunodeficiency virus type 1 subtype E envelope recombinant peptides containing naturally immunogenic epitopes. J Infect Dis. Aug. 2000;182(2):442-50. doi: 10.1086/315730. Epub Jul. 21, 2000.
Genbank Submission, NIH/NCBI, Accession No. NP_848495.2 arrestin domain-containing protein 1 isoform b [Mus musculus], Sundberg et al., Feb. 23, 2019. 2 pages.
Genbank Submission; NIH/NCBI, Accession No. NC_021284.1 Spiroplasma syrphidicola EA-1, complete genome, Ku et al., Aug. 26, 2019. 2 pages.
Genbank Submission; NIH/NCBI, Accession No. NC_015683.1 Corynebacterium ulcerans BR-AD22, complete genome, Trost et al., Aug. 26, 2019. 2 pages.
Genbank Submission; NIH/NCBI, Accession No. NC_016782.1 Corynebacterium diphtheriae 241, complete genome, Trost et al., Aug. 26, 2019. 2 pages.
Genbank Submission; NIH/NCBI, Accession No. NC_016786.1 Corynebacterium diphtheriae HC01, complete genome, Trost et al., Aug. 26, 2019. 2 pages.
Genbank Submission; NIH/NCBI, Accession No. NC_017053.1 *Streptococcus pyogenes* MBAS1882, complete genome, Fittipaldi et al., Mar. 22, 2017. 2 pages.
Genbank Submission; NIH/NCBI, Accession No. NC_017317.1 Corynebacterium ulcerans 809, complete genome, Trost et al., Mar. 30, 2017. 2 pages.
Genbank Submission; NIH/NCBI, Accession No. NC_017861.1 Prevotella intermedia 17 chromosome II, complete sequence, Heidelberg et al., Mar. 30, 2017. 2 pages.
Genbank Submission; NIH/NCBI, Accession No. NC_018010.1 Belliella baltica DSM 15883, complete genome, Lucas et al., May 18, 2017. 3 pages.
Genbank Submission; NIH/NCBI, Accession No. NC_018721.1 Psychroflexus torquis ATCC 700755, complete genome, Feng et al., May 19, 2017. 2 pages.
Genbank Submission; NIH/NCBI, Accession No. NC_021846.1 Spiroplasma Taiwanese CT-1, complete genome, Lo et al., Aug. 26, 2019. 2 pages.
Genbank Submission; NIH/NCBI, Accession No. NC_023414.1 *lStreptococcus iniae* SF1, complete genome, Zhang et al., Dec. 18, 2014. 1 page.
Genbank Submission; NIH/NCBI, Accession No. NM_015277.6 *Homo sapiens* NEDD4 like E3 ubiquitin protein ligase (NEDD4L), transcript variant d, mRNA, Todaro et al., Sep. 22, 2019. 8 pages.
Genbank Submission; NIH/NCBI, Accession No. NP_001155957.1 arrestin domain-containing protein 1 isoform a [Mus musculus], Sundberg et al., Feb. 22, 2019. 2 pages.
Genbank Submission; NIH/NCBI, Accession No. NP_056092.2 E3 ubiquitin-protein ligase NEDD4-like isoform 3 [*Homo sapiens*], Todaro et al., Sep. 22, 2019. 3 pages.
Genbank Submission; NIH/NCBI, Accession No. NP_472073.1 Hypothetical protein lin2744 [Listeria innocua Clipl 1262], Glaser et al., Dec. 17, 2014. 2 pages.
Genbank Submission; NIH/NCBI, Accession No. NP_689498.1 arrestin domain-containing protein 1 isoform 1 [*Homo sapiens*], Mackenzie et al., May 2, 2019. 3 pages.
Genbank Submission; NIH/NCBI, Accession No. YP_002342100.1 Hypothetical protein NMA0631 [Neisseria meningitidis Z2491], Bernardini et al., Dec. 19, 2014. 2 pages.
Genbank Submission; NIH/NCBI, Accession No. YP_002344900.1 CRISPR-associated protein [*Campylobacter jejuni* subsp. jejuni NCTC 11168=ATCC 700819], Gundogdu et al., Aug. 3, 2016. 2 pages.
Genbank Submission; NIH/NCBI, Accession No. YP_820832.1 CRISPR-system-like protein [*Streptococcus thermophilus* LMD-9], Makarova et al., Dec. 16, 2014. 2 pages.
Hall et al., Delivery of Therapeutic Proteins via Extracellular Vesicles: Review and Potential Treatments for Parkinson's Disease, Glioma, and Schwannoma. Cell Mol Neurobiol. Apr. 2016;36(3):417-27. doi: 10.1007/s10571-015-0309-0. Epub Mar. 26, 2016.
Ikediobi et al., Mutation analysis of 24 known cancer genes in the NCI-60 cell line set. Mol Cancer Ther. Nov. 2006;5(11):2606-12. doi: 10.1158/1535-7163.MCT-06-0433. Epub Nov. 6, 2006.
Ingham et al., WW domains provide a platform for the assembly of multiprotein networks. Mol Cell Biol. Aug. 2005;25(16):7092-106. doi: 10.1128/MCB.25.16.7092-7106.2005.
Lake, A human alpha-arrestin protein with a potential role in cargo protein trafficking within the endocytic system. PhD thesis, University of Nottingham. Jul. 2012. 238 pages.
Lee et al., PIK3CA gene is frequently mutated in breast carcinomas and hepatocellular carcinomas. Oncogene. Feb. 1, 20057;24(8):1477-80. doi: 10.1038/sj.one.1208304.
Lefkowitz et al., Transduction of receptor signals by beta-arrestins. Science. Apr. 22, 2005;308(5721):512-7. doi: 10.1126/science.1109237.
Liu et al., Design strategies and application progress of therapeutic exosomes. Theranostics. 2019;9(4):1015-1028. doi: 10.7150/thno.30853.
Marciniak et al., HIV-1 Tat protein trans-activates transcription in vitro. Cell. Nov. 16, 1990;63(4):791-802. doi: 10.1016/0092-8674(90)90145-5.
No Author Listed, A minimal ARRDC1 for ARMM budding and Cargo Packaging powerpoint and written description. Feb. 21, 2019. 7 pages.
Perrin et al., Role of the HIV-1 envelope transmembrane domain in intracellular sorting. BMC Cell Biol. Mar. 15, 2018;19(1):3. doi: 10.1186/s12860-018-0153-4.
Rouet et al., Engineering CRISPR-Cas9 RNA-Protein Complexes for Improved Function and Delivery. CRISPR J. Dec. 2018;1(6):367-378. doi: 10.1089/crispr.2018.0037.
Weeks et al., RNA recognition by Tat-derived peptides: Interaction in the major groove? Cell. Aug. 9, 1991;66(3):577-88. doi: 10.1016/0092-8674(81)90020-9.
U.S. Appl. No. 17/764,013, filed Mar. 25, 2022, Lu et al.
PCT/US2020/052784, Jan. 27, 2021, International Search Report and Written Opinion.
PCT/US2020/052784, Apr. 7, 2022, International Preliminary Report on Patentability.
PCT/US2021/037053, Oct. 6, 2021, International Search Report and Written Opinion.
PCT/US2021/055203, Dec. 29, 2021, Invitation to Pay Additional Fees.
PCT/US2021/055203, Mar. 17, 2022, International Search Report and Written Opinion.
PCT/US2021/055158, Dec. 8, 2021 Invitation to Pay Additional Fees.
PCT/US2021/055158, Feb. 23, 2022, International Search Report and Written Opinion.
PCT/US2021/055154, Dec. 23, 2021, Invitation to Pay Additional Fees.
PCT/US2021/055154, Mar. 10, 2022, International Search Report and Written Opinion.

* cited by examiner

A

B

A

B

A

B

G

F

SEQUENCE LISTING

<160> NUMBER OF SEQ ID NOS: 116

<210> SEQ ID NO 1
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 1

Pro Ser Ala Pro
1

<210> SEQ ID NO 2
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 2

Pro Pro Xaa Tyr
1

<210> SEQ ID NO 3
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 3

Ala Gly Val Phe
1

<210> SEQ ID NO 4
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 4

Gly Phe Leu Gly
1

<210> SEQ ID NO 5
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 5

Ala Leu Ala Leu
1

<210> SEQ ID NO 6
<211> LENGTH: 922
<212> TYPE: PRT
<213> ORGANISM: Homo sapiens

<400> SEQUENCE: 6

-continued

```
Met Ala Thr Ala Ser Pro Arg Ser Asp Thr Ser Asn Asn His Ser Gly
1               5                   10                  15

Arg Leu Gln Leu Gln Val Thr Val Ser Ser Ala Lys Leu Lys Arg Lys
            20                  25                  30

Lys Asn Trp Phe Gly Thr Ala Ile Tyr Thr Glu Val Val Val Asp Gly
                35                  40                  45

Glu Ile Thr Lys Thr Ala Lys Ser Ser Ser Ser Asn Pro Lys Trp
    50                  55                  60

Asp Glu Gln Leu Thr Val Asn Val Thr Pro Gln Thr Thr Leu Glu Phe
65                  70                  75                  80

Gln Val Trp Ser His Arg Thr Leu Lys Ala Asp Ala Leu Leu Gly Lys
                85                  90                  95

Ala Thr Ile Asp Leu Lys Gln Ala Leu Leu Ile His Asn Arg Lys Leu
                100                 105                 110

Glu Arg Val Lys Glu Gln Leu Lys Leu Ser Leu Glu Asn Lys Asn Gly
            115                 120                 125

Ile Ala Gln Thr Gly Glu Leu Thr Val Val Leu Asp Gly Leu Val Ile
            130                 135                 140

Glu Gln Glu Asn Ile Thr Asn Cys Ser Ser Pro Thr Ile Glu Ile
145                 150                 155                 160

Gln Glu Asn Gly Asp Ala Leu His Glu Asn Gly Glu Pro Ser Ala Arg
                165                 170                 175

Thr Thr Ala Arg Leu Ala Val Glu Gly Thr Asn Gly Ile Asp Asn His
                180                 185                 190

Val Pro Thr Ser Thr Leu Val Gln Asn Ser Cys Cys Ser Tyr Val Val
                195                 200                 205

Asn Gly Asp Asn Thr Pro Ser Ser Pro Ser Gln Val Ala Ala Arg Pro
210                 215                 220

Lys Asn Thr Pro Ala Pro Lys Pro Leu Ala Ser Glu Pro Ala Asp Asp
225                 230                 235                 240

Thr Val Asn Gly Glu Ser Ser Phe Ala Pro Thr Asn Ala Ser
                245                 250                 255

Val Thr Gly Thr Pro Val Val Ser Glu Glu Asn Ala Leu Ser Pro Asn
                260                 265                 270

Cys Thr Ser Thr Thr Val Glu Asp Pro Pro Val Gln Glu Ile Leu Thr
            275                 280                 285

Ser Ser Glu Asn Asn Glu Cys Ile Pro Ser Thr Ser Ala Glu Leu Glu
        290                 295                 300

Ser Glu Ala Arg Ser Ile Leu Glu Pro Asp Thr Ser Asn Ser Arg Ser
305                 310                 315                 320

Ser Ser Ala Phe Glu Ala Ala Lys Ser Arg Gln Pro Asp Gly Cys Met
                325                 330                 335

Asp Pro Val Arg Gln Gln Ser Gly Asn Ala Asn Thr Glu Thr Leu Pro
                340                 345                 350

Ser Gly Trp Glu Gln Arg Lys Asp Pro His Gly Arg Thr Tyr Tyr Val
            355                 360                 365

Asp His Asn Thr Arg Thr Thr Thr Trp Glu Arg Pro Gln Pro Leu Pro
        370                 375                 380

Pro Gly Trp Glu Arg Arg Val Asp Asp Arg Arg Val Tyr Tyr Val
385                 390                 395                 400

Asp His Asn Thr Arg Thr Thr Thr Trp Gln Arg Pro Thr Met Glu Ser
        405                 410                 415

Val Arg Asn Phe Glu Gln Trp Gln Ser Gln Arg Asn Gln Leu Gln Gly
```

```
            420                 425                 430
Ala Met Gln Gln Phe Asn Gln Arg Tyr Leu Tyr Ser Ala Ser Met Leu
            435                 440                 445

Ala Ala Glu Asn Asp Pro Tyr Gly Leu Pro Pro Gly Trp Glu Lys
450                 455                 460

Arg Val Asp Ser Thr Asp Arg Val Tyr Phe Val Asn His Asn Thr Lys
465                 470                 475                 480

Thr Thr Gln Trp Glu Asp Pro Arg Thr Gln Gly Leu Gln Asn Glu Glu
                    485                 490                 495

Pro Leu Pro Glu Gly Trp Glu Ile Arg Tyr Thr Arg Glu Gly Val Arg
                500                 505                 510

Tyr Phe Val Asp His Asn Thr Arg Thr Thr Thr Phe Lys Asp Pro Arg
            515                 520                 525

Asn Gly Lys Ser Ser Val Thr Lys Gly Gly Pro Gln Ile Ala Tyr Glu
        530                 535                 540

Arg Gly Phe Arg Trp Lys Leu Ala His Phe Arg Tyr Leu Cys Gln Ser
545                 550                 555                 560

Asn Ala Leu Pro Ser His Val Lys Ile Asn Val Ser Arg Gln Thr Leu
                565                 570                 575

Phe Glu Asp Ser Phe Gln Gln Ile Met Ala Leu Lys Pro Tyr Asp Leu
                580                 585                 590

Arg Arg Arg Leu Tyr Val Ile Phe Arg Gly Glu Glu Gly Leu Asp Tyr
            595                 600                 605

Gly Gly Leu Ala Arg Glu Trp Phe Phe Leu Leu Ser His Glu Val Leu
        610                 615                 620

Asn Pro Met Tyr Cys Leu Phe Glu Tyr Ala Gly Lys Asn Asn Tyr Cys
625                 630                 635                 640

Leu Gln Ile Asn Pro Ala Ser Thr Ile Asn Pro Asp His Leu Ser Tyr
                645                 650                 655

Phe Cys Phe Ile Gly Arg Phe Ile Ala Met Ala Leu Phe His Gly Lys
                660                 665                 670

Phe Ile Asp Thr Gly Phe Ser Leu Pro Phe Tyr Lys Arg Met Leu Ser
            675                 680                 685

Lys Lys Leu Thr Ile Lys Asp Leu Glu Ser Ile Asp Thr Glu Phe Tyr
        690                 695                 700

Asn Ser Leu Ile Trp Ile Arg Asp Asn Asn Ile Glu Glu Cys Gly Leu
705                 710                 715                 720

Glu Met Tyr Phe Ser Val Asp Met Glu Ile Leu Gly Lys Val Thr Ser
                725                 730                 735

His Asp Leu Lys Leu Gly Gly Ser Asn Ile Leu Val Thr Glu Glu Asn
                740                 745                 750

Lys Asp Glu Tyr Ile Gly Leu Met Thr Glu Trp Arg Phe Ser Arg Gly
            755                 760                 765

Val Gln Glu Gln Thr Lys Ala Phe Leu Asp Gly Phe Asn Glu Val Val
        770                 775                 780

Pro Leu Gln Trp Leu Gln Tyr Phe Asp Glu Lys Glu Leu Glu Val Met
785                 790                 795                 800

Leu Cys Gly Met Gln Glu Val Asp Leu Ala Asp Trp Gln Arg Asn Thr
                805                 810                 815

Val Tyr Arg His Tyr Thr Arg Asn Ser Lys Gln Ile Ile Trp Phe Trp
            820                 825                 830

Gln Phe Val Lys Glu Thr Asp Asn Glu Val Arg Met Arg Leu Leu Gln
        835                 840                 845
```

```
Phe Val Thr Gly Thr Cys Arg Leu Pro Leu Gly Gly Phe Ala Glu Leu
    850                 855                 860
Met Gly Ser Asn Gly Pro Gln Lys Phe Cys Ile Glu Lys Val Gly Lys
865                 870                 875                 880
Asp Thr Trp Leu Pro Arg Ser His Thr Cys Phe Asn Arg Leu Asp Leu
                885                 890                 895
Pro Pro Tyr Lys Ser Tyr Glu Gln Leu Lys Glu Lys Leu Leu Phe Ala
            900                 905                 910
Ile Glu Glu Thr Glu Gly Phe Gly Gln Glu
                915                 920

<210> SEQ ID NO 7
<211> LENGTH: 870
<212> TYPE: PRT
<213> ORGANISM: Homo sapiens

<400> SEQUENCE: 7

Met Ala Ser Ala Ser Ser Arg Ala Gly Val Ala Leu Pro Phe Glu
1               5                   10                  15
Lys Ser Gln Leu Thr Leu Lys Val Val Ser Ala Lys Pro Lys Val His
                20                  25                  30
Asn Arg Gln Pro Arg Ile Asn Ser Tyr Val Glu Val Ala Val Asp Gly
            35                  40                  45
Leu Pro Ser Glu Thr Lys Lys Thr Gly Lys Arg Ile Gly Ser Ser Glu
50                  55                  60
Leu Leu Trp Asn Glu Ile Ile Ile Leu Asn Val Thr Ala Gln Ser His
65                  70                  75                  80
Leu Asp Leu Lys Val Trp Ser Cys His Thr Leu Arg Asn Glu Leu Leu
                85                  90                  95
Gly Thr Ala Ser Val Asn Leu Ser Asn Val Leu Lys Asn Asn Gly Gly
            100                 105                 110
Lys Met Glu Asn Met Gln Leu Thr Leu Asn Leu Gln Thr Glu Asn Lys
        115                 120                 125
Gly Ser Val Val Ser Gly Gly Glu Leu Thr Ile Phe Leu Asp Gly Pro
130                 135                 140
Thr Val Asp Leu Gly Asn Val Pro Asn Gly Ser Ala Leu Thr Asp Gly
145                 150                 155                 160
Ser Gln Leu Pro Ser Arg Asp Ser Ser Gly Thr Ala Val Ala Pro Glu
                165                 170                 175
Asn Arg His Gln Pro Pro Ser Thr Asn Cys Phe Gly Gly Arg Ser Arg
            180                 185                 190
Thr His Arg His Ser Gly Ala Ser Ala Arg Thr Thr Pro Ala Thr Gly
        195                 200                 205
Glu Gln Ser Pro Gly Ala Arg Ser Arg His Arg Gln Pro Val Lys Asn
210                 215                 220
Ser Gly His Ser Gly Leu Ala Asn Gly Thr Val Asn Asp Glu Pro Thr
225                 230                 235                 240
Thr Ala Thr Asp Pro Glu Glu Pro Ser Val Val Gly Val Thr Ser Pro
                245                 250                 255
Pro Ala Ala Pro Leu Ser Val Thr Pro Asn Pro Asn Thr Thr Ser Leu
            260                 265                 270
Pro Ala Pro Ala Thr Pro Ala Glu Gly Glu Glu Pro Ser Thr Ser Gly
        275                 280                 285
Thr Gln Gln Leu Pro Ala Ala Ala Gln Ala Pro Asp Ala Leu Pro Ala
```

```
                290                 295                 300
Gly Trp Glu Gln Arg Glu Leu Pro Asn Gly Arg Val Tyr Tyr Val Asp
305                 310                 315                 320

His Asn Thr Lys Thr Thr Thr Trp Glu Arg Pro Leu Pro Pro Gly Trp
                    325                 330                 335

Glu Lys Arg Thr Asp Pro Arg Gly Arg Phe Tyr Tyr Val Asp His Asn
                340                 345                 350

Thr Arg Thr Thr Thr Trp Gln Arg Pro Thr Ala Glu Tyr Val Arg Asn
            355                 360                 365

Tyr Glu Gln Trp Gln Ser Gln Arg Asn Gln Leu Gln Gly Ala Met Gln
    370                 375                 380

His Phe Ser Gln Arg Phe Leu Tyr Gln Ser Ser Ser Ala Ser Thr Asp
385                 390                 395                 400

His Asp Pro Leu Gly Pro Leu Pro Pro Gly Trp Glu Lys Arg Gln Asp
                405                 410                 415

Asn Gly Arg Val Tyr Tyr Val Asn His Asn Thr Arg Thr Thr Gln Trp
                420                 425                 430

Glu Asp Pro Arg Thr Gln Gly Met Ile Gln Glu Pro Ala Leu Pro Pro
            435                 440                 445

Gly Trp Glu Met Lys Tyr Thr Ser Glu Gly Val Arg Tyr Phe Val Asp
    450                 455                 460

His Asn Thr Arg Thr Thr Thr Phe Lys Asp Pro Arg Pro Gly Phe Glu
465                 470                 475                 480

Ser Gly Thr Lys Gln Gly Ser Pro Gly Ala Tyr Asp Arg Ser Phe Arg
                485                 490                 495

Trp Lys Tyr His Gln Phe Arg Phe Leu Cys His Ser Asn Ala Leu Pro
                500                 505                 510

Ser His Val Lys Ile Ser Val Ser Arg Gln Thr Leu Phe Glu Asp Ser
            515                 520                 525

Phe Gln Gln Ile Met Asn Met Lys Pro Tyr Asp Leu Arg Arg Arg Leu
    530                 535                 540

Tyr Ile Ile Met Arg Gly Glu Glu Gly Leu Asp Tyr Gly Gly Ile Ala
545                 550                 555                 560

Arg Glu Trp Phe Phe Leu Leu Ser His Glu Val Leu Asn Pro Met Tyr
                565                 570                 575

Cys Leu Phe Glu Tyr Ala Gly Lys Asn Asn Tyr Cys Leu Gln Ile Asn
                580                 585                 590

Pro Ala Ser Ser Ile Asn Pro Asp His Leu Thr Tyr Phe Arg Phe Ile
            595                 600                 605

Gly Arg Phe Ile Ala Met Ala Leu Tyr His Gly Lys Phe Ile Asp Thr
    610                 615                 620

Gly Phe Thr Leu Pro Phe Tyr Lys Arg Met Leu Asn Lys Arg Pro Thr
625                 630                 635                 640

Leu Lys Asp Leu Glu Ser Ile Asp Pro Glu Phe Tyr Asn Ser Ile Val
                645                 650                 655

Trp Ile Lys Glu Asn Asn Leu Glu Glu Cys Gly Leu Glu Leu Tyr Phe
                660                 665                 670

Ile Gln Asp Met Glu Ile Leu Gly Lys Val Thr Thr His Glu Leu Lys
            675                 680                 685

Glu Gly Gly Glu Ser Ile Arg Val Thr Glu Glu Asn Lys Glu Glu Tyr
    690                 695                 700

Ile Met Leu Leu Thr Asp Trp Arg Phe Thr Arg Gly Val Glu Glu Gln
705                 710                 715                 720
```

Thr Lys Ala Phe Leu Asp Gly Phe Asn Glu Val Ala Pro Leu Glu Trp
                725                 730                 735

Leu Arg Tyr Phe Asp Glu Lys Glu Leu Glu Leu Met Leu Cys Gly Met
            740                 745                 750

Gln Glu Ile Asp Met Ser Asp Trp Gln Lys Ser Thr Ile Tyr Arg His
        755                 760                 765

Tyr Thr Lys Asn Ser Lys Gln Ile Gln Trp Phe Trp Gln Val Val Lys
770                 775                 780

Glu Met Asp Asn Glu Lys Arg Ile Arg Leu Leu Gln Phe Val Thr Gly
785                 790                 795                 800

Thr Cys Arg Leu Pro Val Gly Gly Phe Ala Glu Leu Ile Gly Ser Asn
                805                 810                 815

Gly Pro Gln Lys Phe Cys Ile Asp Lys Val Gly Lys Glu Thr Trp Leu
            820                 825                 830

Pro Arg Ser His Thr Cys Phe Asn Arg Leu Asp Leu Pro Pro Tyr Lys
        835                 840                 845

Ser Tyr Glu Gln Leu Arg Glu Lys Leu Leu Tyr Ala Ile Glu Glu Thr
    850                 855                 860

Glu Gly Phe Gly Gln Glu
865                 870

<210> SEQ ID NO 8
<211> LENGTH: 1319
<212> TYPE: PRT
<213> ORGANISM: Homo sapiens

<400> SEQUENCE: 8

Met Ala Gln Ser Leu Arg Leu His Phe Ala Ala Arg Arg Ser Asn Thr
1               5                   10                  15

Tyr Pro Leu Ser Glu Thr Ser Gly Asp Asp Leu Asp Ser His Val His
            20                  25                  30

Met Cys Phe Lys Arg Pro Thr Arg Ile Ser Thr Ser Asn Val Val Gln
        35                  40                  45

Met Lys Leu Thr Pro Arg Gln Thr Ala Leu Ala Pro Leu Ile Lys Glu
50                  55                  60

Asn Val Gln Ser Gln Glu Arg Ser Ser Val Pro Ser Ser Glu Asn Val
65                  70                  75                  80

Asn Lys Lys Ser Ser Cys Leu Gln Ile Ser Leu Gln Pro Thr Arg Tyr
                85                  90                  95

Ser Gly Tyr Leu Gln Ser Ser Asn Val Leu Ala Asp Ser Asp Asp Ala
            100                 105                 110

Ser Phe Thr Cys Ile Leu Lys Asp Gly Ile Tyr Ser Ser Ala Val Val
        115                 120                 125

Asp Asn Glu Leu Asn Ala Val Asn Asp Gly His Leu Val Ser Ser Pro
130                 135                 140

Ala Ile Cys Ser Gly Ser Leu Ser Asn Phe Ser Thr Ser Asp Asn Gly
145                 150                 155                 160

Ser Tyr Ser Ser Asn Gly Ser Asp Phe Gly Ser Cys Ala Ser Ile Thr
                165                 170                 175

Ser Gly Gly Ser Tyr Thr Asn Ser Val Ile Ser Asp Ser Ser Ser Tyr
            180                 185                 190

Thr Phe Pro Pro Ser Asp Asp Thr Phe Leu Gly Gly Asn Leu Pro Ser
        195                 200                 205

Asp Ser Thr Ser Asn Arg Ser Val Pro Asn Arg Asn Thr Thr Pro Cys

-continued

```
              210                 215                 220
Glu Ile Phe Ser Arg Ser Thr Ser Thr Asp Pro Phe Val Gln Asp Asp
225                 230                 235                 240

Leu Glu His Gly Leu Glu Ile Met Lys Leu Pro Val Ser Arg Asn Thr
                245                 250                 255

Lys Ile Pro Leu Lys Arg Tyr Ser Ser Leu Val Ile Phe Pro Arg Ser
                260                 265                 270

Pro Ser Thr Thr Arg Pro Thr Ser Pro Thr Ser Leu Cys Thr Leu Leu
                275                 280                 285

Ser Lys Gly Ser Tyr Gln Thr Ser His Gln Phe Ile Ile Ser Pro Ser
                290                 295                 300

Glu Ile Ala His Asn Glu Asp Gly Thr Ser Ala Lys Gly Phe Leu Ser
305                 310                 315                 320

Thr Ala Val Asn Gly Leu Arg Leu Ser Lys Thr Ile Cys Thr Pro Gly
                325                 330                 335

Glu Val Arg Asp Ile Arg Pro Leu His Arg Lys Gly Ser Leu Gln Lys
                340                 345                 350

Lys Ile Val Leu Ser Asn Asn Thr Pro Arg Gln Thr Val Cys Glu Lys
                355                 360                 365

Ser Ser Glu Gly Tyr Ser Cys Val Ser Val His Phe Thr Gln Arg Lys
370                 375                 380

Ala Ala Thr Leu Asp Cys Glu Thr Thr Asn Gly Asp Cys Lys Pro Glu
385                 390                 395                 400

Met Ser Glu Ile Lys Leu Asn Ser Asp Ser Glu Tyr Ile Lys Leu Met
                405                 410                 415

His Arg Thr Ser Ala Cys Leu Pro Ser Ser Gln Asn Val Asp Cys Gln
                420                 425                 430

Ile Asn Ile Asn Gly Glu Leu Glu Arg Pro His Ser Gln Met Asn Lys
                435                 440                 445

Asn His Gly Ile Leu Arg Arg Ser Ile Ser Leu Gly Gly Ala Tyr Pro
450                 455                 460

Asn Ile Ser Cys Leu Ser Ser Leu Lys His Asn Cys Ser Lys Gly Gly
465                 470                 475                 480

Pro Ser Gln Leu Leu Ile Lys Phe Ala Ser Gly Asn Glu Gly Lys Val
                485                 490                 495

Asp Asn Leu Ser Arg Asp Ser Asn Arg Asp Cys Thr Asn Glu Leu Ser
                500                 505                 510

Asn Ser Cys Lys Thr Arg Asp Asp Phe Leu Gly Gln Val Asp Val Pro
                515                 520                 525

Leu Tyr Pro Leu Pro Thr Glu Asn Pro Arg Leu Glu Arg Pro Tyr Thr
                530                 535                 540

Phe Lys Asp Phe Val Leu His Pro Arg Ser His Lys Ser Arg Val Lys
545                 550                 555                 560

Gly Tyr Leu Arg Leu Lys Met Thr Tyr Leu Pro Lys Thr Ser Gly Ser
                565                 570                 575

Glu Asp Asp Asn Ala Glu Gln Ala Glu Glu Leu Glu Pro Gly Trp Val
                580                 585                 590

Val Leu Asp Gln Pro Asp Ala Ala Cys His Leu Gln Gln Gln Gln Glu
                595                 600                 605

Pro Ser Pro Leu Pro Pro Gly Trp Glu Glu Arg Gln Asp Ile Leu Gly
                610                 615                 620

Arg Thr Tyr Tyr Val Asn His Glu Ser Arg Arg Thr Gln Trp Lys Arg
625                 630                 635                 640
```

```
Pro Thr Pro Gln Asp Asn Leu Thr Asp Ala Glu Asn Gly Asn Ile Gln
            645                 650                 655

Leu Gln Ala Gln Arg Ala Phe Thr Thr Arg Arg Gln Ile Ser Glu Glu
            660                 665                 670

Thr Glu Ser Val Asp Asn Arg Glu Ser Ser Glu Asn Trp Glu Ile Ile
            675                 680                 685

Arg Glu Asp Glu Ala Thr Met Tyr Ser Asn Gln Ala Phe Pro Ser Pro
            690                 695                 700

Pro Pro Ser Ser Asn Leu Asp Val Pro Thr His Leu Ala Glu Glu Leu
705                 710                 715                 720

Asn Ala Arg Leu Thr Ile Phe Gly Asn Ser Ala Val Ser Gln Pro Ala
            725                 730                 735

Ser Ser Ser Asn His Ser Ser Arg Arg Gly Ser Leu Gln Ala Tyr Thr
            740                 745                 750

Phe Glu Glu Gln Pro Thr Leu Pro Val Leu Leu Pro Thr Ser Ser Gly
            755                 760                 765

Leu Pro Pro Gly Trp Glu Glu Lys Gln Asp Glu Arg Gly Arg Ser Tyr
            770                 775                 780

Tyr Val Asp His Asn Ser Arg Thr Thr Thr Trp Thr Lys Pro Thr Val
785                 790                 795                 800

Gln Ala Thr Val Glu Thr Ser Gln Leu Thr Ser Ser Gln Ser Ser Ala
            805                 810                 815

Gly Pro Gln Ser Gln Ala Ser Thr Ser Asp Ser Gly Gln Gln Val Thr
            820                 825                 830

Gln Pro Ser Glu Ile Glu Gln Gly Phe Leu Pro Lys Gly Trp Glu Val
            835                 840                 845

Arg His Ala Pro Asn Gly Arg Pro Phe Phe Ile Asp His Asn Thr Lys
            850                 855                 860

Thr Thr Thr Trp Glu Asp Pro Arg Leu Lys Ile Pro Ala His Leu Arg
865                 870                 875                 880

Gly Lys Thr Ser Leu Asp Thr Ser Asn Asp Leu Gly Pro Leu Pro Pro
            885                 890                 895

Gly Trp Glu Glu Arg Thr His Thr Asp Gly Arg Ile Phe Tyr Ile Asn
            900                 905                 910

His Asn Ile Lys Arg Thr Gln Trp Glu Asp Pro Arg Leu Glu Asn Val
            915                 920                 925

Ala Ile Thr Gly Pro Ala Val Pro Tyr Ser Arg Asp Tyr Lys Arg Lys
            930                 935                 940

Tyr Glu Phe Phe Arg Arg Lys Leu Lys Lys Gln Asn Asp Ile Pro Asn
945                 950                 955                 960

Lys Phe Glu Met Lys Leu Arg Arg Ala Thr Val Leu Glu Asp Ser Tyr
            965                 970                 975

Arg Arg Ile Met Gly Val Lys Arg Ala Asp Phe Leu Lys Ala Arg Leu
            980                 985                 990

Trp Ile Glu Phe Asp Gly Glu Lys Gly Leu Asp Tyr Gly Gly Val Ala
            995                 1000                1005

Arg Glu Trp Phe Phe Leu Ile Ser Lys Glu Met Phe Asn Pro Tyr
            1010                1015                1020

Tyr Gly Leu Phe Glu Tyr Ser Ala Thr Asp Asn Tyr Thr Leu Gln
            1025                1030                1035

Ile Asn Pro Asn Ser Gly Leu Cys Asn Glu Asp His Leu Ser Tyr
            1040                1045                1050
```

-continued

```
Phe Lys Phe Ile Gly Arg Val Ala Gly Met Ala Val Tyr His Gly
    1055                1060                1065

Lys Leu Leu Asp Gly Phe Phe Ile Arg Pro Phe Tyr Lys Met Met
    1070                1075                1080

Leu His Lys Pro Ile Thr Leu His Asp Met Glu Ser Val Asp Ser
    1085                1090                1095

Glu Tyr Tyr Asn Ser Leu Arg Trp Ile Leu Glu Asn Asp Pro Thr
    1100                1105                1110

Glu Leu Asp Leu Arg Phe Ile Ile Asp Glu Glu Leu Phe Gly Gln
    1115                1120                1125

Thr His Gln His Glu Leu Lys Asn Gly Gly Ser Glu Ile Val Val
    1130                1135                1140

Thr Asn Lys Asn Lys Lys Glu Tyr Ile Tyr Leu Val Ile Gln Trp
    1145                1150                1155

Arg Phe Val Asn Arg Ile Gln Lys Gln Met Ala Ala Phe Lys Glu
    1160                1165                1170

Gly Phe Phe Glu Leu Ile Pro Gln Asp Leu Ile Lys Ile Phe Asp
    1175                1180                1185

Glu Asn Glu Leu Glu Leu Leu Met Cys Gly Leu Gly Asp Val Asp
    1190                1195                1200

Val Asn Asp Trp Arg Glu His Thr Lys Tyr Lys Asn Gly Tyr Ser
    1205                1210                1215

Ala Asn His Gln Val Ile Gln Trp Phe Trp Lys Ala Val Leu Met
    1220                1225                1230

Met Asp Ser Glu Lys Arg Ile Arg Leu Leu Gln Phe Val Thr Gly
    1235                1240                1245

Thr Ser Arg Val Pro Met Asn Gly Phe Ala Glu Leu Tyr Gly Ser
    1250                1255                1260

Asn Gly Pro Gln Ser Phe Thr Val Glu Gln Trp Gly Thr Pro Glu
    1265                1270                1275

Lys Leu Pro Arg Ala His Thr Cys Phe Asn Arg Leu Asp Leu Pro
    1280                1285                1290

Pro Tyr Glu Ser Phe Glu Glu Leu Trp Asp Lys Leu Gln Met Ala
    1295                1300                1305

Ile Glu Asn Thr Gln Gly Phe Asp Gly Val Asp
    1310                1315

<210> SEQ ID NO 9
<211> LENGTH: 955
<212> TYPE: PRT
<213> ORGANISM: Homo sapiens

<400> SEQUENCE: 9

Met Ala Thr Gly Leu Gly Glu Pro Val Tyr Gly Leu Ser Glu Asp Glu
1               5                   10                  15

Gly Glu Ser Arg Ile Leu Arg Val Lys Val Val Ser Gly Ile Asp Leu
                20                  25                  30

Ala Lys Lys Asp Ile Phe Gly Ala Ser Asp Pro Tyr Val Lys Leu Ser
            35                  40                  45

Leu Tyr Val Ala Asp Glu Asn Arg Glu Leu Ala Leu Val Gln Thr Lys
        50                  55                  60

Thr Ile Lys Lys Thr Leu Asn Pro Lys Trp Asn Glu Glu Phe Tyr Phe
65                  70                  75                  80

Arg Val Asn Pro Ser Asn His Arg Leu Leu Phe Glu Val Phe Asp Glu
                85                  90                  95
```

-continued

```
Asn Arg Leu Thr Arg Asp Asp Phe Leu Gly Gln Val Asp Val Pro Leu
            100                 105                 110

Ser His Leu Pro Thr Glu Asp Pro Thr Met Glu Arg Pro Tyr Thr Phe
            115                 120                 125

Lys Asp Phe Leu Leu Arg Pro Arg Ser His Lys Ser Arg Val Lys Gly
130                 135                 140

Phe Leu Arg Leu Lys Met Ala Tyr Met Pro Lys Asn Gly Gly Gln Asp
145                 150                 155                 160

Glu Glu Asn Ser Asp Gln Arg Asp Asp Met Glu His Gly Trp Glu Val
                165                 170                 175

Val Asp Ser Asn Asp Ser Ala Ser Gln His Gln Glu Glu Leu Pro Pro
            180                 185                 190

Pro Pro Leu Pro Pro Gly Trp Glu Lys Val Asp Asn Leu Gly Arg
            195                 200                 205

Thr Tyr Tyr Val Asn His Asn Asn Arg Thr Thr Gln Trp His Arg Pro
            210                 215                 220

Ser Leu Met Asp Val Ser Ser Glu Ser Asp Asn Asn Ile Arg Gln Ile
225                 230                 235                 240

Asn Gln Glu Ala Ala His Arg Arg Phe Arg Ser Arg His Ile Ser
                245                 250                 255

Glu Asp Leu Glu Pro Glu Pro Ser Glu Gly Gly Asp Val Pro Glu Pro
            260                 265                 270

Trp Glu Thr Ile Ser Glu Glu Val Asn Ile Ala Gly Asp Ser Leu Gly
            275                 280                 285

Leu Ala Leu Pro Pro Pro Ala Ser Pro Gly Ser Arg Thr Ser Pro
290                 295                 300

Gln Glu Leu Ser Glu Glu Leu Ser Arg Arg Leu Gln Ile Thr Pro Asp
305                 310                 315                 320

Ser Asn Gly Glu Gln Phe Ser Ser Leu Ile Gln Arg Glu Pro Ser Ser
                325                 330                 335

Arg Leu Arg Ser Cys Ser Val Thr Asp Ala Val Ala Glu Gln Gly His
            340                 345                 350

Leu Pro Pro Pro Ser Val Ala Tyr Val His Thr Thr Pro Gly Leu Pro
            355                 360                 365

Ser Gly Trp Glu Glu Arg Lys Asp Ala Lys Gly Arg Thr Tyr Tyr Val
370                 375                 380

Asn His Asn Asn Arg Thr Thr Trp Thr Arg Pro Ile Met Gln Leu
385                 390                 395                 400

Ala Glu Asp Gly Ala Ser Gly Ser Ala Thr Asn Ser Asn Asn His Leu
                405                 410                 415

Ile Glu Pro Gln Ile Arg Arg Pro Arg Ser Leu Ser Ser Pro Thr Val
            420                 425                 430

Thr Leu Ser Ala Pro Leu Glu Gly Ala Lys Asp Ser Pro Val Arg Arg
            435                 440                 445

Ala Val Lys Asp Thr Leu Ser Asn Pro Gln Ser Pro Gln Pro Ser Pro
            450                 455                 460

Tyr Asn Ser Pro Lys Pro Gln His Lys Val Thr Gln Ser Phe Leu Pro
465                 470                 475                 480

Pro Gly Trp Glu Met Arg Ile Ala Pro Asn Gly Arg Pro Phe Phe Ile
                485                 490                 495

Asp His Asn Thr Lys Thr Thr Thr Trp Glu Asp Pro Arg Leu Lys Phe
            500                 505                 510
```

```
Pro Val His Met Arg Ser Lys Thr Ser Leu Asn Pro Asn Asp Leu Gly
        515                 520                 525

Pro Leu Pro Pro Gly Trp Glu Arg Ile His Leu Asp Gly Arg Thr
530                 535                 540

Phe Tyr Ile Asp His Asn Ser Lys Ile Thr Gln Trp Glu Asp Pro Arg
545                 550                 555                 560

Leu Gln Asn Pro Ala Ile Thr Gly Pro Ala Val Pro Tyr Ser Arg Glu
                565                 570                 575

Phe Lys Gln Lys Tyr Asp Tyr Phe Arg Lys Lys Leu Lys Pro Ala
            580                 585                 590

Asp Ile Pro Asn Arg Phe Glu Met Lys Leu His Arg Asn Asn Ile Phe
        595                 600                 605

Glu Glu Ser Tyr Arg Arg Ile Met Ser Val Lys Arg Pro Asp Val Leu
        610                 615                 620

Lys Ala Arg Leu Trp Ile Glu Phe Glu Ser Glu Lys Gly Leu Asp Tyr
625                 630                 635                 640

Gly Val Ala Arg Glu Trp Phe Phe Leu Leu Ser Lys Glu Met Phe
            645                 650                 655

Asn Pro Tyr Tyr Gly Leu Phe Glu Tyr Ser Ala Thr Asp Asn Tyr Thr
                660                 665                 670

Leu Gln Ile Asn Pro Asn Ser Gly Leu Cys Asn Glu Asp His Leu Ser
        675                 680                 685

Tyr Phe Thr Phe Ile Gly Arg Val Ala Gly Leu Ala Val Phe His Gly
        690                 695                 700

Lys Leu Leu Asp Gly Phe Phe Ile Arg Pro Phe Tyr Lys Met Met Leu
705                 710                 715                 720

Gly Lys Gln Ile Thr Leu Asn Asp Met Glu Ser Val Asp Ser Glu Tyr
            725                 730                 735

Tyr Asn Ser Leu Lys Trp Ile Leu Glu Asn Asp Pro Thr Glu Leu Asp
                740                 745                 750

Leu Met Phe Cys Ile Asp Glu Glu Asn Phe Gly Gln Thr Tyr Gln Val
        755                 760                 765

Asp Leu Lys Pro Asn Gly Ser Glu Ile Met Val Thr Asn Glu Asn Lys
770                 775                 780

Arg Glu Tyr Ile Asp Leu Val Ile Gln Trp Arg Phe Val Asn Arg Val
785                 790                 795                 800

Gln Lys Gln Met Asn Ala Phe Leu Glu Gly Phe Thr Glu Leu Leu Pro
            805                 810                 815

Ile Asp Leu Ile Lys Ile Phe Asp Glu Asn Glu Leu Glu Leu Leu Met
        820                 825                 830

Cys Gly Leu Gly Asp Val Asp Val Asn Asp Trp Arg Gln His Ser Ile
        835                 840                 845

Tyr Lys Asn Gly Tyr Cys Pro Asn His Pro Val Ile Gln Trp Phe Trp
850                 855                 860

Lys Ala Val Leu Leu Met Asp Ala Glu Lys Arg Ile Arg Leu Leu Gln
865                 870                 875                 880

Phe Val Thr Gly Thr Ser Arg Val Pro Met Asn Gly Phe Ala Glu Leu
            885                 890                 895

Tyr Gly Ser Asn Gly Pro Gln Leu Phe Thr Ile Glu Gln Trp Gly Ser
                900                 905                 910

Pro Glu Lys Leu Pro Arg Ala His Thr Cys Phe Asn Arg Leu Asp Leu
            915                 920                 925

Pro Pro Tyr Glu Thr Phe Glu Asp Leu Arg Glu Lys Leu Leu Met Ala
```

```
                930                 935                 940
Val Glu Asn Ala Gln Gly Phe Glu Gly Val Asp
945                 950                 955

<210> SEQ ID NO 10
<211> LENGTH: 757
<212> TYPE: PRT
<213> ORGANISM: Homo sapiens

<400> SEQUENCE: 10

Met Ser Asn Pro Gly Thr Arg Arg Asn Gly Ser Ser Ile Lys Ile Arg
1               5                   10                  15

Leu Thr Val Leu Cys Ala Lys Asn Leu Ala Lys Lys Asp Phe Phe Arg
            20                  25                  30

Leu Pro Asp Pro Phe Ala Lys Ile Val Val Asp Gly Ser Gly Gln Cys
        35                  40                  45

His Ser Thr Asp Thr Val Lys Asn Thr Leu Asp Pro Lys Trp Asn Gln
    50                  55                  60

His Tyr Asp Leu Tyr Val Gly Lys Thr Asp Ser Ile Thr Ile Ser Val
65                  70                  75                  80

Trp Asn His Lys Lys Ile His Lys Lys Gln Gly Ala Gly Phe Leu Gly
                85                  90                  95

Cys Val Arg Leu Leu Ser Asn Ala Ile Ser Arg Leu Lys Asp Thr Gly
            100                 105                 110

Tyr Gln Arg Leu Asp Leu Cys Lys Leu Asn Pro Ser Asp Thr Asp Ala
        115                 120                 125

Val Arg Gly Gln Ile Val Val Ser Leu Gln Thr Arg Asp Arg Ile Gly
    130                 135                 140

Thr Gly Gly Ser Val Val Asp Cys Arg Gly Leu Leu Glu Asn Glu Gly
145                 150                 155                 160

Thr Val Tyr Glu Asp Ser Gly Pro Gly Arg Pro Leu Ser Cys Phe Met
                165                 170                 175

Glu Glu Pro Ala Pro Tyr Thr Asp Ser Thr Gly Ala Ala Ala Gly Gly
            180                 185                 190

Gly Asn Cys Arg Phe Val Glu Ser Pro Ser Gln Asp Gln Arg Leu Gln
        195                 200                 205

Ala Gln Arg Leu Arg Asn Pro Asp Val Arg Gly Ser Leu Gln Thr Pro
    210                 215                 220

Gln Asn Arg Pro His Gly His Gln Ser Pro Glu Leu Pro Glu Gly Tyr
225                 230                 235                 240

Glu Gln Arg Thr Thr Val Gln Gly Gln Val Tyr Phe Leu His Thr Gln
                245                 250                 255

Thr Gly Val Ser Thr Trp His Asp Pro Arg Ile Pro Ser Pro Ser Gly
            260                 265                 270

Thr Ile Pro Gly Gly Asp Ala Ala Phe Leu Tyr Glu Phe Leu Leu Gln
        275                 280                 285

Gly His Thr Ser Glu Pro Arg Asp Leu Asn Ser Val Asn Cys Asp Glu
    290                 295                 300

Leu Gly Pro Leu Pro Pro Gly Trp Glu Val Arg Ser Thr Val Ser Gly
305                 310                 315                 320

Arg Ile Tyr Phe Val Asp His Asn Asn Arg Thr Thr Gln Phe Thr Asp
                325                 330                 335

Pro Arg Leu His His Ile Met Asn His Gln Cys Gln Leu Lys Glu Pro
            340                 345                 350
```

```
Ser Gln Pro Leu Pro Leu Pro Ser Glu Gly Ser Leu Glu Asp Glu Glu
            355                 360                 365

Leu Pro Ala Gln Arg Tyr Glu Arg Asp Leu Val Gln Lys Leu Lys Val
    370                 375                 380

Leu Arg His Glu Leu Ser Leu Gln Gln Pro Gln Ala Gly His Cys Arg
385                 390                 395                 400

Ile Glu Val Ser Arg Glu Glu Ile Phe Glu Glu Ser Tyr Arg Gln Ile
                405                 410                 415

Met Lys Met Arg Pro Lys Asp Leu Lys Lys Arg Leu Met Val Lys Phe
            420                 425                 430

Arg Gly Glu Glu Gly Leu Asp Tyr Gly Gly Val Ala Arg Glu Trp Leu
        435                 440                 445

Tyr Leu Leu Cys His Glu Met Leu Asn Pro Tyr Tyr Gly Leu Phe Gln
    450                 455                 460

Tyr Ser Thr Asp Asn Ile Tyr Met Leu Gln Ile Asn Pro Asp Ser Ser
465                 470                 475                 480

Ile Asn Pro Asp His Leu Ser Tyr Phe His Phe Val Gly Arg Ile Met
                485                 490                 495

Gly Leu Ala Val Phe His Gly His Tyr Ile Asn Gly Gly Phe Thr Val
            500                 505                 510

Pro Phe Tyr Lys Gln Leu Leu Gly Lys Pro Ile Gln Leu Ser Asp Leu
        515                 520                 525

Glu Ser Val Asp Pro Glu Leu His Lys Ser Leu Val Trp Ile Leu Glu
    530                 535                 540

Asn Asp Ile Thr Pro Val Leu Asp His Thr Phe Cys Val Glu His Asn
545                 550                 555                 560

Ala Phe Gly Arg Ile Leu Gln His Glu Leu Lys Pro Asn Gly Arg Asn
                565                 570                 575

Val Pro Val Thr Glu Glu Asn Lys Lys Glu Tyr Val Arg Leu Tyr Val
            580                 585                 590

Asn Trp Arg Phe Met Arg Gly Ile Glu Ala Gln Phe Leu Ala Leu Gln
        595                 600                 605

Lys Gly Phe Asn Glu Leu Ile Pro Gln His Leu Leu Lys Pro Phe Asp
    610                 615                 620

Gln Lys Glu Leu Glu Leu Ile Ile Gly Gly Leu Asp Lys Ile Asp Leu
625                 630                 635                 640

Asn Asp Trp Lys Ser Asn Thr Arg Leu Lys His Cys Val Ala Asp Ser
                645                 650                 655

Asn Ile Val Arg Trp Phe Trp Gln Ala Val Glu Thr Phe Asp Glu Glu
            660                 665                 670

Arg Arg Ala Arg Leu Leu Gln Phe Val Thr Gly Ser Thr Arg Val Pro
        675                 680                 685

Leu Gln Gly Phe Lys Ala Leu Gln Gly Ser Thr Gly Ala Ala Gly Pro
    690                 695                 700

Arg Leu Phe Thr Ile His Leu Ile Asp Ala Asn Thr Asp Asn Leu Pro
705                 710                 715                 720

Lys Ala His Thr Cys Phe Asn Arg Ile Asp Ile Pro Pro Tyr Glu Ser
                725                 730                 735

Tyr Glu Lys Leu Tyr Glu Lys Leu Leu Thr Ala Val Glu Glu Thr Cys
            740                 745                 750

Gly Phe Ala Val Glu
        755
```

```
<210> SEQ ID NO 11
<211> LENGTH: 748
<212> TYPE: PRT
<213> ORGANISM: Homo sapiens

<400> SEQUENCE: 11

Met Ser Asn Pro Gly Gly Arg Arg Asn Gly Pro Val Lys Leu Arg Leu
1               5                   10                  15

Thr Val Leu Cys Ala Lys Asn Leu Val Lys Lys Asp Phe Phe Arg Leu
            20                  25                  30

Pro Asp Pro Phe Ala Lys Val Val Val Asp Gly Ser Gly Gln Cys His
        35                  40                  45

Ser Thr Asp Thr Val Lys Asn Thr Leu Asp Pro Lys Trp Asn Gln His
    50                  55                  60

Tyr Asp Leu Tyr Ile Gly Lys Ser Asp Ser Val Thr Ile Ser Val Trp
65                  70                  75                  80

Asn His Lys Lys Ile His Lys Lys Gln Gly Ala Gly Phe Leu Gly Cys
                85                  90                  95

Val Arg Leu Leu Ser Asn Ala Ile Asn Arg Leu Lys Asp Thr Gly Tyr
            100                 105                 110

Gln Arg Leu Asp Leu Cys Lys Leu Gly Pro Asn Asp Asn Asp Thr Val
        115                 120                 125

Arg Gly Gln Ile Val Val Ser Leu Gln Ser Arg Asp Arg Ile Gly Thr
    130                 135                 140

Gly Gly Gln Val Val Asp Cys Ser Arg Leu Phe Asp Asn Asp Leu Pro
145                 150                 155                 160

Asp Gly Trp Glu Glu Arg Arg Thr Ala Ser Gly Arg Ile Gln Tyr Leu
                165                 170                 175

Asn His Ile Thr Arg Thr Thr Gln Trp Glu Arg Pro Thr Arg Pro Ala
            180                 185                 190

Ser Glu Tyr Ser Ser Pro Gly Arg Pro Leu Ser Cys Phe Val Asp Glu
        195                 200                 205

Asn Thr Pro Ile Ser Gly Thr Asn Gly Ala Thr Cys Gly Gln Ser Ser
    210                 215                 220

Asp Pro Arg Leu Ala Glu Arg Arg Val Arg Ser Gln Arg His Arg Asn
225                 230                 235                 240

Tyr Met Ser Arg Thr His Leu His Thr Pro Asp Leu Pro Glu Gly
                245                 250                 255

Tyr Glu Gln Arg Thr Thr Gln Gln Gly Gln Val Tyr Phe Leu His Thr
            260                 265                 270

Gln Thr Gly Val Ser Thr Trp His Asp Pro Arg Val Pro Arg Asp Leu
        275                 280                 285

Ser Asn Ile Asn Cys Glu Glu Leu Gly Pro Leu Pro Pro Gly Trp Glu
    290                 295                 300

Ile Arg Asn Thr Ala Thr Gly Arg Val Tyr Phe Val Asp His Asn Asn
305                 310                 315                 320

Arg Thr Thr Gln Phe Thr Asp Pro Arg Leu Ser Ala Asn Leu His Leu
                325                 330                 335

Val Leu Asn Arg Gln Asn Gln Leu Lys Asp Gln Gln Gln Gln Val
            340                 345                 350

Val Ser Leu Cys Pro Asp Asp Thr Glu Cys Leu Thr Val Pro Arg Tyr
        355                 360                 365

Lys Arg Asp Leu Val Gln Lys Leu Lys Ile Leu Arg Gln Glu Leu Ser
    370                 375                 380
```

```
Gln Gln Gln Pro Gln Ala Gly His Cys Arg Ile Glu Val Ser Arg Glu
385                 390                 395                 400

Glu Ile Phe Glu Glu Ser Tyr Arg Gln Val Met Lys Met Arg Pro Lys
            405                 410                 415

Asp Leu Trp Lys Arg Leu Met Ile Lys Phe Arg Gly Glu Glu Gly Leu
        420                 425                 430

Asp Tyr Gly Gly Val Ala Arg Glu Trp Leu Tyr Leu Ser His Glu
    435                 440                 445

Met Leu Asn Pro Tyr Tyr Gly Leu Phe Gln Tyr Ser Arg Asp Asp Ile
450                 455                 460

Tyr Thr Leu Gln Ile Asn Pro Asp Ser Ala Val Asn Pro Glu His Leu
465                 470                 475                 480

Ser Tyr Phe His Phe Val Gly Arg Ile Met Gly Met Ala Val Phe His
                485                 490                 495

Gly His Tyr Ile Asp Gly Gly Phe Thr Leu Pro Phe Tyr Lys Gln Leu
            500                 505                 510

Leu Gly Lys Ser Ile Thr Leu Asp Asp Met Glu Leu Val Asp Pro Asp
        515                 520                 525

Leu His Asn Ser Leu Val Trp Ile Leu Glu Asn Asp Ile Thr Gly Val
    530                 535                 540

Leu Asp His Thr Phe Cys Val Glu His Asn Ala Tyr Gly Glu Ile Ile
545                 550                 555                 560

Gln His Glu Leu Lys Pro Asn Gly Lys Ser Ile Pro Val Asn Glu Glu
                565                 570                 575

Asn Lys Lys Glu Tyr Val Arg Leu Tyr Val Asn Trp Arg Phe Leu Arg
            580                 585                 590

Gly Ile Glu Ala Gln Phe Leu Ala Leu Gln Lys Gly Phe Asn Glu Val
        595                 600                 605

Ile Pro Gln His Leu Leu Lys Thr Phe Asp Glu Lys Glu Leu Glu Leu
    610                 615                 620

Ile Ile Cys Gly Leu Gly Lys Ile Asp Val Asn Asp Trp Lys Val Asn
625                 630                 635                 640

Thr Arg Leu Lys His Cys Thr Pro Asp Ser Asn Ile Val Lys Trp Phe
                645                 650                 655

Trp Lys Ala Val Glu Phe Phe Asp Glu Glu Arg Arg Ala Arg Leu Leu
            660                 665                 670

Gln Phe Val Thr Gly Ser Ser Arg Val Pro Leu Gln Gly Phe Lys Ala
        675                 680                 685

Leu Gln Gly Ala Ala Gly Pro Arg Leu Phe Thr Ile His Gln Ile Asp
    690                 695                 700

Ala Cys Thr Asn Asn Leu Pro Lys Ala His Thr Cys Phe Asn Arg Ile
705                 710                 715                 720

Asp Ile Pro Pro Tyr Glu Ser Tyr Glu Lys Leu Tyr Glu Lys Leu Leu
                725                 730                 735

Thr Ala Ile Glu Glu Thr Cys Gly Phe Ala Val Glu
            740                 745

<210> SEQ ID NO 12
<211> LENGTH: 903
<212> TYPE: PRT
<213> ORGANISM: Homo sapiens

<400> SEQUENCE: 12

Met Ser Asp Ser Gly Ser Gln Leu Gly Ser Met Gly Ser Leu Thr Met
1               5                   10                  15
```

```
Lys Ser Gln Leu Gln Ile Thr Val Ile Ser Ala Lys Leu Lys Glu Asn
             20                  25                  30

Lys Lys Asn Trp Phe Gly Pro Ser Pro Tyr Val Glu Val Thr Val Asp
         35                  40                  45

Gly Gln Ser Lys Lys Thr Glu Lys Cys Asn Asn Thr Asn Ser Pro Lys
 50                  55                  60

Trp Lys Gln Pro Leu Thr Val Ile Val Thr Pro Val Ser Lys Leu His
 65                  70                  75                  80

Phe Arg Val Trp Ser His Gln Thr Leu Lys Ser Asp Val Leu Leu Gly
             85                  90                  95

Thr Ala Ala Leu Asp Ile Tyr Glu Thr Leu Lys Ser Asn Asn Met Lys
            100                 105                 110

Leu Glu Glu Val Val Val Thr Leu Gln Leu Gly Gly Asp Lys Glu Pro
            115                 120                 125

Thr Glu Thr Ile Gly Asp Leu Ser Ile Cys Leu Asp Gly Leu Gln Leu
130                 135                 140

Glu Ser Glu Val Val Thr Asn Gly Glu Thr Thr Cys Ser Glu Asn Gly
145                 150                 155                 160

Val Ser Leu Cys Leu Pro Arg Leu Glu Cys Asn Ser Ala Ile Ser Ala
                165                 170                 175

His Cys Asn Leu Cys Leu Pro Gly Leu Ser Asp Ser Pro Ile Ser Ala
                180                 185                 190

Ser Arg Val Ala Gly Phe Thr Gly Ala Ser Gln Asn Asp Asp Gly Ser
            195                 200                 205

Arg Ser Lys Asp Glu Thr Arg Val Ser Thr Asn Gly Ser Asp Asp Pro
            210                 215                 220

Glu Asp Ala Gly Ala Gly Glu Asn Arg Arg Val Ser Gly Asn Asn Ser
225                 230                 235                 240

Pro Ser Leu Ser Asn Gly Gly Phe Lys Pro Ser Arg Pro Pro Arg Pro
                245                 250                 255

Ser Arg Pro Pro Pro Thr Pro Arg Arg Pro Ala Ser Val Asn Gly
            260                 265                 270

Ser Pro Ser Ala Thr Ser Glu Ser Asp Gly Ser Ser Thr Gly Ser Leu
            275                 280                 285

Pro Pro Thr Asn Thr Asn Thr Asn Thr Ser Glu Gly Ala Thr Ser Gly
290                 295                 300

Leu Ile Ile Pro Leu Thr Ile Ser Gly Gly Ser Gly Pro Arg Pro Leu
305                 310                 315                 320

Asn Pro Val Thr Gln Ala Pro Leu Pro Pro Gly Trp Glu Gln Arg Val
                325                 330                 335

Asp Gln His Gly Arg Val Tyr Tyr Val Asp His Val Glu Lys Arg Thr
            340                 345                 350

Thr Trp Asp Arg Pro Glu Pro Leu Pro Pro Gly Trp Glu Arg Arg Val
            355                 360                 365

Asp Asn Met Gly Arg Ile Tyr Tyr Val Asp His Phe Thr Arg Thr Thr
370                 375                 380

Thr Trp Gln Arg Pro Thr Leu Glu Ser Val Arg Asn Tyr Glu Gln Trp
385                 390                 395                 400

Gln Leu Gln Arg Ser Gln Leu Gln Gly Ala Met Gln Phe Asn Gln
                405                 410                 415

Arg Phe Ile Tyr Gly Asn Gln Asp Leu Phe Ala Thr Ser Gln Ser Lys
            420                 425                 430
```

```
Glu Phe Asp Pro Leu Gly Pro Leu Pro Pro Gly Trp Glu Lys Arg Thr
            435                 440                 445

Asp Ser Asn Gly Arg Val Tyr Phe Val Asn His Asn Thr Arg Ile Thr
450                 455                 460

Gln Trp Glu Asp Pro Arg Ser Gln Gly Gln Leu Asn Glu Lys Pro Leu
465                 470                 475                 480

Pro Glu Gly Trp Glu Met Arg Phe Thr Val Asp Gly Ile Pro Tyr Phe
                485                 490                 495

Val Asp His Asn Arg Arg Thr Thr Tyr Ile Asp Pro Arg Thr Gly
                500                 505                 510

Lys Ser Ala Leu Asp Asn Gly Pro Gln Ile Ala Tyr Val Arg Asp Phe
            515                 520                 525

Lys Ala Lys Val Gln Tyr Phe Arg Phe Trp Cys Gln Gln Leu Ala Met
530                 535                 540

Pro Gln His Ile Lys Ile Thr Val Thr Arg Lys Thr Leu Phe Glu Asp
545                 550                 555                 560

Ser Phe Gln Gln Ile Met Ser Phe Ser Pro Gln Asp Leu Arg Arg Arg
                565                 570                 575

Leu Trp Val Ile Phe Pro Gly Glu Glu Gly Leu Asp Tyr Gly Gly Val
            580                 585                 590

Ala Arg Glu Trp Phe Phe Leu Leu Ser His Glu Val Leu Asn Pro Met
            595                 600                 605

Tyr Cys Leu Phe Glu Tyr Ala Gly Lys Asp Asn Tyr Cys Leu Gln Ile
            610                 615                 620

Asn Pro Ala Ser Tyr Ile Asn Pro Asp His Leu Lys Tyr Phe Arg Phe
625                 630                 635                 640

Ile Gly Arg Phe Ile Ala Met Ala Leu Phe His Gly Lys Phe Ile Asp
                645                 650                 655

Thr Gly Phe Ser Leu Pro Phe Tyr Lys Arg Ile Leu Asn Lys Pro Val
            660                 665                 670

Gly Leu Lys Asp Leu Glu Ser Ile Asp Pro Glu Phe Tyr Asn Ser Leu
            675                 680                 685

Ile Trp Val Lys Glu Asn Asn Ile Glu Glu Cys Asp Leu Glu Met Tyr
690                 695                 700

Phe Ser Val Asp Lys Glu Ile Leu Gly Glu Ile Lys Ser His Asp Leu
705                 710                 715                 720

Lys Pro Asn Gly Gly Asn Ile Leu Val Thr Glu Glu Asn Lys Glu Glu
                725                 730                 735

Tyr Ile Arg Met Val Ala Glu Trp Arg Leu Ser Arg Gly Val Glu Glu
            740                 745                 750

Gln Thr Gln Ala Phe Phe Glu Gly Phe Asn Glu Ile Leu Pro Gln Gln
            755                 760                 765

Tyr Leu Gln Tyr Phe Asp Ala Lys Glu Leu Glu Val Leu Leu Cys Gly
770                 775                 780

Met Gln Glu Ile Asp Leu Asn Asp Trp Gln Arg His Ala Ile Tyr Arg
785                 790                 795                 800

His Tyr Ala Arg Thr Ser Lys Gln Ile Met Trp Phe Trp Gln Phe Val
                805                 810                 815

Lys Glu Ile Asp Asn Glu Lys Arg Met Arg Leu Leu Gln Phe Val Thr
            820                 825                 830

Gly Thr Cys Arg Leu Pro Val Gly Gly Phe Ala Asp Leu Met Gly Ser
            835                 840                 845

Asn Gly Pro Gln Lys Phe Cys Ile Glu Lys Val Gly Lys Glu Asn Trp
```

```
                    850                 855                 860
Leu Pro Arg Ser His Thr Cys Phe Asn Arg Leu Asp Leu Pro Pro Tyr
865                 870                 875                 880

Lys Ser Tyr Glu Gln Leu Lys Glu Lys Leu Leu Phe Ala Ile Glu Glu
                885                 890                 895

Thr Glu Gly Phe Gly Gln Glu
            900

<210> SEQ ID NO 13
<211> LENGTH: 1606
<212> TYPE: PRT
<213> ORGANISM: Homo sapiens

<400> SEQUENCE: 13

Met Leu Leu His Leu Cys Ser Val Lys Asn Leu Tyr Gln Asn Arg Phe
1               5                   10                  15

Leu Gly Leu Ala Ala Met Ala Ser Pro Ser Arg Asn Ser Gln Ser Arg
                20                  25                  30

Arg Arg Cys Lys Glu Pro Leu Arg Tyr Ser Tyr Asn Pro Asp Gln Phe
            35                  40                  45

His Asn Met Asp Leu Arg Gly Gly Pro His Asp Gly Val Thr Ile Pro
        50                  55                  60

Arg Ser Thr Ser Asp Thr Asp Leu Val Thr Ser Asp Ser Arg Ser Thr
65                  70                  75                  80

Leu Met Val Ser Ser Tyr Tyr Ser Ile Gly His Ser Gln Asp Leu
                85                  90                  95

Val Ile His Trp Asp Ile Lys Glu Val Asp Ala Gly Asp Trp Ile
                100                 105                 110

Gly Met Tyr Leu Ile Asp Glu Val Leu Ser Glu Asn Phe Leu Asp Tyr
            115                 120                 125

Lys Asn Arg Gly Val Asn Gly Ser His Arg Gly Gln Ile Ile Trp Lys
        130                 135                 140

Ile Asp Ala Ser Ser Tyr Phe Val Glu Pro Glu Thr Lys Ile Cys Phe
145                 150                 155                 160

Lys Tyr Tyr His Gly Val Ser Gly Ala Leu Arg Ala Thr Thr Pro Ser
                165                 170                 175

Val Thr Val Lys Asn Ser Ala Ala Pro Ile Phe Lys Ser Ile Gly Ala
            180                 185                 190

Asp Glu Thr Val Gln Gly Gln Gly Ser Arg Arg Leu Ile Ser Phe Ser
        195                 200                 205

Leu Ser Asp Phe Gln Ala Met Gly Leu Lys Lys Gly Met Phe Phe Asn
210                 215                 220

Pro Asp Pro Tyr Leu Lys Ile Ser Ile Gln Pro Gly Lys His Ser Ile
225                 230                 235                 240

Phe Pro Ala Leu Pro His His Gly Gln Glu Arg Arg Ser Lys Ile Ile
                245                 250                 255

Gly Asn Thr Val Asn Pro Ile Trp Gln Ala Glu Gln Phe Ser Phe Val
            260                 265                 270

Ser Leu Pro Thr Asp Val Leu Glu Ile Glu Val Lys Asp Lys Phe Ala
        275                 280                 285

Lys Ser Arg Pro Ile Ile Lys Arg Phe Leu Gly Lys Leu Ser Met Pro
    290                 295                 300

Val Gln Arg Leu Leu Glu Arg His Ala Ile Gly Asp Arg Val Val Ser
305                 310                 315                 320
```

-continued

```
Tyr Thr Leu Gly Arg Arg Leu Pro Thr Asp His Val Ser Gly Gln Leu
                325                 330                 335
Gln Phe Arg Phe Glu Ile Thr Ser Ser Ile His Pro Asp Asp Glu Glu
            340                 345                 350
Ile Ser Leu Ser Thr Glu Pro Glu Ser Ala Gln Ile Gln Asp Ser Pro
        355                 360                 365
Met Asn Asn Leu Met Glu Ser Gly Ser Gly Glu Pro Arg Ser Glu Ala
    370                 375                 380
Pro Glu Ser Ser Glu Ser Trp Lys Pro Glu Gln Leu Gly Glu Gly Ser
385                 390                 395                 400
Val Pro Asp Gly Pro Gly Asn Gln Ser Ile Glu Leu Ser Arg Pro Ala
                405                 410                 415
Glu Glu Ala Ala Val Ile Thr Glu Ala Gly Asp Gln Gly Met Val Ser
            420                 425                 430
Val Gly Pro Glu Gly Ala Gly Glu Leu Leu Ala Gln Val Gln Lys Asp
        435                 440                 445
Ile Gln Pro Ala Pro Ser Ala Glu Glu Leu Ala Glu Gln Leu Asp Leu
    450                 455                 460
Gly Glu Glu Ala Ser Ala Leu Leu Leu Glu Asp Gly Glu Ala Pro Ala
465                 470                 475                 480
Ser Thr Lys Glu Glu Pro Leu Glu Glu Glu Ala Thr Thr Gln Ser Arg
                485                 490                 495
Ala Gly Arg Glu Glu Glu Lys Glu Gln Glu Glu Glu Gly Asp Val
            500                 505                 510
Ser Thr Leu Glu Gln Gly Glu Gly Arg Leu Gln Leu Arg Ala Ser Val
        515                 520                 525
Lys Arg Lys Ser Arg Pro Cys Ser Leu Pro Val Ser Glu Leu Glu Thr
    530                 535                 540
Val Ile Ala Ser Ala Cys Gly Asp Pro Glu Thr Pro Arg Thr His Tyr
545                 550                 555                 560
Ile Arg Ile His Thr Leu Leu His Ser Met Pro Ser Ala Gln Gly Gly
                565                 570                 575
Ser Ala Ala Glu Glu Glu Asp Gly Ala Glu Glu Glu Ser Thr Leu Lys
            580                 585                 590
Asp Ser Ser Glu Lys Asp Gly Leu Ser Glu Val Asp Thr Val Ala Ala
        595                 600                 605
Asp Pro Ser Ala Leu Glu Glu Asp Arg Glu Glu Pro Glu Gly Ala Thr
    610                 615                 620
Pro Gly Thr Ala His Pro Gly His Ser Gly His Phe Pro Ser Leu
625                 630                 635                 640
Ala Asn Gly Ala Ala Gln Asp Gly Asp Thr His Pro Ser Thr Gly Ser
                645                 650                 655
Glu Ser Asp Ser Ser Pro Arg Gln Gly Gly Asp His Ser Cys Glu Gly
            660                 665                 670
Cys Asp Ala Ser Cys Cys Ser Pro Ser Cys Tyr Ser Ser Ser Cys Tyr
        675                 680                 685
Ser Thr Ser Cys Tyr Ser Ser Cys Tyr Ser Ala Ser Cys Tyr Ser
    690                 695                 700
Pro Ser Cys Tyr Asn Gly Asn Arg Phe Ala His Thr Arg Phe Ser
705                 710                 715                 720
Ser Val Asp Ser Ala Lys Ile Ser Glu Ser Thr Val Phe Ser Ser Gln
                725                 730                 735
Asp Asp Glu Glu Glu Glu Asn Ser Ala Phe Glu Ser Val Pro Asp Ser
```

-continued

```
                740                 745                 750
Met Gln Ser Pro Glu Leu Asp Pro Glu Ser Thr Asn Gly Ala Gly Pro
            755                 760                 765

Trp Gln Asp Glu Leu Ala Ala Pro Ser Gly His Val Glu Arg Ser Pro
            770                 775                 780

Glu Gly Leu Glu Ser Pro Val Ala Gly Pro Ser Asn Arg Arg Glu Gly
785                 790                 795                 800

Glu Cys Pro Ile Leu His Asn Ser Gln Pro Val Ser Gln Leu Pro Ser
                805                 810                 815

Leu Arg Pro Glu His His His Tyr Pro Thr Ile Asp Glu Pro Leu Pro
                820                 825                 830

Pro Asn Trp Glu Ala Arg Ile Asp Ser His Gly Arg Val Phe Tyr Val
                835                 840                 845

Asp His Val Asn Arg Thr Thr Thr Trp Gln Arg Pro Thr Ala Ala Ala
            850                 855                 860

Thr Pro Asp Gly Met Arg Arg Ser Gly Ser Ile Gln Gln Met Glu Gln
865                 870                 875                 880

Leu Asn Arg Arg Tyr Gln Asn Ile Gln Arg Thr Ile Ala Thr Glu Arg
                885                 890                 895

Ser Glu Glu Asp Ser Gly Ser Gln Ser Cys Glu Gln Ala Pro Ala Gly
                900                 905                 910

Gly Gly Gly Gly Gly Ser Asp Ser Glu Ala Glu Ser Ser Gln Ser
            915                 920                 925

Ser Leu Asp Leu Arg Arg Glu Gly Ser Leu Ser Pro Val Asn Ser Gln
        930                 935                 940

Lys Ile Thr Leu Leu Leu Gln Ser Pro Ala Val Lys Phe Ile Thr Asn
945                 950                 955                 960

Pro Glu Phe Phe Thr Val Leu His Ala Asn Tyr Ser Ala Tyr Arg Val
                965                 970                 975

Phe Thr Ser Ser Thr Cys Leu Lys His Met Ile Leu Lys Val Arg Arg
            980                 985                 990

Asp Ala Arg Asn Phe Glu Arg Tyr  Gln His Asn Arg  Asp Leu Val Asn
        995                 1000                1005

Phe Ile  Asn Met Phe Ala Asp  Thr Arg Leu Glu Leu  Pro Arg Gly
    1010                1015                1020

Trp Glu  Ile Lys Thr Asp Gln  Gly Lys Ser Phe  Phe Val Asp
    1025                1030                1035

His Asn  Ser Arg Ala Thr Thr  Phe Ile Asp Pro Arg  Ile Pro Leu
    1040                1045                1050

Gln Asn  Gly Arg Leu Pro Asn  His Leu Thr His Arg  Gln His Leu
    1055                1060                1065

Gln Arg  Leu Arg Ser Tyr Ser  Ala Gly Glu Ala Ser  Glu Val Ser
    1070                1075                1080

Arg Asn  Arg Gly Ala Ser Leu  Leu Ala Arg Pro Gly  His Ser Leu
    1085                1090                1095

Val Ala  Ala Ile Arg Ser Gln  His Gln His Glu Ser  Leu Pro Leu
    1100                1105                1110

Ala Tyr  Asn Asp Lys Ile Val  Ala Phe Leu Arg Gln  Pro Asn Ile
    1115                1120                1125

Phe Glu  Met Leu Gln Glu Arg  Gln Pro Ser Leu Ala  Arg Asn His
    1130                1135                1140

Thr Leu  Arg Glu Lys Ile His  Tyr Ile Arg Thr Glu  Gly Asn His
    1145                1150                1155
```

-continued

```
Gly Leu Glu Lys Leu Ser Cys Asp Ala Asp Leu Val Ile Leu Leu
    1160                1165                1170

Ser Leu Phe Glu Glu Glu Ile Met Ser Tyr Val Pro Leu Gln Ala
    1175                1180                1185

Ala Phe His Pro Gly Tyr Ser Phe Ser Pro Arg Cys Ser Pro Cys
    1190                1195                1200

Ser Ser Pro Gln Asn Ser Pro Gly Leu Gln Arg Ala Ser Ala Arg
    1205                1210                1215

Ala Pro Ser Pro Tyr Arg Arg Asp Phe Glu Ala Lys Leu Arg Asn
    1220                1225                1230

Phe Tyr Arg Lys Leu Glu Ala Lys Gly Phe Gly Gln Gly Pro Gly
    1235                1240                1245

Lys Ile Lys Leu Ile Ile Arg Arg Asp His Leu Leu Glu Gly Thr
    1250                1255                1260

Phe Asn Gln Val Met Ala Tyr Ser Arg Lys Glu Leu Gln Arg Asn
    1265                1270                1275

Lys Leu Tyr Val Thr Phe Val Gly Glu Gly Leu Asp Tyr Ser
    1280                1285                1290

Gly Pro Ser Arg Glu Phe Phe Phe Leu Leu Ser Gln Glu Leu Phe
    1295                1300                1305

Asn Pro Tyr Tyr Gly Leu Phe Glu Tyr Ser Ala Asn Asp Thr Tyr
    1310                1315                1320

Thr Val Gln Ile Ser Pro Met Ser Ala Phe Val Glu Asn His Leu
    1325                1330                1335

Glu Trp Phe Arg Phe Ser Gly Arg Ile Leu Gly Leu Ala Leu Ile
    1340                1345                1350

His Gln Tyr Leu Leu Asp Ala Phe Phe Thr Arg Pro Phe Tyr Lys
    1355                1360                1365

Ala Leu Leu Arg Leu Pro Cys Asp Leu Ser Asp Leu Glu Tyr Leu
    1370                1375                1380

Asp Glu Glu Phe His Gln Ser Leu Gln Trp Met Lys Asp Asn Asn
    1385                1390                1395

Ile Thr Asp Ile Leu Asp Leu Thr Phe Thr Val Asn Glu Glu Val
    1400                1405                1410

Phe Gly Gln Val Thr Glu Arg Glu Leu Lys Ser Gly Gly Ala Asn
    1415                1420                1425

Thr Gln Val Thr Glu Lys Asn Lys Lys Glu Tyr Ile Glu Arg Met
    1430                1435                1440

Val Lys Trp Arg Val Glu Arg Gly Val Val Gln Gln Thr Glu Ala
    1445                1450                1455

Leu Val Arg Gly Phe Tyr Glu Val Val Asp Ser Arg Leu Val Ser
    1460                1465                1470

Val Phe Asp Ala Arg Glu Leu Glu Leu Val Ile Ala Gly Thr Ala
    1475                1480                1485

Glu Ile Asp Leu Asn Asp Trp Arg Asn Asn Thr Glu Tyr Arg Gly
    1490                1495                1500

Gly Tyr His Asp Gly His Leu Val Ile Arg Trp Phe Trp Ala Ala
    1505                1510                1515

Val Glu Arg Phe Asn Asn Glu Gln Arg Leu Arg Leu Leu Gln Phe
    1520                1525                1530

Val Thr Gly Thr Ser Ser Val Pro Tyr Glu Gly Phe Ala Ala Leu
    1535                1540                1545
```

-continued

Arg Gly Ser Asn Gly Leu Arg Arg Phe Cys Ile Glu Lys Trp Gly
          1550                1555                1560

Lys Ile Thr Ser Leu Pro Arg Ala His Thr Cys Phe Asn Arg Leu
    1565                1570                1575

Asp Leu Pro Pro Tyr Pro Ser Tyr Ser Met Leu Tyr Glu Lys Leu
    1580                1585                1590

Leu Thr Ala Val Glu Glu Thr Ser Thr Phe Gly Leu Glu
    1595                1600                1605

<210> SEQ ID NO 14
<211> LENGTH: 1572
<212> TYPE: PRT
<213> ORGANISM: Homo sapiens

<400> SEQUENCE: 14

Met Ala Ser Ser Ala Arg Glu His Leu Leu Phe Val Arg Arg Arg Asn
1               5                   10                  15

Pro Gln Met Arg Tyr Thr Leu Ser Pro Glu Asn Leu Gln Ser Leu Ala
            20                  25                  30

Ala Gln Ser Ser Met Pro Glu Asn Met Thr Leu Gln Arg Ala Asn Ser
        35                  40                  45

Asp Thr Asp Leu Val Thr Ser Glu Ser Arg Ser Ser Leu Thr Ala Ser
    50                  55                  60

Met Tyr Glu Tyr Thr Leu Gly Gln Ala Gln Asn Leu Ile Ile Phe Trp
65                  70                  75                  80

Asp Ile Lys Glu Glu Val Asp Pro Ser Asp Trp Ile Gly Leu Tyr His
                85                  90                  95

Ile Asp Glu Asn Ser Pro Ala Asn Phe Trp Asp Ser Lys Asn Arg Gly
            100                 105                 110

Val Thr Gly Thr Gln Lys Gly Gln Ile Val Trp Arg Ile Glu Pro Gly
        115                 120                 125

Pro Tyr Phe Met Glu Pro Glu Ile Lys Ile Cys Phe Lys Tyr Tyr His
    130                 135                 140

Gly Ile Ser Gly Ala Leu Arg Ala Thr Thr Pro Cys Ile Thr Val Lys
145                 150                 155                 160

Asn Pro Ala Val Met Met Gly Ala Glu Gly Met Glu Gly Gly Ala Ser
                165                 170                 175

Gly Asn Leu His Ser Arg Lys Leu Val Ser Phe Thr Leu Ser Asp Leu
            180                 185                 190

Arg Ala Val Gly Leu Lys Lys Gly Met Phe Phe Asn Pro Asp Pro Tyr
        195                 200                 205

Leu Lys Met Ser Ile Gln Pro Gly Lys Lys Ser Ser Phe Pro Thr Cys
    210                 215                 220

Ala His His Gly Gln Glu Arg Arg Ser Thr Ile Ile Ser Asn Thr Thr
225                 230                 235                 240

Asn Pro Ile Trp His Arg Glu Lys Tyr Ser Phe Phe Ala Leu Leu Thr
                245                 250                 255

Asp Val Leu Glu Ile Glu Ile Lys Asp Lys Phe Ala Lys Ser Arg Pro
            260                 265                 270

Ile Ile Lys Arg Phe Leu Gly Lys Leu Thr Ile Pro Val Gln Arg Leu
        275                 280                 285

Leu Glu Arg Gln Ala Ile Gly Asp Gln Met Leu Ser Tyr Asn Leu Gly
    290                 295                 300

Arg Arg Leu Pro Ala Asp His Val Ser Gly Tyr Leu Gln Phe Lys Val
305                 310                 315                 320

```
Glu Val Thr Ser Ser Val His Glu Asp Ala Ser Pro Glu Ala Val Gly
                325                 330                 335

Thr Ile Leu Gly Val Asn Ser Val Asn Gly Asp Leu Gly Ser Pro Ser
                340                 345                 350

Asp Asp Glu Asp Met Pro Gly Ser His His Asp Ser Gln Val Cys Ser
                355                 360                 365

Asn Gly Pro Val Ser Glu Asp Ser Ala Ala Asp Gly Thr Pro Lys His
            370                 375                 380

Ser Phe Arg Thr Ser Ser Thr Leu Glu Ile Asp Thr Glu Glu Leu Thr
385                 390                 395                 400

Ser Thr Ser Ser Arg Thr Ser Pro Pro Arg Gly Arg Gln Asp Ser Leu
                405                 410                 415

Asn Asp Tyr Leu Asp Ala Ile Glu His Asn Gly His Ser Arg Pro Gly
                420                 425                 430

Thr Ala Thr Cys Ser Glu Arg Ser Met Gly Ala Ser Pro Lys Leu Arg
                435                 440                 445

Ser Ser Phe Pro Thr Asp Thr Arg Leu Asn Ala Met Leu His Ile Asp
                450                 455                 460

Ser Asp Glu Glu Asp His Glu Phe Gln Gln Asp Leu Gly Tyr Pro Ser
465                 470                 475                 480

Ser Leu Glu Glu Glu Gly Gly Leu Ile Met Phe Ser Arg Ala Ser Arg
                485                 490                 495

Ala Asp Asp Gly Ser Leu Thr Ser Gln Thr Lys Leu Glu Asp Asn Pro
                500                 505                 510

Val Glu Asn Glu Glu Ala Ser Thr His Glu Ala Ala Ser Phe Glu Asp
                515                 520                 525

Lys Pro Glu Asn Leu Pro Glu Leu Ala Glu Ser Ser Leu Pro Ala Gly
                530                 535                 540

Pro Ala Pro Glu Glu Gly Glu Gly Pro Glu Pro Gln Pro Ser Ala
545                 550                 555                 560

Asp Gln Gly Ser Ala Glu Leu Cys Gly Ser Gln Glu Val Asp Gln Pro
                565                 570                 575

Thr Ser Gly Ala Asp Thr Gly Thr Ser Asp Ala Ser Gly Gly Ser Arg
                580                 585                 590

Arg Ala Val Ser Glu Thr Glu Ser Leu Asp Gln Gly Ser Glu Pro Ser
                595                 600                 605

Gln Val Ser Ser Glu Thr Glu Pro Ser Asp Pro Ala Arg Thr Glu Ser
                610                 615                 620

Val Ser Glu Ala Ser Thr Arg Pro Glu Gly Glu Ser Asp Leu Glu Cys
625                 630                 635                 640

Ala Asp Ser Ser Cys Asn Glu Ser Val Thr Thr Gln Leu Ser Ser Val
                645                 650                 655

Asp Thr Arg Cys Ser Ser Leu Glu Ser Ala Arg Phe Pro Glu Thr Pro
                660                 665                 670

Ala Phe Ser Ser Gln Glu Glu Asp Gly Ala Cys Ala Ala Glu Pro
                675                 680                 685

Thr Ser Ser Gly Pro Ala Glu Gly Ser Gln Glu Ser Val Cys Thr Ala
                690                 695                 700

Gly Ser Leu Pro Val Val Gln Val Pro Ser Gly Glu Asp Glu Gly Pro
705                 710                 715                 720

Gly Ala Glu Ser Ala Thr Val Pro Asp Gln Glu Glu Leu Gly Glu Val
                725                 730                 735
```

-continued

```
Trp Gln Arg Arg Gly Ser Leu Glu Gly Ala Ala Ala Ala Glu Ser
            740                 745                 750

Pro Pro Gln Glu Glu Gly Ser Ala Gly Glu Ala Gln Gly Thr Cys Glu
            755                 760                 765

Gly Ala Thr Ala Gln Glu Glu Gly Ala Thr Gly Gly Ser Gln Ala Asn
            770                 775                 780

Gly His Gln Pro Leu Arg Ser Leu Pro Ser Val Arg Gln Asp Val Ser
785                 790                 795                 800

Arg Tyr Gln Arg Val Asp Glu Ala Leu Pro Pro Asn Trp Glu Ala Arg
                805                 810                 815

Ile Asp Ser His Gly Arg Ile Phe Tyr Val Asp His Val Asn Arg Thr
            820                 825                 830

Thr Thr Trp Gln Arg Pro Thr Ala Pro Pro Ala Pro Gln Val Leu Gln
            835                 840                 845

Arg Ser Asn Ser Ile Gln Gln Met Glu Gln Leu Asn Arg Arg Tyr Gln
            850                 855                 860

Ser Ile Arg Arg Thr Met Thr Asn Glu Arg Pro Glu Glu Asn Thr Asn
865                 870                 875                 880

Ala Ile Asp Gly Ala Gly Glu Glu Ala Asp Phe His Gln Ala Ser Ala
                885                 890                 895

Asp Phe Arg Arg Glu Asn Ile Leu Pro His Ser Thr Ser Arg Ser Arg
            900                 905                 910

Ile Thr Leu Leu Leu Gln Ser Pro Pro Val Lys Phe Leu Ile Ser Pro
            915                 920                 925

Glu Phe Phe Thr Val Leu His Ser Asn Pro Ser Ala Tyr Arg Met Phe
            930                 935                 940

Thr Asn Asn Thr Cys Leu Lys His Met Ile Thr Lys Val Arg Arg Asp
945                 950                 955                 960

Thr His His Phe Glu Arg Tyr Gln His Asn Arg Asp Leu Val Gly Phe
                965                 970                 975

Leu Asn Met Phe Ala Asn Lys Gln Leu Glu Leu Pro Arg Gly Trp Glu
            980                 985                 990

Met Lys His Asp His Gln Gly Lys Ala Phe Phe Val Asp His Asn Ser
            995                 1000                1005

Arg Thr Thr Thr Phe Ile Asp Pro Arg Leu Pro Leu Gln Ser Ser
            1010                1015                1020

Arg Pro Thr Ser Ala Leu Val His Arg Gln His Leu Thr Arg Gln
            1025                1030                1035

Arg Ser His Ser Ala Gly Glu Val Gly Glu Asp Ser Arg His Ala
            1040                1045                1050

Gly Pro Pro Val Leu Pro Arg Pro Ser Ser Thr Phe Asn Thr Val
            1055                1060                1065

Ser Arg Pro Gln Tyr Gln Asp Met Val Pro Val Ala Tyr Asn Asp
            1070                1075                1080

Lys Ile Val Ala Phe Leu Arg Gln Pro Asn Ile Phe Glu Ile Leu
            1085                1090                1095

Gln Glu Arg Gln Pro Asp Leu Thr Arg Asn His Ser Leu Arg Glu
            1100                1105                1110

Lys Ile Gln Phe Ile Arg Thr Glu Gly Thr Pro Gly Leu Val Arg
            1115                1120                1125

Leu Ser Ser Asp Ala Asp Leu Val Met Leu Leu Ser Leu Phe Glu
            1130                1135                1140

Glu Glu Ile Met Ser Tyr Val Pro Pro His Ala Leu Leu His Pro
```

```
            1145                1150                1155
Ser  Tyr  Cys  Gln  Ser  Pro  Arg  Gly  Ser  Pro  Val  Ser  Ser  Pro  Gln
         1160                1165                1170
Asn  Ser  Pro  Gly  Thr  Gln  Arg  Ala  Asn  Ala  Arg  Ala  Pro  Ala  Pro
         1175                1180                1185
Tyr  Lys  Arg  Asp  Phe  Glu  Ala  Lys  Leu  Arg  Asn  Phe  Tyr  Arg  Lys
         1190                1195                1200
Leu  Glu  Thr  Lys  Gly  Tyr  Gly  Gln  Gly  Pro  Gly  Lys  Leu  Lys  Leu
         1205                1210                1215
Ile  Ile  Arg  Arg  Asp  His  Leu  Leu  Glu  Asp  Ala  Phe  Asn  Gln  Ile
         1220                1225                1230
Met  Gly  Tyr  Ser  Arg  Lys  Asp  Leu  Gln  Arg  Asn  Lys  Leu  Tyr  Val
         1235                1240                1245
Thr  Phe  Val  Gly  Glu  Glu  Gly  Leu  Asp  Tyr  Ser  Gly  Pro  Ser  Arg
         1250                1255                1260
Glu  Phe  Phe  Phe  Leu  Val  Ser  Arg  Glu  Leu  Phe  Asn  Pro  Tyr  Tyr
         1265                1270                1275
Gly  Leu  Phe  Glu  Tyr  Ser  Ala  Asn  Asp  Thr  Tyr  Thr  Val  Gln  Ile
         1280                1285                1290
Ser  Pro  Met  Ser  Ala  Phe  Val  Asp  Asn  His  His  Glu  Trp  Phe  Arg
         1295                1300                1305
Phe  Ser  Gly  Arg  Ile  Leu  Gly  Leu  Ala  Leu  Ile  His  Gln  Tyr  Leu
         1310                1315                1320
Leu  Asp  Ala  Phe  Phe  Thr  Arg  Pro  Phe  Tyr  Lys  Ala  Leu  Leu  Arg
         1325                1330                1335
Ile  Leu  Cys  Asp  Leu  Ser  Asp  Leu  Glu  Tyr  Leu  Asp  Glu  Glu  Phe
         1340                1345                1350
His  Gln  Ser  Leu  Gln  Trp  Met  Lys  Asp  Asn  Asp  Ile  His  Asp  Ile
         1355                1360                1365
Leu  Asp  Leu  Thr  Phe  Thr  Val  Asn  Glu  Glu  Val  Phe  Gly  Gln  Ile
         1370                1375                1380
Thr  Glu  Arg  Glu  Leu  Lys  Pro  Gly  Gly  Ala  Asn  Ile  Pro  Val  Thr
         1385                1390                1395
Glu  Lys  Asn  Lys  Lys  Glu  Tyr  Ile  Glu  Arg  Met  Val  Lys  Trp  Arg
         1400                1405                1410
Ile  Glu  Arg  Gly  Val  Val  Gln  Gln  Thr  Glu  Ser  Leu  Val  Arg  Gly
         1415                1420                1425
Phe  Tyr  Glu  Val  Val  Asp  Ala  Arg  Leu  Val  Ser  Val  Phe  Asp  Ala
         1430                1435                1440
Arg  Glu  Leu  Glu  Leu  Val  Ile  Ala  Gly  Thr  Ala  Glu  Ile  Asp  Leu
         1445                1450                1455
Ser  Asp  Trp  Arg  Asn  Asn  Thr  Glu  Tyr  Arg  Gly  Gly  Tyr  His  Asp
         1460                1465                1470
Asn  His  Ile  Val  Ile  Arg  Trp  Phe  Trp  Ala  Ala  Val  Glu  Arg  Phe
         1475                1480                1485
Asn  Asn  Glu  Gln  Arg  Leu  Arg  Leu  Leu  Gln  Phe  Val  Thr  Gly  Thr
         1490                1495                1500
Ser  Ser  Ile  Pro  Tyr  Glu  Gly  Phe  Ala  Ser  Leu  Arg  Gly  Ser  Asn
         1505                1510                1515
Gly  Pro  Arg  Arg  Phe  Cys  Val  Glu  Lys  Trp  Gly  Lys  Ile  Thr  Ala
         1520                1525                1530
Leu  Pro  Arg  Ala  His  Thr  Cys  Phe  Asn  Arg  Leu  Asp  Leu  Pro  Pro
         1535                1540                1545
```

```
Tyr Pro Ser Phe Ser Met Leu Tyr Glu Lys Leu Leu Thr Ala Val
    1550                1555                1560

Glu Glu Thr Ser Thr Phe Gly Leu Glu
    1565                1570

<210> SEQ ID NO 15
<211> LENGTH: 433
<212> TYPE: PRT
<213> ORGANISM: Homo sapiens

<400> SEQUENCE: 15

Met Gly Arg Val Gln Leu Phe Glu Ile Ser Leu Ser His Gly Arg Val
1               5                   10                  15

Val Tyr Ser Pro Gly Glu Pro Leu Ala Gly Thr Val Arg Val Arg Leu
            20                  25                  30

Gly Ala Pro Leu Pro Phe Arg Ala Ile Arg Val Thr Cys Ile Gly Ser
        35                  40                  45

Cys Gly Val Ser Asn Lys Ala Asn Asp Thr Ala Trp Val Val Glu Glu
    50                  55                  60

Gly Tyr Phe Asn Ser Ser Leu Ser Leu Ala Asp Lys Gly Ser Leu Pro
65                  70                  75                  80

Ala Gly Glu His Ser Phe Pro Phe Gln Phe Leu Leu Pro Ala Thr Ala
                85                  90                  95

Pro Thr Ser Phe Glu Gly Pro Phe Gly Lys Ile Val His Gln Val Arg
            100                 105                 110

Ala Ala Ile His Thr Pro Arg Phe Ser Lys Asp His Lys Cys Ser Leu
        115                 120                 125

Val Phe Tyr Ile Leu Ser Pro Leu Asn Leu Asn Ser Ile Pro Asp Ile
130                 135                 140

Glu Gln Pro Asn Val Ala Ser Ala Thr Lys Lys Phe Ser Tyr Lys Leu
145                 150                 155                 160

Val Lys Thr Gly Ser Val Val Leu Thr Ala Ser Thr Asp Leu Arg Gly
                165                 170                 175

Tyr Val Val Gly Gln Ala Leu Gln Leu His Ala Asp Val Glu Asn Gln
            180                 185                 190

Ser Gly Lys Asp Thr Ser Pro Val Val Ala Ser Leu Leu Gln Lys Val
        195                 200                 205

Ser Tyr Lys Ala Lys Arg Trp Ile His Asp Val Arg Thr Ile Ala Glu
210                 215                 220

Val Glu Gly Ala Gly Val Lys Ala Trp Arg Arg Ala Gln Trp His Glu
225                 230                 235                 240

Gln Ile Leu Val Pro Ala Leu Pro Gln Ser Ala Leu Pro Gly Cys Ser
                245                 250                 255

Leu Ile His Ile Asp Tyr Tyr Leu Gln Val Ser Leu Lys Ala Pro Glu
            260                 265                 270

Ala Thr Val Thr Leu Pro Val Phe Ile Gly Asn Ile Ala Val Asn His
        275                 280                 285

Ala Pro Val Ser Pro Arg Pro Gly Leu Gly Leu Pro Pro Gly Ala Pro
    290                 295                 300

Pro Leu Val Val Pro Ser Ala Pro Pro Gln Glu Ala Glu Ala Glu
305                 310                 315                 320

Ala Ala Ala Gly Gly Pro His Phe Leu Asp Pro Val Phe Leu Ser Thr
                325                 330                 335

Lys Ser His Ser Gln Arg Gln Pro Leu Leu Ala Thr Leu Ser Ser Val
```

```
                340             345             350
Pro Gly Ala Pro Glu Pro Cys Pro Gln Asp Gly Ser Pro Ala Ser His
            355                 360                 365
Pro Leu His Pro Pro Leu Cys Ile Ser Thr Gly Ala Thr Val Pro Tyr
        370                 375                 380
Phe Ala Glu Gly Ser Gly Gly Pro Val Pro Thr Thr Ser Thr Leu Ile
385                 390                 395                 400
Leu Pro Pro Glu Tyr Ser Ser Trp Gly Tyr Pro Tyr Glu Ala Pro Pro
                405                 410                 415
Ser Tyr Glu Gln Ser Cys Gly Gly Val Glu Pro Ser Leu Thr Pro Glu
            420                 425                 430
Ser

<210> SEQ ID NO 16
<211> LENGTH: 434
<212> TYPE: PRT
<213> ORGANISM: Mus musculus

<400> SEQUENCE: 16

Met Gly Arg Val Gln Leu Phe Glu Ile Arg Leu Ser Gln Gly Arg Val
1               5                   10                  15
Val Tyr Gly Pro Gly Glu Pro Leu Ala Gly Thr Val His Leu Arg Leu
            20                  25                  30
Gly Ala Pro Leu Pro Phe Arg Ala Ile Arg Val Thr Cys Met Gly Ser
        35                  40                  45
Cys Gly Val Ser Thr Lys Ala Asn Asp Gly Ala Trp Val Val Glu Glu
    50                  55                  60
Ser Tyr Phe Asn Ser Ser Leu Ser Leu Ala Asp Lys Gly Ser Leu Pro
65                  70                  75                  80
Ala Gly Glu His Asn Phe Pro Phe Gln Phe Leu Leu Pro Ala Thr Ala
                85                  90                  95
Pro Thr Ser Phe Glu Gly Pro Phe Gly Lys Ile Val His Gln Val Arg
            100                 105                 110
Ala Ser Ile Asp Thr Pro Arg Phe Ser Lys Asp His Lys Cys Ser Leu
        115                 120                 125
Val Phe Tyr Ile Leu Ser Pro Leu Asn Leu Asn Ser Ile Pro Asp Ile
    130                 135                 140
Glu Gln Pro Asn Val Ala Ser Thr Thr Lys Lys Phe Ser Tyr Lys Leu
145                 150                 155                 160
Val Lys Thr Gly Asn Val Val Leu Thr Ala Ser Thr Asp Leu Arg Gly
                165                 170                 175
Tyr Val Val Gly Gln Val Leu Arg Leu Gln Ala Asp Ile Glu Asn Gln
            180                 185                 190
Ser Gly Lys Asp Thr Ser Pro Val Ala Ser Leu Leu Gln Lys Val
        195                 200                 205
Ser Tyr Lys Ala Lys Arg Trp Ile Tyr Asp Val Arg Thr Ile Ala Glu
    210                 215                 220
Val Glu Gly Thr Gly Val Lys Ala Trp Arg Arg Ala Gln Trp Gln Glu
225                 230                 235                 240
Gln Ile Leu Val Pro Ala Leu Pro Gln Ser Ala Leu Pro Gly Cys Ser
                245                 250                 255
Leu Ile His Ile Asp Tyr Tyr Leu Gln Val Ser Met Lys Ala Pro Glu
            260                 265                 270
Ala Thr Val Thr Leu Pro Leu Phe Val Gly Asn Ile Ala Val Asn Gln
```

```
              275                 280                 285
Thr Pro Leu Ser Pro Cys Pro Gly Arg Glu Ser Ser Pro Gly Thr Leu
        290                 295                 300

Ser Leu Val Val Pro Ser Ala Pro Pro Gln Glu Ala Glu Ala Val
305                 310                 315                 320

Ala Ser Gly Pro His Phe Ser Asp Pro Val Ser Leu Ser Thr Lys Ser
                325                 330                 335

His Ser Gln Gln Gln Pro Leu Ser Ala Pro Leu Gly Ser Val Ser Val
            340                 345                 350

Thr Thr Thr Glu Pro Trp Val Gln Val Gly Ser Pro Ala Arg His Ser
        355                 360                 365

Leu His Pro Pro Leu Cys Ile Ser Ile Gly Ala Thr Val Pro Tyr Phe
    370                 375                 380

Ala Glu Gly Ser Ala Gly Pro Val Pro Thr Thr Ser Ala Leu Ile Leu
385                 390                 395                 400

Pro Pro Glu Tyr Ser Ser Trp Gly Tyr Pro Tyr Glu Ala Pro Pro Ser
                405                 410                 415

Tyr Glu Gln Ser Cys Gly Ala Ala Gly Thr Asp Leu Gly Leu Ile Pro
            420                 425                 430

Gly Ser

<210> SEQ ID NO 17
<211> LENGTH: 433
<212> TYPE: PRT
<213> ORGANISM: Mus musculus

<400> SEQUENCE: 17

Met Gly Arg Val Gln Leu Phe Glu Ile Arg Leu Ser Gln Gly Arg Val
1               5                   10                  15

Val Tyr Gly Pro Gly Glu Pro Leu Ala Gly Thr Val His Leu Arg Leu
                20                  25                  30

Gly Ala Pro Leu Pro Phe Arg Ala Ile Arg Val Thr Cys Met Gly Ser
            35                  40                  45

Cys Gly Val Ser Thr Lys Ala Asn Asp Gly Ala Trp Val Val Glu Glu
    50                  55                  60

Ser Tyr Phe Asn Ser Ser Leu Ser Leu Ala Asp Lys Gly Ser Leu Pro
65              70                  75                  80

Ala Gly Glu His Asn Phe Pro Phe Gln Phe Leu Leu Pro Ala Thr Ala
                85                  90                  95

Pro Thr Ser Phe Glu Gly Pro Phe Gly Lys Ile Val His Gln Val Arg
            100                 105                 110

Ala Ser Ile Asp Thr Pro Arg Phe Ser Lys Asp His Lys Cys Ser Leu
        115                 120                 125

Val Phe Tyr Ile Leu Ser Pro Leu Asn Leu Asn Ser Ile Pro Asp Ile
    130                 135                 140

Glu Gln Pro Asn Val Ala Ser Thr Thr Lys Lys Phe Ser Tyr Lys Leu
145                 150                 155                 160

Val Lys Thr Gly Asn Val Val Leu Thr Ala Ser Thr Asp Leu Arg Gly
                165                 170                 175

Tyr Val Val Gly Gln Val Leu Arg Leu Gln Ala Asp Ile Glu Asn Gln
            180                 185                 190

Ser Gly Lys Asp Thr Ser Pro Val Val Ala Ser Leu Leu Gln Val Ser
        195                 200                 205

Tyr Lys Ala Lys Arg Trp Ile Tyr Asp Val Arg Thr Ile Ala Glu Val
```

```
                    210                 215                 220
Glu Gly Thr Gly Val Lys Ala Trp Arg Arg Ala Gln Trp Gln Glu Gln
225                 230                 235                 240

Ile Leu Val Pro Ala Leu Pro Gln Ser Ala Leu Pro Gly Cys Ser Leu
                    245                 250                 255

Ile His Ile Asp Tyr Tyr Leu Gln Val Ser Met Lys Ala Pro Glu Ala
                    260                 265                 270

Thr Val Thr Leu Pro Leu Phe Val Gly Asn Ile Ala Val Asn Gln Thr
                    275                 280                 285

Pro Leu Ser Pro Cys Pro Gly Arg Glu Ser Ser Pro Gly Thr Leu Ser
                    290                 295                 300

Leu Val Val Pro Ser Ala Pro Pro Gln Glu Glu Ala Glu Ala Val Ala
305                 310                 315                 320

Ser Gly Pro His Phe Ser Asp Pro Val Ser Leu Ser Thr Lys Ser His
                    325                 330                 335

Ser Gln Gln Gln Pro Leu Ser Ala Pro Leu Gly Ser Val Ser Val Thr
                    340                 345                 350

Thr Thr Glu Pro Trp Val Gln Val Gly Ser Pro Ala Arg His Ser Leu
                    355                 360                 365

His Pro Pro Leu Cys Ile Ser Ile Gly Ala Thr Val Pro Tyr Phe Ala
                    370                 375                 380

Glu Gly Ser Ala Gly Pro Val Pro Thr Thr Ser Ala Leu Ile Leu Pro
385                 390                 395                 400

Pro Glu Tyr Ser Ser Trp Gly Tyr Pro Tyr Glu Ala Pro Pro Ser Tyr
                    405                 410                 415

Glu Gln Ser Cys Gly Ala Ala Gly Thr Asp Leu Gly Leu Ile Pro Gly
                    420                 425                 430

Ser

<210> SEQ ID NO 18
<211> LENGTH: 65
<212> TYPE: PRT
<213> ORGANISM: Homo sapiens

<400> SEQUENCE: 18

Pro Leu Pro Pro Gly Trp Glu Gln Arg Val Asp Gln His Gly Arg Val
1               5                   10                  15

Tyr Tyr Val Asp His Val Glu Lys Arg Thr Thr Trp Asp Arg Pro Glu
                20                  25                  30

Pro Leu Pro Pro Gly Trp Glu Arg Arg Val Asp Asn Met Gly Arg Ile
            35                  40                  45

Tyr Tyr Val Asp His Phe Thr Arg Thr Thr Trp Gln Arg Pro Thr
    50                  55                  60

Leu
65

<210> SEQ ID NO 19
<211> LENGTH: 185
<212> TYPE: PRT
<213> ORGANISM: Homo sapiens

<400> SEQUENCE: 19

Pro Leu Pro Pro Gly Trp Glu Gln Arg Val Asp Gln His Gly Arg Val
1               5                   10                  15

Tyr Tyr Val Asp His Val Glu Lys Arg Thr Thr Trp Asp Arg Pro Glu
                20                  25                  30
```

```
Pro Leu Pro Pro Gly Trp Glu Arg Arg Val Asp Asn Met Gly Arg Ile
        35                  40                  45

Tyr Tyr Val Asp His Phe Thr Arg Thr Thr Trp Gln Arg Pro Thr
 50                  55                  60

Leu Glu Ser Val Arg Asn Tyr Glu Gln Trp Gln Leu Gln Arg Ser Gln
 65                  70                  75                  80

Leu Gln Gly Ala Met Gln Gln Phe Asn Gln Arg Phe Ile Tyr Gly Asn
                 85                  90                  95

Gln Asp Leu Phe Ala Thr Ser Gln Ser Lys Glu Phe Asp Pro Leu Gly
            100                 105                 110

Pro Leu Pro Pro Gly Trp Glu Lys Arg Thr Asp Ser Asn Gly Arg Val
        115                 120                 125

Tyr Phe Val Asn His Asn Thr Arg Ile Thr Gln Trp Glu Asp Pro Arg
130                 135                 140

Ser Gln Gly Gln Leu Asn Glu Lys Pro Leu Pro Glu Gly Trp Glu Met
145                 150                 155                 160

Arg Phe Thr Val Asp Gly Ile Pro Tyr Phe Val Asp His Asn Arg Arg
                165                 170                 175

Thr Thr Thr Tyr Ile Asp Pro Arg Thr
            180                 185

<210> SEQ ID NO 20
<211> LENGTH: 390
<212> TYPE: PRT
<213> ORGANISM: Mus musculus

<400> SEQUENCE: 20

Met Ala Val Ser Glu Ser Gln Leu Lys Lys Met Val Ser Lys Tyr Lys
  1               5                  10                  15

Tyr Arg Asp Leu Thr Val Arg Glu Thr Val Asn Val Ile Thr Leu Tyr
             20                  25                  30

Lys Asp Leu Lys Pro Val Leu Asp Ser Tyr Val Phe Asn Asp Gly Ser
         35                  40                  45

Ser Arg Glu Leu Met Asn Leu Thr Gly Thr Ile Pro Val Pro Tyr Arg
 50                  55                  60

Gly Asn Thr Tyr Asn Ile Pro Ile Cys Leu Trp Leu Leu Asp Thr Tyr
 65                  70                  75                  80

Pro Tyr Asn Pro Pro Ile Cys Phe Val Lys Pro Thr Ser Ser Met Thr
                 85                  90                  95

Ile Lys Thr Gly Lys His Val Asp Ala Asn Gly Lys Ile Tyr Leu Pro
            100                 105                 110

Tyr Leu His Glu Trp Lys His Pro Gln Ser Asp Leu Leu Gly Leu Ile
        115                 120                 125

Gln Val Met Ile Val Val Phe Gly Asp Glu Pro Pro Val Phe Ser Arg
130                 135                 140

Pro Ile Ser Ala Ser Tyr Pro Pro Tyr Gln Ala Thr Gly Pro Pro Asn
145                 150                 155                 160

Thr Ser Tyr Met Pro Gly Met Pro Gly Gly Ile Ser Pro Tyr Pro Ser
                165                 170                 175

Gly Tyr Pro Pro Asn Pro Ser Gly Tyr Pro Gly Cys Pro Tyr Pro Pro
            180                 185                 190

Gly Gly Pro Tyr Pro Ala Thr Thr Ser Ser Gln Tyr Pro Ser Gln Pro
        195                 200                 205

Pro Val Thr Thr Val Gly Pro Ser Arg Asp Gly Thr Ile Ser Glu Asp
```

```
                    210                 215                 220
Thr Ile Arg Ala Ser Leu Ile Ser Ala Val Ser Asp Lys Leu Arg Trp
225                 230                 235                 240

Arg Met Lys Glu Glu Met Asp Arg Ala Gln Ala Glu Leu Asn Ala Leu
                245                 250                 255

Lys Arg Thr Glu Glu Asp Leu Lys Lys Gly His Gln Lys Leu Glu Glu
            260                 265                 270

Met Val Thr Arg Leu Asp Gln Glu Val Ala Glu Val Asp Lys Asn Ile
        275                 280                 285

Glu Leu Leu Lys Lys Lys Asp Glu Glu Leu Ser Ser Ala Leu Glu Lys
    290                 295                 300

Met Glu Asn Gln Ser Glu Asn Asn Asp Ile Asp Glu Val Ile Ile Pro
305                 310                 315                 320

Thr Ala Pro Leu Tyr Lys Gln Ile Leu Asn Leu Tyr Ala Glu Glu Asn
                325                 330                 335

Ala Ile Glu Asp Thr Ile Phe Tyr Leu Gly Glu Ala Leu Arg Arg Gly
            340                 345                 350

Val Ile Asp Leu Asp Val Phe Leu Lys His Val Arg Leu Leu Ser Arg
        355                 360                 365

Lys Gln Phe Gln Leu Arg Ala Leu Met Gln Lys Ala Arg Lys Thr Ala
    370                 375                 380

Gly Leu Ser Asp Leu Tyr
385                 390

<210> SEQ ID NO 21
<211> LENGTH: 391
<212> TYPE: PRT
<213> ORGANISM: Mus musculus

<400> SEQUENCE: 21

Met Ala Val Ser Glu Ser Gln Leu Lys Lys Met Met Ser Lys Tyr Lys
1               5                   10                  15

Tyr Arg Asp Leu Thr Val Arg Gln Thr Val Asn Val Ile Ala Met Tyr
            20                  25                  30

Lys Asp Leu Lys Pro Val Leu Asp Ser Tyr Val Phe Asn Asp Gly Ser
        35                  40                  45

Ser Arg Glu Leu Val Asn Leu Thr Gly Thr Ile Pro Val Arg Tyr Arg
    50                  55                  60

Gly Asn Ile Tyr Asn Ile Pro Ile Cys Leu Trp Leu Leu Asp Thr Tyr
65                  70                  75                  80

Pro Tyr Asn Pro Pro Ile Cys Phe Val Lys Pro Thr Ser Ser Met Thr
                85                  90                  95

Ile Lys Thr Gly Lys His Val Asp Ala Asn Gly Lys Ile Tyr Leu Pro
            100                 105                 110

Tyr Leu His Asp Trp Lys His Pro Arg Ser Glu Leu Leu Glu Leu Ile
        115                 120                 125

Gln Ile Met Ile Val Ile Phe Gly Glu Glu Pro Val Phe Ser Arg
    130                 135                 140

Pro Thr Val Ser Ala Ser Tyr Pro Tyr Thr Ala Thr Gly Pro Pro
145                 150                 155                 160

Asn Thr Ser Tyr Met Pro Gly Met Pro Ser Gly Ile Ser Ala Tyr Pro
                165                 170                 175

Ser Gly Tyr Pro Pro Asn Pro Ser Gly Tyr Pro Gly Cys Pro Tyr Pro
            180                 185                 190
```

```
Pro Ala Gly Pro Tyr Pro Ala Thr Thr Ser Ser Gln Tyr Pro Ser Gln
            195                 200                 205

Pro Pro Val Thr Thr Val Gly Pro Ser Arg Asp Gly Thr Ile Ser Glu
210                 215                 220

Asp Thr Ile Arg Ala Ser Leu Ile Ser Ala Val Ser Asp Lys Leu Arg
225                 230                 235                 240

Trp Arg Met Lys Glu Met Asp Gly Ala Gln Ala Glu Leu Asn Ala
            245                 250                 255

Leu Lys Arg Thr Glu Glu Asp Leu Lys Gly His Gln Lys Leu Glu
            260                 265                 270

Glu Met Val Thr Arg Leu Asp Gln Glu Val Ala Glu Val Asp Lys Asn
            275                 280                 285

Ile Glu Leu Leu Lys Lys Lys Asp Glu Glu Leu Ser Ser Ala Leu Glu
290                 295                 300

Lys Met Glu Asn Gln Ser Glu Asn Asn Asp Ile Asp Glu Val Ile Ile
305                 310                 315                 320

Pro Thr Ala Pro Leu Tyr Lys Gln Ile Leu Asn Leu Tyr Ala Glu Glu
            325                 330                 335

Asn Ala Ile Glu Asp Thr Ile Phe Tyr Leu Gly Glu Ala Leu Arg Arg
            340                 345                 350

Gly Val Ile Asp Leu Asp Val Phe Leu Lys His Val Arg Leu Leu Ser
            355                 360                 365

Arg Lys Gln Phe Gln Leu Arg Ala Leu Met Gln Lys Ala Arg Lys Thr
            370                 375                 380

Ala Gly Leu Ser Asp Leu Tyr
385                 390

<210> SEQ ID NO 22
<211> LENGTH: 391
<212> TYPE: PRT
<213> ORGANISM: Rattus norvegicus

<400> SEQUENCE: 22

Met Ala Val Ser Glu Ser Gln Leu Lys Lys Met Met Ser Lys Tyr Lys
1               5                   10                  15

Tyr Arg Asp Leu Thr Val Arg Gln Thr Val Asn Val Ile Ala Met Tyr
            20                  25                  30

Lys Asp Leu Lys Pro Val Leu Asp Ser Tyr Val Phe Asn Asp Gly Ser
            35                  40                  45

Ser Arg Glu Leu Val Asn Leu Thr Gly Thr Ile Pro Val Arg Tyr Arg
50                  55                  60

Gly Asn Ile Tyr Asn Ile Pro Ile Cys Leu Trp Leu Leu Asp Thr Tyr
65                  70                  75                  80

Pro Tyr Asn Pro Pro Ile Cys Phe Val Lys Pro Thr Ser Ser Met Thr
            85                  90                  95

Ile Lys Thr Gly Lys His Val Asp Ala Asn Gly Lys Ile Tyr Leu Pro
            100                 105                 110

Tyr Leu His Asp Trp Lys His Pro Arg Ser Glu Leu Leu Glu Leu Ile
            115                 120                 125

Gln Ile Met Ile Val Ile Phe Gly Glu Glu Pro Val Phe Ser Arg
            130                 135                 140

Pro Thr Val Ser Ala Ser Tyr Pro Tyr Thr Ala Ala Gly Pro Pro
145                 150                 155                 160

Asn Thr Ser Tyr Leu Pro Ser Met Pro Ser Gly Ile Ser Ala Tyr Pro
            165                 170                 175
```

```
Ser Gly Tyr Pro Pro Asn Pro Ser Gly Tyr Pro Gly Cys Pro Tyr Pro
            180                 185                 190

Pro Ala Gly Pro Tyr Pro Ala Thr Thr Ser Ser Gln Tyr Pro Ser Gln
        195                 200                 205

Pro Pro Val Thr Thr Ala Gly Pro Ser Arg Asp Gly Thr Ile Ser Glu
    210                 215                 220

Asp Thr Ile Arg Ala Ser Leu Ile Ser Ala Val Ser Asp Lys Leu Arg
225                 230                 235                 240

Trp Arg Met Lys Glu Met Asp Gly Ala Gln Ala Glu Leu Asn Ala
                245                 250                 255

Leu Lys Arg Thr Glu Glu Asp Leu Lys Lys Gly His Gln Lys Leu Glu
            260                 265                 270

Glu Met Val Thr Arg Leu Asp Gln Glu Val Ala Glu Val Asp Lys Asn
        275                 280                 285

Ile Glu Leu Leu Lys Lys Lys Asp Glu Glu Leu Ser Ser Ala Leu Glu
    290                 295                 300

Lys Met Glu Asn Gln Ser Glu Asn Asn Asp Ile Asp Glu Val Ile Ile
305                 310                 315                 320

Pro Thr Ala Pro Leu Tyr Lys Gln Ile Leu Asn Leu Tyr Ala Glu Glu
                325                 330                 335

Asn Ala Ile Glu Asp Thr Ile Phe Tyr Leu Gly Glu Ala Leu Arg Arg
            340                 345                 350

Gly Val Ile Asp Leu Asp Val Phe Leu Lys His Val Arg Leu Leu Ser
        355                 360                 365

Arg Lys Gln Phe Gln Leu Arg Ala Leu Met Gln Lys Ala Arg Lys Thr
    370                 375                 380

Ala Gly Leu Ser Asp Leu Tyr
385                 390

<210> SEQ ID NO 23
<211> LENGTH: 3475
<212> TYPE: DNA
<213> ORGANISM: Homo sapiens

<400> SEQUENCE: 23
gaattcgcgg ccgcgtcgac cgcttctgtg gccacggcag atgaaacaga aaggctaaag      60
agggctggag tcaggggact tctcttccac cagcttcacg gtgatgatat ggcatctgcc     120
agctctagcc gggcaggagt ggccctgcct tttgagaagt ctcagctcac tttgaaagtg     180
gtgtccgcaa agcccaaggt gcataatcgt caacctcgaa ttaactccta cgtggaggtg     240
gcggtggatg gactccccag tgagaccaag aagactggga agcgcattgg gagctctgag     300
cttctctgga atgagatcat cattttgaat gtcacggcac agagtcattt agatttaaag     360
gtctggagct gccataccct gagaaatgaa ctgctaggca ccgcatctgt caacctctcc     420
aacgtcttga agaacaatgg gggcaaaatg gagaacatgc agctgaccct gaacctgcag     480
acggagaaca aaggcagcgt tgtctcaggc ggaaaactga caattttcct ggacgggcca     540
actgttgatc tgggaaatgt gcctaatggc agtgccctga cagatggatc acagctgcct     600
tcgagagact ccagtggaac agcagtagct ccagagaacc ggcaccagcc cccagcaca      660 aactgctttg gtggaagatc ccggacgcac agacattcgg gtgcttcagc cagaacaacc     720
ccagcaaccg cgcagcaaag ccccggtgct cggagccggc accgccagcc cgtcaagaac     780
tcaggccaca gtggcttggc caatggcaca gtgaatgatg aacccacaac agccactgat     840
```

-continued

```
cccgaagaac cttccgttgt tggtgtgacg tccccacctg ctgcacccct gagtgtgacc    900
ccgaatccca acacgacttc tctccctgcc ccagccacac cggctgaagg agaggaaccc    960
agcacttcgg gtacacagca gctcccagcg gctgcccagg cccccgacgc tctgcctgct   1020
ggatgggaac agcgagagct gcccaacgga cgtgtctatt atgttgacca caataccaag   1080
accaccacct gggagcggcc ccttcctcca ggctgggaaa aacgcacaga tccccgaggc   1140
aggttttact atgtggatca caatactcgg accaccacct ggcagcgtcc gaccgcggag   1200
tacgtgcgca actatgagca gtggcagtcg cagcggaatc agctccaggg ggccatgcag   1260
cacttcagcc aaagattcct ataccagttt tggagtgctt cgactgacca tgatcccctg   1320
ggccccctcc ctcctggttg ggagaaaaga caggacaatg gacgggtgta ttacgtgaac   1380
cataacactc gcacgaccca gtgggaggat ccccggaccc aggggatgat ccaggaacca   1440
gctttgcccc caggatggga gatgaaatac accagcgagg gggtgcgata ctttgtggac   1500
cacaataccc gcaccaccac ctttaaggat cctcgcccgg ggtttgagtc ggggacgaag   1560
caaggttccc ctggtgctta tgaccgcagt tttcggtgga agtatcacca gttccgtttc   1620
ctctgccatt caaatgccct acctagccac gtgaagatca gcgtttccag gcagacgctt   1680
ttcgaagatt ccttccaaca gatcatgaac atgaaaccct atgacctgcg ccgccggctt   1740
tacatcatca tgcgtggcga ggagggcctg gactatgggg gcatcgccag agagtggttt   1800
ttcctcctgt ctcacgaggt gctcaaccct atgtattgtt tatttgaata tgccggaaag   1860
aacaattact gcctgcagat caaccccgcc tcctccatca acccggacca cctcacctac   1920
tttcgcttta taggcagatt catcgccatg gcgctgtacc atggaaagtt catcgacacg   1980
ggcttcaccc tccctttcta caagcggatg ctcaataaga gaccaaccct gaaagacctg   2040
gagtccattg accctgagtt ctacaactcc attgtctgga tcaaagagaa caacctggaa   2100
gaatgtggcc tggagctgta cttcatccag gacatggaga tactgggcaa ggtgacgacc   2160
cacgagctga aggagggcgg cgagagcatc cgggtcacgg aggagaacaa ggaagagtac   2220
atcatgctgc tgactgactg gcgtttcacc cgaggcgtgg aagagcagac caaagccttc   2280
ctggatggct tcaacgaggt ggcccccgct gagtggctgc gctactttga cgagaaagag   2340
ctggagctga tgctgtgcgg catgcaggag atagacatga gcgactggca gaagagcacc   2400
atctaccggc actacaccaa gaacagcaag cagatccagt ggttctggca ggtggtgaag   2460
gagatggaca acgagaagag gatccggctg ctgcagtttg tcaccggtac ctgccgcctg   2520
cccgtcgggg gatttgccga actcatcggt agcaacggac cacagaagtt ttgcattgac   2580
aaagttggca aggaaacctg gctgcccaga agccacacct gcttcaaccg tctggatctt   2640
ccaccctaca gagctacgaa acagctgaga gagaagctgc tgtatgccat tgaggagacc   2700
gagggctttg gacaggagta accgaggccg cccctcccac gcccccccagc gcacatgtag   2760
tcctgagtcc tccctgcctg agaggccact ggccccgcag cccttgggag gccccgtgg    2820
atgtggccct gtgtgggacc acactgtcat ctcgctgctg gcagaaaagc ctgatcccag   2880
gaggccctgc agttcccccg acccgcggat ggcagtctgg aataaagccc cctagttgcc   2940
tttggcccca cctttgcaaa gttccagagg gctgaccctc tctgcaaaac tctcccctgt   3000
cctctagacc ccaccctggg tgtatgtgag tgtgcaaggg aaggtgttgc atccccaggg   3060
gctgccgcag aggccggaga cctcctggac tagttcggcg aggagactgg ccactggggg   3120
tggctgttcg ggactgagag cgccaagggt cttgccagc aaaggaggtt ctgcctgtaa    3180
ttgagcctct ctgatgatgg agatgaagtg aaggtctgag ggacgggccc tggggctagg   3240
```

-continued

| | |
|---|---|
| ccatctctgc ctgcctccct agcaggcgcc agcggtggag gctgagtcgc aggacacatg | 3300 |
| ccggccagtt aattcattct cagcaaatga aggtttgtct aagctgcctg ggtatccacg | 3360 |
| ggacaaaaac agcaaactcc ctccagactt tgtccatgtt ataaacttga aagttggttg | 3420 |
| ttgtttgtta ggtttgccag gttttttttgt ttacgcctgc tgtcactttc ctgtc | 3475 |

<210> SEQ ID NO 24
<211> LENGTH: 3475
<212> TYPE: DNA
<213> ORGANISM: Homo sapiens

<400> SEQUENCE: 24

| | |
|---|---|
| gaattcgcgg ccgcgtcgac cgcttctgtg gccacggcag atgaaacaga aaggctaaag | 60 |
| agggctggag tcaggggact tctcttccac cagcttcacg gtgatgatat ggcatctgcc | 120 |
| agctctagcc gggcaggagt ggccctgcct tttgagaagt ctcagctcac tttgaaagtg | 180 |
| gtgtccgcaa agcccaaggt gcataatcgt caacctcgaa ttaactccta cgtggaggtg | 240 |
| gcggtggatg gactccccag tgagaccaag aagactggga agcgcattgg gagctctgag | 300 |
| cttctctgga atgagatcat cattttgaat gtcacggcac agagtcattt agatttaaag | 360 |
| gtctggagct gccataccct gagaaatgaa ctgctaggca ccgcatctgt caacctctcc | 420 |
| aacgtcttga agaacaatgg gggcaaaatg gagaacatgc agctgaccct gaacctgcag | 480 |
| acggagaaca aaggcagcgt tgtctcaggc ggaaaactga cattttcct ggacgggcca | 540 |
| actgttgatc tgggaaatgt gcctaatggc agtgccctga cagatggatc acagctgcct | 600 |
| tcgagagact ccagtggaac agcagtagct ccagagaacc ggcaccagcc cccagcaca | 660 |
| aactgctttg gtggaagatc ccggacgcac agacattcgg gtgcttcagc cagaacaacc | 720 |
| ccagcaaccg gcgagcaaag ccccggtgct cggagccggc accgcagcc cgtcaagaac | 780 |
| tcaggccaca gtggcttggc caatggcaca gtgaatgatg aacccacaac agccactgat | 840 |
| cccgaagaac cttccgttgt tggtgtgacg tccccacctg ctgcacccett gagtgtgacc | 900 |
| ccgaatccca acacgacttc tctccctgcc ccagccacac cggctgaagg agaggaaccc | 960 |
| agcacttcgg gtacacagca gctcccagcg gctgcccagg cccccgacgc tctgcctgct | 1020 |
| ggatgggaac agcgagagct gcccaacgga cgtgtctatt atgttgacca caataccaag | 1080 |
| accaccacct gggagcggcc ccttcctcca ggctgggaaa acgcacaga tccccgaggc | 1140 |
| aggttttact atgtggatca caatactcgg accaccacct ggcagcgtcc gaccgcggag | 1200 |
| tacgtgcgca actatgagca gtggcagtcg cagcggaatc agctccaggg ggccatgcag | 1260 |
| cacttcagcc aaagattcct ataccagttt tggagtgctt cgactgacca tgatcccctg | 1320 |
| ggcccctcc ctcctggttg ggagaaaaga caggacaatg gacgggtgta ttacgtgaac | 1380 |
| cataacactc gcacgaccca gtgggaggat ccccggaccc aggggatgat ccaggaacca | 1440 |
| gctttgcccc caggatggga gatgaaatac accagcgagg gggtgcgata ctttgtggac | 1500 |
| cacaataccc gcaccaccac ctttaaggat cctcgcccgg ggtttgagtc ggggacgaag | 1560 |
| caaggttccc ctggtgctta tgaccgcagt tttcggtgga agtatcacca gttccgtttc | 1620 |
| ctctgccatt caaatgccct acctagccac gtgaagatca gcgttccag gcagacgctt | 1680 |
| ttcgaagatt ccttccaaca gatcatgaac atgaaaccct atgacctgcg ccgccggctt | 1740 |
| tacatcatca tgcgtggcga ggagggcctg gactatgggg gcatcgccag agagtggttt | 1800 |
| ttcctcctgt ctcacgaggt gctcaaccct atgtattgtt tatttgaata tgccggaaag | 1860 |

```
aacaattact gcctgcagat caaccccgcc tcctccatca acccggacca cctcacctac    1920
tttcgcttta taggcagatt catcgccatg gcgctgtacc atggaaagtt catcgacacg    1980
ggcttcaccc tccctttcta caagcggatg ctcaataaga gaccaaccct gaaagacctg    2040
gagtccattg accctgagtt ctacaactcc attgtctgga tcaaagagaa caacctggaa    2100
gaatgtggcc tggagctgta cttcatccag gacatggaga tactgggcaa ggtgacgacc    2160
cacgagctga aggagggcgg cgagagcatc cgggtcacgg aggagaacaa ggaagagtac    2220
atcatgctgc tgactgactg gcgtttcacc cgaggcgtgg aagagcagac caaagccttc    2280
ctggatggct tcaacgaggt ggccccgctg gagtggctgc gctactttga cgagaaagag    2340
ctggagctga tgctgtgcgg catgcaggag atagacatga gcgactggca gaagagcacc    2400
atctaccggc actacaccaa gaacagcaag cagatccagt ggttctggca ggtggtgaag    2460
gagatggaca acgagaagag gatccggctg ctgcagtttg tcaccggtac ctgccgcctg    2520
cccgtcgggg gatttgccga actcatcggt agcaacggac cacagaagtt ttgcattgac    2580
aaagttggca aggaaacctg gctgcccaga agccacacct gcttcaaccg tctggatctt    2640 ccacccctaca agagctacga acagctgaga gagaagctgc tgtatgccat tgaggagacc    2700
gagggctttg acaggagta accgaggccg cccctcccac gccccccagc gcacatgtag    2760
tcctgagtcc tccctgcctg agaggccact ggccccgcag cccttgggag gccccgtgg    2820 atgtggccct gtgtgggacc acactgtcat ctcgctgctg gcagaaaagc ctgatcccag    2880
gaggccctgc agttccccg acccgcggat ggcagtctgg aataaagccc cctagttgcc    2940
tttggcccca cctttgcaaa gttccagagg gctgaccctc tctgcaaaac tctcccctgt    3000
cctctagacc ccaccctggg tgtatgtgag tgtgcaaggg aaggtgttgc atccccaggg    3060
gctgccgcag aggccggaga cctcctggac tagttcggcg aggagactgg ccactggggg    3120
tggctgttcg ggactgagag cgccaagggt cttttgccagc aaaggaggtt ctgcctgtaa    3180
ttgagcctct ctgatgatgg agatgaagtg aaggtctgag ggacgggccc tggggctagg    3240
ccatctctgc ctgcctccct agcaggcgcc agcggtggag gctgagtcgc aggacacatg    3300
ccggccagtt aattcattct cagcaaatga aggtttgtct aagctgcctg ggtatccacg    3360
ggacaaaaac agcaaactcc ctccagactt tgtccatgtt ataaacttga agttggttg    3420 ttgtttgtta ggtttgccag gttttttttgt ttacgcctgc tgtcactttc ctgtc         3475
```

<210> SEQ ID NO 25
<211> LENGTH: 2914
<212> TYPE: DNA
<213> ORGANISM: Homo sapiens

<400> SEQUENCE: 25

```
acagttgcct gccctgggcg ggggcgagcg cgtccggttt gctggaagcg ttcggaaatg      60
gcaacttgcg cggtggaggt gttcgggctc ctggaggacg aggaaaattc acgaattgtg     120
agagtaagag ttatagccgg aataggcctt gccaagaagg atatattggg agctagtgat     180
ccttacgtga gagtgacgtt atatgaccca atgaatggag ttcttacaag tgtgcaaaca     240
aaaaccatta aaaagagttt gaatccaaag tggaatgaag aaatatattatt cagagttcat     300 cctcagcagc accggcttct ttttgaagtg tttgacgaaa accgattgac aagagatgat     360
ttcctaggtc aagtggatgt tccactttat ccattaccga cagaaaatcc aagattggag     420
agaccatata catttaagga ttttgttctt catccaagaa gtcacaaatc aagagttaaa     480
ggttatctga gactaaaaat gacttattta cctaaaacca gtggctcaga agatgataat     540
```

```
gcagaacagg ctgaggaatt agagcctggc tgggttgttt tggaccaacc agatgctgct    600
tgccatttgc agcaacaaca agaaccttct cctctacctc cagggtggga agagaggcag    660
gatatccttg gaaggaccta ttatgtaaac catgaatcta gaagaacaca gtggaaaaga    720
ccaacccctc aggacaacct aacagatgct gagaatggca acattcaact gcaagcacaa    780
cgtgcattta ccaccaggcg gcagatatcc gaggaaacag aaagtgttga caaccaagag    840
tcttccgaga actgggaaat tataagagaa gatgaagcca ccatgtatag cagccaggcc    900
ttcccatcac ctccaccgtc aagtaacttg gatgttccaa ctcatcttgc agaagaattg    960
aatgccagac tcaccatttt tggaaattca gccgtgagcc agccagcatc gagctcaaat   1020
cattccagca gaagaggcag cttacaagcc tatactttg aggaacaacc tacacttcct    1080
gtgcttttgc ctacttcatc tggattacca ccaggttggg aagaaaaaca agatgaaaga   1140
ggaagatcat attatgtaga tcacaattcc agaacgacta cttggacaaa gcccactgta   1200
caggccacag tggagaccag tcagctgacc tcaagccaga gttctgcagg ccctcaatca   1260
caagcctcca ccagtgattc aggccagcag gtgacccagc catctgaaat tgagcaagga   1320
ttccttccta aaggctggga agtccggcat gcaccaaatg ggaggccttt ctttattgac   1380
cacaacacta aaaccaccac ctgggaagat ccaagattga aaattccagc ccatctgaga   1440
ggaaagacat cacttgatac ttccaatgat ctagggcctt acctccagg atgggaagag    1500 agaactcaca cagatggaag aatcttctac ataaatcaca atataaaaag aacacaatgg   1560
gaagatcctc ggttggagaa tgtagcaata actggaccag cagtgcccta ctccagggat   1620
tacaaaagaa agtatgagtt cttccgaaga aagttgaaga agcagaatga cattccaaac   1680
aaatttgaaa tgaaacttcg ccgagcaact gttcttgaag actcttaccg gagaattatg   1740
ggtgtcaaga gagcagactt cctgaaggct cgactgtgga ttgagtttga tggtgaaaag   1800
ggattggatt atgaggagt tgccagagaa tggttcttcc tgatctcaaa ggaaatgttt    1860
aacccttatt atgggttgtt tgaatattct gctacggaca attatacccct acagataaat   1920 ccaaactctg gattgtgtaa cgaagatcac ctctcttact tcaagtttat tggtcgggta   1980
gctggaatgg cagtttatca tggcaaactg ttggatggtt ttttcatccg cccattttac   2040
aagatgatgc ttcacaaacc aataaccctt catgatatgg aatctgtgga tagtgaatat   2100
tacaattccc taagatggat tcttgaaaat gacccaacag aattggacct caggtttatc   2160
atagatgaag aacttttgg acagacacat caacatgagc tgaaaaatgg tggatcagaa    2220
atagttgtca ccaataagaa caaaaaggaa tatatttatc ttgtaataca atggcgattt   2280
gtaaaccgaa tccagaagca aatggctgct tttaaagagg gattctttga actaatacca   2340
caggatctca tcaaaatttt tgatgaaaat gaactagagc ttcttatgtg tggaccggga   2400
gatgttgatg tgaatgactg gagggaacat acaaagtata aaatggcta cagtgcaaat    2460 catcaggtta tacagtggtt ttggaaggct gttttaatga tggattcaga aaaaagaata   2520
agattacttc agtttgtcac tggcacatct cgggtgccta tgaatggatt tgctgaacta   2580
tacggttcaa atggaccaca gtcatttaca gttgaacagt ggggtactcc tgaaaagctg   2640
ccaagagctc atacctgttt taatcgcctg gacttgccac cttatgaatc atttgaagaa   2700
ttatgggata aacttcagat ggcaattgaa acacccagg gctttgatgg agttgattag   2760
attacaaata caatctgta gtgttttac tgccatagtt ttataaccaa aatcttgact     2820
taaaattttc cggggaacta ctaaaatgtg gccactgagt cttcccagat cttgaagaaa   2880
```

|                                                                        |      |
|------------------------------------------------------------------------|------|
| atcatataaa aagcatttga agaaatagta cgac                                  | 2914 |

<210> SEQ ID NO 26
<211> LENGTH: 2868
<212> TYPE: DNA
<213> ORGANISM: Homo sapiens

<400> SEQUENCE: 26

|                                                                        |      |
|------------------------------------------------------------------------|------|
| atggcgaccg ggctcgggga gccggtctat ggactttccg aagacgaggg agagtcccgt      |   60 |
| attctcagag taaaagttgt ttctggaatt gatctcgcca aaaaggacat ctttggagcc      |  120 |
| agtgatccgt atgtgaaact ttcattgtac gtagcggatg agaatagaga acttgctttg      |  180 |
| gtccagacaa aacaattaa aaagacactg aacccaaaat ggaatgaaga attttatttc       |  240 |
| agggtaaacc catctaatca cagactccta tttgaagtat ttgacgaaaa tagactgaca      |  300 |
| cgagacgact tcctgggcca ggtggacgtg ccccttagtc accttccgac agaagatcca     |  360 |
| accatggagc gaccctatac atttaaggac tttctcctca gaccaagaag tcataagtct     |  420 |
| cgagttaagg gattttttgcg attgaaaatg gcctatatgc aaaaaatgg aggtcaagat     |  480 |
| gaagaaaaca gtgaccagag ggatgacatg gagcatggat gggaagttgt tgactcaaat    |  540 |
| gactcggctt ctcagcacca agaggaactt cctcctcctc ctctgcctcc cgggtgggaa    |  600 |
| gaaaaagtgg acaatttagg ccgaacttac tatgtcaacc acaacaaccg gaccactcag    |  660 |
| tggcacagac caagcctgat ggacgtgtcc tcggagtcgg acaataacat cagacagatc    |  720 |
| aaccaggagg cagcacaccg gcgcttccgc tcccgcaggc acatcagcga agacttggag    |  780 |
| cccgagccct cggagggcgg ggatgtcccc gagccttggg agaccatttc agaggaagtg    |  840 |
| aatatcgctg gagactctct cggtctggct ctgccccac caccggcctc cccaggatct     |  900 |
| cggaccagcc ctcaggagct gtcagaggaa ctaagcagaa ggcttcagat cactccagac    |  960 |
| tccaatgggg aacagttcag ctctttgatt caaagagaac cctcctcaag gttgaggtca    | 1020 |
| tgcagtgtca ccgacgcagt tgcagaacag ggccatctac caccgccatc agtggcctat    | 1080 |
| gtacatacca cgccgggtct gccttcaggc tgggaagaaa gaaagatgc taaggggcgc     | 1140 |
| acatactatg tcaatcataa caatcgaacc acaacttgga ctcgacctat catgcagctt    | 1200 |
| gcagaagatg gtgcgtccgg atcagccaca acagtaaca accatctaat cgagcctcag     | 1260 |
| atccgccggc ctcgtagcct cagctcgcca acagtaactt tatctgcccc gctgagggt     | 1320 |
| gccaaggact cacccgtacg tcgggctgtg aaagacaccc tttccaaccc acagtcccca    | 1380 |
| cagccatcac cttacaactc ccccaaaacca caacacaaag tcacacagag cttcttgcca   | 1440 |
| cccggctggg aaatgaggat agcgccaaac ggccggccct tcttcattga tcataacaca    | 1500 |
| aagactacaa cctgggaaga tccacgtttg aaatttccag tacatatgcg gtcaaagaca    | 1560 |
| tctttaaacc ccaatgacct tggcccccctt cctcctggct gggaagaaag aattcacttg   | 1620 |
| gatggccgaa cgtttttatat tgatcataat agcaaaatta ctcagtggga agacccaaga   | 1680 |
| ctgcagaacc cagctattac tggtccggct gtcccttact ccagagaatt taagcagaaa    | 1740 |
| tatgactact tcaggaagaa attaagaaa cctgctgata tccccaatag gtttgaaatg     | 1800 |
| aaacttcaca gaataacat atttgaagag tcctatcgga gaattatgtc cgtgaaaaga     | 1860 |
| ccagatgtcc taaaagctag actgtggatt gagtttgaat cagagaaagg tcttgactat    | 1920 |
| gggggtgtgg ccagagaatg gttcttctta ctgtccaaag agatgttcaa cccctactac    | 1980 |
| ggcctctttg agtactctgc cacgacaac tacacccttc agatcaaccc taattcaggc     | 2040 |
| ctctgtaatg aggatcattt gtcctacttc acttttattg gaagagttgc tggtctggcc    | 2100 |

```
gtatttcatg ggaagctctt agatggtttc ttcattagac cattttacaa gatgatgttg    2160
ggaaagcaga taaccctgaa tgacatggaa tctgtggata gtgaatatta caactctttg    2220
aaatggatcc tggagaatga ccctactgag ctggacctca tgttctgcat agacgaagaa    2280
aactttggac agacatatca agtggatttg aagcccaatg ggtcagaaat aatggtcaca    2340
aatgaaaaca aagggaata tatcgactta gtcatccagt ggagatttgt gaacagggtc    2400
cagaagcaga tgaacgcctt cttggaggga ttcacagaac tacttcctat tgatttgatt    2460 aaaattttg atgaaaatga gctggagttg ctcatgtgcg gcctcggtga tgtggatgtg    2520
aatgactgga gacagcattc tatttacaag aacggctact gcccaaacca ccccgtcatt    2580
cagtggttct ggaaggctgt gctactcatg gacgccgaaa agcgtatccg gttactgcag    2640
tttgtcacag gacatcgcg agtacctatg aatggatttg ccgaactta tggttccaat    2700 ggtcctcagc tgtttacaat agagcaatgg ggcagtcctg agaaactgcc cagagctcac    2760
acatgcttta atcgccttga cttacctcca tatgaaacct ttgaagattt acgagagaaa    2820
cttctcatgg ccgtggaaaa tgctcaagga tttgaagggg tggattaa                2868

<210> SEQ ID NO 27
<211> LENGTH: 2274
<212> TYPE: DNA
<213> ORGANISM: Homo sapiens

<400> SEQUENCE: 27
atgtcgaacc ccgggacacg caggaacggc tccagcatca agatccgtct gacagtgtta      60
tgtgccaaga accttgcaaa gaaagacttc ttcaggctcc ctgacccttt tgcaaagatt     120
gtcgtggatg ggtctgggca gtgccactca accgacactg tgaaaaacac attggaccca     180
aagtggaacc agcactatga tctatatgtt gggaaaacgg attcgataac cattagcgtg     240
tggaaccata gaaaattca caagaaacag ggagctggct tcctgggctg tgtgcggctg     300
ctctccaatg ccatcagcag attaaaagat accggatacc agcgtttgga tctatgcaaa     360
ctaaacccct cagatactga tgcagttcgt ggccagatag tggtcagttt acagacacga     420
gacagaatag gaaccggcgg ctcggtggtg gactgcagag gactgttaga aaatgaagga     480
acggtgtatg aagactccgg gcctgggagg ccgctcagct gcttcatgga ggaaccagcc     540
ccttacacag atagcaccgg tgctgctgct ggaggaggga attgcaggtt cgtggagtcc     600
ccaagtcaag atcaaagact tcaggcacag cggcttcgaa accctgatgt gcgaggttca     660
ctacagacgc cccagaaccg accacacggc caccagtccc cggaactgcc cgaaggctac     720
gaacaaagaa caacagtcca gggccaagtt tacttttgc atacacagac tggagttagc     780
acgtggcacg accccaggat accaagtccc tcggggacca ttcctggggg agatgcagct     840
tttctatacg aattccttct acaaggccat acatctgagc ccagagacct aacagtgtg     900 aactgtgatg aacttggacc actgccgcca ggctgggaag tcagaagtac agtttctggg     960
aggatatatt ttgtagatca taataaccga acaacccagt ttacagaccc aaggttacac    1020
cacatcatga atcaccagtg ccaactcaag gagcccagcc agccgctgcc actgcccagt    1080
gagggctctc tggaggacga ggagcttcct gcccagagat acgaaagaga tctagtccag    1140
aagctgaaag tcctcagaca cgaactgtcg cttcagcagc cccaagctgg tcattgccgc    1200
atcgaagtgt ccagaagaa aatctttgag gagtcttacc gccagataat gaagatgcga    1260
ccgaaagact tgaaaaaacg gctgatggtg aaattccgtg gggaagaagg tttggattac    1320
```

| | |
|---|---|
| ggtggtgtgg ccagggagtg gctttacttg ctgtgccatg aaatgctgaa tccttattac | 1380 |
| gggctcttcc agtattctac ggacaatatt tacatgttgc aaataaatcc ggattcttca | 1440 |
| atcaaccccg accacttgtc ttatttccac tttgtggggc ggatcatggg gctggctgtg | 1500 |
| ttccatggac actacatcaa cgggggcttc acagtgccct tctacaagca gctgctgggg | 1560 |
| aagcccatcc agctctcaga tctggaatct gtggacccag agctgcataa gagcttggtg | 1620 |
| tggatcctag agaacgacat cacgcctgta ctggaccaca ccttctgcgt ggaacacaac | 1680 |
| gccttcgggc ggatcctgca gcatgaactg aaacccaatg gcagaaatgt gccagtcaca | 1740 |
| gaggagaata agaaagaata cgtccggttg tatgtaaact ggaggtttat gagaggaatc | 1800 |
| gaagcccagt tcttagctct gcagaagggg ttcaatgagc tcatccctca acatctgctg | 1860 |
| aagcctttg accagaagga actggagctg atcataggcg gcctggataa aatagacttg | 1920 |
| aacgactgga agtcgaacac gcggctgaag cactgtgtgg ccgacagcaa catcgtgcgg | 1980 |
| tggttctggc aagcggtgga gacgttcgat gaagaaagga gggccaggct cctgcagttt | 2040 |
| gtgactgggt ccacgcgagt cccgctccaa ggcttcaagg ctttgcaagg ttctacaggc | 2100 |
| gcggcagggc cccggctgtt caccatccac ctgatagacg cgaacacaga caaccttccg | 2160 |
| aaggcccata cctgctttaa ccggatcgac attccaccat atgagtccta tgagaagctc | 2220 |
| tacgagaagc tgctgacagc cgtggaggag acctgcgggt tgctgtggag gtga | 2274 |

<210> SEQ ID NO 28
<211> LENGTH: 2247
<212> TYPE: DNA
<213> ORGANISM: Homo sapiens

<400> SEQUENCE: 28

| | |
|---|---|
| atgtctaacc ccgacgccg gaggaacggg cccgtcaagc tgcgcctgac agtactctgt | 60 |
| gcaaaaaacc tggtgaaaaa ggattttttc cgacttcctg atccatttgc taaggtggtg | 120 |
| gttgatggat ctgggcaatg ccattctaca gatactgtga agaatacgct tgatccaaag | 180 |
| tggaatcagc attatgacct gtatattgga aagtctgatt cagttacgat cagtgtatgg | 240 |
| aatcacaaga agatccataa gaaacaaggt gctggatttc tcggttgtgt tcgtcttctt | 300 |
| tccaatgcca tcaaccgcct caaagacact ggttatcaga ggttggattt atgcaaactc | 360 |
| gggccaaatg acaatgatac agttagagga cagatagtag taagtcttca gtccagagac | 420 |
| cgaataggca caggaggaca agttgtggac tgcagtcgtt tatttgataa cgatttacca | 480 |
| gacggctggg aagaaaggag aaccgcctct ggaagaatcc agtatctaaa ccatataaca | 540 |
| agaactacgc aatgggagcg cccaacacga ccggcatccg aatattctag ccctggcaga | 600 |
| cctcttagct gctttgttga tgagaacact ccaattagtg gaacaaatgg tgcaacatgt | 660 |
| ggacagtctt cagatcccag gctggcagag aggagagtca ggtcacaacg acatagaaat | 720 |
| tacatgagca gaacacattt acatactcct ccagacctac agaaggcta tgaacagagg | 780 |
| acaacgcaac aaggccaggt gtatttctta catacacaga ctggtgtgag cacatggcat | 840 |
| gatccaagag tgcccaggga tcttagcaac atcaattgtg aagagcttgg tccattgcct | 900 |
| cctggatggg agatccgtaa tacggcaaca ggcagagttt atttcgttga ccataacaac | 960 |
| agaacaacac aatttacaga tcctcggctg tctgctaact tgcatttagt tttaaatcgg | 1020 |
| cagaaccaat tgaaagacca acagcaacag caagtggtat cgttatgtcc tgatgacaca | 1080 |
| gaatgcctga cagtcccaag gtacaagcga gacctggttc agaaactaaa attttgcgg | 1140 |
| caagaacttt cccaacaaca gcctcaggca ggtcattgcc gcattgaggt ttccagggaa | 1200 |

-continued

```
gagattttg aggaatcata tcgacaggtc atgaaaatga gaccaaaaga tctctggaag    1260
cgattaatga taaaatttcg tggagaagaa ggccttgact atggaggcgt tgccagggaa    1320
tggttgtatc tcttgtcaca tgaaatgttg aatccatact atggcctctt ccagtattca    1380
agagatgata tttatacatt gcagatcaat cctgattctg cagttaatcc ggaacattta    1440
tcctatttcc actttgttgg acgaataatg ggaatggctg tgtttcatgg acattatatt    1500
gatggtggtt tcacattgcc ttttataag caattgcttg ggaagtcaat taccttggat    1560
gacatggagt tagtagatcc ggatcttcac aacagtttag tgtggatact gagaatgat     1620 attacaggtg ttttggacca taccttctgt gttgaacata atgcatatgg tgaaattatt    1680
cagcatgaac ttaaaccaaa tggcaaaagt atccctgtta atgaagaaaa taaaaaagaa    1740
tatgtcaggc tctatgtgaa ctggagattt ttacgaggca ttgaggctca attcttggct    1800
ctgcagaaag gatttaatga agtaattcca caacatctgc tgaagacatt tgatgagaag    1860
gagttagagc tcattatttg tggacttgga aagatagatg ttaatgactg aaggtaaac     1920 acccggttaa aacactgtac accagacagc aacattgtca aatggttctg gaaagctgtg    1980
gagttttttg atgaagagcg acgagcaaga ttgcttcagt ttgtgacagg atcctctcga    2040
gtgcctctgc agggcttcaa agcattgcaa ggtgctgcag gcccgagact ctttaccata    2100
caccagattg atgcctgcac taacaacctg ccgaaagccc acacttgctt caatcgaata    2160
gacattccac cctatgaaag ctatgaaaag ctatatgaaa agctgctaac agccattgaa    2220
gaaacatgtg gatttgctgt ggaatga                                        2247
```

<210> SEQ ID NO 29
<211> LENGTH: 2869
<212> TYPE: DNA
<213> ORGANISM: Homo sapiens

<400> SEQUENCE: 29

```
ggagtcgccg ccgccccgag ttccggtacc atgcatttca cggtggcctt gtggagacaa     60
cgccttaacc caaggaagtg actcaaactg tgagaactcc aggttttcca acctattggt    120
ggtatgtctg acagtggatc acaacttggt tcaatgggta gcctcaccat gaaatcacag    180
cttcagatca ctgtcatctc agcaaaactt aaggaaaata agaagaattg gtttggacca    240
agtccttacg tagaggtcac agtagatgga cagtcaaaga agacagaaaa atgcaacaac    300
acaaacagtc ccaagtggaa gcaacccctt acagttatcg ttaccctgt gagtaaatta     360 cattttcgtg tgtggagtca ccagacactg aaatctgatg ttttgttggg aactgctgca    420
ttagatattt atgaaacatt aaagtcaaac aatatgaaac ttgaagaagt agttgtgact    480
ttgcagcttg gaggtgacaa agagccaaca gagacaatag agacttgtc aatttgtctt     540 gatgggctac agttagagtc tgaagttgtt accaatggtg aaactacatg ttcagaaagt    600
gcttctcaga tgatgatgg ctccagatcc aaggatgaaa caagagtgag cacaaatgga    660
tcagatgacc ctgaagatgc aggagctggt gaaaatagga gagtcagtgg gaataattct    720
ccatcactct caaatggtgg ttttaaacct tctagacctc caagaccttc acgaccacca    780
ccacccaccc cacgtagacc agcatctgtc aatggttcac catctgccac ttctgaaagt    840
gatgggtcta gtacaggctc tctgccgccg acaaatacaa atacaaatac atctgaagga    900
gcaacatctg gattaataat tcctcttact atatctggag ctcaggccc taggccatta     960 aatcctgtaa ctcaagctcc cttgccacct ggttgggagc agagagtgga ccagcacggg   1020
```

| | |
|---|---|
| cgagtttact atgtagatca tgttgagaaa agaacaacat gggatagacc agaacctcta | 1080 |
| cctcctggct gggaacggcg ggttgacaac atgggacgta tttattatgt tgaccatttc | 1140 |
| acaagaacaa caacgtggca gaggccaaca ctggaatccg tccggaacta tgaacaatgg | 1200 |
| cagctacagc gtagtcagct tcaaggagca atgcagcagt ttaaccagag attcatttat | 1260 |
| gggaatcaag atttatttgc tacatcacaa agtaaagaat ttgatcctct tggtccattg | 1320 |
| ccacctggat gggagaagag aacagacagc aatggcagag tatatttcgt caaccacaac | 1380 |
| acacgaatta cacaatggga agaccccaga agtcaaggtc aattaaatga aaagccctta | 1440 |
| cctgaaggtt gggaaatgag attcacagtg gatggaattc catattttgt ggaccacaat | 1500 |
| agaagaacta ccacctatat agatccccgc acaggaaaat ctgccctaga caatggacct | 1560 |
| cagatagcct atgttcggga cttcaaagca aaggttcagt atttccggtt ctggtgtcag | 1620 |
| caactggcca tgccacagca cataaagatt acagtgacaa gaaaaacatt gtttgaggat | 1680 |
| tcctttcaac agataatgag cttcagtccc caagatctgc gaagacgttt gtgggtgatt | 1740 |
| tttccaggag aagaaggttt agattatgga ggtgtagcaa gagaatggtt cttctctttg | 1800 |
| tcacatgaag tgttgaaccc aatgtattgc ctgtttgaat atgcagggaa ggataactac | 1860 |
| tgcttgcaga taaaccccgc ttcttacatc aatccagatc acctgaaata ttttcgtttt | 1920 |
| attggcagat ttattgccat ggctctgttc catgggaaat tcatagacac gggttttct | 1980 |
| ttaccattct ataagcgtat cttgaacaaa ccagttggac tcaaggattt agaatctatt | 2040 |
| gatccagaat tttacaattc tctcatctgg gttaaggaaa acaatattga ggaatgtgat | 2100 |
| ttggaaatgt acttctccgt tgacaaagaa attctaggtg aaattaagag tcatgatctg | 2160 |
| aaacctaatg gtggcaatat tcttgtaaca gaagaaaata agaggaata catcagaatg | 2220 |
| gtagctgagt ggaggttgtc tcgaggtgtt gaagaacaga cacaagcttt ctttgaaggc | 2280 |
| tttaatgaaa ttcttcccca gcaatatttg caatactttg atgcaaagga attagaggtc | 2340 |
| cttttatgtg gaatgcaaga gattgatttg aatgactggc aaagacatgc catctaccgt | 2400 |
| cattatgcaa ggaccagcaa acaaatcatg tggttttggc agtttgttaa agaaattgat | 2460 |
| aatgagaaga gaatgagact tctgcagttt gttactggaa cctgccgatt gccagtagga | 2520 |
| ggatttgctg atctcatggg gagcaatgga ccacagaaat tctgcattga aaaagttggg | 2580 |
| aaagaaaatt ggctacccag aagtcatacc tgtttaatc gcctggacct gccaccatac | 2640 |
| aagagctatg agcaactgaa ggaaaagctg ttgtttgcca tagaagaaac agaaggattt | 2700 |
| ggacaagagt aacttctgag aacttgcacc atgaatgggc aagaactat ttgcaatgtt | 2760 |
| tgtccttctc tgcctgttgc acatcttgta aaattggaca atggctcttt agagagttat | 2820 |
| ctgagtgtaa gtaaattaat gttctcattt aaaaaaaaaa aaaaaaaaa | 2869 |

<210> SEQ ID NO 30
<211> LENGTH: 5169
<212> TYPE: DNA
<213> ORGANISM: Homo sapiens

<400> SEQUENCE: 30

| | |
|---|---|
| gcgcatcagg cgctgttgtt ggagccggaa caccgtgcga ctctgaccga accggccccc | 60 |
| tcctcgcgca cacactcgcc gagccgcgcg cgcccctccg ccgtgacagt ggccgtggcc | 120 |
| tccgctctct cggggcaccc ggcagccaga gcgcagcgag agcgggcggt cgccagggtc | 180 |
| ccctccccag ccagtcccag gcgccccgtg cactatgcgg ggcacgtgcg ccccccagct | 240 |
| ctaatctgcg cgctgacagg agcatgatct gtgcccaggc cagggctgcc aaggaattga | 300 |

```
tgcgcgtaca cgtggtgggt cattatgctg ctacacctgt gtagtgtgaa gaatctgtac      360
cagaacaggt ttttaggcct ggccgccatg gcgtctcctt ctagaaactc ccagagccga      420
cgccggtgca aggagccgct ccgatacagc tacaaccccg accagttcca caacatggac      480
ctcaggggcg gccccacga tggcgtcacc attccccgct ccaccagcga cactgacctg       540
gtcacctcgg acagccgctc cacgctcatg gtcagcagct cctactattc catcgggcac      600
tctcaggacc tggtcatcca ctgggacata aaggaggaag tggacgctgg ggactggatt      660
ggcatgtacc tcattgatga ggtcttgtcc gaaaactttc tggactataa aaaccgtgga      720
gtcaatggtt ctcatcgggg ccagatcatc tggaagatcg atgccagctc gtactttgtg      780
gaacctgaaa ctaagatctg cttcaaatac taccatggag tgagtggggc cctgcgagca      840
accacccca gtgtcacggt caaaaactcg gcagctccta tttttaaaag cattggtgct        900
gatgagaccg tccaaggaca aggaagtcgg aggctgatca gcttctctct ctcagatttc      960
caagccatgg ggttgaagaa agggatgttt ttcaacccag cccttatct gaagatttcc       1020
attcagcctg ggaaacacag catcttcccc gccctccctc accatggaca ggagaggaga     1080
tccaagatca taggcaacac cgtgaacccc atctggcagg ccgagcaatt cagttttgtg      1140
tccttgccca ctgacgtgct ggaaattgag gtgaaggaca gtttgccaa gagccgcccc       1200
atcatcaagc gcttcttggg aaagctgtcg atgcccgttc aaagactcct ggagagacac      1260
gccatagggg atagggtggt cagctacaca cttggccgca ggcttccaac agatcatgtg      1320
agtggacagc tgcaattccg atttgagatc acttcctcca tccacccaga tgatgaggag      1380
atttccctga gtaccgagcc tgagtcagcc caaattcagg acagccccat gaacaacctg      1440
atggaaagcg gcagtgggga acctcggtct gaggcaccag agtcctctga gagctggaag      1500
ccagagcagc tgggtgaggg cagtgtcccc gatggtccag ggaaccaaag catagagctt     1560
tccagaccag ctgaggaagc agcagtcatc acggaggcag gagaccaggg catggtctct      1620
gtgggacctg aaggggctgg ggagctcctg gcccaggtgc aaaaggacat ccagcctgcc      1680
cccagtgcag aagagctggc cgagcagctg gacctgggtg aggaggcatc agcactgctg      1740
ctggaagacg gtgaagcccc agccagcacc aaggaggagc ccttggagga ggaagcaacg      1800
acccagagcc gggctggaag ggaagaagag gagaaggagc aggaggagga gggagatgtg     1860
tctaccctgg agcaggagag gggcaggctg cagctgcggg cctcggtgaa gagaaaagc     1920
aggccctgct ccttgcctgt gtccgagctg gagacggtga tcgcgtcagc ctgcggggac      1980
cccgagaccc cgcggacaca ctacatccgc atccacaccc tgctgcacag catgccctcc      2040
gcccagggcg gcagcgcggc agaggaggag gacggcgcgg aggaggagtc caccctcaag      2100
gactcctcgg agaaggatgg gctcagcgag gtggacacgg tggccgctga cccgtctgcc      2160
ctggaagagg acagagaaga gcccgagggg gctactccag gcacggcgca ccctggccac      2220
tccggggcc acttccccag cctggccaat ggcgcggccc aggatggcga cacgcacccc      2280
agcaccggga gcgagagcga ctccagcccc aggcaaggcg gggaccacag ttgcgagggc     2340
tgtgacgcgt cctgctgcag cccctcgtgc tacagctcct cgtgctacag cacgtcctgc     2400
tacagcagct cgtgctacag cgcctcgtgc tacagcccct cctgctacaa cggcaacagg     2460
ttcgccagcc acacgcgctt ctcctccgtg gacagcgcca agatctccga gagcacggtc      2520
ttctcctcgc aagacgacga ggaggaggag aacagcgcgt tcgagtcggt acccgactcc      2580
atgcagagcc ctgagctgga cccggagtcc acgaacggcg ctgggccgtg gcaagacgag      2640
```

```
ctggccgccc ctagcgggca cgtggaaaga agcccggaag gtctggaatc ccccgtggca   2700
ggtccaagca atcggagaga agactgggaa gctcgaattg acagccacgg gcgggtcttt   2760
tatgtggacc acgtgaaccg cacaaccacc tggcagcgtc cgacggcagc agccaccccg   2820
gatggcatgc ggagatcggg gtccatccag cagatggagc aactcaacag gcggtatcaa   2880
aacattcagc gaaccattgc aacagagagg tccgaagaag attctggcag ccaaagctgc   2940
gagcaagccc cagcaggagg aggcggaggt ggagggagtg actcagaagc cgaatcttcc   3000
cagtccagct tagatctaag gagagagggg tcactttctc cagtgaactc acaaaaaatc   3060
accttgctgc tgcagtcccc agcggtcaag ttcatcacca accccgagtt cttcactgtg   3120
ctacacgcca attatagtgc ctaccgagtc ttcaccagta gcacctgctt aaagcacatg   3180
attctgaaag tccgacggga tgctcgcaat tttgaacgct accagcacaa ccggacttg   3240 gtgaatttca tcaacatgtt cgcagacact cggctggaac tgccccgggg ctgggagatc   3300
aaaacggacc agcagggaaa gtctttttc gtggaccaca acagtcgagc taccactttc   3360
attgaccccc gaatccctct tcagaacggt cgtcttccca tcatctaac tcaccgacag   3420 cacctccaga ggctccgaag ttacagcgcc ggagaggcct cagaagtttc tagaaacaga   3480
ggagcctctt tactggccag gccaggacac agcttagtag ctgctattcg aagccaacat   3540
caacatgagt cattgccact ggcatataat gacaagattg tggcatttct tcgccagcca   3600 aacattttg aaatgctgca agagcgtcag ccaagcttag caagaaacca cacactcagg   3660
gagaaaatcc attacattcg gactgagggt aatcacgggc ttgagaagtt gtcctgtgat   3720
gcggatctgg tcattttgct gagtctcttt gaagaagaga ttatgtccta cgtcccctg   3780 caggctgcct ccaccctgg gtatagcttc tctccccgat gttcaccctg ttcttcacct   3840
cagaactccc caggtttaca gagagccagt gcaagagccc cttccccta ccgaagagac   3900 tttgaggcca agctccgcaa tttctacaga aaactggaag ccaaaggatt tggtcagggt   3960
ccggggaaaa ttaagctcat tattcgccgg gatcatttgt tggagggaac cttcaatcag   4020
gtgatggcct attcgcggaa agagctccag cgaaacaagc tctacgtcac ctttgttgga   4080 gaggagggc tggactacag tggccccctcg cgggagttct tcttccttct gtctcaggag   4140
ctcttcaacc cttactatgg actctttgag tactcggcaa atgatactta cacggtgcag   4200
atcagcccca tgtccgcatt tgtagaaaac catcttgagt ggttcaggtt tagcggtcgc   4260
atcctgggtc tggctctgat ccatcagtac cttcttgacg cttcttcac gaggcccttc   4320 tacaaggcac tcctgagact gcccgtgat ttgagtgacc tggaatattt ggatgaggaa   4380
ttccaccaga gtttgcagtg gatgaaggac aacaacatca cagacatctt agacctcact   4440
ttcactgtta atgaagaggt ttttggacag gtcacggaaa gggagttgaa gtctggagga   4500
gccaacacac aggtgacgga gaaaaacaag aaggagtaca tcgagcgcat ggtgaagtgg   4560
cgggtggagc gcggcgtggt acagcagacc gaggcgctgg tgcgcggctt ctacgaggtt   4620
gtagactcga ggctggtgtc cgtgtttgat gccaggagc tggagctggt gatagctggc   4680
accgcggaaa tcgacctaaa tgactggcgg aataacactg agtaccgggg aggttaccac   4740
gatgggcatc ttgtgatccg ctggttctgg gctgcggtgg agcgcttcaa taatgagcag   4800
aggctgagat tactgcagtt tgtcacggga acatccagcg tgccctacga aggcttcgca   4860
gccctccgtg ggagcaatgg gcttcggcgc ttctgcatag agaaatgggg gaaaattact   4920 tctctccca gggcacacac atgcttcaac cgactggatc ttccaccgta tccctcgtac   4980
tccatgttgt atgaaaagct gttaacagca gtagaggaaa ccagcacctt tggacttgag   5040
```

```
tgaggacatg gaacctcgcc tgacattttc ctggccagtg acatcaccct tcctgggatg    5100
atcccctttt cccttccct  taatcaactc tcctttgatt ttggtattcc atgattttta    5160
ttttcaaac                                                             5169
```

<210> SEQ ID NO 31
<211> LENGTH: 2715
<212> TYPE: DNA
<213> ORGANISM: Homo sapiens

<400> SEQUENCE: 31

```
agagttccat cagagcctgc agtggatgaa agacaatgat atccatgaca tcctagacct      60
cacgttcact gtgaacgaag aagtatttgg gcagataact gaacgagaat aaagccagg     120 gggtgccaat atcccagtta cagagaagaa caagaaggag tacatcgaga ggatggtgaa    180
gtggaggatt gagaggggtg ttgtacagca acagagagc  ttagtgcgtg gcttctatga    240
ggtggtggat gccaggctgg tatctgtttt tgatgcaaga gaactggaat tggtcatcgc    300
aggcacagct gaaatagacc taagtgattg gagaaacaac acagaatata gaggaggata    360
ccatgacaat catattgtaa ttcggtggtt ctgggctgca gtggaaagat tcaacaatga    420
acaacgacta aggttgttac agtttgttac aggcacatcc agcattccct atgaaggatt    480
tgcttcactc cgagggagta acggcccaag aagattctgt gtggagaaat gggggaaaat    540
cactgctctt cccagagcgc atacatgttt taaccgtctg gatctgcctc cctacccatc    600
cttttccatg ctttatgaaa aactgttgac agcagttgaa gaaaccagta cttttggact    660
tgagtgacct ggaagctgaa tgcccatctc tgtggacagg cagtttcaga agctgccttc    720
tagaagaatg attgaacatt ggaagtttca agaggatgct tcctttagga taaagctacg    780
tgctgttgtt ttccaggaac aagtgctctg tcacatttgg ggactggaga tgagtcctct    840
tggaaggatt tgggtgagct tgatgcccag ggaacaaccc aaccgtcttt caatcaacag    900
ttcttgactg ccaaactttt tccatttgtt atgttccaag acaaagatga acccatacat    960
gatcagctcc acgtaatttt tagggactc  aggagaatct tgaaacttac ccttgaacgt   1020
ggttcaagcc aaactggcag catttggccc aatctccaaa ttagagcaag ttaaataata   1080
taataaaagt aaatatattt cctgaaagta cattcattta agccctaagt tataacagaa   1140
tattcatttc ttgcttatga gtgcctgcat ggtgtgcacc ataggtttcc gctttcatgg   1200
gacatgagtg aaaatgaaac caagtcaata tgaggtacct ttacagattt gcaataagat   1260
ggtctgtgac aatgtatatg caagtggtat gtgtgtaatt atggctaaag acaaaccatt   1320
attcagtgaa ttactaatga cagattttat gctttataat gcatgaaaac aattttaaaa   1380
taactagcaa ttaatcacag catatcagga aaaagtacac agtgagttct gtttatttt    1440 tgtaggctca ttatgtttat gttctttaag atgtatataa gaacctactt atcatgctgt   1500
atgtatcact cattccattt tcatgttcca tgcatactcg ggcatcatgc taatatgtat   1560
ccttttaagc actctcaagg aaacaaaagg gccttttatt tttataaagg taaaaaaaat   1620
tccccaaata ttttgcactg aatgtaccaa aggtgaaggg acattacaat atgactaaca   1680
gcaactccat cacttgagaa gtaaataga  aaatagcttc taaatcaaac ttccttcaca   1740
gtgccgtgtc taccactaca aggactgtgc atctaagtaa taattttta agattcacta   1800 tatgtgatag tatgatatgc atttatttaa aatgcattag actctcttcc atccatcaaa   1860
tactttacag gatggcattt aatacagata tttcgtattt cccccactgc tttttatttg   1920
```

| | |
|---|---|
| tacagcatca ttaaacacta agctcagtta aggagccatc agcaacactg aagagatcag | 1980 |
| tagtaagaat tccattttcc ctcatcagtg aagacaccac aaattgaaac tcagaactat | 2040 |
| atttctaagc ctgcattttc actgatgcat aatttctta ttaatattaa gagacagttt | 2100 |
| ttctatggca tctccaaaac tgcatgacat cactagtctt acttctgctt aattttatga | 2160 |
| gaaggtattc ttcattttaa ttgcttttgg gattactcca catctttgtt tatttcttga | 2220 |
| ctaatcagat tttcaataga gtgaagttaa attgggggtc ataaaagcat tggattgaca | 2280 |
| tatggtttgc cagcctatgg gtttacaggc attgcccaaa catttctttg agatctatat | 2340 |
| ttataagcag ccatggaatt cctattatgg gatgttggca atcttacatt ttatagaggt | 2400 |
| catatgcata gttttcatag gtgttttgta agaactgatt gctctcctgt gagttaagct | 2460 |
| atgtttacta ctgggaccct caagaggaat accacttatg ttacactcct gcactaaagg | 2520 |
| cacgtactgc agtgtgaaga aatgttctga aaaagggtta tagaaatctg gaaataagaa | 2580 |
| aggaagagct ctctgtattc tataattgga agagaaaaaa agaaaaactt ttaactggaa | 2640 |
| atgttagttt gtacttattg atcatgaata caagtatata tttaattttg caaaaaaaaa | 2700 |
| aaaaaaaaaa aaaag | 2715 |

<210> SEQ ID NO 32
<211> LENGTH: 195
<212> TYPE: DNA
<213> ORGANISM: Homo sapiens

<400> SEQUENCE: 32

| | |
|---|---|
| cccttgccac ctggttggga gcagagagtg gaccagcacg ggcgagttta ctatgtagat | 60 |
| catgttgaga aaagaacaac atgggataga ccagaacctc tacctcctgg ctgggaacgg | 120 |
| cgggttgaca acatgggacg tatttattat gttgaccatt tcacaagaac aacaacgtgg | 180 |
| cagaggccaa cactg | 195 |

<210> SEQ ID NO 33
<211> LENGTH: 555
<212> TYPE: DNA
<213> ORGANISM: Homo sapiens

<400> SEQUENCE: 33

| | |
|---|---|
| cccttgccac ctggttggga gcagagagtg gaccagcacg ggcgagttta ctatgtagat | 60 |
| catgttgaga aaagaacaac atgggataga ccagaacctc tacctcctgg ctgggaacgg | 120 |
| cgggttgaca acatgggacg tatttattat gttgaccatt tcacaagaac aacaacgtgg | 180 |
| cagaggccaa cactggaatc cgtccggaac tatgaacaat ggcagctaca gcgtagtcag | 240 |
| cttcaaggag caatgcagca gtttaaccag agattcattt atgggaatca agatttattt | 300 |
| gctacatcac aaagtaaaga atttgatcct cttggtccat tgccacctgg atgggagaag | 360 |
| agaacagaca gcaatggcag agtatatttc gtcaaccaca acacgaat tacacaatgg | 420 |
| gaagacccca gaagtcaagg tcaattaaat gaaaagccct tacctgaagg ttgggaaatg | 480 |
| agattcacag tggatggaat tccatatttt gtggaccaca atagaagaac taccacctat | 540 |
| atagatcccc gcaca | 555 |

<210> SEQ ID NO 34
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 34

Ala Leu Ala Leu Ala
1               5

<210> SEQ ID NO 35
<211> LENGTH: 238
<212> TYPE: PRT
<213> ORGANISM: Aequorea victoria

<400> SEQUENCE: 35

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235

<210> SEQ ID NO 36
<211> LENGTH: 34
<212> TYPE: PRT
<213> ORGANISM: Homo sapiens

<400> SEQUENCE: 36

Glu Thr Leu Pro Ser Gly Trp Glu Gln Arg Lys Asp Pro His Gly Arg
1               5                   10                  15

Thr Tyr Tyr Val Asp His Asn Thr Arg Thr Thr Thr Trp Glu Arg Pro
            20                  25                  30

Gln Pro

<210> SEQ ID NO 37
<211> LENGTH: 34
<212> TYPE: PRT

<213> ORGANISM: Homo sapiens

<400> SEQUENCE: 37

Gln Pro Leu Pro Pro Gly Trp Glu Arg Arg Val Asp Asp Arg Arg
1               5                   10                  15
Val Tyr Tyr Val Asp His Asn Thr Arg Thr Thr Thr Gln Arg Pro
                20                  25                  30
Thr Met

<210> SEQ ID NO 38
<211> LENGTH: 39
<212> TYPE: PRT
<213> ORGANISM: Homo sapiens

<400> SEQUENCE: 38

Glu Asn Asp Pro Tyr Gly Pro Leu Pro Pro Gly Trp Glu Lys Arg Val
1               5                   10                  15
Asp Ser Thr Asp Arg Val Tyr Phe Val Asn His Asn Thr Lys Thr Thr
                20                  25                  30
Gln Trp Glu Asp Pro Arg Thr
        35

<210> SEQ ID NO 39
<211> LENGTH: 34
<212> TYPE: PRT
<213> ORGANISM: Homo sapiens

<400> SEQUENCE: 39

Glu Pro Leu Pro Glu Gly Trp Glu Ile Arg Tyr Thr Arg Glu Gly Val
1               5                   10                  15
Arg Tyr Phe Val Asp His Asn Thr Arg Thr Thr Thr Phe Lys Asp Pro
                20                  25                  30
Arg Asn

<210> SEQ ID NO 40
<211> LENGTH: 34
<212> TYPE: PRT
<213> ORGANISM: Homo sapiens

<400> SEQUENCE: 40

Asp Ala Leu Pro Ala Gly Trp Glu Gln Arg Glu Leu Pro Asn Gly Arg
1               5                   10                  15
Val Tyr Tyr Val Asp His Asn Thr Lys Thr Thr Thr Trp Glu Arg Pro
                20                  25                  30
Leu Pro

<210> SEQ ID NO 41
<211> LENGTH: 33
<212> TYPE: PRT
<213> ORGANISM: Homo sapiens

<400> SEQUENCE: 41

Pro Leu Pro Pro Gly Trp Glu Lys Arg Thr Asp Pro Arg Gly Arg Phe
1               5                   10                  15
Tyr Tyr Val Asp His Asn Thr Arg Thr Thr Thr Trp Gln Arg Pro Thr
                20                  25                  30
Ala

<210> SEQ ID NO 42

```
<211> LENGTH: 37
<212> TYPE: PRT
<213> ORGANISM: Homo sapiens

<400> SEQUENCE: 42

His Asp Pro Leu Gly Pro Leu Pro Pro Gly Trp Glu Lys Arg Gln Asp
1               5                   10                  15

Asn Gly Arg Val Tyr Tyr Val Asn His Asn Thr Arg Thr Thr Gln Trp
            20                  25                  30

Glu Asp Pro Arg Thr
            35

<210> SEQ ID NO 43
<211> LENGTH: 34
<212> TYPE: PRT
<213> ORGANISM: Homo sapiens

<400> SEQUENCE: 43

Pro Ala Leu Pro Pro Gly Trp Glu Met Lys Tyr Thr Ser Glu Gly Val
1               5                   10                  15

Arg Tyr Phe Val Asp His Asn Thr Arg Thr Thr Thr Phe Lys Asp Pro
            20                  25                  30

Arg Pro

<210> SEQ ID NO 44
<211> LENGTH: 34
<212> TYPE: PRT
<213> ORGANISM: Homo sapiens

<400> SEQUENCE: 44

Ser Pro Leu Pro Pro Gly Trp Glu Glu Arg Gln Asp Ile Leu Gly Arg
1               5                   10                  15

Thr Tyr Tyr Val Asn His Glu Ser Arg Arg Thr Gln Trp Lys Arg Pro
            20                  25                  30

Thr Pro

<210> SEQ ID NO 45
<211> LENGTH: 34
<212> TYPE: PRT
<213> ORGANISM: Homo sapiens

<400> SEQUENCE: 45

Ser Gly Leu Pro Pro Gly Trp Glu Glu Lys Gln Asp Glu Arg Gly Arg
1               5                   10                  15

Ser Tyr Tyr Val Asp His Asn Ser Arg Thr Thr Thr Trp Thr Lys Pro
            20                  25                  30

Thr Val

<210> SEQ ID NO 46
<211> LENGTH: 34
<212> TYPE: PRT
<213> ORGANISM: Homo sapiens

<400> SEQUENCE: 46

Gly Phe Leu Pro Lys Gly Trp Glu Val Arg His Ala Pro Asn Gly Arg
1               5                   10                  15

Pro Phe Phe Ile Asp His Asn Thr Lys Thr Thr Thr Trp Glu Asp Pro
            20                  25                  30

Arg Leu
```

<210> SEQ ID NO 47
<211> LENGTH: 34
<212> TYPE: PRT
<213> ORGANISM: Homo sapiens

<400> SEQUENCE: 47

Gly Pro Leu Pro Pro Gly Trp Glu Glu Arg Thr His Thr Asp Gly Arg
1               5                   10                  15

Ile Phe Tyr Ile Asn His Asn Ile Lys Arg Thr Gln Trp Glu Asp Pro
            20                  25                  30

Arg Leu

<210> SEQ ID NO 48
<211> LENGTH: 34
<212> TYPE: PRT
<213> ORGANISM: Homo sapiens

<400> SEQUENCE: 48

Pro Glu Leu Pro Glu Gly Tyr Glu Gln Arg Thr Thr Val Gln Gly Gln
1               5                   10                  15

Val Tyr Phe Leu His Thr Gln Thr Gly Val Ser Thr Trp His Asp Pro
            20                  25                  30

Arg Ile

<210> SEQ ID NO 49
<211> LENGTH: 34
<212> TYPE: PRT
<213> ORGANISM: Homo sapiens

<400> SEQUENCE: 49

Gly Pro Leu Pro Pro Gly Trp Glu Val Arg Ser Thr Val Ser Gly Arg
1               5                   10                  15

Ile Tyr Phe Val Asp His Asn Asn Arg Thr Thr Gln Phe Thr Asp Pro
            20                  25                  30

Arg Leu

<210> SEQ ID NO 50
<211> LENGTH: 34
<212> TYPE: PRT
<213> ORGANISM: Homo sapiens

<400> SEQUENCE: 50

Asn Asp Leu Pro Asp Gly Trp Glu Glu Arg Arg Thr Ala Ser Gly Arg
1               5                   10                  15

Ile Gln Tyr Leu Asn His Ile Thr Arg Thr Thr Gln Trp Glu Arg Pro
            20                  25                  30

Thr Arg

<210> SEQ ID NO 51
<211> LENGTH: 34
<212> TYPE: PRT
<213> ORGANISM: Homo sapiens

<400> SEQUENCE: 51

Pro Asp Leu Pro Glu Gly Tyr Glu Gln Arg Thr Thr Gln Gln Gly Gln
1               5                   10                  15

Val Tyr Phe Leu His Thr Gln Thr Gly Val Ser Thr Trp His Asp Pro
            20                  25                  30

Arg Val

<210> SEQ ID NO 52
<211> LENGTH: 34
<212> TYPE: PRT
<213> ORGANISM: Homo sapiens

<400> SEQUENCE: 52

Gly Pro Leu Pro Pro Gly Trp Glu Ile Arg Asn Thr Ala Thr Gly Arg
1               5                   10                  15

Val Tyr Phe Val Asp His Asn Asn Arg Thr Thr Gln Phe Thr Asp Pro
            20                  25                  30

Arg Leu

<210> SEQ ID NO 53
<211> LENGTH: 34
<212> TYPE: PRT
<213> ORGANISM: Homo sapiens

<400> SEQUENCE: 53

Ala Pro Leu Pro Pro Gly Trp Glu Gln Arg Val Asp Gln His Gly Arg
1               5                   10                  15

Val Tyr Tyr Val Asp His Val Glu Lys Arg Thr Thr Trp Asp Arg Pro
            20                  25                  30

Glu Pro

<210> SEQ ID NO 54
<211> LENGTH: 34
<212> TYPE: PRT
<213> ORGANISM: Homo sapiens

<400> SEQUENCE: 54

Glu Pro Leu Pro Pro Gly Trp Glu Arg Arg Val Asp Asn Met Gly Arg
1               5                   10                  15

Ile Tyr Tyr Val Asp His Phe Thr Arg Thr Thr Thr Trp Gln Arg Pro
            20                  25                  30

Thr Leu

<210> SEQ ID NO 55
<211> LENGTH: 34
<212> TYPE: PRT
<213> ORGANISM: Homo sapiens

<400> SEQUENCE: 55

Gly Pro Leu Pro Pro Gly Trp Glu Lys Arg Thr Asp Ser Asn Gly Arg
1               5                   10                  15

Val Tyr Phe Val Asn His Asn Thr Arg Ile Thr Gln Trp Glu Asp Pro
            20                  25                  30

Arg Ser

<210> SEQ ID NO 56
<211> LENGTH: 34
<212> TYPE: PRT
<213> ORGANISM: Homo sapiens

<400> SEQUENCE: 56

Lys Pro Leu Pro Glu Gly Trp Glu Met Arg Phe Thr Val Asp Gly Ile
1               5                   10                  15

Pro Tyr Phe Val Asp His Asn Arg Arg Thr Thr Thr Tyr Ile Asp Pro
            20                  25                  30

-continued

Arg Thr

<210> SEQ ID NO 57
<211> LENGTH: 33
<212> TYPE: PRT
<213> ORGANISM: Homo sapiens

<400> SEQUENCE: 57

Pro Leu Pro Pro Asn Trp Glu Ala Arg Ile Asp Ser His Gly Arg Val
1               5                   10                  15

Phe Tyr Val Asp His Val Asn Arg Thr Thr Thr Trp Gln Arg Pro Thr
            20                  25                  30

Ala

<210> SEQ ID NO 58
<211> LENGTH: 34
<212> TYPE: PRT
<213> ORGANISM: Homo sapiens

<400> SEQUENCE: 58

Leu Glu Leu Pro Arg Gly Trp Glu Ile Lys Thr Asp Gln Gln Gly Lys
1               5                   10                  15

Ser Phe Phe Val Asp His Asn Ser Arg Ala Thr Thr Phe Ile Asp Pro
            20                  25                  30

Arg Ile

<210> SEQ ID NO 59
<211> LENGTH: 34
<212> TYPE: PRT
<213> ORGANISM: Homo sapiens

<400> SEQUENCE: 59

Glu Ala Leu Pro Pro Asn Trp Glu Ala Arg Ile Asp Ser His Gly Arg
1               5                   10                  15

Ile Phe Tyr Val Asp His Val Asn Arg Thr Thr Thr Trp Gln Arg Pro
            20                  25                  30

Thr Ala

<210> SEQ ID NO 60
<211> LENGTH: 34
<212> TYPE: PRT
<213> ORGANISM: Homo sapiens

<400> SEQUENCE: 60

Leu Glu Leu Pro Arg Gly Trp Glu Met Lys His Asp His Gln Gly Lys
1               5                   10                  15

Ala Phe Phe Val Asp His Asn Ser Arg Thr Thr Thr Phe Ile Asp Pro
            20                  25                  30

Arg Leu

<210> SEQ ID NO 61
<211> LENGTH: 27
<212> TYPE: PRT
<213> ORGANISM: Homo sapiens

<400> SEQUENCE: 61

Gly Trp Glu Glu Lys Val Asp Asn Leu Gly Arg Thr Tyr Tyr Val Asn
1               5                   10                  15

His Asn Asn Arg Thr Thr Gln Trp His Arg Pro
            20                  25

<210> SEQ ID NO 62
<211> LENGTH: 29
<212> TYPE: PRT
<213> ORGANISM: Homo sapiens

<400> SEQUENCE: 62

Pro Ser Gly Trp Glu Glu Arg Lys Asp Ala Lys Gly Arg Thr Tyr Tyr
1               5                   10                  15

Val Asn His Asn Asn Arg Thr Thr Thr Trp Thr Arg Pro
            20                  25

<210> SEQ ID NO 63
<211> LENGTH: 31
<212> TYPE: PRT
<213> ORGANISM: Homo sapiens

<400> SEQUENCE: 63

Pro Pro Gly Trp Glu Met Arg Ile Ala Pro Asn Gly Arg Pro Phe Phe
1               5                   10                  15

Ile Asp His Asn Thr Lys Thr Thr Thr Trp Glu Asp Pro Arg Leu
            20                  25                  30

<210> SEQ ID NO 64
<211> LENGTH: 31
<212> TYPE: PRT
<213> ORGANISM: Homo sapiens

<400> SEQUENCE: 64

Pro Pro Gly Trp Glu Glu Arg Ile His Leu Asp Gly Arg Thr Phe Tyr
1               5                   10                  15

Ile Asp His Asn Ser Lys Ile Thr Gln Trp Glu Asp Pro Arg Leu
            20                  25                  30

<210> SEQ ID NO 65
<211> LENGTH: 101
<212> TYPE: PRT
<213> ORGANISM: Artificial Sequence
<220> FEATURE:
<223> OTHER INFORMATION: Synthetic polypeptide

<400> SEQUENCE: 65

Met Glu Pro Val Asp Pro Arg Leu Glu Pro Trp Lys His Pro Gly Ser
1               5                   10                  15

Gln Pro Arg Thr Pro Cys Thr Thr Cys Tyr Cys Lys Lys Cys Cys Phe
            20                  25                  30

His Cys Gln Val Cys Phe Thr Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Ser Ser Gln Pro Arg Gly Asp
65                  70                  75                  80

Gln Thr Gly Pro Lys Glu Ser Lys Lys Val Glu Arg Glu Thr Glu
                85                  90                  95

Ala Asp Pro Lys Pro
            100

<210> SEQ ID NO 66
<211> LENGTH: 86
<212> TYPE: PRT
<213> ORGANISM: Artificial Sequence
<220> FEATURE:
<223> OTHER INFORMATION: Synthetic polypeptide

<400> SEQUENCE: 66

Met Glu Pro Val Asp Pro Arg Leu Glu Pro Trp Lys His Pro Gly Ser
1               5                   10                  15

Gln Pro Arg Thr Pro Cys Thr Thr Cys Tyr Cys Lys Lys Cys Cys Phe
            20                  25                  30

His Cys Gln Val Cys Phe Thr Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Ser Ser Gln Pro Arg Gly Asp
65                  70                  75                  80

Gln Thr Gly Pro Lys Glu
                85

<210> SEQ ID NO 67
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 67

Cys Phe Thr Thr Lys Ala Leu Gly Ile Ser Tyr Gly Arg Lys Lys Arg
1               5                   10                  15

Arg Gln Arg Arg Arg Pro Pro Gln Gly Ser Gln Thr His Gln Val Ser
            20                  25                  30

Leu Ser Lys Gln
        35

<210> SEQ ID NO 68
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 68

Met Glu Pro Val Asp Pro Arg Leu Glu Pro Trp Lys His Pro Gly Ser
1               5                   10                  15

Gln Pro Arg Thr Pro Cys Thr Thr Cys Tyr Cys Lys Lys Cys Cys Phe
            20                  25                  30

His Cys Gln Val Cys Phe Thr Thr Lys Ala Leu Gly Ile
        35                  40                  45

<210> SEQ ID NO 69
<211> LENGTH: 38
<212> TYPE: PRT
<213> ORGANISM: Artificial Sequence
<220> FEATURE:
<223> OTHER INFORMATION: Synthetic polypeptide

<400> SEQUENCE: 69

Arg Lys Lys Arg Arg Gln Arg Arg Arg Pro Pro Gln Gly Ser Gln Thr
1               5                   10                  15

His Gln Val Ser Leu Ser Lys Gln Pro Ser Ser Gln Pro Arg Gly Asp
            20                  25                  30

Gln Thr Gly Pro Lys Glu
        35

```
<210> SEQ ID NO 70
<211> LENGTH: 35
<212> TYPE: PRT
<213> ORGANISM: Artificial Sequence
<220> FEATURE:
<223> OTHER INFORMATION: Synthetic polypeptide

<400> SEQUENCE: 70

Arg Arg Gln Arg Arg Pro Pro Gln Gly Ser Gln Thr His Gln Val
1               5                   10                  15

Ser Leu Ser Lys Gln Pro Ser Ser Gln Pro Arg Gly Asp Gln Thr Gly
            20                  25                  30

Pro Lys Glu
        35

<210> SEQ ID NO 71
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 71

Arg Arg Arg Pro Pro Gln Gly Ser Gln Thr His Gln Val Ser Leu Ser
1               5                   10                  15

Lys Gln Pro Ser Ser Gln Pro Arg Gly Asp Gln Thr Gly Pro Lys Glu
            20                  25                  30

<210> SEQ ID NO 72
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 72

Pro Pro Gln Gly Ser Gln Thr His Gln Val Ser Leu Ser Lys Gln Pro
1               5                   10                  15

Ser Ser Gln Pro Arg Gly Asp Gln Thr Gly Pro Lys Glu
            20                  25

<210> SEQ ID NO 73
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 73

Arg Lys Lys Arg Arg Gln Arg Arg Arg
1               5

<210> SEQ ID NO 74
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 74

Arg Lys Lys Arg Arg Gln Arg Arg Arg Pro Pro
1               5                   10
```

-continued

<210> SEQ ID NO 75
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 75

Arg Lys Lys Arg Arg Gln Arg Arg Pro Pro Gln Gly
1               5                   10

<210> SEQ ID NO 76
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 76

Arg Lys Lys Arg Arg Gln Arg Arg Pro Pro Gln Gly Ser Gln
1               5                   10                  15

<210> SEQ ID NO 77
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 77

Arg Lys Lys Arg Arg Gln Arg Arg Pro Pro Gln Gly Ser Gln Thr
1               5                   10                  15

His

<210> SEQ ID NO 78
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 78

Cys Phe Thr Thr Lys Ala Leu Gly Ile Ser Tyr Gly Arg Lys Lys Arg
1               5                   10                  15

Arg Gln Arg Arg Arg
            20

<210> SEQ ID NO 79
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 79

Cys Phe Thr Thr Lys Ala Leu Gly Ile Ser Tyr Gly Arg Lys Lys Arg
1               5                   10                  15

Arg Gln Arg Arg Arg Pro Pro Gln Gly Ser Gln
            20                  25

<210> SEQ ID NO 80
<211> LENGTH: 12
<212> TYPE: PRT
<213> ORGANISM: Artificial Sequence
<220> FEATURE:
<223> OTHER INFORMATION: Synthetic polypeptide

```
<400> SEQUENCE: 80

Gly Arg Arg Lys Lys Arg Arg Gln Arg Arg Pro
1               5                   10

<210> SEQ ID NO 81
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 81

Arg Lys Lys Arg Arg Gln Arg Arg Pro Pro Gln Gly Ser Gln Thr
1               5                   10                  15

His

<210> SEQ ID NO 82
<211> LENGTH: 130
<212> TYPE: PRT
<213> ORGANISM: Artificial Sequence
<220> FEATURE:
<223> OTHER INFORMATION: Synthetic polypeptide

<400> SEQUENCE: 82

Met Glu Thr Pro Leu Lys Ala Pro Glu Gly Ser Leu Gly Ser Tyr Asn
1               5                   10                  15

Glu Pro Ser Ser Cys Thr Ser Glu Gln Asp Ala Ala Gln Gly Leu
            20                  25                  30

Val Ser Pro Gly Asp Glu Ile Leu Tyr Gln Leu Tyr Gln Pro Leu Glu
            35                  40                  45

Ala Cys Asp Asn Lys Cys Tyr Cys Lys Cys Cys Tyr His Cys Gln
        50                  55                  60

Met Cys Phe Leu Asn Lys Gly Leu Gly Ile Trp Tyr Glu Arg Lys Gly
65                  70                  75                  80

Arg Arg Arg Arg Thr Pro Lys Lys Thr Lys Ala His Ser Ser Ser Ala
                85                  90                  95

Ser Asp Lys Ser Ile Ser Thr Arg Thr Gly Asn Ser Gly Pro Glu Lys
            100                 105                 110

Lys Gln Lys Lys Thr Leu Glu Thr Ala Leu Glu Thr Ile Gly Gly Pro
        115                 120                 125

Gly Arg
    130

<210> SEQ ID NO 83
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 83

Met Pro Gly Pro Trp Val Ala Met Ile Met Leu Pro Gln Pro Lys Glu
1               5                   10                  15

Ser Phe Gly Gly Lys Pro Ile Gly Trp Leu Phe Trp Asn Thr Cys Lys
            20                  25                  30

Gly Pro Arg Arg Asp Cys Pro His Cys Cys Pro Ile Cys Ser Trp
        35                  40                  45

His Cys Gln Leu Cys Phe Leu Gln Lys Asn Leu Gly Ile Asn Tyr Gly
        50                  55                  60
```

Ser Gly Pro Arg Arg Arg Gly Thr Arg Gly Lys Gly Arg Arg Ile Arg
65                  70                  75                  80

Arg Thr Ala Ser Gly Gly Asp Gln Arg Glu Ala Asp Ser Gln Arg
                85                  90                  95

Ser Phe Thr Asn Met Asp Gln
            100

<210> SEQ ID NO 84
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 84

Ser Gly Pro Arg Pro Arg Gly Thr Arg Gly Lys Gly Arg Arg Ile Arg
1               5                   10                  15

Arg

<210> SEQ ID NO 85
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 85
gggcccggag accagacgag ccgggagccc ggcaacaggg aacccacg                48

<210> SEQ ID NO 86
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 86
gggcccggag accagacgag ccgggccggc aacagggaac ccacg                   45

<210> SEQ ID NO 87
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 87
gggcccggag accagacgag ccgggagccc ggcaacaggg aacc                    44

<210> SEQ ID NO 88
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 88
agacgagccg ggagccc                                                  17

<210> SEQ ID NO 89
<211> LENGTH: 22
<212> TYPE: DNA
<213> ORGANISM: Artificial Sequence
<220> FEATURE:

<223> OTHER INFORMATION: Synthetic polynucleotide

<400> SEQUENCE: 89
gccggagccg ggaagcccga gc                                           22

<210> SEQ ID NO 90
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 90
cggagccaag cccga                                                   15

<210> SEQ ID NO 91
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 91
ggcgggcgca gcgcaagcga cggacaggcc                                   30

<210> SEQ ID NO 92
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 92
ggcggaccga ccggacggag aaacagcc                                     28

<210> SEQ ID NO 93
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 93

Met Ala Gly Arg Ser Gly Asp Ser Asp Glu Glu Leu Ile Arg Thr Val
1               5                   10                  15

Arg Leu Ile Lys Leu Leu Tyr Gln Ser Asn Pro Pro Asn Pro Glu
            20                  25                  30

Gly Thr Arg Gln Ala Arg Arg Asn Arg Arg Arg Arg Trp Arg Glu Arg
        35                  40                  45

Gln Arg Gln Ile His Ser Ile Ser Glu Arg Ile Leu Gly Thr Tyr Leu
    50                  55                  60

Gly Arg Ser Ala Glu Pro Val Pro Leu Gln Leu Pro Pro Leu Glu Arg
65                  70                  75                  80

Leu Thr Leu Asp Cys Asn Glu Asp Cys Gly Thr Ser Gly Thr Gln Gly
                85                  90                  95

Val Gly Ser Pro Gln Ile Leu Val Glu Ser Pro Thr Val Leu Glu Ser
            100                 105                 110

Gly Thr Lys Glu
        115

<210> SEQ ID NO 94
<211> LENGTH: 17

```
<212> TYPE: PRT
<213> ORGANISM: Artificial Sequence
<220> FEATURE:
<223> OTHER INFORMATION: Synthetic polypeptide

<400> SEQUENCE: 94

Thr Arg Gln Ala Arg Arg Asn Arg Arg Arg Trp Arg Glu Arg Gln
1               5                   10                  15

Arg

<210> SEQ ID NO 95
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 95

Arg Asp Arg Arg Arg Arg Gly Ser Arg Pro Ser Gly Ala Glu Arg Arg
1               5                   10                  15

Arg Arg Arg Ala Ala Ala Ala
            20

<210> SEQ ID NO 96
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 96
acagaggaac ccag                                                     14

<210> SEQ ID NO 97
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 97
ccggaggaca ccacggg                                                  17

<210> SEQ ID NO 98
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 98
ccacagcacg gg                                                       12

<210> SEQ ID NO 99
<211> LENGTH: 129
<212> TYPE: PRT
<213> ORGANISM: Artificial Sequence
<220> FEATURE:
<223> OTHER INFORMATION: Synthetic polypeptide

<400> SEQUENCE: 99

Ala Ser Asn Phe Thr Gln Phe Val Leu Val Asp Asn Gly Gly Thr Gly
1               5                   10                  15

Asp Val Thr Val Ala Pro Ser Asn Phe Ala Asn Gly Val Ala Glu Trp
            20                  25                  30
```

```
Ile Ser Ser Asn Ser Arg Ser Gln Ala Tyr Lys Val Thr Cys Ser Val
         35                  40                  45

Arg Gln Ser Ser Ala Gln Asn Arg Lys Tyr Thr Ile Lys Val Glu Val
     50                  55                  60

Pro Lys Val Ala Thr Gln Thr Val Gly Gly Val Glu Leu Pro Val Ala
 65                  70                  75                  80

Ala Trp Arg Ser Tyr Leu Asn Met Glu Leu Thr Ile Pro Ile Phe Ala
             85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
            115                 120                 125

Tyr

<210> SEQ ID NO 100
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 100

Asn Ala Lys Thr Arg Arg His Glu Arg Arg Arg Lys Leu Ala Ile Glu
1               5                   10                  15

Arg Asp Thr Ile
            20

<210> SEQ ID NO 101
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 101

Gly Ser Met Asp Ala Gln Thr Arg Arg Arg Glu Arg Arg Ala Glu Lys
1               5                   10                  15

Gln Ala Gln Trp Lys Ala Ala Asn
            20

<210> SEQ ID NO 102
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 102

Gly Thr Ala Lys Ser Arg Tyr Lys Ala Arg Arg Ala Glu Leu Ile Ala
1               5                   10                  15

Glu Arg Arg

<210> SEQ ID NO 103
<211> LENGTH: 55
<212> TYPE: PRT
<213> ORGANISM: Artificial Sequence
<220> FEATURE:
<223> OTHER INFORMATION: Synthetic polypeptide

<400> SEQUENCE: 103

Met Gln Lys Gly Asn Phe Arg Asn Gln Arg Lys Thr Val Lys Cys Phe
```

```
                1               5                      10                     15
Asn Cys Gly Lys Glu Gly His Ile Ala Lys Asn Cys Arg Ala Pro Arg
                20                     25                     30

Lys Lys Gly Cys Trp Lys Cys Gly Lys Glu Gly His Gln Met Lys Asp
        35                     40                     45

Cys Thr Glu Arg Gln Ala Asn
    50                 55
```

<210> SEQ ID NO 104
<211> LENGTH: 15
<212> TYPE: RNA
<213> ORGANISM: Artificial Sequence
<220> FEATURE:
<223> OTHER INFORMATION: Synthetic polynucleotide

<400> SEQUENCE: 104
gcgcugacaa agcgc                                                    15

<210> SEQ ID NO 105
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 105
gggcccugaa gaagggccc                                                19

<210> SEQ ID NO 106
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 106
ucucaaccua accguugaga                                               20

<210> SEQ ID NO 107
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 107
ggacuagcgg aggcuagucc                                               20

<210> SEQ ID NO 108
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 108

```
Ser Gly Phe Ala Asn Glu Leu Gly Pro Arg Leu Met Gly His
1               5                   10
```

<210> SEQ ID NO 109
<211> LENGTH: 8
<212> TYPE: PRT
<213> ORGANISM: Artificial Sequence
<220> FEATURE:
<223> OTHER INFORMATION: Synthetic polypeptide

```
<400> SEQUENCE: 109

Pro Pro Lys Lys Lys Arg Lys Val
1               5

<210> SEQ ID NO 110
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 110

Met Met Ser Phe Val Ser Leu Leu Leu Val Gly Ile Leu Phe Trp Ala
1               5                   10                  15

Thr Glu Ala Glu Gln Leu Thr Lys Cys Glu Val Phe Gln
            20                  25

<210> SEQ ID NO 111
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 111

Lys Asp Glu Leu
1

<210> SEQ ID NO 112
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 112

Met Leu Ser Leu Arg Gln Ser Ile Arg Phe Phe Leu Pro Ala Thr Arg
1               5                   10                  15

Thr Leu Cys Ser Ser Arg Tyr Leu Leu
            20                  25

<210> SEQ ID NO 113
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(7)
<223> OTHER INFORMATION: Xaa can be any naturally occurring amino acid

<400> SEQUENCE: 113

Arg Leu Xaa Xaa Xaa Xaa Xaa His Leu
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 114

Pro Lys Lys Lys Arg Lys Val
```

```
<210> SEQ ID NO 115
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 115

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys
            20                  25                  30

<210> SEQ ID NO 116
<211> LENGTH: 57
<212> TYPE: RNA
<213> ORGANISM: Artificial Sequence
<220> FEATURE:
<223> OTHER INFORMATION: Synthetic polynucleotide

<400> SEQUENCE: 116
ccaagggauc aaucgucuc ucgagggucc gagucuagac cagauugguc ucucugg          57
```

DELIVERY OF THERAPEUTIC RNAS VIA ARRDC1-MEDIATED MICROVESICLES

RELATED APPLICATIONS

This application is a national stage filing under 35 U.S.C. § 371 of international PCT application, PCT/US2017/054912, filed Oct. 3, 2017, which claims priority under 35 U.S.C. § 119(e) to U.S. Provisional Application, U.S. Ser. No. 62/403,678, filed on Oct. 3, 2016, each of which is incorporated herein by reference.

GOVERNMENT SUPPORT

This invention was made with government support under HL114769 awarded by National Institutes of Health. The government has certain rights in the invention.

BACKGROUND OF THE INVENTION

The delivery of ribonucleic acids (e.g., therapeutic RNAs) to cells is limited by a number of factors, including the immunogenicity of viral delivery systems as well as the ability to a target a specific cell type when using viral or non-viral transduction methods. Therefore, there is a need to develop methods, compositions, and systems for effectively delivering therapeutic RNAs, such as mRNAs or siRNAs, to a desired targeted cell in order to realize the full potential of RNA-based therapeutics.

SUMMARY OF THE INVENTION

This invention relates to the discovery that ribonucleic acids (RNAs) can be loaded into microvesicles, specifically ARRDC1-mediated microvesicles (ARMMs), for delivery to a targeted cell. The ARMM delivery system, described herein, addresses many limitations of current delivery systems that prevent the safe and efficient delivery of therapeutic RNAs to cells. As ARMMS are derived from an endogenous budding pathway, they are unlikely to elicit a strong immune response, unlike viral delivery systems, which are known to trigger an inflammatory response (Sen et al., "Cellular unfolded protein response against viruses used in gene therapy." *Front Microbiology.* 2014; 5:250, 1-16.). Additionally, ARMMs allow for the specific packaging of any cargo RNA of interest (e.g., a mRNA or a siRNA). These cargo RNAs can then be delivered by fusion with or uptake by specific recipient cells/tissues by incorporating antibodies or other types of molecules in the ARMMs that recognize tissue-specific markers. ARMMs are microvesicles that are distinct from exosomes and, like budding viruses, are produced by direct plasma membrane budding (DPMB). DPMB is driven by a specific interaction of TSG101 with a tetrapeptide PSAP (SEQ ID NO: 1) motif of the arrestin-domain-containing protein ARRDC1 accessory protein, which is localized to the plasma membrane through its arrestin domain. ARMMS have been described in detail, for example, in PCT application number PCT/US2013/024839, filed Feb. 6, 2013 (published as WO 2013/119602 A1 on Aug. 15, 2013) by Lu et al., and entitled "Arrdc1-Mediated Microvesicles (ARMMs) and Uses Thereof," the entire contents of which are incorporated herein by reference. The ARRDC1/TSG101 interaction results in relocation of TSG101 from endosomes to the plasma membrane and mediates the release of microvesicles that contain TSG101, ARRDC1, and other cellular components as well as the cargo RNA of interest.

Non-naturally occurring RNAs including, for example, a binding RNA (e.g., a TAR element) associated with a cargo RNA (e.g., an RNA that expresses GFP, p53, Bims, or other protein) can associate with one or more ARMM proteins (e.g., ARRDC1), facilitating their incorporation into ARMMs, which in turn can be used to deliver the cargo RNA into a targeted cell. As one example, a cargo RNA fused to a TAR element can associate with an ARRDC1 protein that is fused to an RNA binding protein, such as a Tat protein. A non-limiting example of an ARRDC1 protein fused to a Tat protein is shown in FIG. 1, Panel A. As another example, a cargo RNA fused to a TAR element can associate with a WW domain-containing protein that is fused to an RNA binding protein, such as a Tat protein. The WW domain-containing protein that is fused to the RNA binding protein (e.g., Tat protein) can associate with ARRDC1, for example, by binding to the PPXY (SEQ ID NO: 2) motif of ARRDC1. A non-limiting example of a Tat protein fused to a WW domain that associates with the PPXY (SEQ ID NO: 2) motif of ARRDC1 is shown in FIG. 1, Panel B. The association of a cargo RNA to an ARMM protein (e.g., ARRDC1), for example, via the Tat/TAR interaction, facilitates loading of the cargo RNA into the ARRDC1-containing ARMM. For example, a cargo RNA fused to a TAR element may associate with an ARRDC1 protein fused to a Tat protein via the association between Tat and TAR, as illustrated in FIG. 2. As another example a cargo RNA fused to a TAR element may associate with a Tat protein that is fused to a WW domain, which may associate with an ARRDC1 protein via the association between the WW domain and the PPXY (SEQ ID NO: 2) motif of the ARRDC1 protein. In certain instances, the cargo RNA can be fused to or associated with a binding RNA via a linker, which may be cleaved upon delivery into a target cell. The binding RNA (e.g. TAR element) and the RNA binding protein (e.g., Tat protein) may be any suitable RNA and protein pair that sufficiently associates to facilitate loading of a cargo RNA into an ARMM.

Other advantages, features, and uses of the invention will be apparent from the detailed description of certain exemplary, non-limiting embodiments; the drawings; the non-limiting working examples; and the claims.

DEFINITIONS

Figure 1:
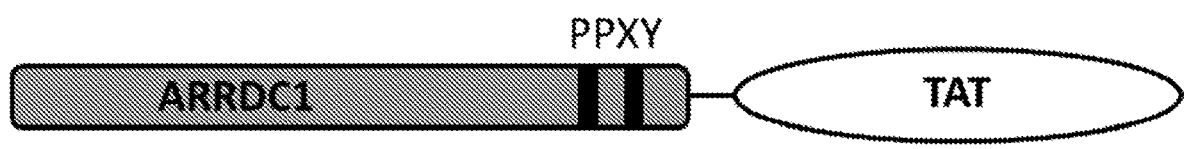
FIG. 1 shows non-limiting schematic representations of fusion proteins used for packaging RNAs into ARMMs. (A) is a schematic of an ARRDC1 protein, containing a PPXY (SEQ ID NO: 2) motif, that is fused to a Tat protein. (B) is a schematic of a WW domain fused to a Tat protein, which may bind the PPXY (SEQ ID NO: 2) motif of ARRDC1 via the interaction between the WW domain and the PPXY (SEQ ID NO: 2) motif.
Figure 1:
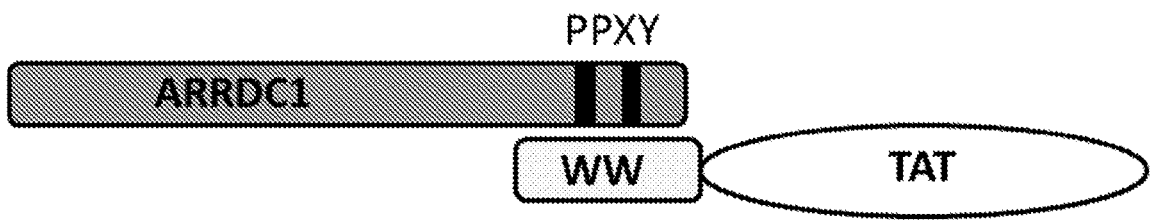

The term "ARMM," as used herein, refers to a microvesicle comprising an ARRDC1 protein or variant thereof, and/or TSG101 protein or variant thereof. In some embodiments, the ARMM is shed from a cell, and comprises a molecule, for example, a nucleic acid, protein, or small molecule, present in the cytoplasm or associated with the membrane of the cell. In some embodiments, the ARMM is shed from a transgenic cell comprising a recombinant expression construct that includes the transgene, and the ARMM comprises a gene product, for example, a transcript and/or a protein (e.g., an ARRDC1-Tat fusion protein and a TAR-cargo RNA) encoded by the expression construct. In some embodiments, the protein encoded by the expression construct is a Tat protein fused to at least one WW domain, or variant thereof, which may associate with the ARRDC1 protein to facilitate loading of cargo RNA fused to a TAR into the ARMM. In some embodiments, the ARMM is produced synthetically, for example, by contacting a lipid bilayer within ARRDC1 protein, or variant thereof, in a cell-free system in the presence of TSG101, or a variant thereof. In other embodiments, the ARMM is synthetically produced by further contacting a lipid bilayer with HECT domain ligase, and VPS4a. In some embodiments, an ARMM lacks a late endosomal marker. Some ARMMs as provided herein do not include, or are negative for, one or more exosomal biomarker. Exosomal biomarkers are known to those of skill in the art and include, but are not limited to, CD63, Lamp-1, Lamp-2, CD9, HSPA8, GAPDH, CD81, SDCBP, PDCD6IP, ENO1, ANXA2, ACTB, YWHAZ, HSP90AA1, ANXA5, EEF1A1, YWHAE, PPIA, MSN, CFL1, ALDOA, PGK1, EEF2, ANXA1, PKM2, HLA-DRA, and YWHAB. For example, some ARMMs provided herein lack CD63, some ARMMs lack LAMP1, some ARMMs lack CD9, some ARMMs lack CD81, some ARMMs lack CD63 and Lamp-1, some ARMMs lack CD63, Lamp-1, and CD9, some ARMMs lack CD63, Lamp-1, CD81, and CD9, and so forth. Certain ARMMs provided herein may include an exosomal biomarker. Accordingly, some ARMMs may be negative for one or more exosomal biomarker, but positive for one or more different exosomal biomarker. For example, such an ARMM may be negative for CD63 and Lamp-1, but may include PGK1 or GAPDH; or may be negative for CD63, Lamp-1, CD9, and CD81, but may be positive for HLA-DRA. In some embodiments, ARMMs include an exosomal biomarker, but at a lower level than a level found in exosomes. For example, some ARMMs include one or more exosomal biomarkers at a level of less than about 1%, less than about 5%, less than about 10%, less than about 20%, less than about 30%, less than about 40%, or less than about 50% of the level of that biomarker found in exosomes. To give a non-limiting example, in some embodiments, an ARMM may be negative for CD63 and Lamp-1, include CD9 at a level of less than about 5% of the level of CD9 typically found in exosomes, and be positive for ACTB. Exosomal biomarkers in addition to those listed above are known to those of skill in the art, and the invention is not limited in this regard.

The term "binding RNA", as used herein, refers to a ribonucleic acid (RNA) that binds to an RNA binding protein, for example, any of the RNA binding proteins known in the art and/or provided herein. In some embodiments, a binding RNA is an RNA that specifically binds to an RNA binding protein. A binding RNA that "specifically binds" to an RNA binding protein, binds to the RNA binding protein with greater affinity, avidity, more readily, and/or with greater duration than it binds to another protein, such as a protein that does not bind the RNA or a protein that weakly binds to the binding RNA. In some embodiments, the binding RNA is a naturally-occurring RNA, or non-naturally-occurring variant thereof, that binds to a specific RNA binding protein. For example, the binding RNA may be a TAR element, a Rev response element, an MS2 RNA, or any variant thereof that specifically binds an RNA binding protein. In some embodiments, the binding RNA may be a trans-activating response element (TAR element), or variant thereof, which is an RNA stem-loop structure that is found at the 5' ends of nascent HIV-1 transcripts and specifically binds to the trans-activator of transcription (Tat) protein. In some embodiments, the binding RNA is a Rev response element (RRE), or variant thereof, that specifically binds to the accessory protein Rev (e.g., Rev from HIV-1). In some embodiments, the binding RNA is an MS2 RNA that specifically binds to a MS2 phage coat protein. The binding RNAs of the present disclosure may be designed to specifically bind a protein (e.g., an RNA binding protein fused to ARRDC1) in order to facilitate loading of the binding RNA (e.g., a binding RNA fused to a cargo RNA) into an ARMM.

The term "aptamer", as used herein, refers to nucleic acids that bind to a specific target molecule, e.g., an RNA binding protein. In some embodiments, nucleic acid (e.g., DNA or RNA) aptamers are engineered through repeated rounds of in vitro selection or equivalently, SELEX (systematic evolution of ligands by exponential enrichment) methodology to bind to various molecular targets, for example, proteins, small molecules, macromolecules, metabolites, carbohydrates, metals, nucleic acids, cells, tissues, and organisms. Methods for engineering aptamers to bind to various molecular targets, such as proteins, are known in the art and include those described in U.S. Pat Nos. 6,376,19; and 9,061,043; Shui B., et al., "RNA aptamers that functionally interact with green fluorescent protein and its derivatives." *Nucleic Acids Res.*, March; 40(5): e39 (2012); Trujillo U. H., et al., "DNA and RNA aptamers: from tools for basic research towards therapeutic applications". *Comb Chem High Throughput Screen* 9 (8): 619-32 (2006); Srisawat C., et al., "Streptavidin aptamers: Affinity tags for the study of RNAs and ribonucleoproteins." RNA, 7:632-641 (2001); and Tuerk and Gold, "Systematic evolution of ligands by exponential enrichment: RNA ligands to bacteriophage T4 DNA polymerase." Science. 1990; the entire contents of each of which are hereby incorporated by reference in their entirety.

The term "RNA binding protein", as used herein refers to a polypeptide molecule that binds to a binding RNA, for example, any of the binding RNAs known in the art and/or provided herein. In some embodiments, an RNA binding protein is a protein that specifically binds to a binding RNA. An RNA binding protein that "specifically binds" to a binding RNA, binds to the binding RNA with greater affinity, avidity, more readily, and/or with greater duration than it binds to another RNA, such as a control RNA (e.g., an RNA having a random nucleic acid sequence) or an RNA that weakly binds to the RNA binding protein. In some embodiments, the RNA binding protein is a naturally-occurring protein, or non-naturally-occurring variant thereof, that binds to a specific RNA. For example, in some embodiments, the RNA binding protein may be a trans-activator of transcription (Tat) protein that specifically binds a trans-activating response element (TAR element). In some embodiments, the RNA binding protein is a regulator of virion expression (Rev) protein (e.g., Rev from HIV-1) or variant thereof, that specifically binds to a Rev response element (RRE). In some embodiments, the RNA binding protein is a coat protein of an MS2 bacteriophage that specifically binds to an MS2 RNA. The RNA binding proteins useful in the present disclosure (e.g., a binding protein fused to ARRDC1) may be designed to specifically bind a binding RNA (e.g., a binding RNA fused to a cargo RNA) in order to facilitate loading of the binding RNA into an ARMM.

The term "cargo RNA", as used herein, refers to a ribonucleic acid that may be incorporated into an ARMM, for example, into the liquid phase of the ARMM (e.g., by associating the cargo RNA with an RNA binding protein fused to an ARRDC1 protein). The term "cargo RNA to be delivered" refers to any RNA that can be delivered via its association with or inclusion in an ARMM to a subject, organ, tissue, or cell. In some embodiments, the cargo RNA is to be delivered to a targeted cell in vitro, in vivo, or ex vivo. In some embodiments, the cargo RNA to be delivered is a biologically active agent, i.e., it has activity in a cell, organ, tissue, and/or subject. For instance, an RNA that, when administered to a subject, has a biological effect on that subject or is considered to be biologically active. In certain embodiments, the cargo RNA is a messenger RNA or an RNA that expresses a protein in a cell. In certain embodiments, the cargo RNA is a small interfering RNA (siRNA) that inhibits the expression of one or more genes in a cell. In some embodiments, a cargo RNA to be delivered is a therapeutic agent. As used herein, the term "therapeutic agent" refers to any agent that, when administered to a subject, has a beneficial effect. In some embodiments, the cargo RNA to be delivered to a cell is an RNA that expresses a transcription factor, a tumor suppressor, a developmental regulator, a growth factor, a metastasis suppressor, a pro-apoptotic protein, a nuclease, or a recombinase. In certain embodiments, the cargo RNA is associated with a binding RNA, either covalently or non-covalently (e.g., via nucleotide base pairing) to facilitate loading of the cargo RNA into an ARMM.

The term "linker," as used herein, refers to a chemical moiety linking two molecules or moieties, e.g., an ARRDC1 protein and a Tat protein, or a WW domain and a Tat protein. Typically, the linker is positioned between, or flanked by, two groups, molecules, or other moieties and connected to each one via a covalent bond, thus connecting the two. In some embodiments, the linker comprises an amino acid or a plurality of amino acids (e.g., a peptide or protein). In some embodiments, the linker comprises a nucleotide (e.g., DNA or RNA) or a plurality of nucleotides (e.g., a nucleic acid). In some embodiments, the linker is an organic molecule, group, polymer, or other chemical moiety. In some embodiments, the linker is a cleavable linker, e.g., the linker comprises a bond that can be cleaved upon exposure to, for example, UV light or a hydrolytic enzyme, such as a lysosomal protease. In some embodiments, the linker is any stretch of amino acids having at least 1, at least 2, at least 3, at least 4, at least 5, at least 6, at least 7, at least 8, at least 9, at least 10, at least 15, at least 20, at least 25, at least 30, at least 40, at least 50, or more amino acids (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids). In other embodiments, the linker is a chemical bond (e.g., a covalent bond).

As used herein, the term "animal" refers to any member of the animal kingdom. In some embodiments, the term "animal" refers to a human of either sex at any stage of development. In some embodiments, the term "animal" refers to a non-human animal at any stage of development. In certain embodiments, the non-human animal is a mammal (e.g., a rodent, a mouse, a rat, a rabbit, a monkey, a dog, a cat, a sheep, cattle, a primate, or a pig). Animals include, but are not limited to, mammals, birds, reptiles, amphibians, fish, and worms. In some embodiments, the animal is a transgenic animal, genetically-engineered animal, or a clone. In some embodiments, the animal is a transgenic non-human animal, genetically-engineered non-human animal, or a non-human clone.

As used herein, the term "associated with," when used with respect to two or more entities, for example, with chemical moieties, molecules, and/or ARMMs, means that the entities are physically associated or connected with one another, either directly or via one or more additional moieties that serves as a linker, to form a structure that is sufficiently stable so that the entities remain physically associated under the conditions in which the structure is used, e.g., physiological conditions. An ARMM is typically associated with an agent, for example, a nucleic acid, protein, or small molecule, by a mechanism that involves a covalent (e.g., via an amide bond) or non-covalent association (e.g., between ARRDC1 and a WW domain, or between a Tat protein and a TAR element). In certain embodiments, the agent to be delivered (e.g., a cargo RNA) is covalently bound to a molecule (e.g., a TAR element) that associates non-covalently with a part of the ARMM, for example, a Tat protein, or variant thereof, that is fused to an ARRCD1 protein, or variant thereof. In some embodiments, the agent to be delivered (e.g., a cargo RNA) is covalently bound to a molecule (e.g., a TAR element) that associates non-covalently with a Tat protein, or variant thereof, that is fused to a WW domain, where the WW domain non-covalently associates with ARRDC1 in an ARMM. In some embodiments, the association is via a linker, for example, a cleavable linker. In some embodiments, an entity (e.g., a cargo RNA) is associated with an ARMM by inclusion in the ARMM, for example, by encapsulation of an entity (e.g., a cargo RNA) within the ARMM. For example, in some embodiments, an agent (e.g., a cargo RNA) present in the cytoplasm of an ARMM-producing cell is associated with an ARMM by encapsulation of the cytoplasm with the agent in the ARMM upon ARMM budding.

Similarly, a membrane protein or other molecule associated with the cell membrane of an ARMM producing cell may be associated with an ARMM produced by the cell by inclusion into the ARMM's membrane upon budding.

As used herein, the phrase "biologically active" refers to a characteristic of any substance that has activity in a cell, organ, tissue, and/or subject. For instance, a substance that, when administered to an organism, has a biological effect on that organism, is considered to be biologically active. As one example, a cargo RNA may be considered biologically active if it increases or decreases the expression of a gene product when administered to a subject or cell.

As used herein, the term "conserved" refers to nucleotides or amino acid residues of a polynucleotide sequence or amino acid sequence, respectively, that are those that occur unaltered in the same position of two or more related sequences being compared. Nucleotides or amino acids that are relatively conserved are those that are conserved amongst more related sequences than nucleotides or amino acids appearing elsewhere in the sequences. In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95% identical, about 98% identical, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another.

The term "engineered," as used herein refers to a protein, nucleic acid, complex, substance, or entity that has been designed, produced, prepared, synthesized, and/or manufactured by a human. Accordingly, an engineered product is a product that does not occur in nature. In some embodiments, an engineered protein or nucleic acid is a protein or nucleic acid that has been designed to meet particular requirements or to have particular design features. For example, a cargo RNA may be engineered to associate with the ARRDC1 by fusing one or more WW domains to a Tat protein and fusing the cargo RNA to a TAR element to facilitate loading of the cargo RNA into an ARMM. As another example, a cargo RNA may be engineered to associate with the ARRDC1 by fusing a Tat protein to the ARRDC1 and by fusing the cargo RNA to a TAR element to facilitate loading of the cargo RNA into an ARMM.

As used herein, "expression" of a nucleic acid sequence refers to one or more of the following events: (1) production of an RNA transcript from a DNA sequence (e.g., by transcription); (2) processing of an RNA transcript (e.g., by splicing, editing, 5' cap formation, and/or 3' end processing); (3) translation of an RNA transcript into a polypeptide or protein; and (4) post-translational modification of a polypeptide or protein.

As used herein, a "fusion protein" includes a first protein moiety, e.g., an ARRCD1 protein or variant thereof, associated with a second protein moiety, for example, a Tat protein to be delivered to a target cell through a peptide linkage. In certain embodiments, the fusion protein is encoded by a single fusion gene.

As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that the definition of gene includes references to nucleic acids that do not encode proteins but rather encode functional RNA molecules, such as gRNAs, RNAi agents, ribozymes, tRNAs, etc. For the purpose of clarity it should be noted that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein—coding expression units but rather to clarify that, in most cases, the term as used herein refers to a protein-coding nucleic acid.

As used herein, the term "gene product" or "expression product" generally refers to an RNA transcribed from the gene (pre- and/or post-processing) or a polypeptide (pre- and/or post-modification) encoded by an RNA transcribed from the gene.

As used herein, the term "green fluorescent protein" (GFP) refers to a protein originally isolated from the jellyfish *Aequorea victoria* that fluoresces green when exposed to blue light or a derivative of such a protein (e.g., an enhanced or wavelength-shifted version of the protein). The amino acid sequence of wild type GFP is as follows:

```
                                       (SEQ ID NO: 35)
MSKGEELFTGVVPILVELDGDVNGHKFSVSGEGEGDATYGKLTLKFIC

TTGKLPVPWPTLVTTFSYGVQCFSRYPDHMKQHDFFKSAMPEGYVQE

RTIFFKDDGNYKTRAEVKFEGDTLVNRIELKGIDFKEDGNILGHKLEY

NYNSHNVYIMADKQKNGIKVNFKIRHNIEDGSVQLADHYQQNTPIGD

GPVLLPDNHYLSTQSALSKDPNEKRDHMVLLEFVTAAGITHGMDELY

K
```

Proteins that are at least 70%, at least 75%, at least 80%, at least 85%, at least 90%, at least 95%, at least 98%, or at least 99% homologous to SEQ ID NO: 35 are also considered to be green fluorescent proteins.

As used herein, the term "homology" refers to the overall relatedness between nucleic acids (e.g. DNA molecules and/or RNA molecules) or polypeptides. In some embodiments, nucleic acids or proteins are considered to be "homologous" to one another if their sequences are at least 50%, at least 55%, at least 60%, at least 65%, at least 70%, at least 75%, at least 80%, at least 85%, at least 90%, at least 95%, or at least 99% identical. In some embodiments, nucleic acids or proteins are considered to be "homologous" to one another if their sequences are at least 50%, at least 55%, at least 60%, at least 65%, at least 70%, at least 75%, at least 80%, at least 85%, at least 90%, at least 95%, or at least 99% similar. The term "homologous" necessarily refers to a comparison between at least two sequences (nucleotide sequences or amino acid sequences). In accordance with the invention, two nucleotide sequences are considered to be homologous if the polypeptides they encode are at least about 50% identical, at least about 60% identical, at least about 70% identical, at least about 80% identical, or at least about 90% identical for at least one stretch of at least about 20 amino acids. In some embodiments, homologous nucleotide sequences are characterized by the ability to encode a stretch of at least 4-5 uniquely specified amino acids. Both the identity and the approximate spacing of these amino acids relative to one another must be considered for sequences to be considered homologous. For nucleotide sequences less than 60 nucleotides in length, homology is determined by the ability to encode a stretch of at least 4-5 uniquely specified amino acids. In accordance with the invention, two protein sequences are considered to be homologous if the proteins are at least about 50% identical, at least about 60% identical, at least about 70% identical, at least about 80% identical, or at least about 90% identical for at least one stretch of at least about 20 amino acids.

As used herein, the term "identity" refers to the overall relatedness between nucleic acids or proteins (e.g. DNA molecules, RNA molecules, and/or polypeptides). Calculation of the percent identity of two nucleic acid sequences, for example, can be performed by aligning the two sequences for optimal comparison purposes (e.g., gaps can be introduced in one or both of a first and second nucleic acid sequence for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in *Computational Molecular Biology*, Lesk, A. M., ed., Oxford University Press, New York, 1988; *Biocomputing: Informatics and Genome Projects*, Smith, D. W., ed., Academic Press, New York, 1993; *Sequence Analysis in Molecular Biology*, von Heinje, G., Academic Press, 1987; *Computer Analysis of Sequence Data, Part I*, Griffin, A. M., and Griffin, H. G., eds., Humana Press, New Jersey, 1994; and *Sequence Analysis Primer*, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., *SIAM J Applied Math.*, 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research*, 12(1), 387 (1984)), BLASTP, BLASTN, and FASTA Atschul, S. F. et al., *J. Molec. Biol.*, 215, 403 (1990)).

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe).

As used herein, the term "isolated" refers to a substance or entity that has been (1) separated from at least some of the components with which it was associated when initially produced (whether in nature or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated substances are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

As used herein, the term "nucleic acid," in its broadest sense, refers to a compound and/or substance that is or can be incorporated into an oligonucleotide chain via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising individual nucleotides. As used herein, the terms "oligonucleotide" and "polynucleotide" can be used interchangeably to refer to a polymer of nucleotides (e.g., a string of at least two nucleotides). In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, at least 4, at least 5, at least 6, at least 7, at least 8, at least 9, at least 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadeno sine, 7-deazaadenosine, 7-deazaguanosine, 8-oxoadenosine, 8-oxoguanosine, 0(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g. polynucleotides and residues, including nucleotides and/or nucleosides) that have not been chemically modified in order to facilitate or achieve delivery.

As used herein, the term "protein" refers to a string of at least two amino acids linked to one another by one or more peptide bonds. Proteins may include moieties other than amino acids (e.g., may be glycoproteins) and/or may be otherwise processed or modified. Those of ordinary skill in the art will appreciate that a "protein" can be a complete protein chain as produced by a cell (with or without a signal sequence), or can be a functional portion thereof. Those of ordinary skill will further appreciate that a protein can sometimes include more than one protein chain, for example linked by one or more disulfide bonds or associated by other means. Proteins may contain L-amino acids, D-amino acids, or both and may contain any of a variety of amino acid modifications or analogs known in the art. Useful modifications include, e.g., addition of a chemical entity such as a carbohydrate group, a phosphate group, a farnesyl group, an isofarnesyl group, a fatty acid group, an amide group, a terminal acetyl group, a linker for conjugation, functionalization, or other modification (e.g., alpha amidation), etc. In certain embodiments, the modifications of the protein lead to a more stable protein (e.g., greater half-life in vivo). These modifications may include cyclization of the protein, the incorporation of D-amino acids, etc. None of the modifications should substantially interfere with the desired biological activity of the protein. In certain embodiments, the modifications of the protein lead to a more biologically active protein. In some embodiments, proteins may comprise natural amino acids, non-natural amino acids, synthetic amino acids, amino acid analogs, and combinations thereof.

As used herein, the term "reprogramming factor" refers to a factor that, alone or in combination with other factors, can change the state of a cell from a somatic, differentiated state into a pluripotent stem cell state. Non-limiting examples of reprogramming factors include a protein (e.g., a transcription factor), a peptide, a nucleic acid, or a small molecule. Known reprogramming factors that are useful for cell reprogramming include, but are not limited to, Oct4, Sox2, Klf4, and c-myc. Similarly, a programming factor may be used to modulate cell differentiation, for example, to facilitate or induce cell differentiation towards a desired lineage.

As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals, such as mice, rats, rabbits, non-human primates, and humans) and/or plants. In some embodiments, the subject is a patient having or suspected of having a disease or disorder. In other embodiments, the subject is a healthy volunteer.

As used herein, the term "therapeutically effective amount" means an amount of an agent to be delivered (e.g., nucleic acid, protein, drug, therapeutic agent, diagnostic agent, prophylactic agent, RNA, ARMM, or ARMM comprising a cargo RNA) that is sufficient, when administered to a subject suffering from or susceptible to a disease, disorder, and/or condition, to treat, improve symptoms of, diagnose, prevent, and/or delay the onset of the disease, disorder, and/or condition.

As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules. Examples of transcription factors include, but are not limited to, Sp1, NF1, CCAAT, GATA, HNF, PIT-1, MyoD, Myf5, Hox, Winged Helix, SREBP, p53, CREB, AP-1, Mef2, STAT, R-SMAD, NF-KB, Notch, TUBBY, and NFAT.

As used herein, the term "treating" refers to partially or completely preventing, and/or reducing the incidence of one or more symptoms or features of a particular disease or condition. For example, "treating" cancer may refer to inhibiting survival, growth, and/or spread of the cancer. Treatment may be administered to a subject who does not exhibit signs or symptoms of a disease, disorder, and/or condition and/or to a subject who exhibits only early signs or symptoms of a disease, or condition for the purpose of decreasing the risk of developing more severe effects associated with the disease, disorder, or condition.

As used herein, "vector" refers to a nucleic acid molecule which can transport another nucleic acid to which it has been linked. In some embodiment, vectors can achieve extrachromosomal replication and/or expression of nucleic acids to which they are linked in a host cell such as a eukaryotic and/or prokaryotic cell. Vectors capable of directing the expression of operatively linked genes are referred to herein as "expression vectors."

The term "WW domain" as used herein, refers to a protein domain having two basic residues at the C-terminus that mediates protein-protein interactions with short proline-rich or proline-containing motifs. It should be appreciated that the two basic residues (e.g., H, R, and K) of the WW domain are not required to be at the absolute C-terminal end of the WW protein domain. Rather, the two basic residues may be at a C-terminal portion of the WW protein domain (e.g., the C-terminal half of the WW protein domain). In some embodiments, the WW domain contains at least 1, 2, 3, 4, 5, 6, 7, 8, 9, or 10 W residues. In some embodiments, the WW domain contains at least two W residues. In some embodiments, the at least two W residues are spaced apart by from 15-25 amino acids. In some embodiments, the at least two W residues are spaced apart by from 19-23 amino acids. In some embodiments, the at least two W residues are spaced apart by from 20-22 amino acids. The WW domain possessing the two basic C-terminal amino acid residues may have the ability to associate with short proline-rich or proline-containing motifs (e.g., a PPXY (SEQ ID NO: 2) motif). WW domains bind a variety of distinct peptide ligands including motifs with core proline-rich sequences, such as PPXY (SEQ ID NO: 2), which is found in AARDC1. A WW domain may be a 30-40 amino acid protein interaction domain with two signature tryptophan residues spaced by 20-22 amino acids. The three-dimensional structure of WW domains shows that they generally fold into a three-stranded, antiparallel β sheet with two ligand-binding grooves.

Figure 3:
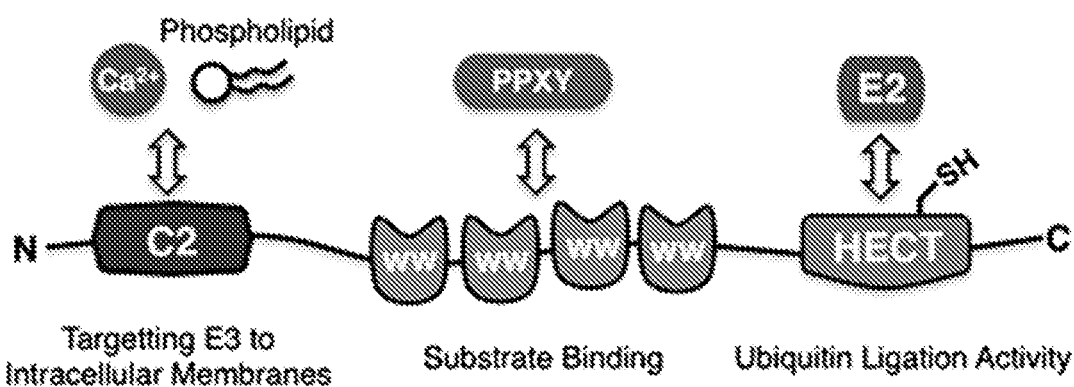
FIG. 3 is a non-limiting schematic of a ubiquitin ligase protein (top) showing the conserved protein domains including the phospholipid binding C2 domain, four WW domains that bind PPXY (SEQ ID NO: 2) motifs, and the HECT ubiquitin ligase domain. Exemplary ubiquitin ligases (bottom) include Nedd4-1, Nedd4-2, WWP1, WWP2, Smurf1, Smurf2, ITCH, NEDL1, and NEDL2.
Figure 3:
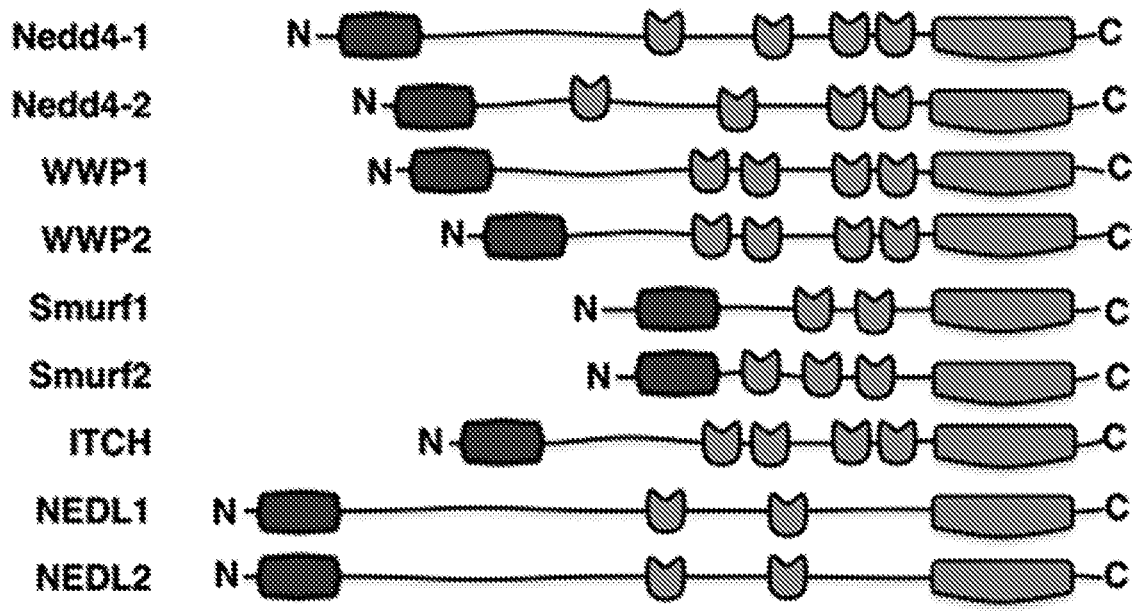
Figure 4:
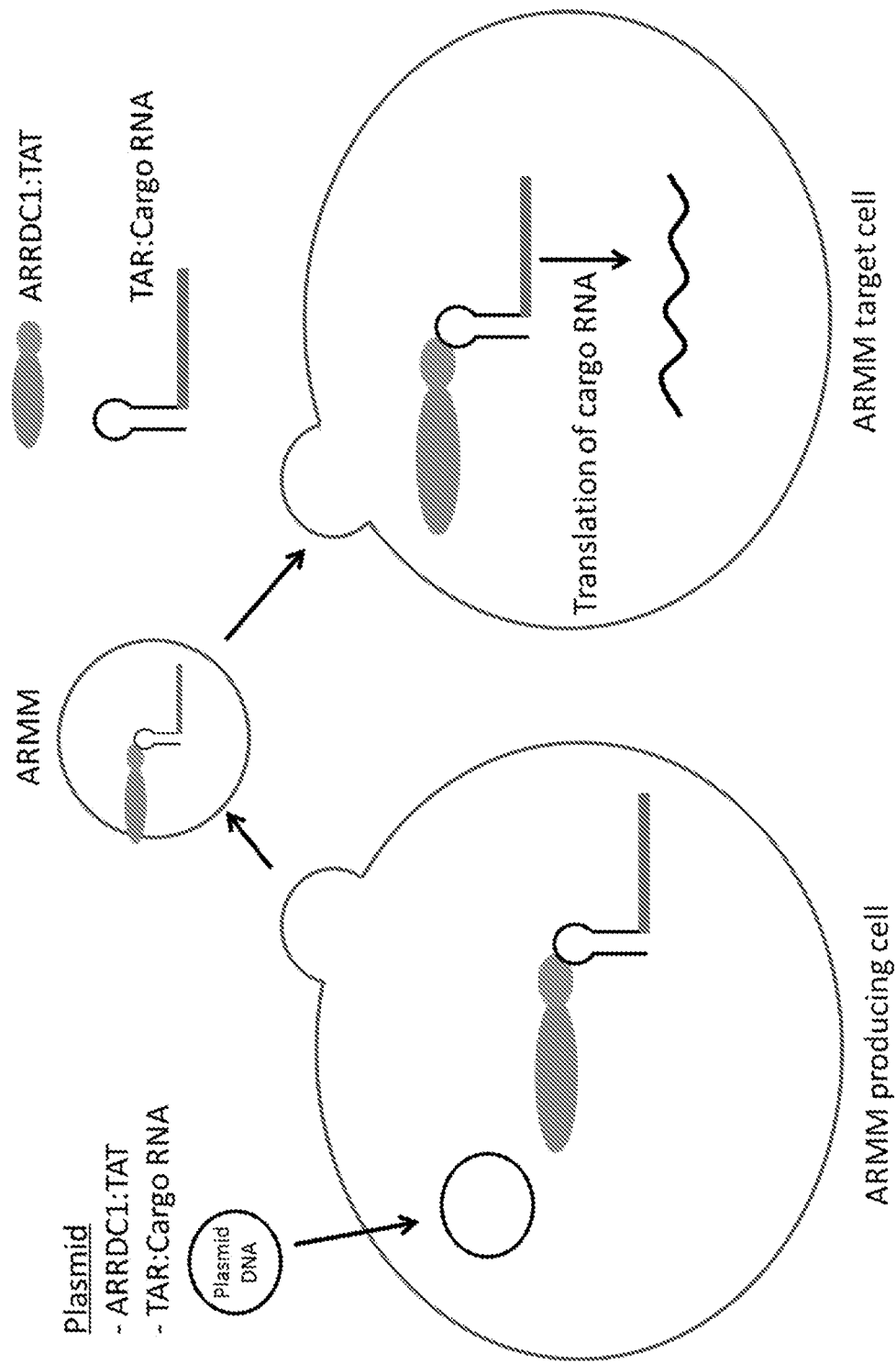
FIG. 4 is a schematic demonstrating the production of an ARMM in a microvesicle-producing cell (ARMM producing cell) that contains an ARRDC1-Tat fusion protein, which associates with a TAR molecule fused to a cargo RNA to facilitate the loading of the cargo RNA into the ARMM. The ARRDC1-Tat fusion protein may be co-expressed in an ARMM producing cell with the TAR:cargoRNA fusion (e.g., from a plasmid DNA) so they are co-incorporated into ARMMs (left). The ARMM may then be delivered to an ARMM target cell (right), where the cargo RNA fused to the TAR is released into the cytoplasm of the target cell. The cargo RNA may then be translated into protein, for example, if the RNA is an mRNA. Alternatively, the cargo RNA may be a siRNA, which may be processed by a Dicer complex to stimulate the RNA interference (RNAi) pathway.

WW domains are found in many eukaryotes and are present in approximately 50 human proteins (Bork, P. & Sudol, M. The WW domain: a signaling site in dystrophin? Trends Biochem Sci 19, 531-533 (1994)). WW domains may be present together with several other interaction domains, including membrane targeting domains, such as C2 in the NEDD4 family proteins, the phosphotyrosine-binding (PTB) domain in FE65 protein, FF domains in CA150 and FBPI1, and pleckstrin homology (PH) domains in PLEKHAS. WW domains are also linked to a variety of catalytic domains, including HECT E3 protein-ubiquitin ligase domains in NEDD4 family proteins, rotomerase or peptidyl prolyisomerase domains in Pinl, and Rho GAP domains in ArhGAP9 and ArhGAP12. Exemplary proteins containing WW domains are illustrated in FIG. 3.

In the instant disclosure, the WW domain may be a WW domain that naturally possesses two basic amino acids at the C-terminus. In some embodiments, a WW domain or WW domain variant may be from the human ubiquitin ligase WWP1, WWP2, Nedd4-1, Nedd4-2, Smurf1, Smurf2, ITCH, NEDL1, or NEDL2. Exemplary amino acid sequences of WW domain containing proteins (WW domains underlined) are listed below. It should be appreciated that any of the WW domains or WW domain variants of the exemplary proteins may be used in the invention, described herein, and are not meant to be limiting.

Human WWP1 amino acid sequence (uniprot.org/uniprot/ Q9H0M0). The four underlined WW domains correspond to amino acids 349-382 (WW1), 381-414 (WW2), 456-489 (WW3), and 496-529 (WW4).

```
                                                                    (SEQ ID NO: 6)
MATASPRSDT  SNNHSGRLQL  QVTVSSAKLK  RKKNWFGTAI  YTEVVVDGEI      50

TKTAKSSSSS  NPKWDEQLTV  NVTPQTTLEF  QVWSHRTLKA  DALLGKATID     100

LKQALLIHNR  KLERVKEQLK  LSLENKNGIA  QTGELTVVLD  GLVIEQENIT     150

NCSSSPTIEI  QENGDALHEN  GEPSARTTAR  LAVEGTNGID  NHVPTSTLVQ     200

NSCCSYVVNG  DNTPSSPSQV  AARPKNTPAP  KPLASERADD  TVNGESSSFA     250

PTDNASVTGT  PVVSEENALS  PNCTSTTVED  PPVQEILTSS  ENNECIPSTS     300

AELESEARSI  LEPDTSNSRS  SSAFEAAKSR  QPDGCMDPVR  QQSGNANTET     350

LPSGWEQRKD  PHGRTYYVDH  NTRTTTWERP  QPLPPGWERR  VDDRRRVYYV     400

DHNTRTTTWQ  RPTMESVRNF  EQWQSQRNQL  QGAMQQFNQR  YLYSASMLAA     450

ENDPYGPLPP  GWEKRVDSTD  RVYFVNHNTK  TTQWEDPRTQ  GLQNEEPLPE     500

GWEIRYTREG  VRYFVDHNTR  TTTFKDPRNG  KSSVTKGGPQ  IAYERGFRWK     550

LAHFRYLCQS  NALPSHVKIN  VSRQTLFEDS  FQQIMALKPY  DLRRRLYVIF     600

RGEEGLDYGG  LAREWFFLLS  HEVLNPMYCL  FEYAGKNNYC  LQINPASTIN     650

PDHLSYFCFI  GRFIAMALFH  GKFIDTGFSL  PFYKRMLSKK  LTIKDLESID     700

TEFYNSLIWI  RDNNIEECGL  EMYFSVDMEI  LGKVTSHDLK  LGGSNILVTE     750

ENKDEYIGLM  TEWRFSRGVQ  EQTKAFLDGF  NEVVPLQWLQ  YFDEKELEVM     800

LCGMQEVDLA  DWQRNTVYRH  YTRNSKQIIW  FWQFVKETDN  EVRMRLLQFV     850

TGTCRLPLGG  FAELMGSNGP  QKFCIEKVGK  DTWLPRSHTC  FNRLDLPPYK     900

SYEQLKEKLL  FAIEETEGFG  QE                                     922
```

WW1 (349-382):
ETLPSGWEQRKDPHGRTYYVDHNTRTTTWERPQP
(SEQ ID NO: 36).

WW2 (381-414):
QPLPPGWERRVDDRRRVYYVDHNTRTTTWQRPTM
(SEQ ID NO: 37).

WW3 (456-489):
ENDPYGPLPPGWEKRVDSTDRVYFVNHNTKTTQW-
EDPRT (SEQ ID NO: 38).

WW4 (496-529):
EPLPEGWEIRYTREGVRYFVDHNTRTTTFKDPRN
(SEQ ID NO: 39).

Human WWP2 amino acid sequence (uniprot.org/uniprot/O00308). The four underlined WW domains correspond to amino acids 300-333 (WW1), 330-363 (WW2), 405-437 (WW3), and 444-547 (WW4).

```
                                                                    (SEQ ID NO: 7)
MASASSSRAG  VALPFEKSQL  TLKVVSAKPK  VHNRQPRINS  YVEVAVDGLP      50

SETKKTGKRI  GSSELLWNEI  IILNVTAQSH  LDLKVWSCHT  LRNELLGTAS     100

VNLSNVLKNN  GGKMENMQLT  LNLQTENKGS  VVSGGELTIF  LDGPTVDLGN     150

VPNGSALTDG  SQLPSRDSSG  TAVAPENRHQ  PPSTNCFGGR  SRTHRHSGAS     200

ARTTPATGEQ  SPGARSRHRQ  PVKNSGHSGL  ANGTVNDEPT  TATDPEEPSV     250

VGVTSPPAAP  LSVTPNPNTT  SLPAPATPAE  GEEPSTSGTQ  QLPAAAQAPD     300

ALPAGWEQRE  LPNGRVYYVD  HNTKTTTWER  PLPPGWEKRT  DPRGRFYYVD     350

HNTRTTTWQR  PTAEYVRNYE  QWQSQRNQLQ  GAMQHFSQRF  LYQSSSASTD     400

HDPLGPLPPG  WEKRQDNGRV  YYVNHNTRTT  QWEDPRTQGM  IQEPALPPGW     450

EMKYTSEGVR  YFVDHNTRTT  TFKDPRPGFE  SGTKQGSPGA  YDRSFRWKYH     500

QFRFLCHSNA  LPSHVKISVS  RQTLFEDSFQ  QIMNMKPYDL  RRRLYIIMRG     550

EEGLDYGGIA  REWFFLLSHE  VLNPMYCLFE  YAGKNNYCLQ  INPASSINPD     600

HLTYFRFIGR  FIAMALYHGK  FIDTGFTLPF  YKRMLNKRPT  LKDLESIDPE     650

FYNSIVWIKE  NNLEECGLEL  YFIQDMEILG  KVTTHELKEG  GESIRVTEEN     700
```

```
KEEYIMLLTD WRFTRGVEEQ TKAFLDGFNE VAPLEWLRYF DEKELELMLC      750

GMQEIDMSDW QKSTIYRHYT KNSKQIQWFW QVVKEMDNEK RIRLLQFVTG      800

TCRLPVGGFA ELIGSNGPQK FCIDKVGKET WLPRSHTCFN RLDLPPYKSY      850

EQLREKLLYA IEETEGFGQE                                      870
```

WW1 (300-333):
DALPAGWEQRELPNGRVYYVDHNTKTTTWERPLP
(SEQ ID NO: 40).
WW2 (330-363):
PLPPGWEKRT       DPRGRFYYVDHNTRTTTWQRPTA
(SEQ ID NO: 41).
WW3 (405-437):
HDPLGPLPPGWEKRQDNGRVYYVNHNTRTTQW-
EDPRT (SEQ ID NO: 42).

WW4 (444-477):
PALPPGWEMKYTSEGVRYFVDHNTRTTTFKDPRP
(SEQ ID NO: 43).

Human Nedd4-1 amino acid sequence (uniprot.org/uniprot/P46934). The four underlined WW domains correspond to amino acids 610-643 (WW1), 767-800 (WW2), 840-873 (WW3), and 892-925 (WW4).

```
                                                    (SEQ ID NO: 8)
           MAQSLRLHFA ARRSNTYPLS ETSGDDLDSH VHMCFKRPTR TSTSNVVQMK       50

LTPRQTALAP LIKENVQSQE RSSVPSSENV NKKSSCLQIS LQPTRYSGYL      100

QSSNVLADSD DASFTCILKD GIYSSAVVDN ELNAVNDGHL VSSPAICSGS      150

LSNFSTSDNG SYSSNGSDFG SCASITSGGS YTNSVISDSS SYTFPPSDDT      200

FLGGNLPSDS TSNRSVPNRN TTPCEIFSRS TSTDPFVQDD LEHGLEIMKL      250

PVSRNTKIPL KRYSSLVIFP RSPSTTRPTS PTSLCTLLSK GSYQTSHQFI      300

ISPSEIAHNE DGTSAKGFLS TAVNGLRLSK TICTPGEVRD IRPLHRKGSL      350

QKKIVLSNNT PRQTVCEKSS EGYSCVSVHF TQRKAATLDC ETTNGDCKPE      400

MSEIKLNSDS EYIKLMHRTS ACLPSSQNVD CQININGELE RPHSQMNKNH      450

GILRRSISLG GAYPNISCLS SLKHNCSKGG PSQLLIKFAS GNEGKVDNLS      500

RDSNRDCTNE LSNSCKTRDD FLGQVDVPLY PLPTENPRLE RPYTFKDFVL      550

HPRSHKSRVK GYLRLKMTYL PKTSGSEDDN AEQAEELEPG WVVLDQPDAA      600

CHLQQQQEPS PLPPGWEERQ DILGRTYYVN HESRRTQWKR PTPQDNLTDA      650

ENGNIQLQAQ RAFTTRRQIS EETESVDNRE SSENWEIIRE DEATMYSNQA      700

FPSPPPSSNL DVPTHLAEEL NARLTIFGNS AVSQPASSSN HSSRRGSLQA      750

YTFEEQPTLP VLLPTSSGLP PGWEEKQDER GRSYYVDHNS RTTTWTKPTV      800

QATVETSQLT SSQSSAGPQS QASTSDSGQQ VTQPSEIEQG FLPKGWEVRH      850

APNGRPFFID HNTKTTTWED PRLKIPAHLR GKTSLDTSND LGPLPPGWEE      900

RTHTDGRIFY INHNIKRTQW EDPRLENVAI TGPAVPYSRD YKRKYEFFRR      950

KLKKQNDIPN KFEMKLRRAT VLEDSYRRIM GVKRADFLKA RLWIEFDGEK     1000

GLDYGGVARE WFFLISKEMF NPYYGLFEYS ATDNYTLQIN PNSGLCNEDH     1050

LSYFKFIGRV AGMAVYHGKL LDGFFIRPFY KMMLHKPITL HDMESVDSEY     1100

YNSLRWILEN DPTELDLRFI IDEELFGQTH QHELKNGGSE IVVTNKNKKE     1150

YIYLVIQWRE VNRIQKQMAA FKEGFFELIP QDLIKIFDEN ELELLMCGLG     1200

DVDVNDWREH TKYKNGYSAN HQVIQWFWKA VLMMDSEKRI RLLQFVTGTS     1250

RVPMNGFAEL YGSNGPQSFT VEQWGTPEKL PRAHTCFNRL DLPPYESFEE     1300

LWDKLQMAIE NTQGFDGVD                                     1319
```

WW1 (610-643):
SPLPPGWEERQDILGRTYYVNHESRRTQWKRPTP
(SEQ ID NO: 44).
WW2 (767-800):
SGLPPGWEEKQDERGRSYYVDHNSRTTTWTKPTV
(SEQ ID NO: 45).
WW3 (840-873):
GFLPKGWEVRHAPNGRPFFIDHNTKTTTWEDPRL
(SEQ ID NO: 46).
WW4 (892-925):
GPLPPGWEERTHTDGRIFYINHNIKRTQWEDPRL
(SEQ ID NO: 47).

Human Nedd4-2 amino acid sequence (>gi|21361472|ref|NP_056092.2| E3 ubiquitin-protein ligase NEDD4-like isoform 3 [Homo sapiens]). The four underlined WW domains correspond to amino acids 198-224 (WW1), 368-396 (WW2), 480-510 (WW3), and 531-561 (WW4).

(SEQ ID NO: 9)
MATGLGEPVYGLSEDEGESRILRVKVVSGIDLAKKDIFGASDPYVKLSL
YVADENRELALVQTKTIKKTLNPKWNEEFYFRVNPSNHRLLFEVFDENR
LTRDDFLGQVDVPLSHLPTEDPTMERPYTFKDFLLRPRSHKSRVKGFLR
LKMAYMPKNGGQDEENSDQRDDMEHGWEVVDSNDSASQHQEELPPPPLP
PGWEEKVDNLGRTYYVNHNNRTTQWHRPSLMDVSSESDNNIRQINQEAA
HRRFRSRRHISEDLEPEPSEGGDVPEPWETISEEVNIAGDSLGLALPPP
PASPGSRTSPQELSEELSRRLQITPDSNGEQFSSLIQREPSSRLRSCSV
TDAVAEQGHLPPPSVAYVHTTPGLPSGWEERKDAKGRTYYVNHNNRTTT
WTRPIMQLAEDGASGSATNSNNHLIEPQIRRPRSLSSPTVTLSAPLEGA
KDSPVRRAVKDTLSNPQSPQPSPYNSPKPQHKVTQSFLPPGWEMRIAPN
GRPFFIDHNTKTTTWEDPRLKFPVHMRSKTSLNPNDLGPLPPGWEERIH
LDGRTFYIDHNSKITQWEDPRLQNPAITGPAVPYSREFKQKYDYFRKKL
KKPADIPNRFEMKLHRNNIFEESYRRIMSVKRPDVLKARLWIEFESEKG
LDYGGVAREWFFLLSKEMFNPYYGLFEYSATDNYTLQINPNSGLCNEDH
LSYFTFIGRVAGLAVFHGKLLDGFFIRPFYKMMLGKQITLNDMESVDSE
YYNSLKWILENDPTELDLMFCIDEENFGQTYQVDLKPNGSEIMVTNENK
REYIDLVIQWRFVNRVQKQMNAFLEGFTELLPIDLIKIFDENELELLMC
GLGDVDVNDWRQHSIYKNGYCPNHPVIQWFWKAVLLMDAEKRIRLLQFV
TGTSRVPMNGFAELYGSNGPQLFTIEQWGSPEKLPRAHTCFNRLDLPPY
ETFEDLREKLLMAVENAQGFEGVD

WW1 (198-224):
GWEEKVDNLGRTYYVNHNNRTTQWHRP (SEQ ID NO: 61).
WW2 (368-396):
PSGWEERKDAKGRTYYVNHNNRTTTWTRP (SEQ ID NO: 62).
WW3 (480-510):
PPGWEMRIAPNGRPFFIDHNTKTTTWEDPRL (SEQ ID NO: 63).
WW4 (531-561):
PPGWEERIHLDGRTFYIDHNSKITQWEDPRL (SEQ ID NO: 64).

Human Smurf1 amino acid sequence (uniprot.org/uniprot/Q9HCE7). The two underlined WW domains correspond to amino acids 234-267 (WW1) and 306-339 (WW2).

```
                                                    (SEQ ID NO: 10)
         MSNPGTRRNG SSIKIRLTVL CAKNLAKKDF FRLPDPFAKI VVDGSGQCHS    50

TDTVKNTLDP KWNQHYDLYV GKTDSITISV WNHKKIHKKQ GAGFLGCVRL   100

LSNAISRLKD TGYQRLDLCK LNPSDTDAVR GQIVVSLQTR DRIGTGGSVV   150

DCRGLLENEG TVYEDSGPGR PLSCFMEEPA PYTDSTGAAA GGGNCRFVES   200

PSQDQRLQAQ RLRNPDVRGS LQTPQNRPHG HQSPELPEGY EQRTTVQGQV   250

YFLHTQTGVS TWHDPRIPSP SGTIPGGDAA FLYEFLLQGH TSEPRDLNSV   300

NCDELGPLPP GWEVRSTVSG RIYFVDHNNR TTQFTDPRLH HIMNHQCQLK   350

EPSQPLPLPS EGSLEDEELP AQRYERDLVQ KLKVLRHELS LQQPQAGHCR   400

IEVSREEIFE ESYRQIMKMR PKDLKKRLMV KFRGEEGLDY GGVAREWLYL   450

LCHEMLNPYY GLFQYSTDNI YMLQINPDSS INPDHLSYFH FVGRIMGLAV   500

FHGHYINGGE TVPFYKQLLG KPIQLSDLES VDPELHKSLV WILENDITPV   550

LDHTFCVEHN AFGRILQHEL KPNGRNVPVT EENKKEYVRL YVNWRFMRGI   600

EAQFLALQKG FNELIPQHLL KPFDQKELEL IIGGLDKIDL NDWKSNTRLK   650

HCVADSNIVR WFWQAVETFD EERRARLLQF VTGSTRVPLQ GFKALQGSTG   700

AAGPRLFTIH LIDANTDNLP KAHTCFNRID IPPYESYEKL YEKLLTAVEE   750

TCGFAVE                                                  757
```

WW1 (234-267):
PELPEGYEQRTTVQGQVYFLHTQTGVSTWHDPRI
(SEQ ID NO: 48).
WW2 (306-339):
GPLPPGWEVRSTVSGRIYFVDHNNRTTQFTDPRL
(SEQ ID NO: 49).

Human Smurf2 amino acid sequence (uniprot.org/uniprot/Q9HAU4). The three underlined WW domains correspond to amino acids 157-190 (WW1), 251-284 (WW2), and 297-330 (WW3).

```
                                                    (SEQ ID NO: 11)
MSNPGGRRNG PVKLRLTVLC AKNLVKKDFF RLPDPFAKVV VDGSGQCHST    50

DTVKNTLDPK WNQHYDLYIG KSDSVTISVW NHKKIHKKQG AGFLGCVRLL   100

SNAINRLKDT GYQRLDLCKL GPNDNDTVRG QIVVSLQSRD RIGTGGQVVD   150

CSRLFDNDLP DGWEERRTAS GRIQYLNHIT RTTQWERPTR PASEYSSPGR   200

PLSCFVDENT PISGTNGATC GQSSDPRLAE RRVRSQRHRN YMSRTHLHTP   250

PDLPEGYEQR TTQQGQVYFL HTQTGVSTWH DPRVPRDLSN INCEELGPLP   300

PGWEIRNTAT GRVYFVDHNN RTTQFTDPRL SANLHLVLNR QNQLKDQQQQ   350

QVVSLCPDDT ECLTVPRYKR DLVQKLKILR QELSQQQPQA GHCRIEVSRE   400

EIFEESYRQV MKMRPKDLWK RLMIKFRGEE GLDYGGVARE WLYLLSHEML   450

NPYYGLFQYS RDDIYTLQIN PDSAVNPEHL SYFHFVGRIM GMAVFHGHYI   500

DGGFTLPFYK QLLGKSITLD DMELVDPDLH NSLVWILEND ITGVLDHTFC   550

VEHNAYGEII QHELKPNGKS IPVNEENKKE YVRLYVNWRF LRGIEAQFLA   600

LQKGFNEVIP QHLLKTFDEK ELELIICGLG KIDVNDWKVN TRLKHCTPDS   650

NIVKWFWKAV EFFDEERRAR LLQFVTGSSR VPLQGFKALQ GAAGPRLFTI   700

HQIDACTNNL PKAHTCFNRI DIPPYESYEK LYEKLLTAIE ETCGFAVE    748
```

WW1 (157-190):
NDLPDGWEERRTASGRIQYLNHITRTTQWERPTR
(SEQ ID NO: 50).
WW2 (251-284):
PDLPEGYEQRTTQQGQVYFLHTQTGVSTWHDPRV
(SEQ ID NO: 51).
WW3 (297-330):
GPLPPGWEIRNTATGRVYFVDHNNRTTQFTDPRL
(SEQ ID NO: 52).

Human ITCH amino acid sequence (uniprot.org/uniprot/Q96J02). The four underlined WW domains correspond to amino acids 326-359 (WW1), 358-391 (WW2), 438-471 (WW3), and 478-511 (WW4).

```
                                                    (SEQ ID NO: 12)
MSDSGSQLGS MGSLTMKSQL QITVISAKLK ENKKNWFGPS PYVEVTVDGQ    50

SKKTEKCNNT NSPKWKQPLT VIVTPVSKLH FRVWSHQTLK SDVLLGTAAL   100

DIYETLKSNN MKLEEVVVTL QLGGDKEPTE TIGDLSICLD GLQLESEVVT   150

NGETTCSENG VSLCLPRLEC NSAISAHCNL CLPGLSDSPI SASRVAGFTG   200

ASQNDDGSRS KDETRVSTNG SDDPEDAGAG ENRRVSGNNS PSLSNGGFKP   250

SRPPRPSRPP PPTPRRPASV NGSPSATSES DGSSTGSLPP TNTNTNTSEG   300

ATSGLIIPLT ISGGSGPRPL NPVTQAPLPP GWEQRVDQHG RVYYVDHVEK   350

RTTWDRPEPL PPGWERRVDN MGRIYYVDHF TRTTTWQRPT LESVRNYEQW   400

QLQRSQLQGA MQQFNQRFIY GNQDLFATSQ SKEFDPLGPL PPGWEKRTDS   450
```

-continued

```
NGRVYFVNHN TRITQWEDPR SQGQLNEKPL PEGWEMRFTV DGIPYFVDHN        500
RRTTTYIDPR TGKSALDNGP QIAYVRDFKA KVQYFRFWCQ QLAMPQHIKI        550
TVTRKTLFED SFQQIMSFSP QDLRRRLWVI FPGEEGLDYG GVAREWFFLL        600
SHEVLNPMYC LFEYAGKDNY CLQINPASYI NPDHLKYFRF IGRFIAMALF        650
HGKFIDTGFS LPFYKRILNK PVGLKDLESI DPEFYNSLIW VKENNIEECD        700
LEMYFSVDKE ILGEIKSHDL KPNGGNILVT EENKEEYIRM VAEWRLSRGV        750
EEQTQAFFEG FNEILPQQYL QYFDAKELEV LLCGMQEIDL NDWQRHAIYR        800
HYARTSKQIM WFWQFVKEID NEKRMRLLQF VTGTCRLPVG GFADLMGSNG        850
PQKFCIEKVG KENWLPRSHT CFNRLDLPPY KSYEQLKEKL LFAIEETEGF        900
GQE                                                          903
```

ITCH WW1 (326-359):
APLPPGWEQRVDQHGRVYYVDHVEKRTTWDRPEP
(SEQ ID NO: 53).
ITCH WW2 (358-391):
EPLPPGWERRVDNMGRIYYVDHFTRTTTWQRPTL
(SEQ ID NO: 54).
ITCH WW3 (438-471):
GPLPPGWEKRTDSNGRVYFVNHNTRITQWEDPRS
(SEQ ID NO: 55).

ITCH WW4 (478-511):
KPLPEGWEMRFTVDGIPYFVDHNRRTTTYIDPRT
(SEQ ID NO: 56).

Human NEDL1 amino acid sequence (uniprot.org/uniprot/Q76N89). The two underlined WW domains correspond to amino acids 829-862 (WW1), and 1018-1051 (WW2).

```
                                                   (SEQ ID NO: 13)
                MLLHLCSVKN LYQNRFLGLA AMASPSRNSQ SRRRCKEPLR YSYNPDQFHN        50
                MDLRGGPHDG VTIPRSTSDT DLVTSDSRST LMVSSSYYSI GHSQDLVIHW       100
                DIKEEVDAGD WIGMYLIDEV LSENFLDYKN RGVNGSHRGQ IIWKIDASSY       150
                FVEPETKICF KYYHGVSGAL RATTPSVTVK NSAAPIFKSI GADETVQGQG       200
                SRRLISFSLS DFQAMGLKKG MFFNPDPYLK ISIQPGKHSI FPALPHHGQE       250
                RRSKIIGNTV NPIWQAEQFS FVSLPTDVLE IEVKDKFAKS RPIIKRFLGK       300
                LSMPVQRLLE RHAIGDRVVS YTLGRRLPTD HVSGQLQFRF EITSSIHPDD       350
                EEISLSTEPE SAQIQDSPMN NLMESGSGEP RSEAPESSES WKPEQLGEGS       400
                VPDGPGNQSI ELSRPAEEAA VITEAGDQGM VSVGPEGAGE LLAQVQKDIQ       450
                PAPSAEELAE QLDLGEEASA LLLEDGEAPA STKEEPLEEE ATTQSRAGRE       500
                EEEKEQEEEG DVSTLEQGEG RLQLRASVKR KSRPCSLPVS ELETVIASAC       550
                GDPETPRTHY IRIHTLLHSM PSAQGGSAAE EEDGAEEEST LKDSSEKDGL       600
                SEVDTVAADP SALEEDREEP EGATPGTAHP GHSGGHFPSL ANGAAQDGDT       650
                HPSTGSESDS SPRQGGDHSC EGCDASCCSP SCYSSSCYST SCYSSSCYSA       700
                SCYSPSCYNG NRFASHTRFS SVDSAKISES TVFSSQDDEE EENSAFESVP       750
                DSMQSPELDP ESTNGAGPWQ DELAAPSGHV ERSPEGLESP VAGPSNRREG       800
                ECPILHNSQP VSQLPSLRPE HHHYPTIDEP LPPNWEARID SHGRVFYVDH       850
                VNRTTTWQRP TAAATPDGMR RSGSIQQMEQ LNRRYQNIQR TIATERSEED       900
                SGSQSCEQAP AGGGGGGGSD SEAESSQSSL DLRREGSLSP VNSQKITLLL       950
                QSPAVKFITN PEFFTVLHAN YSAYRVFTSS TCLKHMILKV RRDARNFERY      1000
                QHNRDLVNFI NMFADTRLEL PRGWEIKTDQ QGKSFFVDHN SRATTFIDPR      1050
                IPLQNGRLPN HLTHRQHLQR LRSYSAGEAS EVSRNRGASL LARPGHSLVA      1100
                AIRSQHQHES LPLAYNDKIV AFLRQPNIFE MLQERQPSLA RNHTLREKIH      1150
```

```
                           -continued
YIRTEGNHGL EKLSCDADLV ILLSLFEEEI MSYVPLQAAF HPGYSFSPRC   1200

SPCSSPQNSP GLQRASARAP SPYRRDFEAK LRNFYRKLEA KGFGQGPGKI   1250

KLIIRRDHLL EGTFNQVMAY SRKELQRNKL YVTFVGEEGL DYSGPSREFF   1300

FLLSQELFNP YYGLFEYSAN DTYTVQISPM SAFVENHLEW FRFSGRILGL   1350

ALIHQYLLDA FFTRPFYKAL LRLPCDLSDL EYLDEEFHQS LQWMKDNNIT   1400

DILDLTFTVN EEVFGQVTER ELKSGGANTQ VTEKNKKEYI ERMVKWRVER   1450

GVVQQTEALV RGFYEVVDSR LVSVFDAREL ELVIAGTAEI DLNDWRNNTE   1500

YRGGYHDGHL VIRWFWAAVE RFNNEQRLRL LQFVTGTSSV PYEGFAALRG   1550

SNGLRRFCIE KWGKITSLPR AHTCFNRLDL PPYPSYSMLY EKLLTAVEET   1600

STFGLE                                                  1606
```

WW1 (829-862):
PLPPNWEARIDSHGRVFYVDHVNRTTTWQRPTA (SEQ ID NO: 57).
WW2 (1018-1051):
LELPRGWEIKTDQQGKSFFVDHNSRATTFIDPRI (SEQ ID NO: 58).

Human NEDL2 amino acid sequence (uniprot.org/uniprot/Q9P2P5). The two underlined WW domains correspond to amino acids 807-840 (WW1) and 985-1018 (WW2).

```
                                                (SEQ ID NO: 14)
MASSAREHLL FVRRRNPQMR YTLSPENLQS LAAQSSMPEN MTLQRANSDT    50

DLVTSESRSS LTASMYEYTL GQAQNLIIFW DIKEEVDPSD WIGLYHIDEN   100

SPANFWDSKN RGVTGTQKGQ IVWRIEPGPY FMEPEIKICF KYYHGISGAL   150

RATTPCITVK NPAVMMGAEG MEGGASGNLH SRKLVSFTLS DLRAVGLKKG   200

MFFNPDPYLK MSIQPGKKSS FPTCAHHGQE RRSTIISNTT NPIWHREKYS   250

FFALLTDVLE IEIKDKFAKS RPIIKRFLGK LTIPVQRLLE RQAIGDQMLS   300

YNLGRRLPAD HVSGYLQFKV EVTSSVHEDA SPEAVGTILG VNSVNGDLGS   350

PSDDEDMPGS HHDSQVCSNG PVSEDSAADG TPKHSFRTSS TLEIDTEELT   400

STSSRTSPPR GRQDSLNDYL DAIEHNGHSR PGTATCSERS MGASPKLRSS   450

FPTDTRLNAM LHIDSDEEDH EFQQDLGYPS SLEEEGGLIM FSRASRADDG   500

SLTSQTKLED NPVENEEAST HEAASFEDKP ENLPELAESS LPAGPAPEEG   550

EGGPEPQPSA DQGSAELCGS QEVDQPTSGA DTGTSDASGG SRRAVSETES   600

LDQGSEPSQV SSETEPSDPA RTESVSEAST RPEGESDLEC ADSSCNESVT   650

TQLSSVDTRC SSLESARFPE TPAFSSQEEE DGACAAEPTS SGPAEGSQES   700

VCTAGSLPVV QVPSGEDEGP GAESATVPDQ EELGEVWQRR GSLEGAAAAA   750

ESPPQEEGSA GEAQGTCEGA TAQEEGATGG SQANGHQPLR SLPSVRQDVS   800

RYQRVDEALP PNWEARIDSH GRIFYVDHVN RTTTWQRPTA PPAPQVLQRS   850

NSIQQMEQLN RRYQSIRRTM TNERPEENTN AIDGAGEEAD FHQASADFRR   900

ENILPHSTSR SRITLLLQSP PVKFLISPEF FTVLHSNPSA YRMFTNNTCL   950

KHMITKVRRD THHFERYQHN RDLVGFLNMF ANKQLELPRG WEMKHDHQGK  1000

AFFVDHNSRT TTFIDPRLPL QSSRPTSALV HRQHLTRQRS HSAGEVGEDS  1050

RHAGPPVLPR PSSTFNTVSR PQYQDMVPVA YNDKIVAFLR QPNIFEILQE  1100

RQPDLTRNHS LREKIQFIRT EGTPGLVRLS SDADLVMLLS LFEEEIMSYV  1150
```

```
                      -continued
PPHALLHPSY CQSPRGSPVS SPQNSPGTQR ANARAPAPYK RDFEAKLRNF  1200

YRKLETKGYG QGPGKLKLII RRDHLLEDAF NQIMGYSRKD LQRNKLYVTE  1250

VGEEGLDYSG PSREFFFLVS RELFNPYYGL FEYSANDTYT VQISPMSAFV  1300

DNHHEWFRFS GRILGLALIH QYLLDAFFTR PFYKALLRIL CDLSDLEYLD  1350

EEFHQSLQWM KDNDIHDILD LTFTVNEEVE GQITERELKP GGANIPVTEK  1400

NKKEYIERMV KWRIERGVVQ QTESLVRGFY EVVDARLVSV FDARELELVI  1450

AGTAEIDLSD WRNNTEYRGG YHDNHIVIRW FWAAVERFNN EQRLRLLQFV  1500

TGTSSIPYEG FASLRGSNGP RRFCVEKWGK ITALPRAHTC FNRLDLPPYP  1550

SFSMLYEKLL TAVEETSTFG LE                               1572
```

WW1 (807-840):
EALPPNWEARIDSHGRIFYVDHVNRTTTWQRPTA
(SEQ ID NO: 59).
WW2 (985-1018):
LELPRGWEMKHDHQGKAFFVDHNSRTTTFIDPRL
(SEQ ID NO: 60).

In some embodiments, the WW domain comprises a WW domain or WW domain variant from the amino acid sequence (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14). In other embodiments, the WW domain consists of a WW domain or WW domain variant from the amino acid sequence (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14). In another embodiment, the WW domain consists essentially of a WW domain or WW domain variant from the amino acid sequence (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14). Consists essentially of means that a domain, peptide, or polypeptide consists essentially of an amino acid sequence when such an amino acid sequence is present with only a few additional amino acid residues, for example, from about 1 to about 10 or so additional residues, typically from 1 to about 5 additional residues in the domain, peptide, or polypeptide.

Alternatively, the WW domain may be a WW domain that has been modified to include two basic amino acids at the C-terminus of the domain. Techniques are known in the art and are described in the art, for example, in Sambrook et al. ((2001) Molecular Cloning: a Laboratory Manual, 3rd ed., Cold Spring Harbour Laboratory Press). Thus, a skilled person could readily modify an existing WW domain that does not normally have two C-terminal basic residues so as to include two basic residues at the C-terminus.

Basic amino acids are amino acids that possess a side-chain functional group that has a pKa of greater than 7 and includes lysine, arginine, and histidine, as well as basic amino acids that are not included in the twenty α-amino acids commonly included in proteins. The two basic amino acids at the C-terminus of the WW domain may be the same basic amino acid or may be different basic amino acids. In one embodiment, the two basic amino acids are two arginines.

The term WW domain also includes variants of a WW domain provided that any such variant possesses two basic amino acids at its C-terminus and maintains the ability of the WW domain to associate with the PPXY (SEQ ID NO: 2) motif. A variant of such a WW domain refers to a WW domain which retains the ability of the variant to associate with the PPXY (SEQ ID NO: 2) motif (i.e., the PPXY (SEQ ID NO: 2) motif of ARRDC1) and that has been mutated at one or more amino acids, including point, insertion, and/or deletion mutations, but still retains the ability to associate with the PPXY (SEQ ID NO: 2) motif. A variant or derivative therefore includes deletions, including truncations and fragments; insertions and additions, for example conservative substitutions, site-directed mutants and allelic variants; and modifications, including one or more non-amino acyl groups (e.g., sugar, lipid, etc.) covalently linked to the peptide and post-translational modifications. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

The WW domain may be part of a longer protein. Thus, the protein, in various different embodiments, comprises the WW domain, consists of the WW domain or consists essentially of the WW domain, as defined herein. The polypeptide may be a protein that includes a WW domain as a functional domain within the protein sequence. In some embodiments, the polypeptide comprises the sequence set forth in (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14), consists of (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14), or consists essentially of (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14).

DETAILED DESCRIPTION OF CERTAIN EMBODIMENTS OF THE INVENTION

The instant disclosure relates, at least in part, to the discovery that a GFP-encoding cargo RNA fused to a TAR element can be loaded into ARMMs by co-expressing the TAR:cargo RNA fusion with an ARRDC1:Tat fusion protein in a cell. The disclosure also demonstrates that ARMMs containing a GFP-encoding cargo RNA were able to deliver their GFP-encoding cargo RNA into targeted cells. Furthermore, fusing of the TAR element with the GFP-encoding cargo RNA did not inhibit GFP expression from the cargo RNA. As described in more detail herein, cargo RNAs (e.g., RNAs that encode proteins (e.g., therapeutic proteins) or siRNAs that inhibit the expression of one or more proteins) may be associated (covalently or non-covalently) with one or more binding RNAs (e.g., a TAR element) in order to facilitate loading of the cargo RNA into an ARMM, for example, by binding to an ARMM protein (e.g., ARRDC1 or fragment thereof). Loading a cargo RNA into an ARMM may be performed by expressing an ARRDC1 protein, or fragment thereof, fused to a RNA binding protein (e.g., Tat), or fragment thereof, so that a cargo RNA associated with a binding RNA (e.g., TAR element) binds to the fusion protein of ARRDC1:RNA binding protein and is loaded into an ARMM. Alternatively, a fusion protein, such as an RNA binding protein:WW domain fusion protein (e.g., Tat:WW), may be used to recruit a cargo RNA associated with a binding RNA (e.g., a TAR element) to ARRDC1 in order to load the cargo RNA into an ARMM. For example, a cargo RNA associated with a TAR element may bind to the Tat portion of a Tat:WW fusion protein. The WW domain of the Tat:WW fusion protein may bind to ARRDC1 (e.g., via the PPXY (SEQ ID NO: 2) motif of ARRDC1), thereby recruiting the cargo RNA into an ARMM by associating it with the ARMM protein ARRDC1.

ARMMs containing cargo RNAs, such as RNAs that express therapeutic proteins or siRNAs that inhibit the expression of one or more proteins, may be used to deliver the cargo RNA to a cell. The ARMMs may be delivered to cells in vitro or in vivo. For example, ARMMs may be incubated with cells in culture (e.g., by adding them to the cell culture medium) in order to deliver the contents of the ARMMs into the cultured cells. As another example, ARMMs may be delivered to the cells of a subject, e.g., by administering the ARMMs to the subject. ARMMs may also be modified to target one or more cell types. For example, ARMMs may be associated with one or more binding agents that selectively bind an antigen on the surface of the target cell. Methods for producing membrane-bound binding agents, for example, membrane-bound immunoglobulins, membrane-bound antibodies or antibody fragments that specifically bind a surface antigen expressed on the surface of cells (e.g., cancer cells), are known to those of skill in the art. Cell surface antigens specifically expressed on various types of cells that can be targeted by ARMMs comprising membrane-bound binding agents in order to deliver the contents of the ARMMs into one or more targeted cells.

Microvesicles with ARRDC1 and Binding RNAs

Figure 2:
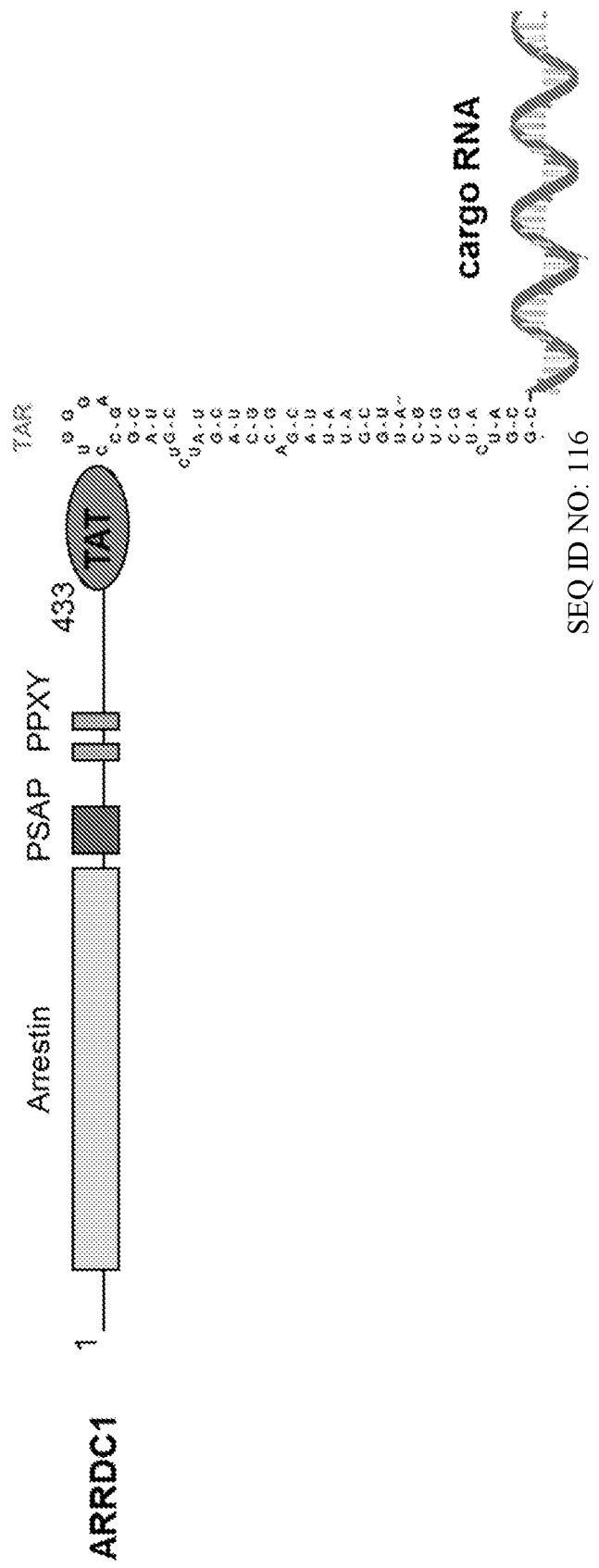
FIG. 2 shows a non-limiting schematic representation of an ARRDC1 protein fused to a Tat protein that associates with a TAR molecule that is fused to a cargo RNA. The nucleotide sequence of a TAR is set forth in SEQ ID NO: 116.

Some aspects of this invention provide arrestin domain-containing protein 1 (ARRDC1)-mediated microvesicles (ARMMs) containing an ARRDC1 protein, or variant thereof, associated with a binding RNA. The binding RNA may associate with the ARRDC1 protein in different ways. For example, the ARRDC1 may be fused to an RNA binding protein, or variant thereof, that associates with the binding RNA, thereby associating the binding RNA with the ARRDC1 via the RNA binding protein. See, for example, the schematic of FIG. 2 showing AARDC1 fused to a Tat protein, which associates with a TAR binding RNA. As another example, an ARMM may comprise an RNA binding protein fused to one or more WW domains, which associates with ARRDC1 via at least one WW domain and also associates with a binding RNA via the RNA binding protein, thereby associating the binding RNA with ARRDC1.

Some aspects of this invention provide arrestin domain-containing protein 1 (ARRDC1)-mediated microvesicles (ARMMs) containing an ARRDC1 protein, or variant thereof, that is associated with an RNA binding protein, or variant thereof, and a binding RNA that is associated with the RNA binding protein. Such ARMMs typically include a lipid bilayer and an ARRDC1 protein or variant thereof. In some embodiments, the ARRDC1 protein is non-covalently associated with the RNA binding protein. In some embodiments, ARRDC1 protein is covalently associated with the RNA binding protein. In some embodiments, the RNA binding protein is fused to the N-terminus of the ARRDC1 protein. In some embodiments, the RNA binding protein is fused to the C-terminus of the ARRDC1 protein. In some embodiments, the RNA binding protein is non-covalently associated with the binding RNA.

Some aspects of this invention provide arrestin domain-containing protein 1 (ARRDC1)-mediated microvesicles (ARMMs) containing an ARRDC1 protein, or variant thereof, and an RNA binding protein fused to at least one WW domain, or variant thereof, and a binding RNA that is associated with the RNA binding protein. Such ARMMs typically include a lipid bilayer and an ARRDC1 protein, or variant thereof. In some embodiments, the RNA binding protein fused to a WW domain associates with the PPXY (SEQ ID NO: 2) (where x=any amino acid) domain of ARRDC1, via the WW domain, which may facilitate loading of the binding RNA into an ARMM. In some embodiments, at least one WW domain is fused to the N-terminus of an RNA binding protein. In some embodiments, 1, 2, 3, 4, 5, 6, 7, 8, 9, or 10 WW domains are fused to the N-terminus of an RNA binding protein. In some embodiments, at least one WW domain is fused to the C-terminus of an RNA binding protein. In some embodiments, 1, 2, 3, 4, 5, 6, 7, 8, 9, or 10 WW domains are fused to the C-terminus of an RNA binding protein.

In some embodiments, the binding RNA is associated with a cargo RNA, which may facilitate loading of the cargo RNA into an ARMM. In some embodiments, the binding RNA is covalently associated with the cargo RNA. In some embodiments, the binding RNA and the cargo RNA are part of the same RNA molecule (e.g., an RNA from a single transcript). In some embodiments, the binding RNA and the cargo RNA are covalently associated via a linker. In some embodiments, the linker comprises a nucleotide or nucleic acid (e.g., DNA or RNA). In some embodiments, the linker comprises RNA. In some embodiments, the linker comprises DNA. In some embodiments, the linker comprises at least 1, at least 2, at least 3, at least 4, at least 5, at least 6, at least 7, at least 8, at least 9, at least 10, at least 15, at least 20, at least 25, at least 30, at least 40, at least 50, at least 100, at least 150, at least 200, at least 250, at least 300, at least 400, or at least 500 nucleotides (e.g., DNA or RNA).

In other embodiments, the binding RNA is non-covalently associated with the cargo RNA. For example, the binding RNA may associate with the cargo RNA via complementary base pairing. In some embodiments, the binding RNA is bound to the cargo RNA via at least 2, at least 3, at least 4, at least 5, at least 6, at least 7, at least 8, at least 9, at least 10, at least 15, at least 20, at least 25, at least 30, at least 40, at least 50 complementary base pairs, which may be contiguous or non-contiguous. In some embodiments, the binding RNA is bound to the cargo RNA via at least 2, at least 3, at least 4, at least 5, at least 6, at least 7, at least 8, at least 9, at least 10, at least 15, at least 20, at least 25, at least 30, at least 40, or at least 50 contiguous complementary base pairs.

It should be appreciated that any number of cargo RNAs can be associated with a binding RNA, for example, to facilitate loading of the cargo RNA into an ARMM. A cargo RNA may, for example, encode a reprogramming factor (e.g., Oct4, Sox2, c-Myc, or KLF4), which may be loaded into an ARMM by associating it with an ARRDC1 fused to an RNA binding protein via a binding RNA. In some embodiments, the cargo RNA is an mRNA that encodes a therapeutic protein (e.g., a transcription factor, a tumor suppressor, a developmental regulator, a growth factor, a metastasis suppressor, a pro-apoptotic protein, a zinc finger nuclease, or a recombinase). In other embodiments, the cargo RNA is an siRNA that inhibits expression of a protein (e.g., a transcription factor, a tumor suppressor, a developmental regulator, a growth factor, a metastasis suppressor, a metastasis promoter, an oncogene, a pro-apoptotic protein, a zinc finger nuclease, or a recombinase). In other embodiments, an ARMM further includes a a TSG101 protein, or variant thereof, to facilitate the release of ARMMs. Without wishing to be bount by any particular theory, the TSG101 protein interacts with ARRDC1, which results in relocation of TSG101 from endosomes to the plasma membrane and mediates the release of microvesicles that contain TSG101, ARRDC1, and other cellular components, including, for example, cargoRNAs (e.g., TAR:cargoRNA) and RNA binding proteins (e.g., ARRDC1:Tat).

ARRDC1

ARRDC1 is a protein that comprises a PSAP (SEQ ID NO: 1) motif and a PPXY (SEQ ID NO: 2) motif, also referred to herein as a PSAP (SEQ ID NO: 1) and PPXY (SEQ ID NO: 2) motif, respectively, in its C-terminus, and interacts with TSG101 as shown herein. It should be appreciated that the PSAP (SEQ ID NO: 1) motif and the PPXY (SEQ ID NO: 2) motif are not required to be at the absolute C-terminal end of the ARRDC1. Rather, they may be at a C-terminal portion of the ARRDC1 protein (e.g., the C-terminal half of the ARRDC1). The disclosure also contemplates variants of ARRDC1, such as fragments of ARRDC1 and/or ARRDC1 proteins that have a degree of identity (e.g., 60%, 70%, 80%, 85%, 90%, 95%, 98%, or 99% identity) to an ARRDC1 protein and are capable if interacting with TSG101. Accordingly, an ARRDC1 protein may be a protein that comprises a PSAP (SEQ ID NO: 1) motif and a PPXY (SEQ ID NO: 2) motif, and interacts with TSG101. In some embodiments, the ARRDC1 protein is at least 60%, 65%, 70%, 75%, 80%, 85%, 90%, 95%, 98%, or 99% identical to the amino acid sequence of any one of SEQ ID NOs: 15-17, comprises a PSAP (SEQ ID NO: 1) motif and a PPXY (SEQ ID NO: 2) motif, and interacts with TSG101. In some embodiments, the ARRDC1 protein has at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, at least 350, at least 360, at least 370, at least 380, at least 390, at least 400, at least 410, at least 420, or at least 430 identical contiguous amino acids of any one of SEQ ID NOs: 15-17, comprises a PSAP (SEQ ID NO: 1) motif and a PPXY (SEQ ID NO: 2) motif, and interacts with TSG101. In some embodiments, the ARRDC1 protein has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more mutations compared to any one of the amino acid sequences set forth in SEQ ID NOs: 15-17 comprises a PSAP (SEQ ID NO: 1) motif and a PPXY (SEQ ID NO: 2) motif, and interacts with TSG101. In some embodiments, the ARRDC1 protein comprises any one of the amino acid sequences set forth in SEQ ID NOs: 15-17. Exemplary, non-limiting ARRDC1 protein sequences are provided herein, and additional, suitable ARRDC1 protein variants according to aspects of this invention are known in the art. It will be appreciated by those of skill in the art that this invention is not limited in this respect. Exemplary ARRDC1 sequences include the following (PSAP (SEQ ID NO: 1) and PPXY (SEQ ID NO: 2) motifs are marked):

```
>gi|22748653|ref|NP_689498.1| arrestin domain-
containing protein 1 [Homo sapiens]
                                     (SEQ ID NO: 15)
MGRVQLFEISLSHGRVVYSPGEPLAGTVRVRLGAPLPFRAIRVTCIGSCG

VSNKANDTAWVVEEGYFNSSLSLADKGSLPAGEHSFPFQFLLPATAPTSF

EGPFGKIVHQVRAAIHTPRFSKDHKCSLVFYILSPLNLNSIPDIEQPNVA

SATKKFSYKLVKTGSVVLTASTDLRGYVVGQALQLHADVENQSGKDTSPV

VASLLQKVSYKAKRWIHDVRTIAEVEGAGVKAWRRAQWHEQILVPALPQS

ALPGCSLIHIDYYLQVSLKAPEATVTLPVFIGNIAVNHAPVSPRPGLGLP

PGAPPLVV PSAP PQEEAEAEAAAGGPHFLDPVFLSTKSHSQRQPLLAT

LSSVPGAPEPCPQDGSPASHPLHPPLCISTGATVPYFAEGSGGPVPTTST

LIL PPEY SWGYPYEAPPSYEQSCGGVEPSLTPES

>gi|244798004|ref|NP_001155957.1| arrestin
domain-containing protein 1 isoform a [Mus
musculus]
                                     (SEQ ID NO: 16)
MGRVQLFEIRLSQGRVVYGPGEPLAGTVHLRLGAPLPFRAIRVTCMGSCG

VSTKANDGAWVVEESYFNSSLSLADKGSLPAGEHNFPFQFLLPATAPTSF

EGPFGKIVHQVRASIDTPRFSKDHKCSLVFYILSPLNLNSIPDIEQPNVA

STTKKFSYKLVKTGNVVLTASTDLRGYVVGQVLRLQADIENQSGKDTSPV

VASLLQKVSYKAKRWIYDVRTIAEVEGTGVKAWRRAQWQEQILVPALPQS

ALPGCSLIHIDYYLQVSMKAPEATVTLPLFVGNIAVNQTPLSPCPGRESS

PGTLSLVV PSAP PQEEAEAVASGPHFSDPVSLSTKSHSQQQPLSAPLG

SVSVTTTEPWVQVGSPARHSLHPPLCISIGATVPYFAEGSAGPVPTTSAL

IL PPEY  SSWGYPYEAPPSYEQSCGAAGTDLGLIPGS

>gi|244798112|ref|NP_848495.2| arrestin domain-
containing protein 1 isoform b [Mus musculus]
                                     (SEQ ID NO: 17)
MGRVQLFEIRLSQGRVVYGPGEPLAGTVHLRLGAPLPFRAIRVTCMGSCG

VSTKANDGAWVVEESYFNSSLSLADKGSLPAGEHNFPFQFLLPATAPTSF

EGPFGKIVHQVRASIDTPRFSKDHKCSLVFYILSPLNLNSIPDIEQPNVA

STTKKFSYKLVKTGNVVLTASTDLRGYVVGQVLRLQADIENQSGKDTSPV

VASLLQVSYKAKRWIYDVRTIAEVEGTGVKAWRRAQWQEQILVPALPQSA

LPGCSLIHIDYYLQVSMKAPEATVTLPLFVGNIAVNQTPLSPCPGRESSP

GTLSLVV PSAP   PQEEAEAVASGPHFSDPVSLSTKSHSQQQPLSAPLG

SVSVTTTEPWVQVGSPARHSLHPPLCISIGATVPYFAEGSAGPVPTTSAL

IL PPEY  SSWGYPYEAPPSYEQSCGAAGTDLGLIPGS
```

TSG101

In certain embodiments, the inventive microvesicles further comprise TSG101. Tumor susceptibility gene 101, also referred to herein as TSG101, is a protein encoded by this gene and belonging to a group of apparently inactive homologs of ubiquitin-conjugating enzymes. The protein contains a coiled-coil domain that interacts with stathmin, a cytosolic phosphoprotein implicated in tumorigenesis. TSG101 is a protein that comprises a UEV domain, and interacts with ARRDC1. The disclosure also contemplates variants of TSG101, such as fragments of TSG101 and/or TSG101 proteins that have a degree of identity (e.g., 60%, 70%, 80%, 85%, 90%, 95%, 98%, or 99% identity) to a TSG101 protein and are capable if interacting with ARRDC1. Accordingly, an TSG101 protein may be a protein that comprises a UEV domain, and interacts with ARRDC. In some embodiments, the TSG101 protein is at least 60%, 65%, 70%, 75%, 80%, 85%, 90%, 95%, 98%, or 99% identical to the amino acid sequence of any one of SEQ ID NOs: 20-22, comprises a UEV domain, and interacts with ARRDC1. In some embodiments, the TSG101 protein has at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, at least 350, at least 360, at least 370, at least 380, or at least 390, identical amino acids of any one of SEQ ID NOs: 20-22, comprises a UEV domain, and interacts with ARRDC1. In some embodiments, the TSG101 protein has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more mutations compared to any one of the amino acid sequences set forth in SEQ ID NOs: 20-22 and comprises a UEV domain. In some embodiments, the ARRDC1 protein comprises any one of the amino acid sequences set forth in SEQ ID NOs: 20-22. Exemplary, non-limiting TSG101 protein sequences are provided herein, and additional, suitable TSG101 protein sequences, isoforms, and variants according to aspects of this invention are known in the art. It will be appreciated by those of skill in the art that this invention is not limited in this respect. Exemplary TSG101 sequences include the following:

```
>gi|5454140|ref|NP_006283.1| tumor susceptibility
gene 101 protein [Homo sapiens]
                                    (SEQ ID NO: 20)
MAVSESQLKKMVSKYKYRDLTVRETVNVITLYKDLKPVLDSYVFNDGSSR

ELMNLTGTIPVPYRGNTYNIPICLWLLDTYPYNPPICFVKPTSSMTIKTG

KHVDANGKIYLPYLHEWKHPQSDLLGLIQVMIVVFGDEPPVFSRPISASY

PPYQATGPPNTSYMPGMPGGISPYPSGYPPNPSGYPGCPYPPGGPYPATT

SSQYPSQPPVTTVGPSRDGTISEDTIRASLISAVSDKLRWRMKEEMDRAQ

AELNALKRTEEDLKKGHQKLEEMVTRLDQEVAEVDKNIELLKKKDEELSS

ALEKMENQSENNDIDEVIIPTAPLYKQILNLYAEENAIEDTIFYLGEALR

RGVIDLDVFLKHVRLLSRKQFQLRALMQKARKTAGLSDLY

>gi|11230780|ref|NP_068684.1| tumor susceptibility
gene 101 protein [Mus musculus]
                                    (SEQ ID NO: 21)
MAVSESQLKKMMSKYKYRDLTVRQTVNVIAMYKDLKPVLDSYVFNDGSSR

ELVNLTGTIPVRYRGNIYNIPICLWLLDTYPYNPPICFVKPTSSMTIKTG

KHVDANGKIYLPYLHDWKHPRSELLELIQIMIVIFGEEPPVFSRPTVSAS

YPPYTATGPPNTSYMPGMPSGISAYPSGYPPNPSGYPGCPYPPAGPYPAT

TSSQYPSQPPVTTVGPSRDGTISEDTIRASLISAVSDKLRWRMKEEMDGA

QAELNALKRTEEDLKKGHQKLEEMVTRLDQEVAEVDKNIELLKKKDEELS

SALEKMENQSENNDIDEVIIPTAPLYKQILNLYAEENAIEDTIFYLGEAL

RRGVIDLDVFLKHVRLLSRKQFQLRALMQKARKTAGLSDLY

>gi|48374087|ref|NP_853659.2| tumor susceptibility
gene 101 protein [Rattus norvegicus]
                                    (SEQ ID NO: 22)
MAVSESQLKKMMSKYKYRDLTVRQTVNVIAMYKDLKPVLDSYVFNDGSSR

ELVNLTGTIPVRYRGNIYNIPICLWLLDTYPYNPPICFVKPTSSMTIKTG

KHVDANGKIYLPYLHDWKHPRSELLELIQIMIVIFGEEPPVFSRPTVSAS

YPPYTAAGPPNTSYLPSMPSGISAYPSGYPPNPSGYPGCPYPPAGPYPAT

TSSQYPSQPPVTTAGPSRDGTISEDTIRASLISAVSDKLRWRMKEEMDGA

QAELNALKRTEEDLKKGHQKLEEMVTRLDQEVAEVDKNIELLKKKDEELS

SALEKMENQSENNDIDEVIIPTAPLYKQILNLYAEENAIEDTIFYLGEAL

RRGVIDLDVFLKHVRLLSRKQFQLRALMQKARKTAGLSDLY
```

The UEV domain in these sequences includes amino acids 1-145 (underlined in the sequences above). The structure of UEV domains is known to those of skill in the art (see, e.g., Owen Pornillos et al., Structure and functional interactions of the Tsg101 UEV domain, EMBO J. 2002 May 15; 21(10): 2397-2406, the entire contents of which are incorporated herein by reference).

Fusion Proteins

RNA Binding Proteins Fused to ARRDC1

In some aspects, microvesicles, e.g., ARMMs, are provided that comprise an ARRDC1 protein, or variant thereof, fused to an RNA binding protein, or variant thereof. In some aspects, fusion proteins are provided that comprise an ARRDC1 protein, or variant thereof, fused to a Tat protein, or variant thereof. In some aspects, expression constructs are provided that encode an ARRDC1 protein, or variant thereof, fused to an RNA binding protein (e.g., Tat), or variant thereof. In some embodiments, the ARRDC1 protein variant is a C-terminal ARRDC1 protein variant. In some embodiments, the ARRDC1 protein variant has a PSAP (SEQ ID NO: 1) motif and at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 contiguous amino acids of the ARRCD1 sequence.

Some aspects of this invention provide ARRDC1 fusion proteins that comprise an ARRDC1 protein, or a variant thereof, and an RNA binding protein, or RNA binding protein variant, associated with the ARRDC1 protein or variant thereof. In some embodiments the RNA binding protein is non-covalently linked to the ARRDC1 protein, or variant thereof. In some embodiments the RNA binding protein is covalently linked to the ARRDC1 protein, or variant thereof. The RNA binding protein, for example, may be covalently linked to the N-terminus, the C-terminus, or within the amino acid sequence of the ARRDC1 protein. In some embodiments, the ARRDC1 variant comprises a PSAP (SEQ ID NO: 1) motif (comprising the amino acid sequence PSAP (SEQ ID NO: 1)). In some embodiments, the ARRDC1 protein variant comprises the PSAP (SEQ ID NO: 1) motif and at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 contiguous amino acids of the ARRCD1 sequence.

In certain embodiments, the RNA binding protein or RNA binding protein variant is fused to the C-terminus of the ARRDC1 protein or protein variant thereof. The RNA binding protein or RNA binding variant may also be fused to the N terminus of the ARRDC1 protein or variant thereof. In some embodiments, the RNA binding protein or RNA binding protein variant may be within the ARRDC1 protein or variant thereof. A schematic representation of a Tat RNA binding protein fused to the C-terminus of ARRDC1 can be seen in FIG. 1A.

In certain embodiments, the RNA binding protein is associated with an ARRDC1 protein, or variant thereof, via a covalent bond. In some embodiments, the RNA binding protein is associated with the ARRDC1 protein, or the ARRDC1 protein variant, via a linker. In some embodiments, the linker is a cleavable linker, for example, the linker may contain a protease recognition site or a disulfide bond. The protease recognition site of the linker may be recognized by a protease expressed in a target cell, resulting in the RNA binding protein fused to the ARRDC1 protein or variant thereof being released into the cytoplasm of the target cell upon uptake of the ARMM. A person skilled in the art would appreciate that any number of linkers may be used to fuse the RNA binding protein or RNA binding protein variant to the ARRDC1 protein, or variant thereof.

The linker may be cleavable or uncleavable. In some embodiments, the linker comprises an amide, ester, ether, carbon-carbon, or disulfide bond, although any covalent bond in the chemical art may be used. In some embodiments, the linker comprises a labile bond, cleavage of which results in separation of the RNA binding protein from the ARRDC1 protein, or variant thereof. In some embodiments, the linker is cleaved under conditions found in the target cell (e.g., a specific pH, a reductive environment, or the presence of a cellular enzyme). In some embodiments, the linker is cleaved by a cellular enzyme. In some embodiments, the cellular enzyme is a cellular protease or a cellular esterase. In some embodiments, the cellular enzyme is a cytoplasmic protease, an endosomal protease, or an endosomal esterase. In some embodiments, the cellular enzyme is specifically expressed in a target cell or cell type, resulting in preferential or specific release of the RNA binding protein in the target cell or cell type. The target sequence of the protease may be engineered into the linker between the RNA binding protein and the ARRDC1 protein, or variant thereof. The target cell may be any cell type found in a subject, including normal and pathologic or diseased cells, and the linker is cleaved by an enzyme or based on a characteristic specific to the target cell, or chemical environment (e.g., a cellular compartment). In some embodiments, the linker comprises an amino acid sequence chosen from the group including, but not limited to, AGVF (SEQ ID NO: 3), GFLG (SEQ ID NO: 4), FK, AL, ALAL (SEQ ID NO: 5), or ALALA (SEQ ID NO: 34). Additional linkers that may be used in accordance with the disclosure include, without limitation, those described in Chen et al., "Fusion Protein Linkers: Property, Design and Functionality" *Adv Drug Deliv Rev.* 2013 Oct. 15; 65(10): 1357-1369; and Choi et al., "Protease-Activated Drug Development" *Theranostics,* 2012; 2(2): 156-178; the entire contents of each of which are incorporated herein by reference in their entirety. Other suitable linkers will be apparent to those of skill in the art and are within the scope of this disclosure.

In some embodiments, the linker comprises a disulfide bond, which may be cleaved by reduction of the disulfide bond, for example, in vivo. In some embodiments, a disulfide bond refers to a functional group having the general structure R—S—S—R', wherein R and R' are alkyl groups. In some embodiments, the linker comprises one or more thiol groups. In some embodiments, the linker comprises one or more cysteine amino acid residues. In some embodiments, the disulfide bond is formed by an oxidation reaction between two cysteine residues to generate a cysteine with a disulfide bond (e.g., —S—S—). In some embodiments, the linker consists of a disulfide bond. Cleavable disulfide linkers are known in the art and have been described previously, for example, in Chen et al., "Design of an in vivo cleavable disulfide linker in recombinant fusion proteins" *Biotechniques.* 2010 July; 49(1): 513-518; the entire contents of which are incorporated herein by reference. However, it should be appreciated that additional cleavable linkers comprising disulfide bonds would be apparent to the skilled artisan and are within the scope of this disclosure. In some embodiments, the disulfide bond is cleaved within a cell (e.g., a target cell). As one example, any of the fusion proteins provided herein comprising a disulfide bond may be produced in a cell where the disulfide bond is not cleaved, for example, in a cell that expresses a sulfhydryl oxidase enzyme (e.g., Erv1p), which may prevent reduction of the disulfide bond. Such enzymes have been described in the art, for example, in Hatahet et al., "Disruption of reducing pathways is not essential for efficient disulfide bond formation in the cytoplasm of *E. coli*" *Microb Cell Fact.* 2010, 9: 67; the entire contents of which are incorporated herein by reference. It should be appreciated that certain cellular compartments are reducing environments (e.g., the cytosol of a cell), where the disulfide bond may be cleaved.

In some embodiments, the linker is a photo-cleavable linker. In some embodiments, the linker is a UV-cleavable moiety, which may be cleaved upon exposure to ultravilot (UV) irradiation. Suitable photo-cleavable linkers, for example, linkers comprising a UV cleavable moiety are known to those of skill in the art. For example, photo-cleavable linkers have been described in Kakiyama et al., "A peptide release system using a photo-cleavable linker in a cell array format for cell-toxicity analysis" *Polymer Journal* (2013) 45, 535-539; Baccile, J. A., et al., "Modular synthesis of photocleavable peptides using click chemistry." *Tetrahedron Letters volume* 53, Issue 15, 11 Apr. 2012, p. 1933-1935; and Olejnik J. et al., "Photocleavable biotin phosphoramidite for 5'-end-labeling, affinity purification and phosphorylation of synthetic oligonucleotides." *Nucleic Acids Res.* 1996 Jan. 15; 24(2):361-6; the entire contents of each are incorporated herein by reference. It should be appreciated, however, that additional photo-cleavable linkers would be apparent to the skilled artisan and are within the scope of this disclosure.

In some embodiments, the RNA binding protein is associated with the ARRDC1 protein, or variant thereof, via a sortase or transpeptidation reaction, and the linker comprises an LPXTG (e.g., for *S. aureus* sortase A), or LPXTA (e.g., for *S. pyogenes* sortase A) motif, where "X" represents any amino acid. A sortase refers to a group of prokaryotic enzymes that modify surface proteins by recognizing and cleaving a carboxyl-terminal sorting signal, for example, a sorting signal comprising the motif LPXTG or LPXTA. It should be appreciated, however, that additional sortase sorting signals would be recognized by the skilled artisan and are within the sope of this disclosure. Methods and reagents for conjugating proteins (e.g., an RNA binding protein and an ARRDC1 protein) using a sortase are known in the art and have been described previously, for example, in Levary, "Protein-Protein Fusion Catalyzed by Sortase A." *PLOS One*, 2011 6(4): e18342; and Theile et al., "Site-specific N-terminal labeling of proteins using sortase-mediated reactions." *Nature Protocols*. (2013) 8, 1800-1807; the entire contents of each are incorporated herein by reference. Accordingly, suitable methods for conjugating proteins as well as RNA binding proteins fused to an ARRDC1 protein, or variant thereof, to be included in an ARMM will be apparent to those of skill in the art based on this disclosure and knowledge in the art.

Any of the linkers, described herein, may be fused to the C-terminus of the ARRDC1 protein, or variant thereof, and the N-terminus of the RNA binding protein, or variant thereof, thereby linking the ARRDC1 protein, or variant thereof, to the RNA binding protein or RNA binding protein variant. In other embodiments, the linker may be fused to the C-terminus of the RNA binding protein, or variant thereof, and the N-terminus of the ARRDC1 protein, or variant thereof.

Any of the fusion proteins or linkers provided herein may comprise one or more additional features. Exemplary features that may be present include, without limitation, target peptides and protein tags. In some embodiments, any of the fusion proteins or linkers provided herein comprise one or more target peptides. In some embodiments, the fusion protein or linker comprises 1, 2, 3, 4, 5, 6, 7, 8, 9, or 10 target peptides. A fusion protein or linker comprising more than one target peptide may comprise the same target peptide, or different target peptides. As used herein, a "target peptide" refers to a peptide sequence, typically from 3-70 amino acids in length, that directs the transport of a protein to a specific region in the cell, including the nucleus, mitochondria, endoplasmic reticulum, peroxisome, and plasma membrane, however additional target peptides that target proteins to other regions of the cell would be apparent to the skilled artisan and are within the scope of this disclosure. In some embodiments, the target peptide is a peptide that directs a protein (e.g., a RNA binding protein bound to a binding RNA) to the nucleus. In some embodiments, the target peptide is a nuclear localization sequence. In some embodiments, the target peptide comprises the amino acid sequence PPKKKRKV (SEQ ID NO: 109). In some embodiments, the target peptide is a peptide that directs the protein to the secretory pathway. In some embodiments, the target peptide is a peptide that directs a protein (e.g., a RNA binding protein bound to a binding RNA) to the plasma membrane or the endoplasmic reticulum. In some embodiments, the target peptide that directs a protein to the plasma membrane or the endoplasmic reticulum is fused to the N-terminus of any of the fusion proteins provided herein. In some embodiments, the target peptide comprises the amino acid sequence MMSFVSLLLVGILFWATEAEQLTKCEVFQ (SEQ ID NO: 110). In some embodiments, the target peptide is a peptide that directs a protein to be retained at the endoplasmic reticulum. In some embodiments, the target peptide that directs a protein to be retained at the endoplasmic reticulum is fused to the C-terminus of any of the fusion proteins provided herein. In some embodiments, the target peptide comprises the amino acid sequence KDEL (SEQ ID NO: 111). In some embodiments, the target peptide is a peptide that directs a protein to the mitochondrial matrix. In some embodiments, the target peptide that directs a protein to the mitochondrial matrix is fused to the N-terminus of any of the fusion proteins provided herein. In some embodiments, the target peptide comprises the amino acid sequence MLSLRQSIRFFLPATRTLCSSRYLL(SEQ ID NO: 112). In some embodiments, the target peptide is a peptide that directs a protein to a peroxisome. In some embodiments, the target peptide is a PTS1 signal. In some embodiments, the PTS1 signal comprises the amino acid sequence SKL. In some embodiments, the target peptide is a PTS2 signal. In some embodiments, the PTS2 signal comprises the amino acid sequence RLXXXXXHL (SEQ ID NO: 113), wherein X is any amino acid. It should be appreciated, however, that the target peptides provided herein are exemplary and additional target peptides are also within the scope of this disclosure.

In some embodiments, any of the fusion proteins or linkers provided herein comprise one or more nuclear localization sequence (NLS). As used herein, a nuclear localization sequence refers to an amino acid sequence that promotes locatlization of a protein, for example, an RNA binding protein bound to a binding RNA having an NLS, into the nucleus of the cell (e.g., via nuclear transport). Typically, an NLS comprises one or more short amino acid sequences of positively charged lysines or arginines exposed on the protein surface. Nuclear localization sequences are known in the art and would be apparent to those skilled artisan. For example, nuclear localization sequences have been described in Kosugi et al., "Six Classes of Nuclear Localization Signals Specific to Different Binding Grooves of Importin a" *J. Biol. Chem. Jan.* 2, 2008, 284 p. 4'78-85; Kalderon et al., "A short amino acid sequence able to specify nuclear location" *Cell* (1984) 39 (3 Pt 2): 499-509; Dingwall et al., "The nucleoplasmin nuclear location sequence is larger and more complex than that of SV-40 large T antigen". *J Cell Biol.* (1988) 107 (3): 841-9; Makkerh, et al., "Comparative mutagenesis of nuclear localization signals reveals the importance of neutral and acidic amino acids". *Curr Biol.* (1996) 6 (8): 1025-7; and Ray et al., "Quantitative tracking of protein trafficking to the nucleus using cytosolic protein delivery by nanoparticle-stabilized nanocapsules". *Bioconjug. Chem.* (2015) 26 (6): 1004-7; the entire contents of each of which are incorporated herein by reference. Additional nuclear localization sequences are described, for example, in Plank et al., international PCT application, PCT/EP2000/011690, the entire contents of which are incorporated herein by reference. In some embodiments, a NLS comprises the amino acid sequence PKKKRKV (SEQ ID NO: 114) or MDSLLMNRRKFLYQFKNVRWAKGRRETYLC (SEQ ID NO: 115).

In some embodiments, the RNA binding protein is fused to at least one NLS. In some embodiments, one or more nuclear localization sequences (NLSs) are fused to the N-terminus of an RNA binding protein. In some embodiments, one or more NLSs are fused to the C-terminus of an RNA binding protein. In some embodiments, an RNA binding protein is fused to at least one, at least two, at least three, at least four, at least five, at least six, at least seven, at least eight, at least nine, at least ten, or more NLSs. It should be appreciated that one or more NLSs may be fused to an RNA binding protein to allow localization of the RNA binding protein into the nucleus of a target cell. In some embodiments, the RNA binding protein fused to at least one NLS is associated with ARRDC1, or an ARRDC1 protein variant.

In some embodiments, any of the fusion proteins or linkers provided herein comprise one or more protein tags, which may be useful for solubilization, purification, or detection of the fusion proteins. In some embodiments, the fusion protein or linker comprises 1, 2, 3, 4, 5, 6, 7, 8, 9, or 10 protein tags. Suitable protein tags are provided herein, and include, without limitation, biotin carboxylase carrier protein (BCCP) tags, myc-tags, calmodulin-tags, FLAG-tags, hemagglutinin (HA)-tags, polyhistidine tags, also referred to as histidine tags or His-tags, maltose binding protein (MBP)-tags, nus-tags, glutathione-S-transferase (GST)-tags, green fluorescent protein (GFP)-tags, thioredoxin-tags, S-tags, Softags (e.g., Softag 1, Softag 3), streptags, biotin ligase tags, FlAsH tags, V5 tags, and SBP-tags. Additional suitable protein tags will be apparent to those of skill in the art and are within the scope of this disclosure.

WW Domain Containing RNA Binding Proteins

Aspects of the disclosure relate to ARMMs comprising an RNA binding protein associated with at least one WW domain (e.g., WW:Tat). In some aspects, fusion proteins are provided that comprise an RNA binding protein with at least one WW domain. In some aspects, expression constructs are provided that encode an RNA binding protein associated with at least one WW domain. The WW domain of a cargo protein may associate with the PPXY (SEQ ID NO: 2) motif of the ARRDC1 protein, or variant thereof, to facilitate association with or inclusion of the RNA binding protein into an ARMM. A schematic representation of a Tat RNA binding protein fused to a WW domain that associates with the PPXY (SEQ ID NO: 2) motif of ARRDC1 can be seen in FIG. 1B. In some embodiments, the RNA binding protein is fused to at least one, at least two, at least three, at least four, at least five, at least six, at least seven, at least eight, at least nine, at least ten, or more WW domains. The WW domain may be derived from a WW domain of ubiquitin ligase WWP1, WWP2, Nedd4-1, Nedd4-2, Smurf1, Smurf2, ITCH, NEDL1, or NEDL2 (FIG. 3). For example, the WW domain may comprise a WW domain or WW domain variant from the amino acid sequence set forth in (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14). In certain embodiments, the RNA binding proteins may comprise two WW domains, or WW domain variants, from the human ITCH protein having the amino acid sequence:

(SEQ ID NO: 18)
PLPPGWEQRVDQHGRVYYVDHVEKRTTWDRPEPLPPGWERRVDNMGRIYY

VDHFTRTTTWQRPTL.

In other embodiments, RNA binding proteins may comprise four WW domains, or WW domain variants, from the human ITCH protein having the amino acid sequence:

(SEQ ID NO: 19)
PLPPGWEQRVDQHGRVYYVDHVEKRTTWDRPEPLPPGWERRVDNMGRIYY

VDHFTRTTTWQRPTLESVRNYEQWQLQRSQLQGAMQQFNQRFIYGNQDLF

ATSQSKEFDPLGPLPPGWEKRTDSNGRVYFVNHNTRITQWEDPRSQGQLN

EKPLPEGWEMRFTVDGIPYFVDHNRRTTTYIDPRT.

The RNA binding proteins, described herein, that are fused to at least one WW domain or WW domain variant are non-naturally occurring, that is, they do not exist in nature.

In some embodiments, one or more WW domains may be fused to the N-terminus of an RNA binding protein. In other embodiments, one or more WW domains may be fused to the C-terminus of an RNA binding protein. In yet other embodiments, one or more WW domains may be inserted into an RNA binding protein. It should be appreciated that the WW domains may be configured in any number of ways to maintain function of the RNA binding protein, which can be tested by methods known to one of ordinary skill in the art. In some embodiments, at least one WW domain is fused to the N-terminus of an RNA binding protein. In some embodiments, 1, 2, 3, 4, 5, 6, 7, 8, 9, or 10 WW domains are fused to the N-terminus of an RNA binding protein. In some embodiments, at least one WW domain is fused to the C-terminus of an RNA binding protein. In some embodiments, 1, 2, 3, 4, 5, 6, 7, 8, 9, or 10 WW domains are fused to the C-terminus of an RNA binding protein.

The RNA binding protein of the inventive microvesicles may be a protein comprising at least one WW domain. For example, the RNA binding protein may be a WW domain containing protein or a protein fused to at least one WW domain. In some embodiments, the RNA binding protein may be a Tat protein or Tat protein variant fused to at least one WW domain.

RNA Binding Proteins

Some aspects of the disclosure relate to proteins that bind to RNA. In some embodiments, the RNA binding protein is a naturally-occurring protein, or non-naturally-occurring variant thereof, or a non-naturally occurring protein that binds to an RNA, for example, an RNA with a specific sequence or structure.

In certain embodiments, the RNA binding protein is a trans-activator of transcription (Tat) protein that specifically binds a trans-activating response element (TAR element). An exemplary Tat protein comprises the amino acid sequence as set forth in SEQ ID NO: 65 (Table 1). Exemplary amino acid sequences of Tat proteins, as well as Tat protein fragments that bind TAR elements, are shown in Table 1. In some embodiments, the RNA binding protein is at least 60%, 65%, 70%, 75%, 80%, 85%, 90%, 95%, 98%, or 99% identical to the amino acid sequence of any one of SEQ ID NOs: 65-84, and binds a TAR element. In some embodiments, the RNA binding protein has at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, or at least 130 identical contiguous amino acids of any one of SEQ ID NOs: 65-84, and binds a TAR element. In some embodiments, the RNA binding protein has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more mutations compared to any one of the amino acid sequences set forth in SEQ ID NOs: 65-84, and binds a TAR element. In some embodiments, the RNA binding protein comprises any one of the amino acid sequences set forth in SEQ ID NOs: 65-84. In some embodiments, the Tat protein comprises an amino acid sequence as set forth in any one of SEQ ID NOs: 65-84. The RNA binding protein may also be a variant of a Tat protein that is capable of associating with a TAR element. Tat proteins, as well as variants of Tat proteins that bind to a TAR element, are known in the art and have been described previously, for example, in Kamine et al., "Mapping of HIV-1 Tat Protein Sequences Required for Binding to Tar RNA", *Virology* 182, 570-577 (1991); and Patel, "Adaptive recognition in RNA complexes with peptides and protein modules" *Curr Opin Struct Biol.* 1999 February; 9(1):74-87; the entire contents of each of which are incorporated herein by reference. In some embodiments, the Tat protein is an HIV-1 Tat protein, or variant thereof. In some embodiments, the Tat protein is bovine immunodeficiency virus (BIV) Tat protein, or variant thereof.

A Tat protein is a nuclear transcriptional activator of viral gene expression that is essential for viral transcription from the LTR promoter and replication; it acts as a sequence-specific molecular adapter, directing components of the cellular transcription machinery to the viral RNA to promote processive transcription elongation by the RNA polymerase II (RNA pol II) complex, thereby increasing the level of full-length transcripts. Tat binds to a hairpin structure at the 5'-end of all nascent viral mRNAs referred to as the trans-activation responsive RNA element (TAR RNA) in a CCNT1-independent mode.

The Tat protein consists of several domains, one is a short lysine and arginine rich region important for nuclear localization. The nine amino acid basic region of HIV-1 Tat is found at positions 49-57 of SEQ ID NO: 65, and is capable of binding a TAR element. In some embodiments, the Tat sequence comprises the nine amino acid basic region of Tat (SEQ ID NO: 73). In some embodiments the RNA binding protein comprises any one of the amino acid sequences as set forth in SEQ ID NOs: 65-67, 69, 70, or 73-84. In some embodiments, the Tat proteins are fusion proteins.

element (RRE). Rev proteins are known in the art and are known to the skilled artisan. For example, Rev proteins have been described in Fernandes et al., "The HIV-1 Rev response element: An RNA scaffold that directs the cooperative assembly of a homo-oligomeric ribonucleoprotein complex" *RNA Biology* 9:1, 6-11; January 2012; Cochrane et al., "The human immunodeficiency virus Rev protein is a nuclear phosphoprotein" *Virology* 171 (1):264-266, 1989; Grate et al., "Role REVersal: understanding how RRE RNA binds its peptide ligand" Structure. 1997 Jan. 15; 5(1):7-11; and Patel, "Adaptive recognition in RNA complexes with peptides and protein modules" *Curr Opin Struct Biol.* 1999 February; 9(1):74-87; the entire contents of each of which are incorporated herein by reference in their entirety. An exemplary Rev protein comprises the amino acid sequence as set forth in SEQ ID NOs: 93-95 (Table 3). In some embodiments, the RNA binding protein is at least 60%, 65%, 70%, 75%, 80%, 85%, 90%, 95%, 98%, or 99% identical to the amino acid sequence of any one of SEQ ID NOs: 93-95, and binds a Rev response element. In some embodiments, the RNA binding protein has at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, or at least 115 identical contiguous amino acids of any one of SEQ ID NOs: 93-95, and binds a Rev response element. In some embodiments, the RNA binding protein has 1, 2, 3, 4, 5, 6, 7, 8, 9, 10, 11, 12, 13, 14, 15, 16, 17, 18,

TABLE 1

Tat Sequences

| Tat (Residue NOs) | Sequence | SEQ ID NO |
|---|---|---|
| HIV-1 Tat (1-101) | MEPVDPRLEPWKHPGSQPRT PCTTCYCKKC CFHCQVCFTT KALGISYGRK KRRQRRRPPQ GSQTHQVSLS KQPSSQPRGD QTGPKESKKK VERETEADPKP | 65 |
| HIV-1 Tat (1-86) | MEPVDPRLEP WKHPGSQPRT PCTTCYCKKC CFHCQVCFTT KALGISYGRK KRRQRRRPPQ GSQTHQVSLS KQPSSQPRGD QTGPKE | 66 |
| HIV-1 Tat (37-72) | CFTT KALGISYGRK KRRQRRRPPQ GSQTHQVSLS KQ | 67 |
| HIV-1 Tat (1-45) | MEPVDPRLEP WKHPGSQPRT PCTTCYCKKC CFHCQVCFTT KALGI | 68 |
| HIV-1 Tat (49-86) | RK KRRQRRRPPQ GSQTHQVSLS KQPSSQPRGD QTGPKE | 69 |
| HIV-1 Tat (52-86) | RRQRRRPPQ GSQTHQVSLS KQPSSQPRGD QTGPKE | 70 |
| HIV-1 Tat (55-86) | RRRPPQ GSQTHQVSLS KQPSSQPRGD QTGPKE | 71 |
| HIV-1 Tat (58-86) | PPQ GSQTHQVSLS KQPSSQPRGD QTGPKE | 72 |
| HIV-1 Tat (49-57) | RK KRRQRRR | 73 |
| HIV-1 Tat (49-59) | RK KRRQRRRPP | 74 |
| HIV-1 Tat (49-61) | RK KRRQRRRPPQ G | 75 |
| HIV-1 Tat (49-63) | RK KRRQRRRPPQ GSQ | 76 |
| HIV-1 Tat (49-65) | RK KRRQRRRPPQ GSQTH | 77 |
| HIV-1 Tat (37-57) | CFTT KALGISYGRK KRRQRRR | 78 |
| HIV-1 Tat (38-62) | CFTT KALGISYGRK KRRQRRRPPQ GSQ | 79 |
| HIV-1 Tat (47-58) | GRRK KRRQRRRP | 80 |
| HIV-1 Tat (46-65) | RK KRRQRRRPPQ GSQTH | 81 |
| HIV-2 Tat (1-130) | METPLKAPEG SLGSYNEPSS CTSEQDAAAQ GLVSPGDEIL YQLYQPLEAC DNKCYCKKCC YHCQMCFLNK GLGIWYERKG RRRRTPKKTK AHSSSASDKS ISTRTGNSQP EKKQKKTLET ALETIGGPGR | 82 |
| BIV Tat | MPGPWVAMIM LPQPKESFGG KPIGWLFWNT CKGPRRDCPH CCCPICSWHC QLCFLQKNLG INYGSGPRRR GTRGKGRRIR RTASGGDQRR EADSQRSFTN MDQ | 83 |
| BIV Tat | SGPRPRGTRGKGRRIRR | 84 |

In some embodiments, the RNA binding protein is a regulator of virion expression (Rev) protein (e.g., Rev from HIV-1), or variant thereof, that binds to a Rev response 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more mutations compared to any one of the amino acid sequences set forth in SEQ ID NOs: 93-95, and binds a Rev response element. In some embodiments, the RNA binding protein comprises any one of the amino acid sequences set forth in SEQ ID NOs: 93-95. In some embodiments, the RNA binding protein comprises a variant of any one of the amino acid sequences as set forth in SEQ ID NOs: 93-95 that are capable of binding an RRE. Such variants would be apparent to the skilled artisan based on this disclosure and knowledge in the art and may be tested (e.g. for binding to an RRE) using routine methods known in the art.

In some embodiments, the RNA binding protein is a coat protein of an MS2 bacteriophage that specifically binds to an MS2 RNA. MS2 bacteriophage coat proteins that specifically bind MS2 RNAs are known in the art. For example MS2 phage coat proteins have been described in Parrott et al., "RNA aptamers for the MS2 bacteriophage coat protein and the wild-type RNA operator have similar solution behavior" Nucl. Acids Res. 28(2):489-497 (2000); Keryer-Bibens et al., "Tethering of proteins to RNAs by bacteriophage proteins" Biol. Cell. 100(2): 125-38 (2008); and Patel, "Adaptive recognition in RNA complexes with peptides and protein modules" Curr Opin Struct Biol. 1999 February; 9(1):74-87; the entire contents of each are hereby incorporated by reference in their entirety. An exemplary MS2 phage coat protein comprises the amino acid sequence as set forth in SEQ ID NO: 99 (Table 4). In some embodiments, the RNA binding protein is at least 60%, 65%, 70%, 75%, 80%, 85%, 90%, 95%, 98%, or 99% identical to the amino acid sequence of SEQ ID NO: 99, and binds an MS2 RNA. In some embodiments, the RNA binding protein has at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, or at least 115 identical contiguous amino acids of SEQ ID NO: 99, and binds an MS2 RNA. In some embodiments, the RNA binding protein has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more mutations compared to SEQ ID NO: 99, and binds an MS2 RNA. In some embodiments, the RNA binding protein comprises the amino acid sequence set forth in SEQ ID NO: 99. In some embodiments, the RNA binding protein comprises a fragment or variant of SEQ ID NO: 99 that is capable of binding to an MS2 RNA. Methods for testing whether variants or fragments of MS2 phage coat proteins bind to MS2 RNAs (e.g., SEQ ID NO: 99) can be performed using routine experimentation and would be apparent to the skilled artisan.

In some embodiments, the RNA binding protein is a P22 N protein (e.g., P22 N from bacteriophage), or variant thereof, that binds to a P22 boxB RNA. P22 N proteins are known in the art and would be apparent to the skilled artisan. For example, P22 N proteins have been described in Cal et al., "Solution structure of P22 transcriptional antitermination N peptide-boxB RNA complex" Nat Struct Biol. 1998 March; 5(3):203-12; and Patel, "Adaptive recognition in RNA complexes with peptides and protein modules" Curr Opin Struct Biol. 1999 February; 9(1):74-87; the entire contents of each are incorporated by reference herein. An exemplary P22 N that specifically binds to a protein P22 boxB RNA comprises the amino acid sequence NAKTRRHERRRKLAIERDTI (SEQ ID NO: 100).

In some embodiments, the RNA binding protein is a λ N protein (e.g., λ N from bacteriophage), or variant thereof, that binds to a λ boxB RNA. λ N proteins are known in the art and would be apparent to the skilled artisan. For example, λ N proteins have been described in Keryer-Bibens et al., "Tethering of proteins to RNAs by bacteriophage proteins" Biol Cell. 2008 February; 100(2):125-38; Legault et al., "NMR structure of the bacteriophage lambda N peptide/boxB RNA complex: recognition of a GNRA fold by an arginine-rich motif" Cell. 1998 Apr. 17; 93(2):289-99; and Patel, "Adaptive recognition in RNA complexes with peptides and protein modules" Curr Opin Struct Biol. 1999 February; 9(1):74-87; the entire contents of each are incorporated by reference herein. An exemplary λ N protein that specifically binds to a λ boxB comprises the amino acid sequence GSMDAQTRRRERRAEKQAQWKAAN (SEQ ID NO: 101).

In some embodiments, the RNA binding protein is a φ21 N protein (e.g., φ21 N from bacteriophage), or variant thereof, that binds to a φ21 boxB RNA. φ21 N proteins are known in the art and would be apparent to the skilled artisan. For example, φ21 proteins have been described in Cilley et al. "Structural mimicry in the phage φ21 N peptide-boxB RNA complex." RNA. 2003; 9(6):663-676; and Patel, "Adaptive recognition in RNA complexes with peptides and protein modules" Curr Opin Struct Biol. 1999 February; 9(1):74-87; the entire contents of each are incorporated by reference herein. An exemplary φ21 N protein that specifically binds to a φ21 boxB RNA comprises amino acid sequence GTAKSRYKARRAELIAERR(SEQ ID NO: 102). The N peptide binds as an α-helix and interacts predominately with the major groove side of the 5' half of the boxB RNA stem-loop. This binding interface is defined by surface complementarity of polar and nonpolar interactions. The N peptide complexed with the exposed face of the φ21 boxB loop is similar to the GNRA tetraloop-like folds of the related λ and P22 bacteriophage N peptide-boxB RNA complexes.

In some embodiments, the RNA binding protein is a HIV-1 nucleocapsid (e.g., nucleocapsid from HIV-1), or variant thereof, that binds to a SL3 ψ RNA. HIV-1 nucleocapsid proteins are known in the art and would be apparent to the skilled artisan. For example, HIV-1 nucleocapsid proteins have been described in Patel, "Adaptive recognition in RNA complexes with peptides and protein modules" Curr Opin Struct Biol. 1999 February; 9(1):74-87; the entire contents of which is incorporated by reference herein. An exemplary HIV-1 nucleocapsid that specifically binds to a SL3 ψ RNA comprises amino acid sequence (SEQ ID NO: 103)
MQKGNFRNQRKTVKCFNCGKEGHIAKNCRAPRKKGCWKCGKEGHQMKDCT
ERQAN.

Binding RNAs

Some aspects of the disclosure relate to RNA molecules that bind proteins. In some embodiments, the binding RNA is a naturally occurring RNA, or non-naturally occurring variant thereof, or a non-naturally occurring RNA, that binds to a protein having a specific amino acid sequence or structure.

In certain embodiments, the binding RNA is a trans-activating response element (TAR element), which is an RNA stem-loop structure that is found at the 5' ends of nascent human immunodeficiency virus-1 (HIV-1) transcripts and specifically bind to a trans-activator of transcription (Tat) protein. In some embodiments, the TAR element is a bovine immunodeficiency virus (BIV) TAR. An exemplary TAR element comprises the nucleic acid sequence as set forth in SEQ ID NO: 84. Further exemplary TAR sequences can be found in Table 2; however, these sequences are not meant to be limiting and additional TAR element sequences that bind to a Tat protein, or variant thereof, are also within the scope of this disclosure. The binding RNA may also be a variant of a TAR element that is capable of associating with the RNA binding protein, trans-activator of transcription (Tat protein), which is a regulatory protein that is involved in transcription of the viral genome. Variants of TAR elements that are capable of associating with Tat proteins would be apparent to the skilled artisan based on this disclosure and knowledge in the art, and are within the scope of this disclosure. Further, the association between a TAR variant and a Tat protein, or Tat protein variant, may be tested using routine methods. TAR elements and variants of TAR elements that bind to Tat proteins are known in the art and have been described previously, for example in Kamine et al., "Mapping of HIV-1 Tat Protein Sequences Required for Binding to Tar RNA" *Virology* 182, 570-577 (1991); and Patel, "Adaptive recognition in RNA complexes with peptides and protein modules" *Curr Opin Struct Biol.* 1999 February; 9(1):74-87; the entire contents of each are incorporated by reference herein. In some embodiments, the binding RNA comprises the nucleic acid sequence as set forth in SEQ ID NOs: 85-90. In some embodiments, the binding RNA comprises a variant of any of the nucleic acid sequences set forth in SEQ ID NOs: 85-90 that are capable of binding to a Tat protein or variant thereof.

Without wishing to be bound by any particular theory, a TAR element is capable of forming a stable stem-loop structure (Muesing et al., 1987) in the native viral RNA. On the stem of TAR, a three nucleotide bulge, has been demonstrated to play a role in high-affinity binding of the Tat protein to the TAR element (Roy et al., 1990; Cordingley et al., 1990; Dingwall et al., 1989; Weeks et al., 1990). In the TAR element, the integrity of the stem and the initial U22 of the bulge may contribute to Tat protein binding (Roy et al., 1990b). Other sequences that may not affect the binding of the Tat protein to the TAR site play a role in trans-activation of transcription in vivo. One such region is the sequence at the loop, which is required for the binding of cellular factors that may interact with the Tat protein to mediate transactivation (Gatignol et al., 1989; Gaynor et al., 1989; Marciniak et al., 1990a; Gatignol et al., 1991).

In some embodiments, the binding RNA is a Rev response element (RRE), or variant thereof, that binds to a Rev protein (e.g., Rev from HIV-1). Rev response elements are known in the art and would be apparent to the skilled artisan for use in the present invention. For example, Rev response elements have been described in Fernandes et al., "The HIV-1 Rev response element: An RNA scaffold that directs the cooperative assembly of a homo-oligomeric ribonucleoprotein complex." *RNA Biology* 9:1, 6-11, January 2012; Cook et al., "Characterization of HIV-1 REV protein: binding stoichiometry and minimal RNA substrate." *Nucleic Acids Res.* April 11; 19(7):1577-1583, 1991; Grate et al., "Role REVersal: understanding how RRE RNA binds its peptide ligand" *Structure.* 1997 Jan. 15; 5(1):7-11; and Patel, "Adaptive recognition in RNA complexes with peptides and protein modules" *Curr Opin Struct Biol.* 1999 February; 9(1):74-87; the entire contents of each are incorporated herein by reference. Any of the RRE nucleic acid sequences or any of the fragments of RRE nucleic acid sequences described in the above references may be used as binding RNAs in accordance with this disclosure. Exemplary RRE nucleic acid sequences that bind Rev include, without limitation, those nucleic acid sequences set forth in SEQ ID NOs: 91 and 92 (Table 3).

In some embodiments, the Rev peptide may adopt a particular structure and several amino acids, rather than a single arginine, may participate in sequence-specific RNA interactions. Without wishing to be bound by any particular theory, Rev recognition of the RRE, like Tat recognition of TAR, is due to direct binding. Binding can be tight (Kd=1-3 nM) and highly specific for the RRE. As the concentration of Rev increases, progressively larger complexes with RRE RNA are formed, whereas Tat forms one-to-one complexes with TAR RNA.

Generally, a Rev protein may bind initially to a high affinity site and subsequently additional Rev molecules occupy lower affinity sites. RNAs that bind Rev have been described in Heaphy et al., "HIV-1 regulator of virion expression (Rev) protein binds to an RNA stem-loop structure located within the Rev-response element region" *Cell,* 1990. 60, 685-693; the entire contents of which is incorporated by reference herein.

TABLE 2

TAR Sequences

| TAR | Sequence | SEQ ID NO |
|---|---|---|
| HIV-1 TAR RNA + 1-59 | gggucucucugguuagaccagaucugagccugggagcucucuggcuaa cuagggaacccacug | 85 |
| Δ TAR | gggucucucugguuagaccagaucugagccugggcucuggcuaacuag ggaacccacug | 86 |
| HIV-1TAR (shown in Figure 2) | gggucucucugguuagaccagaucugagccugggagcucucuggcuaa cuagggaacc | 87 |
| HIV-1 TAR | agaucugagccugggagcucucu | 88 |
| Hybrid TAR | gcucguugagcucugggaagcuccgagc | 89 |
| BIV TAR | ucguguagcucauuagcuccga | 90 |

TABLE 3

RRE/Rev Sequences

| | Sequence | SEQ ID NO |
|---|---|---|
| HIV-1 RRE | ggucugggcgcagcgcaagcugacgguacaggcc | 91 |
| HIV-1 RRE aptamer | ggcuggacucguacuucgguacuggagaaacagcc | 92 |
| HIV-1 Rev | MAGRSGDSDEELIRTVRLIKLLYQSNPPPNPEGTRQ ARRNRRRRWRERQRQIHSISERILGTYLGRSAEPVP LQLPPLERLTLDCNEDCGTSGTQGVGSPQILVESPT VLESGTKE | 93 |
| HIV-1 Rev peptide | TRQARRNRRRRWRERQR | 94 |
| Evolved HIV-1 RRE-binding peptide | RDRRRRGSRPSGAERRRRRAAAA | 95 |

In some embodiments, the binding RNA is an MS2 RNA that specifically binds to a MS2 phage coat protein. Typically, the coat protein of the RNA bacteriophage MS2 binds a specific stem-loop structure in viral RNA (e.g., MS2 RNA) to accomplish encapsidation of the genome and translational repression of replicase synthesis. RNAs that specifically bind MS2 phage coat proteins are known in the art and would be apparent the skilled artisan. For example RNAs that bind MS2 phage coat proteins have been described in Parrott et al., "RNA aptamers for the MS2 bacteriophage coat protein and the wild-type RNA operator have similar solution behavior." *Nucl. Acids Res.* 28(2): 489-497 (2000); Witherell et al., "Specific interaction between RNA phage coat proteins and RNA." *Prog Nucleic Acid Res Mol Biol.* 1991; 40:185-220; Stockley et al., "Probing sequence-specific RNA recognition by the bacteriophage MS2 coat protein." *Nucleic Acids Res.* 1995 Jul. 11; 23(13):2512-8; Keryer-Bibens C., et al., "Tethering of proteins to RNAs by bacteriophage proteins." *Biol. Cell.* 100(2): 125-38 (2008); and Patel. "Adaptive recognition in RNA complexes with peptides and protein modules." *Curr Opin Struct Biol.* 1999 February; 9(1):74-87; the entire contents of each are hereby incorporated by reference in their entirety. In some embodiments, an exemplary MS2 RNA that specifically binds to a MS2 phage coat protein comprises a nucleic acid sequence as set forth in any one of SEQ ID NOs: 96-98 (Table 4). In some embodiments, the binding RNA comprises the nucleic acid sequence of any one of SEQ ID NOs: 96, 97, or 98.

TABLE 4

MS2 Sequences

| MS2 | Sequence | SEQ ID NO |
|---|---|---|
| Bacteriophage MS2 RNA | acaugaggauuacccaugu | 96 |
| MS2 RNA | ccggaggaucaccacggg | 97 |
| MS2 RNA | ccacagucacuggg | 98 |
| Bacteriophage MS2 Coat Protein | ASNFTQFVLVDNGGTGDVTVAPSNFANGVAEWIS SNSRSQAYKVTCSVRQSSAQNRKYTIKVEVPKVAT QTVGGVELPVAAWRSYLNMELTIPIFATNSDCELI VKAMQ GLLKDGNPIP SAIAANSGIY | 99 |

In some embodiments, the binding RNA is an RNA that specifically binds to a P22 N protein (e.g., P22 N from bacteriophage), or variant thereof. P22 N proteins are known in the art and would be apparent to the skilled artisan. For example, P22 N proteins have been described in Cal et al., "Solution structure of P22 transcriptional antitermination N peptide-boxB RNA complex" *Nat Struct Biol.* 1998 March; 5(3):203-12; Weiss, "RNA-mediated signaling in transcrip-tion" *Nat Struct Biol.* 1998 May; 5(5):329-33; and Patel, "Adaptive recognition in RNA complexes with peptides and protein modules" *Curr Opin Struct Biol.* 1999 February; 9(1):74-87; the entire contents of each are incorporated by reference herein. An exemplary P22 boxB RNA that specifically binds to a P22 N protein comprises a nucleic acid sequence as set forth in gcgcugacaaagcgc (SEQ ID NO: 104).

In some embodiments, the binding RNA is an RNA that specifically binds to a λ N protein (e.g., λ N from bacteriophage), or variant thereof. λ N proteins are known in the art and would be apparent to the skilled artisan. For example, λ N proteins have been described in Keryer-Bibens et al., "Tethering of proteins to RNAs by bacteriophage proteins." *Biol Cell.* 2008 February; 100(2):125-38; Weiss. "RNA-mediated signaling in transcription." *Nat Struct Biol.* 1998 May; 5(5):329-33; Legault et al., "NMR structure of the bacteriophage lambda N peptide/boxB RNA complex: recognition of a GNRA fold by an arginine-rich motif." *Cell.* 1998 Apr. 17; 93(2):289-99; and Patel, "Adaptive recognition in RNA complexes with peptides and protein modules." *Curr Opin Struct Biol.* 1999 February; 9(1):74-87; the entire contents of each are incorporated by reference herein. An exemplary λ boxB RNA that specifically binds to a λ N protein comprises a nucleic acid sequence as set forth in gggcccugaagaagggccc (SEQ ID NO: 105).

In some embodiments, the binding RNA is an RNA that specifically binds to a φ21 N protein (e.g., φ21 N from bacteriophage), or variant thereof. φ21 N proteins are known in the art and would be apparent to the skilled artisan. For example, φ21 proteins have been described in Cilley et al. "Structural mimicry in the phage φ21 N peptide-boxB RNA complex." *RNA.* 2003; 9(6):663-676; and Patel, "Adaptive recognition in RNA complexes with peptides and protein modules." *Curr Opin Struct Biol.* 1999 February; 9(1):74-87; the entire contents of each are incorporated by reference herein. An exemplary φ21 boxB RNA that specifically binds to a φ21 N protein comprises a nucleic acid sequence as set forth in ucucaaccuaaccguugaga (SEQ ID NO: 106).

In some embodiments, the binding RNA is an RNA that specifically binds to an HIV-1 nucleocapsid protein (e.g., nucleocapsid from HIV-1) or variant thereof. HIV-1 nucleocapsid proteins are known in the art and would be apparent to the skilled artisan. For example, HIV-1 nucleocapsid proteins have been described in Patel, "Adaptive recognition in RNA complexes with peptides and protein modules." *Curr Opin Struct Biol.* 1999 February; 9(1):74-87; the entire contents of which is incorporated by reference herein. An exemplary SL3 ψ RNA that specifically binds to a HIV-1 nucleocapsid comprises a nucleic acid sequence as set forth in ggacuagcggaggcuagucc (SEQ ID NO: 107).

It should be appreciated that the binding RNAs of the present disclosure need not be limited to naturally-occurring RNAs or non-naturally-occurring variants thereof, that have recognized protein binding partners. In some embodiments, the binding RNA may also be a synthetically produced RNA, for example an RNA that is designed to specifically bind to a protein (e.g., an RNA binding protein). In some embodiments, the binding RNA is designed to specifically bind to any protein of interest, for example ARRDC1. In some embodiments, the binding RNA is an RNA produced by the systematic evolution of ligands by exponential enrichment (SELEX). SELEX methodology would be apparent to the skilled artisan and has been described previously, for example in U.S. Pat. Nos. 5,270,163; 5,817,785; 5,595,887; 5,496,938; 5,475,096; 5,861,254; 5,958,691; 5,962,219; 6,013,443; 6,030,776; 6,083,696; 6,110,900; 6,127,119; and 6,147,204; U.S. Appln 20030175703 and 20030083294, Potti et al., Expert Opin. Biol. Ther. 4:1641-1647 (2004), and Nimjee et al., Annu. Rev. Med. 56:555-83 (2005). The technique of SELEX has been used to evolve aptamers to have extremely high binding affinity to a variety of target proteins. See, for example, Trujillo U. H., et al., "DNA and RNA aptamers: from tools for basic research towards therapeutic applications". *Comb Chem High Throughput Screen* 9 (8): 619-32 (2006) for its disclosure of using SELEX to design aptamers that bind vascular endothelial growth factor (VEGF). In some embodiments, the binding RNA is an aptamer that specifically binds a target protein, for example a protein found in an ARMM (e.g., ARRDC1 or TSG101).

Cargo RNAs

Some aspects of the disclosure provide RNAs that are associated with, for example, incorporated into the liquid phase of, an ARMM. In some embodiments, a cargo RNA is an RNA molecule that can be delivered via its association with or inclusion in an ARMM to a subject, organ, tissue, or cell. In some embodiments, the cargo RNA is to be delivered to a target cell in vitro, in vivo, or ex vivo. In some embodiments, the cargo RNA to be delivered is a biologically active agent, i.e., it has activity in a cell, organ, tissue, and/or subject. For instance, an RNA that, when administered to a subject, has a biological effect on that subject, or is considered to be biologically active. In certain embodiments the cargo RNA is a messenger RNA or an RNA that expresses a protein in a cell. In certain embodiments, the cargo RNA is a small interfering RNA (siRNA) that inhibits the expression of one or more genes in a cell. In some embodiments, a cargo RNA to be delivered is a therapeutic agent, for example, an agent that has a beneficial effect on a subject when administered to a subject. In some embodiments, the cargo RNA to be delivered to a cell is an RNA that expresses a transcription factor, a tumor suppressor, a developmental regulator, a growth factor, a metastasis suppressor, a pro-apoptotic protein, a nuclease, or a recombinase. In some embodiments, the cargo RNA to be delivered is an RNA that expresses p53, Rb (retinoblastoma protein), a BIM protein, BRCA1, BRCA2, PTEN, adenomatous polyposis *coli* (APC), CDKN1B, cyclin-dependent kinase inhibitor 1C, HEPACAM, INK4, Mir-145, p16, p63, p73, SDHB, SDHD, secreted frizzled-related protein 1, TCF21, TIG1, TP53, tuberous sclerosis complex tumor suppressors, Von Hippel-Lindau (VHL) tumor suppressor, CD95, ST7, ST14, a BCL-2 family protein, a caspase; BRMS1, CRSP3, DRG1, KAI1, KISS1, NM23, a TIMP-family protein, a BMP-family growth factor, EGF, EPO, FGF, G-CSF, GM-CSF, a GDF-family growth factor, HGF, HDGF, IGF, PDGF, TPO, TGF-α, TGF-β, VEGF; a zinc finger nuclease, Cre, Dre, or FLP recombinase.

In some embodiments, the cargo RNA may be an RNA that inhibits expression of one or more genes in a cell. For example, in some embodiments, the cargo RNA is a microRNA (miRNA), a small interfering RNA (siRNA) or an antisense RNA (asRNA).

In some embodiments, the cargo RNA to be delivered comprises a messenger RNA (mRNA), a ribosomal RNA (rRNA), a signal recognition particle RNA (SRP RNA), or a transfer RNA (tRNA). In some embodiments, the cargo RNA to be delivered comprises a small nuclear RNA (snRNA), a small nucleolar (snoRNA), a SmY RNA (smY), a guide RNA (gRNA), a ribonuclease P (RNase P), a ribonuclease MRP (RNase MRP), a Y RNA, a telomerase RNA component (TERC), or a spliced leader RNA (SL RNA). In some embodiments, the cargo RNA to be delivered comprises an antisense RNA (asRNA), a cis-natural antisense sequence (cis-NAT), a CRISPR RNA (crRNA), a long noncoding RNA (lncRNA), a microRNA (miRNA), a piwi-interacting RNA (piRNA), a small interfering RNA (siRNA), or a trans-acting siRNA (tasiRNA).

In some embodiments, the cargo RNA to be delivered is a diagnostic agent. In some embodiments, the cargo RNA to be delivered is a prophylactic agent. In some embodiments, the cargo RNA to be delivered is useful as an imaging agent. In some of these embodiments, the diagnostic or imaging agent is, and in others it is not, biologically active.

In some embodiments, any of the cargo RNAs provided herein are associated with a binding RNA. In some embodiments, the cargo RNA is covalently associated with the binding RNA. In some embodiments, the cargo RNA and the binding RNA are part of the same RNA molecule, (e.g., an RNA from a single transcript). In some embodiments, the cargo RNA and the binding RNA are covalently associated via a linker. In some embodiments, the linker comprises a nucleotide or nucleic acid (e.g., DNA or RNA). In some embodiments, the linker comprises RNA. In some embodiments, the linker comprises at least 1, at least 2, at least 3, at least 4, at least 5, at least 6, at least 7, at least 8, at least 9, at least 10, at least 15, at least 20, at least 25, at least 30, at least 40, at least 50, at least 100, at least 150, at least 200, at least 250, at least 300, at least 400, or at least 500 nucleotides (e.g., DNA or RNA).

In other embodiments, the cargo RNA is non-covalently associated with the binding RNA. For example, the cargo RNA may associate with the binding RNA via complementary base pairing. In some embodiments, the cargo RNA is bound to the binding RNA via at least 2, at least 3, at least 4, at least 5, at least 6, at least 7, at least 8, at least 9, at least 10, at least 15, at least 20, at least 25, at least 30, at least 40, at least 50, complementary base pairs, which may be contiguous or non-contiguous. In some embodiments, the cargo RNA is bound to the binding RNA via at least 2, at least 3, at least 4, at least 5, at least 6, at least 7, at least 8, at least 9, at least 10, at least 15, at least 20, at least 25, at least 30, at least 40, at least 50 contiguous complementary base pairs.

It should be appreciated that any of the RNAs provided herein (e.g., binding RNAs, cargo RNAs, and/or binding RNAs fused to cargo RNAs) may comprise one or more modified oligonucleotides. In some embodiments, any of the RNAs described herein may be modified, e.g., comprise a modified sugar moiety, a modified internucleoside linkage, a modified nucleotide and/or combinations thereof. In some embodiments, RNA oligonucleotides of the invention can be stabilized against nucleolytic degradation such as by the incorporation of a modification, e.g., a nucleotide modification. For example, nucleic acid sequences of the invention include a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), T dimethylaminoethyl (2'-O-DMAOE), 2'-O-dimethylaminopropyl (2'-O-DMAP), 2' dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom.

Any of the modified chemistries or formats of RNA oligonucleotides described herein can be combined with each other, and that one, two, three, four, five, or more different types of modifications can be included within the same molecule.

In some embodiments, the RNA oligonucleotide may comprise at least one bridged nucleotide. In some embodiments, the oligonucleotide may comprise a bridged nucleotide, such as a locked nucleic acid (LNA) nucleotide, a constrained ethyl (cEt) nucleotide, or an ethylene bridged nucleic acid (ENA) nucleotide. Examples of such nucleotides are disclosed herein and known in the art. In some embodiments, the oligonucleotide comprises a nucleotide analog disclosed in one of the following United States Patent or Patent Application Publications: U.S. Pat. Nos. 7,399,845, 7,741,457, 8,022,193, 7,569,686, 7,335,765, 7,314,923, 7,335,765, and 7,816,333, US 20110009471, the entire contents of each of which are incorporated herein by reference for all purposes. The oligonucleotide may have one or more 2' O-methyl nucleotides. The oligonucleotide may consist entirely of 2' O-methyl nucleotides.

Expression Constructs

Some aspects of this invention provide expression constructs that encode any of the fusion proteins described herein. For example the expression constructs may encode an RNA binding protein fused to an ARRDC1 protein (e.g., ARRDC1:Tat) or an RNA binding protein fused to one or more WW domains. In some embodiments, the expression constructs described herein may further encode, or encode separately, a binding RNA. It should be appreciated that the binding RNA may be expressed under the control of the same promoter sequence or a different promoter sequence as any of the fusion proteins described herein. In some embodiments, an expression construct encoding a binding RNA is co-expressed with any of the expression constructs described herein. In some embodiments, the expression constructs described herein may further encode, or encode separately, a cargo RNA. In some embodiments, the cargo RNA is expressed under the control of the same promoter sequence or a different promoter sequence as any of the fusion proteins or binding RNAs provided herein. In some embodiments, the cargo RNA is expressed as part of the same transcript as the binding RNA. For example, the binding RNA and the cargo RNA may be expressed as a single transcript. In some embodiments, the construct encodes a cargo RNA that is fused 5' to the binding RNA. In some embodiments, the construct encodes a cargo RNA that is fused 3' to the binding RNA. In some embodiments, the construct encodes a cargo RNA and a binding RNA that are fused via one or more linkers. It should be appreciated that the cargo RNA may also be expressed as a separate transcript from the binding RNA. When expressed as a separate transcript, the cargo RNA may comprise a sequence that binds to the binding RNA (e.g., via complementary base pairing). Accordingly, in some embodiments, the construct encodes a cargo RNA that may comprise a nucleotide sequence that is complementary to a sequence of a binding RNA. In some embodiments, the cargo RNA is expressed from a separate expression construct from the construct encoding the RNA binding protein and/or the binding RNA. In some embodiments, the cargo RNA is expressed from the same construct (e.g., expression vector) encoding the RNA binding protein and/or the binding RNA, but under a different promoter.

In some embodiments, the expression constructs described herein may further encode a gene product or gene products that induce or facilitate the generation of ARMMs in cells harboring such a construct. In some embodiments, the expression constructs encode an ARRDC1 protein, or variant thereof, and/or a TSG101 protein, or variant thereof. In some embodiments, overexpression of either or both of these gene products in a cell increase the production of ARMMs in the cell, thus turning the cell into a microvesicle producing cell. In some embodiments, such an expression construct comprises at least one restriction or recombination site that allows in-frame cloning of an RNA binding protein sequence to be fused, either at the C-terminus, or at the N-terminus of the encoded ARRDC1, or variant thereof. As another example an expression construct comprises at least one restriction or recombination site that allows in-frame cloning of an RNA binding protein sequence to be fused either at the C-terminus, or at the N-terminus of one ore more encoded WW domains.

In some embodiments, the expression construct comprises (a) a nucleotide sequence encoding an ARRDC1 protein, or variant thereof, operably linked to a heterologous promoter, and (b) a restriction site or a recombination site positioned adjacent to the ARRDC1-encoding nucleotide sequence allowing for the insertion of an RNA binding protein or RNA binding protein variant sequence in frame with the ARRDC1-encoding nucleotide sequence. In certain embodiments, the expression constructs encode a fusion protein comprising an ARRDC1 protein, or variant thereof, and a Tat protein or variant thereof.

Some aspects of this invention provide an expression construct comprising (a) a nucleotide sequence encoding a WW domain, or variant thereof, operably linked to a heterologous promoter, and (b) a restriction site or a recombination site positioned adjacent to the WW domain-encoding nucleotide sequence allowing for the insertion of an RNA binding protein or RNA binding protein variant sequence in frame with the WW domain-encoding nucleotide sequence. The expression constructs may encode an RNA binding protein fused to at least one WW domain. In some embodiments, the expression constructs encode an RNA binding protein, or variant thereof, fused to at least one WW domain, or variant thereof. Any of the expression constructs, described herein, may encode any WW domain or variant thereof. For example, the expression constructs may comprise any nucleotide sequence capable of encoding a WW domain or variant thereof from the poly peptide sequence (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); (SEQ ID NO: 14); (SEQ ID NO: 18) or (SEQ ID NO: 19).

The expression constructs, described herein, may comprise any nucleic acid sequence capable of encoding a WW domain or variant thereof. For example a nucleic acid sequence encoding a WW domain or WW domain variant may be from the human ubiquitin ligase WWP1, WWP2, Nedd4-1, Nedd4-2, Smurf1, Smurf2, ITCH, NEDL1, or NEDL2. Exemplary nucleic acid sequences of WW domain containing proteins are listed below. It should be appreciated that any of the nucleic acids encoding WW domains or WW domain variants of the exemplary proteins may be used in the invention, described herein, and are not meant to be limiting.

```
Human WWP1 nucleic acid sequence (uniprot.org/uniprot/Q9H0M0).
                                                                    (SEQ ID NO: 23)
GAATTCGCGGCCGCGTCGACCGCTTCTGTGGCCACGGCAGATGAAACAGAAAGGCTAAAG

AGGGCTGGAGTCAGGGGACTTCTCTTCCACCAGCTTCACGGTGATGATATGGCATCTGCC

AGCTCTAGCCGGGCAGGAGTGGCCCTGCCTTTTGAGAAGTCTCAGCTCACTTTGAAAGTG

GTGTCCGCAAAGCCCAAGGTGCATAATCGTCAACCTCGAATTAACTCCTACGTGGAGGTG

GCGGTGGATGGACTCCCCAGTGAGACCAAGAAGACTGGGAAGCGCATTGGGAGCTCTGAG

CTTCTCTGGAATGAGATCATCATTTTGAATGTCACGGCACAGAGTCATTTAGATTTAAAG

GTCTGGAGCTGCCATACCTTGAGAAATGAACTGCTAGGCACCGCATCTGTCAACCTCTCC

AACGTCTTGAAGAACAATGGGGGCAAAATGGAGAACATGCAGCTGACCCTGAACCTGCAG

ACGGAGAACAAAGGCAGCGTTGTCTCAGGCGGAAAACTGACAATTTTCCTGGACGGGCCA

ACTGTTGATCTGGGAAATGTGCCTAATGGCAGTGCCCTGACAGATGGATCACAGCTGCCT

TCGAGAGACTCCAGTGGAACAGCAGTAGCTCCAGAGAACCGGCACCAGCCCCCCAGCACA

AACTGCTTTGGTGGAAGATCCCGGACGCACAGACATTCGGGTGCTTCAGCCAGAACAACC

CCAGCAACCGGCGAGCAAAGCCCCGGTGCTCGGAGCCGGCACCGCCAGCCCGTCAAGAAC

TCAGGCCACAGTGGCTTGGCCAATGGCACAGTGAATGATGAACCCACAACAGCCACTGAT

CCCGAAGAACCTTCCGTTGTTGGTGTGACGTCCCCACCTGCTGCACCCTTGAGTGTGACC

CCGAATCCCAACACGACTTCTCTCCCTGCCCCAGCCACACCGGCTGAAGGAGAGGAACCC

AGCACTTCGGGTACACAGCAGCTCCCAGCGGCTGCCCAGGCCCCCGACGCTCTGCCTGCT

GGATGGGAACAGCGAGAGCTGCCCAACGGACGTGTCTATTATGTTGACCACAATACCAAG

ACCACCACCTGGGAGCGGCCCCTTCCTCCAGGCTGGGAAAAACGCACAGATCCCCGAGGC

AGGTTTTACTATGTGGATCACAATACTCGGACCACCACCTGGCAGCGTCCGACCGCGGAG

TACGTGCGCAACTATGAGCAGTGGCAGTCGCAGCGGAATCAGCTCCAGGGGGCCATGCAG

CACTTCAGCCAAAGATTCCTATACCAGTTTTGGAGTGCTTCGACTGACCATGATCCCCTG

GGCCCCCTCCCTCCTGGTTGGGAGAAAAGACAGGACAATGGACGGGTGTATTACGTGAAC

CATAACACTCGCACGACCCAGTGGGAGGATCCCCGGACCCAGGGGATGATCCAGGAACCA

GCTTTGCCCCAGGATGGGAGATGAAATACACCAGCGAGGGGTGCGATACTTTGTGGAC

CACAATACCCGCACCACCACCTTTAAGGATCCTCGCCCGGGGTTTGAGTCGGGGACGAAG

CAAGGTTCCCCTGGTGCTTATGACCGCAGTTTTCGGTGGAAGTATCACCAGTTCCGTTTC

CTCTGCCATTCAAATGCCCTACCTAGCCACGTGAAGATCAGCGTTTCCAGGCAGACGCTT

TTCGAAGATTCCTTCCAACAGATCATGAACATGAAACCCTATGACCTGCGCCGCCGGCTT

TACATCATCATGCGTGGCGAGGAGGGCCTGGACTATGGGGGCATCGCCAGAGAGTGGTTT

TTCCTCCTGTCTCACGAGGTGCTCAACCCTATGTATTGTTTATTTGAATATGCCGGAAAG

AACAATTACTGCCTGCAGATCAACCCCGCCTCCTCCATCAACCCGGACCACCTCACCTAC
```

```
TTTCGCTTTATAGGCAGATTCATCGCCATGGCGCTGTACCATGGAAAGTTCATCGACACG

GGCTTCACCCTCCCTTTCTACAAGCGGATGCTCAATAAGAGACCAACCCTGAAAGACCTG

GAGTCCATTGACCCTGAGTTCTACAACTCCATTGTCTGGATCAAAGAGAACAACCTGGAA

GAATGTGGCCTGGAGCTGTACTTCATCCAGGACATGGAGATACTGGGCAAGGTGACGACC

CACGAGCTGAAGGAGGGCGGCGAGAGCATCCGGGTCACGGAGGAGAACAAGGAAGAGTAC

ATCATGCTGCTGACTGACTGGCGTTTCACCCGAGGCGTGGAAGAGCAGACCAAAGCCTTC

CTGGATGGCTTCAACGAGGTGGCCCCGCTGGAGTGGCTGCGCTACTTTGACGAGAAAGAG

CTGGAGCTGATGCTGTGCGGCATGCAGGAGATAGACATGAGCGACTGGCAGAAGAGCACC

ATCTACCGGCACTACACCAAGAACAGCAAGCAGATCCAGTGGTTCTGGCAGGTGGTGAAG

GAGATGGACAACGAGAAGAGGATCCGGCTGCTGCAGTTTGTCACCGGTACCTGCCGCCTG

CCCGTCGGGGATTTGCCGAACTCATCGGTAGCAACGGACCACAGAAGTTTTGCATTGAC

AAAGTTGGCAAGGAAACCTGGCTGCCCAGAAGCCACACCTGCTTCAACCGTCTGGATCTT

CCACCCTACAAGAGCTACGAACAGCTGAGAGAGAAGCTGCTGTATGCCATTGAGGAGACC

GAGGGCTTTGGACAGGAGTAACCGAGGCCGCCCCTCCCACGCCCCCAGCGCACATGTAG

TCCTGAGTCCTCCCTGCCTGAGAGGCCACTGGCCCCGCAGCCCTTGGGAGGCCCCCGTGG

ATGTGGCCCTGTGTGGGACCACACTGTCATCTCGCTGCTGGCAGAAAAGCCTGATCCCAG

GAGGCCCTGCAGTTCCCCCGACCCGCGGATGGCAGTCTGGAATAAAGCCCCCTAGTTGCC

TTTGGCCCCACCTTTGCAAAGTTCCAGAGGGCTGACCCTCTCTGCAAAACTCTCCCCTGT

CCTCTAGACCCCACCCTGGGTGTATGTGAGTGTGCAAGGGAAGGTGTTGCATCCCCAGGG

GCTGCCGCAGAGGCCGGAGACCTCCTGGACTAGTTCGGCGAGGAGACTGGCCACTGGGGG

TGGCTGTTCGGGACTGAGAGCGCCAAGGGTCTTTGCCAGCAAAGGAGGTTCTGCCTGTAA

TTGAGCCTCTCTGATGATGGAGATGAAGTGAAGGTCTGAGGGACGGGCCCTGGGGCTAGG

CCATCTCTGCCTGCCTCCCTAGCAGGCGCCAGCGGTGGAGGCTGAGTCGCAGGACACATG

CCGGCCAGTTAATTCATTCTCAGCAAATGAAGGTTTGTCTAAGCTGCCTGGGTATCCACG

GGACAAAAACAGCAAACTCCCTCCAGACTTTGTCCATGTTATAAACTTGAAAGTTGGTTG

TTGTTTGTTAGGTTTGCCAGGTTTTTTTGTTTACGCCTGCTGTCACTTTCCTGTC
```

Human WWP2 nucleic acid sequence (uniprot.org/uniprot/O00308). (SEQ ID NO: 24)

```
GAATTCGCGGCCGCGTCGACCGCTTCTGTGGCCACGGCAGATGAAACAGAAAGGCTAAAG

AGGGCTGGAGTCAGGGGACTTCTCTTCCACCAGCTTCACGGTGATGATATGGCATCTGCC

AGCTCTAGCCGGGCAGGAGTGGCCCTGCCTTTTGAGAAGTCTCAGCTCACTTTGAAAGTG

GTGTCCGCAAAGCCCAAGGTGCATAATCGTCAACCTCGAATTAACTCCTACGTGGAGGTG

GCGGTGGATGGACTCCCCAGTGAGACCAAGAAGACTGGGAAGCGCATTGGGAGCTCTGAG

CTTCTCTGGAATGAGATCATCATTTTGAATGTCACGGCACAGAGTCATTTAGATTTAAAG

GTCTGGAGCTGCCATACCTTGAGAAATGAACTGCTAGGCACCGCATCTGTCAACCTCTCC

AACGTCTTGAAGAACAATGGGGGCAAAATGGAGAACATGCAGCTGACCCTGAACCTGCAG

ACGGAGAACAAAGGCAGCGTTGTCTCAGGCGGAAAACTGACAATTTTCCTGGACGGGCCA

ACTGTTGATCTGGGAAATGTGCCTAATGGCAGTGCCCTGACAGATGGATCACAGCTGCCT

TCGAGAGACTCCAGTGGAACAGCAGTAGCTCCAGAGAACCGGCACCAGCCCCCCAGCACA

AACTGCTTTGGTGGAAGATCCCGGACGCACAGACATTCGGGTGCTTCAGCCAGAACAACC

CCAGCAACCGGCGAGCAAAGCCCCGGTGCTCGGAGCCGGCACCGCCAGCCCGTCAAGAAC
```

-continued
```
TCAGGCCACAGTGGCTTGGCCAATGGCACAGTGAATGATGAACCCACAACAGCCACTGAT
CCCGAAGAACCTTCCGTTGTTGGTGTGACGTCCCCACCTGCTGCACCCTTGAGTGTGACC
CCGAATCCCAACACGACTTCTCTCCCTGCCCCAGCCACACCGGCTGAAGGAGAGGAACCC
AGCACTTCGGGTACACAGCAGCTCCCAGCGGCTGCCCAGGCCCCCGACGCTCTGCCTGCT
GGATGGGAACAGCGAGAGCTGCCCAACGGACGTGTCTATTATGTTGACCACAATACCAAG
ACCACCACCTGGGAGCGGCCCCTTCCTCCAGGCTGGGAAAAACGCACAGATCCCCGAGGC
AGGTTTTACTATGTGGATCACAATACTCGGACCACCACCTGGCAGCGTCCGACCGCGGAG
TACGTGCGCAACTATGAGCAGTGGCAGTCGCAGCGGAATCAGCTCCAGGGGGCCATGCAG
CACTTCAGCCAAAGATTCCTATACCAGTTTTGGAGTGCTTCGACTGACCATGATCCCCTG
GGCCCCCTCCCTCCTGGTTGGGAGAAAAGACAGGACAATGGACGGGTGTATTACGTGAAC
CATAACACTCGCACGACCCAGTGGGAGGATCCCCGGACCCAGGGGATGATCCAGGAACCA
GCTTTGCCCCCAGGATGGGAGATGAAATACACCAGCGAGGGGTGCGATACTTTGTGGAC
CACAATACCCGCACCACCACCTTTAAGGATCCTCGCCCGGGGTTTGAGTCGGGGACGAAG
CAAGGTTCCCCTGGTGCTTATGACCGCAGTTTTCGGTGGAAGTATCACCAGTTCCGTTTC
CTCTGCCATTCAAATGCCCTACCTAGCCACGTGAAGATCAGCGTTTCCAGGCAGACGCTT
TTCGAAGATTCCTTCCAACAGATCATGAACATGAAACCCTATGACCTGCGCCGCCGGCTT
TACATCATCATGCGTGGCGAGGAGGGCCTGGACTATGGGGGCATCGCCAGAGAGTGGTTT
TTCCTCCTGTCTCACGAGGTGCTCAACCCTATGTATTGTTTATTTGAATATGCCGGAAAG
AACAATTACTGCCTGCAGATCAACCCCGCCTCCTCCATCAACCCGGACCACCTCACCTAC
TTTCGCTTTATAGGCAGATTCATCGCCATGGCGCTGTACCATGGAAAGTTCATCGACACG
GGCTTCACCCTCCCTTTCTACAAGCGGATGCTCAATAAGAGACCAACCCTGAAAGACCTG
GAGTCCATTGACCCTGAGTTCTACAACTCCATTGTCTGGATCAAAGAGAACAACCTGGAA
GAATGTGGCCTGGAGCTGTACTTCATCCAGGACATGGAGATACTGGGCAAGGTGACGACC
CACGAGCTGAAGGAGGGCGGCGAGAGCATCCGGGTCACGGAGGAGAACAAGGAAGAGTAC
ATCATGCTGCTGACTGACTGGCGTTTCACCCGAGGCGTGGAAGAGCAGACCAAAGCCTTC
CTGGATGGCTTCAACGAGGTGGCCCCGCTGGAGTGGCTGCGCTACTTTGACGAGAAAGAG
CTGGAGCTGATGCTGTGCGGCATGCAGGAGATAGACATGAGCGACTGGCAGAAGAGCACC
ATCTACCGGCACTACACCAAGAACAGCAAGCAGATCCAGTGGTTCTGGCAGGTGGTGAAG
GAGATGGACAACGAGAAGAGGATCCGGCTGCTGCAGTTTGTCACCGGTACCTGCCGCCTG
CCCGTCGGGGATTTGCCGAACTCATCGGTAGCAACGGACCACAGAAGTTTTGCATTGAC
AAAGTTGGCAAGGAAACCTGGCTGCCCAGAAGCCACACCTGCTTCAACCGTCTGGATCTT
CCACCCTACAAGAGCTACGAACAGCTGAGAGAGAAGCTGCTGTATGCCATTGAGGAGACC
GAGGGCTTTGGACAGGAGTAACCGAGGCCGCCCCTCCCACGCCCCCAGCGCACATGTAG
TCCTGAGTCCTCCCTGCCTGAGAGGCCACTGGCCCCGCAGCCCTTGGGAGGCCCCCGTGG
ATGTGGCCCTGTGTGGGACCACACTGTCATCTCGCTGCTGGCAGAAAAGCCTGATCCCAG
GAGGCCCTGCAGTTCCCCCGACCCGCGGATGGCAGTCTGGAATAAAGCCCCCTAGTTGCC
TTTGGCCCCACCTTTGCAAAGTTCCAGAGGGCTGACCCTCTCTGCAAAACTCTCCCCTGT
CCTCTAGACCCCACCCTGGGTGTATGTGAGTGTGCAAGGGAAGGTGTTGCATCCCCAGGG
GCTGCCGCAGAGGCCGGAGACCTCCTGGACTAGTTCGGCGAGGAGACTGGCCACTGGGGG
TGGCTGTTCGGGACTGAGAGCGCCAAGGGTCTTTGCCAGCAAAGGAGGTTCTGCCTGTAA
TTGAGCCTCTCTGATGATGGAGATGAAGTGAAGGTCTGAGGGACGGGCCCTGGGGCTAGG
```

-continued

```
CCATCTCTGCCTGCCTCCCTAGCAGGCGCCAGCGGTGGAGGCTGAGTCGCAGGACACATG

CCGGCCAGTTAATTCATTCTCAGCAAATGAAGGTTTGTCTAAGCTGCCTGGGTATCCACG

GGACAAAAACAGCAAACTCCCTCCAGACTTTGTCCATGTTATAAACTTGAAAGTTGGTTG

TTGTTTGTTAGGTTTGCCAGGTTTTTTTGTTTACGCCTGCTGTCACTTTCCTGTC
```

Human Nedd4-1 nucleic acid sequence (uniprot.org/uniprot/P46934).

(SEQ ID NO: 25)

```
ACAGTTGCCTGCCCTGGGCGGGGCGAGCGCGTCCGGTTTGCTGGAAGCGTTCGGAAATG

GCAACTTGCGCGGTGGAGGTGTTCGGGCTCCTGGAGGACGAGGAAAATTCACGAATTGTG

AGAGTAAGAGTTATAGCCGGAATAGGCCTTGCCAAGAAGGATATATTGGGAGCTAGTGAT

CCTTACGTGAGAGTGACGTTATATGACCCAATGAATGGAGTTCTTACAAGTGTGCAAACA

AAAACCATTAAAAAGAGTTTGAATCCAAAGTGGAATGAAGAAATATTATTCAGAGTTCAT

CCTCAGCAGCACCGGCTTCTTTTTGAAGTGTTTGACGAAAACCGATTGACAAGAGATGAT

TTCCTAGGTCAAGTGGATGTTCCACTTTATCCATTACCGACAGAAAATCCAAGATTGGAG

AGACCATATACATTTAAGGATTTTGTTCTTCATCCAAGAAGTCACAAATCAAGAGTTAAA

GGTTATCTGAGACTAAAAATGACTTATTTACCTAAAACCAGTGGCTCAGAAGATGATAAT

GCAGAACAGGCTGAGGAATTAGAGCCTGGCTGGGTTGTTTGGACCAACCAGATGCTGCT

TGCCATTTGCAGCAACAACAAGAACCTTCTCCTCTACCTCCAGGGTGGGAAGAGAGGCAG

GATATCCTTGGAAGGACCTATTATGTAAACCATGAATCTAGAAGAACACAGTGGAAAAGA

CCAACCCCTCAGGACAACCTAACAGATGCTGAGAATGGCAACATTCAACTGCAAGCACAA

CGTGCATTTACCACCAGGCGGCAGATATCCGAGGAAACAGAAAGTGTTGACAACCAAGAG

TCTTCCGAGAACTGGGAAATTATAAGAGAAGATGAAGCCACCATGTATAGCAGCCAGGCC

TTCCCATCACCTCCACCGTCAAGTAACTTGGATGTTCCAACTCATCTTGCAGAAGAATTG

AATGCCAGACTCACCATTTTTGGAAATTCAGCCGTGAGCCAGCCAGCATCGAGCTCAAAT

CATTCCAGCAGAAGAGGCAGCTTACAAGCCTATACTTTTGAGGAACAACCTACACTTCCT

GTGCTTTTGCCTACTTCATCTGGATTACCACCAGGTTGGGAAGAAAAACAAGATGAAAGA

GGAAGATCATATTATGTAGATCACAATTCCAGAACGACTACTTGGACAAAGCCCACTGTA

CAGGCCACAGTGGAGACCAGTCAGCTGACCTCAAGCCAGAGTTCTGCAGGCCCTCAATCA

CAAGCCTCCACCAGTGATTCAGGCCAGCAGGTGACCCAGCCATCTGAAATTGAGCAAGGA

TTCCTTCCTAAAGGCTGGGAAGTCCGGCATGCACCAAATGGGAGGCCTTTCTTTATTGAC

CACAACACTAAAACCACCACCTGGGAAGATCCAAGATTGAAAATTCCAGCCCATCTGAGA

GGAAAGACATCACTTGATACTTCCAATGATCTAGGGCCTTTACCTCCAGGATGGGAAGAG

AGAACTCACACAGATGGAAGAATCTTCTACATAAATCACAATATAAAAAGAACACAATGG

GAAGATCCTCGGTTGGAGAATGTAGCAATAACTGGACCAGCAGTGCCCTACTCCAGGGAT

TACAAAAGAAAGTATGAGTTCTTCCGAAGAAAGTTGAAGAAGCAGAATGACATTCCAAAC

AAATTTGAAATGAAACTTCGCCGAGCAACTGTTCTTGAAGACTCTTACCGGAGAATTATG

GGTGTCAAGAGAGCAGACTTCCTGAAGGCTCGACTGTGGATTGAGTTTGATGGTGAAAAG

GGATTGGATTATGGAGGAGTTGCCAGAGAATGGTTCTTCCTGATCTCAAAGGAAATGTTT

AACCCTTATTATGGGTTGTTTGAATATTCTGCTACGGACAATTATACCCTACAGATAAAT

CCAAACTCTGGATTGTGTAACGAAGATCACCTCTCTTACTTCAAGTTTATTGGTCGGGTA

GCTGGAATGGCAGTTTATCATGGCAAACTGTTGGATGGTTTTTCATCCGCCCATTTTAC

AAGATGATGCTTCACAAACCAATAACCCTTCATGATATGGAATCTGTGGATAGTGAATAT
```

-continued

```
TACAATTCCCTAAGATGGATTCTTGAAAATGACCCAACAGAATTGGACCTCAGGTTTATC

ATAGATGAAGAACTTTTTGGACAGACACATCAACATGAGCTGAAAAATGGTGGATCAGAA

ATAGTTGTCACCAATAAGAACAAAAAGGAATATATTTATCTTGTAATACAATGGCGATTT

GTAAACCGAATCCAGAAGCAAATGGCTGCTTTTAAAGAGGGATTCTTTGAACTAATACCA

CAGGATCTCATCAAAATTTTTGATGAAAATGAACTAGAGCTTCTTATGTGTGGACCGGGA

GATGTTGATGTGAATGACTGGAGGGAACATACAAAGTATAAAAATGGCTACAGTGCAAAT

CATCAGGTTATACAGTGGTTTTGGAAGGCTGTTTTAATGATGGATTCAGAAAAAAGAATA

AGATTACTTCAGTTTGTCACTGGCACATCTCGGGTGCCTATGAATGGATTTGCTGAACTA

TACGGTTCAAATGGACCACAGTCATTTACAGTTGAACAGTGGGGTACTCCTGAAAAGCTG

CCAAGAGCTCATACCTGTTTTAATCGCCTGGACTTGCCACCTTATGAATCATTTGAAGAA

TTATGGGATAAACTTCAGATGGCAATTGAAAACACCCAGGGCTTTGATGGAGTTGATTAG

ATTACAAATAACAATCTGTAGTGTTTTTACTGCCATAGTTTTATAACCAAAATCTTGACT

TAAAATTTTCCGGGGAACTACTAAAATGTGGCCACTGAGTCTTCCCAGATCTTGAAGAAA

ATCATATAAAAAGCATTTGAAGAAATAGTACGAC
```

Human Nedd4-2 nucleic acid sequence (>gi|345478679|ref|NM_015277.5| *Homo sapiens* neural precursor cell expressed, developmentally down-regulated 4-like, E3 ubiquitin protein ligase (NEDD4L), transcript variant d, mRNA).

(SEQ ID NO: 26)

```
ATGGCGACCGGGCTCGGGGAGCCGGTCTATGGACTTTCCGAAGACGAGGGAGAGTCCCGTAT

TCTCAGAGTAAAAGTTGTTTCTGGAATTGATCTCGCCAAAAAGGACATCTTTGGAGCCAGTG

ATCCGTATGTGAAACTTTCATTGTACGTAGCGGATGAGAATAGAGAACTTGCTTTGGTCCAG

ACAAAAACAATTAAAAAGACACTGAACCCAAAATGGAATGAAGAATTTTATTTCAGGGTAAA

CCCATCTAATCACAGACTCCTATTTGAAGTATTTGACGAAAATAGACTGACACGAGACGACT

TCCTGGGCCAGGTGGACGTGCCCCTTAGTCACCTTCCGACAGAAGATCCAACCATGGAGCGA

CCCTATACATTTAAGGACTTTCTCCTCAGACCAAGAAGTCATAAGTCTCGAGTTAAGGGATT

TTTGCGATTGAAAATGGCCTATATGCCAAAAAATGGAGGTCAAGATGAAGAAAACAGTGACC

AGAGGGATGACATGGAGCATGGATGGGAAGTTGTTGACTCAAATGACTCGGCTTCTCAGCAC

CAAGAGGAACTTCCTCCTCCTCCTCTGCCTCCCGGGTGGGAAGAAAAAGTGGACAATTTAGG

CCGAACTTACTATGTCAACCACAACAACCGGACCACTCAGTGGCACAGACCAAGCCTGATGG

ACGTGTCCTCGGAGTCGGACAATAACATCAGACAGATCAACCAGGAGGCAGCACACCGGCGC

TTCCGCTCCCGCAGGCACATCAGCGAAGACTTGGAGCCCGAGCCCTCGGAGGGCGGGGATGT

CCCCGAGCCTTGGGAGACCATTTCAGAGGAAGTGAATATCGCTGGAGACTCTCTCGGTCTGG

CTCTGCCCCCACCACCGGCCTCCCCAGGATCTCGGACCAGCCCTCAGGAGCTGTCAGAGGAA

CTAAGCAGAAGGCTTCAGATCACTCCAGACTCCAATGGGGAACAGTTCAGCTCTTTGATTCA

AAGAGAACCCTCCTCAAGGTTGAGGTCATGCAGTGTCACCGACGCAGTTGCAGAACAGGGCC

ATCTACCACCGCCATCAGTGGCCTATGTACATACCACGCCGGGTCTGCCTTCAGGCTGGGAA

GAAAGAAAGATGCTAAGGGGCGCACATACTATGTCAATCATAACAATCGAACCACAACTTG

GACTCGACCTATCATGCAGCTTGCAGAAGATGGTGCGTCCGGATCAGCCACAAACAGTAACA

ACCATCTAATCGAGCCTCGATCCGCCGGCCTCGTAGCCTCAGCTCGCCAACAGTAACTTTA

TCTGCCCCGCTGGAGGGTGCCAAGGACTCACCCGTACGTCGGGCTGTGAAAGACACCCTTTC

CAACCCACAGTCCCCACAGCCATCACCTTACAACTCCCCCAAACCACAACACAAAGTCACAC

AGAGCTTCTTGCCACCCGGCTGGGAAATGAGGATAGCGCCAAACGGCCGGCCCTTCTTCATT

GATCATAACACAAAGACTACAACCTGGGAAGATCCACGTTTGAAATTTCCAGTACATATGCG
```

GTCAAAGACATCTTTAAACCCCAATGACCTTGGCCCCCTTCCTCCTGGCTGGGAAGAAAGAA

TTCACTTGGATGGCCGAACGTTTTATATTGATCATAATAGCAAAATTACTCAGTGGGAAGAC

CCAAGACTGCAGAACCCAGCTATTACTGGTCCGGCTGTCCCTTACTCCAGAGAATTTAAGCA

GAAATATGACTACTTCAGGAAGAAATTAAAGAAACCTGCTGATATCCCCAATAGGTTTGAAA

TGAAACTTCACAGAAATAACATATTTGAAGAGTCCTATCGGAGAATTATGTCCGTGAAAAGA

CCAGATGTCCTAAAAGCTAGACTGTGGATTGAGTTTGAATCAGAGAAAGGTCTTGACTATGG

GGGTGTGGCCAGAGAATGGTTCTTCTTACTGTCCAAAGAGATGTTCAACCCCTACTACGGCC

TCTTTGAGTACTCTGCCACGGACAACTACACCCTTCAGATCAACCCTAATTCAGGCCTCTGT

AATGAGGATCATTTGTCCTACTTCACTTTTATTGGAAGAGTTGCTGGTCTGGCCGTATTTCA

TGGGAAGCTCTTAGATGGTTTCTTCATTAGACCATTTTACAAGATGATGTTGGGAAAGCAGA

TAACCCTGAATGACATGGAATCTGTGGATAGTGAATATTACAACTCTTTGAAATGGATCCTG

GAGAATGACCCTACTGAGCTGGACCTCATGTTCTGCATAGACGAAGAAAACTTTGGACAGAC

ATATCAAGTGGATTTGAAGCCCAATGGGTCAGAAATAATGGTCACAAATGAAAACAAAGGG

AATATATCGACTTAGTCATCCAGTGGAGATTTGTGAACAGGGTCCAGAAGCAGATGAACGCC

TTCTTGGAGGGATTCACAGAACTACTTCCTATTGATTTGATTAAAATTTTTGATGAAAATGA

GCTGGAGTTGCTCATGTGCGGCCTCGGTGATGTGGATGTGAATGACTGGAGACAGCATTCTA

TTTACAAGAACGGCTACTGCCCAAACCACCCCGTCATTCAGTGGTTCTGGAAGGCTGTGCTA

CTCATGGACGCCGAAAAGCGTATCCGGTTACTGCAGTTTGTCACAGGGACATCGCGAGTACC

TATGAATGGATTTGCCGAACTTTATGGTTCCAATGGTCCTCAGCTGTTTACAATAGAGCAAT

GGGGCAGTCCTGAGAAACTGCCCAGAGCTCACACATGCTTTAATCGCCTTGACTTACCTCCA

TATGAAACCTTTGAAGATTTACGAGAGAAACTTCTCATGGCCGTGGAAAATGCTCAAGGATT

TGAAGGGGTGGATTAA

Human Smurf1 nucleic acid sequence (uniprot.org/uniprot/Q9HCE7).
(SEQ ID NO: 27)
ATGTCGAACCCCGGGACACGCAGGAACGGCTCCAGCATCAAGATCCGTCTGACAGTGTTA

TGTGCCAAGAACCTTGCAAAGAAAGACTTCTTCAGGCTCCCTGACCCTTTTGCAAAGATT

GTCGTGGATGGGTCTGGGCAGTGCCACTCAACCGACACTGTGAAAAACACATTGGACCCA

AAGTGGAACCAGCACTATGATCTATATGTTGGGAAAACGGATTCGATAACCATTAGCGTG

TGGAACCATAAGAAAATTCACAAGAAACAGGGAGCTGGCTTCCTGGGCTGTGTGCGGCTG

CTCTCCAATGCCATCAGCAGATTAAAAGATACCGGATACCAGCGTTTGGATCTATGCAAA

CTAAACCCCTCAGATACTGATGCAGTTCGTGGCCAGATAGTGGTCAGTTTACAGACACGA

GACAGAATAGGAACCGGCGGCTCGGTGGTGGACTGCAGAGGACTGTTAGAAAATGAAGGA

ACGGTGTATGAAGACTCCGGGCCTGGGAGGCCGCTCAGCTGCTTCATGGAGGAACCAGCC

CCTTACACAGATAGCACCGGTGCTGCTGCTGGAGGAGGGAATTGCAGGTTCGTGGAGTCC

CCAAGTCAAGATCAAAGACTTCAGGCACAGCGGCTTCGAAACCCTGATGTGCGAGGTTCA

CTACAGACGCCCCAGAACCGACCACACGGCCACCAGTCCCCGGAACTGCCCGAAGGCTAC

GAACAAAGAACAACAGTCCAGGGCCAAGTTTACTTTTTGCATACACAGACTGGAGTTAGC

ACGTGGCACGACCCCAGGATACCAAGTCCCTCGGGGACCATTCCTGGGGGAGATGCAGCT

TTTCTATACGAATTCCTTCTACAAGGCCATACATCTGAGCCCAGAGACCTTAACAGTGTG

AACTGTGATGAACTTGGACCACTGCCGCCAGGCTGGGAAGTCAGAAGTACAGTTTCTGGG

AGGATATATTTTGTAGATCATAATAACCGAACAACCCAGTTTACAGACCCAAGGTTACAC

-continued
```
CACATCATGAATCACCAGTGCCAACTCAAGGAGCCCAGCCAGCCGCTGCCACTGCCCAGT

GAGGGCTCTCTGGAGGACGAGGAGCTTCCTGCCCAGAGATACGAAAGAGATCTAGTCCAG

AAGCTGAAAGTCCTCAGACACGAACTGTCGCTTCAGCAGCCCCAAGCTGGTCATTGCCGC

ATCGAAGTGTCCAGAGAAGAAATCTTTGAGGAGTCTTACCGCCAGATAATGAAGATGCGA

CCGAAAGACTTGAAAAAACGGCTGATGGTGAAATTCCGTGGGGAAGAAGGTTTGGATTAC

GGTGGTGTGGCCAGGGAGTGGCTTTACTTGCTGTGCCATGAAATGCTGAATCCTTATTAC

GGGCTCTTCCAGTATTCTACGGACAATATTTACATGTTGCAAATAAATCCGGATTCTTCA

ATCAACCCCGACCACTTGTCTTATTTCCACTTTGTGGGGCGGATCATGGGGCTGGCTGTG

TTCCATGGACACTACATCAACGGGGGCTTCACAGTGCCCTTCTACAAGCAGCTGCTGGGG

AAGCCCATCCAGCTCTCAGATCTGGAATCTGTGGACCCAGAGCTGCATAAGAGCTTGGTG

TGGATCCTAGAGAACGACATCACGCCTGTACTGGACCACACCTTCTGCGTGGAACACAAC

GCCTTCGGGCGGATCCTGCAGCATGAACTGAAACCCAATGGCAGAAATGTGCCAGTCACA

GAGGAGAATAAGAAAGAATACGTCCGGTTGTATGTAAACTGGAGGTTTATGAGAGGAATC

GAAGCCCAGTTCTTAGCTCTGCAGAAGGGGTTCAATGAGCTCATCCCTCAACATCTGCTG

AAGCCTTTTGACCAGAAGGAACTGGAGCTGATCATAGGCGGCCTGGATAAAATAGACTTG

AACGACTGGAAGTCGAACACGCGGCTGAAGCACTGTGTGGCCGACAGCAACATCGTGCGG

TGGTTCTGGCAAGCGGTGGAGACGTTCGATGAAGAAAGGAGGGCCAGGCTCCTGCAGTTT

GTGACTGGGTCCACGCGAGTCCCGCTCCAAGGCTTCAAGGCTTTGCAAGGTTCTACAGGC

GCGGCAGGGCCCCGGCTGTTCACCATCCACCTGATAGACGCGAACACAGACAACCTTCCG

AAGGCCCATACCTGCTTTAACCGGATCGACATTCCACCATATGAGTCCTATGAGAAGCTC

TACGAGAAGCTGCTGACAGCCGTGGAGGAGACCTGCGGGTTTGCTGTGGAGTGA
```

Human Smurf2 nucleic acid sequence (uniprot.org/uniprot/Q9HAU4).

(SEQ ID NO: 28)
```
ATGTCTAACCCCGGACGCCGGAGGAACGGGCCCGTCAAGCTGCGCCTGACAGTACTCTGT

GCAAAAAACCTGGTGAAAAAGGATTTTTTCCGACTTCCTGATCCATTTGCTAAGGTGGTG

GTTGATGGATCTGGGCAATGCCATTCTACAGATACTGTGAAGAATACGCTTGATCCAAAG

TGGAATCAGCATTATGACCTGTATATTGGAAAGTCTGATTCAGTTACGATCAGTGTATGG

AATCACAAGAAGATCCATAAGAAACAAGGTGCTGGATTTCTCGGTTGTGTTCGTCTTCTT

TCCAATGCCATCAACCGCCTCAAAGACACTGGTTATCAGAGGTTGGATTTATGCAAACTC

GGGCCAAATGACAATGATACAGTTAGAGGACAGATAGTAGTAAGTCTTCAGTCCAGAGAC

CGAATAGGCACAGGAGGACAAGTTGTGGACTGCAGTCGTTTATTTGATAACGATTTACCA

GACGGCTGGGAAGAAAGGAGAACCGCCTCTGGAAGAATCCAGTATCTAAACCATATAACA

AGAACTACGCAATGGGAGCGCCCAACACGACCGGCATCCGAATATTCTAGCCCTGGCAGA

CCTCTTAGCTGCTTTGTTGATGAGAACACTCCAATTAGTGGAACAAATGGTGCAACATGT

GGACAGTCTTCAGATCCCAGGCTGGCAGAGAGGAGAGTCAGGTCACAACGACATAGAAAT

TACATGAGCAGAACACATTTACATACTCCTCCAGACCTACCAGAAGGCTATGAACAGAGG

ACAACGCAACAAGGCCAGGTGTATTTCTTACATACACAGACTGGTGTGAGCACATGGCAT

GATCCAAGAGTGCCCAGGGATCTTAGCAACATCAATTGTGAAGAGCTTGGTCCATTGCCT

CCTGGATGGGAGATCCGTAATACGGCAACAGGCAGAGTTTATTTCGTTGACCATAACAAC

AGAACAACACAATTTACAGATCCTCGGCTGTCTGCTAACTTGCATTTAGTTTTAAATCGG

CAGAACCAATTGAAAGACCAACAGCAACAGCAAGTGGTATCGTTATGTCCTGATGACACA

GAATGCCTGACAGTCCCAAGGTACAAGCGAGACCTGGTTCAGAAACTAAAAATTTTGCGG
```

-continued

```
CAAGAACTTTCCCAACAACAGCCTCAGGCAGGTCATTGCCGCATTGAGGTTTCCAGGGAA
GAGATTTTTGAGGAATCATATCGACAGGTCATGAAAATGAGACCAAAAGATCTCTGGAAG
CGATTAATGATAAAATTTCGTGGAGAAGAAGGCCTTGACTATGGAGGCGTTGCCAGGGAA
TGGTTGTATCTCTTGTCACATGAAATGTTGAATCCATACTATGGCCTCTTCCAGTATTCA
AGAGATGATATTTATACATTGCAGATCAATCCTGATTCTGCAGTTAATCCGGAACATTTA
TCCTATTTCCACTTTGTTGGACGAATAATGGGAATGGCTGTGTTTCATGGACATTATATT
GATGGTGGTTTCACATTGCCTTTTTATAAGCAATTGCTTGGGAAGTCAATTACCTTGGAT
GACATGGAGTTAGTAGATCCGGATCTTCACAACAGTTTAGTGTGGATACTTGAGAATGAT
ATTACAGGTGTTTTGGACCATACCTTCTGTGTTGAACATAATGCATATGGTGAAATTATT
CAGCATGAACTTAAACCAAATGGCAAAAGTATCCCTGTTAATGAAGAAATAAAAAAGAA
TATGTCAGGCTCTATGTGAACTGGAGATTTTTACGAGGCATTGAGGCTCAATTCTTGGCT
CTGCAGAAAGGATTTAATGAAGTAATTCCACAACATCTGCTGAAGACATTTGATGAGAAG
GAGTTAGAGCTCATTATTTGTGGACTTGGAAAGATAGATGTTAATGACTGGAAGGTAAAC
ACCCGGTTAAAACACTGTACACCAGACAGCAACATTGTCAAATGGTTCTGGAAAGCTGTG
GAGTTTTTTGATGAAGAGCGACGAGCAAGATTGCTTCAGTTTGTGACAGGATCCTCTCGA
GTGCCTCTGCAGGGCTTCAAAGCATTGCAAGGTGCTGCAGGCCCGAGACTCTTTACCATA
CACCAGATTGATGCCTGCACTAACAACCTGCCGAAAGCCCACACTTGCTTCAATCGAATA
GACATTCCACCCTATGAAAGCTATGAAAAGCTATATGAAAAGCTGCTAACAGCCATTGAA
GAAACATGTGGATTTGCTGTGGAATGA
```

Human ITCH nucleic acid sequence (uniprot.org/uniprot/Q96J02).

(SEQ ID NO: 29)

```
GGAGTCGCCGCCGCCCCGAGTTCCGGTACCATGCATTTCACGGTGGCCTTGTGGAGACAA
CGCCTTAACCCAAGGAAGTGACTCAAACTGTGAGAACTCCAGGTTTTCCAACCTATTGGT
GGTATGTCTGACAGTGGATCACAACTTGGTTCAATGGGTAGCCTCACCATGAAATCACAG
CTTCAGATCACTGTCATCTCAGCAAAACTTAAGGAAAATAAGAAGAATTGGTTTGGACCA
AGTCCTTACGTAGAGGTCACAGTAGATGGACAGTCAAAGAAGACAGAAAAATGCAACAAC
ACAAACAGTCCCAAGTGGAAGCAACCCCTTACAGTTATCGTTACCCCTGTGAGTAAATTA
CATTTTCGTGTGTGGAGTCACCAGACACTGAAATCTGATGTTTTGTTGGGAACTGCTGCA
TTAGATATTTATGAAACATTAAAGTCAAACAATATGAAACTTGAAGAAGTAGTTGTGACT
TTGCAGCTTGGAGGTGACAAAGAGCCAACAGAGACAATAGGAGACTTGTCAATTTGTCTT
GATGGGCTACAGTTAGAGTCTGAAGTTGTTACCAATGGTGAAACTACATGTTCAGAAAGT
GCTTCTCAGAATGATGATGGCTCCAGATCCAAGGATGAAACAAGAGTGAGCACAAATGGA
TCAGATGACCCTGAAGATGCAGGAGCTGGTGAAAATAGGAGAGTCAGTGGGAATAATTCT
CCATCACTCTCAAATGGTGGTTTTAAACCTTCTAGACCTCCAAGACCTTCACGACCACCA
CCACCCACCCCACGTAGACCAGCATCTGTCAATGGTTCACCATCTGCCACTTCTGAAAGT
GATGGGTCTAGTACAGGCTCTCTGCCGCCGACAAATACAAATACAAATACATCTGAAGGA
GCAACATCTGGATTAATAATTCCTCTTACTATATCTGGAGGCTCAGGCCCTAGGCCATTA
AATCCTGTAACTCAAGCTCCCTTGCCACCTGGTTGGGAGCAGAGAGTGGACCAGCACGGG
CGAGTTTACTATGTAGATCATGTTGAGAAAAGAACAACATGGGATAGACCAGAACCTCTA
CCTCCTGGCTGGGAACGGCGGGTTGACAACATGGGACGTATTTATTATGTTGACCATTTC
ACAAGAACAACAACGTGGCAGAGGCCAACACTGGAATCCGTCCGGAACTATGAACAATGG
```

-continued

```
CAGCTACAGCGTAGTCAGCTTCAAGGAGCAATGCAGCAGTTTAACCAGAGATTCATTTAT

GGGAATCAAGATTTATTTGCTACATCACAAAGTAAAGAATTTGATCCTCTTGGTCCATTG

CCACCTGGATGGGAGAAGAGAACAGACAGCAATGGCAGAGTATATTTCGTCAACCACAAC

ACACGAATTACACAATGGGAAGACCCCAGAAGTCAAGGTCAATTAAATGAAAAGCCCTTA

CCTGAAGGTTGGGAAATGAGATTCACAGTGGATGGAATTCCATATTTTGTGGACCACAAT

AGAAGAACTACCACCTATATAGATCCCCGCACAGGAAAATCTGCCCTAGACAATGGACCT

CAGATAGCCTATGTTCGGGACTTCAAAGCAAAGGTTCAGTATTTCCGGTTCTGGTGTCAG

CAACTGGCCATGCCACAGCACATAAAGATTACAGTGACAAGAAAAACATTGTTTGAGGAT

TCCTTTCAACAGATAATGAGCTTCAGTCCCCAAGATCTGCGAAGACGTTTGTGGGTGATT

TTTCCAGGAGAAGAAGGTTTAGATTATGGAGGTGTAGCAAGAGAATGGTTCTTTCTTTTG

TCACATGAAGTGTTGAACCCAATGTATTGCCTGTTTGAATATGCAGGGAAGGATAACTAC

TGCTTGCAGATAAACCCCGCTTCTTACATCAATCCAGATCACCTGAAATATTTTCGTTTT

ATTGGCAGATTTATTGCCATGGCTCTGTTCCATGGGAAATTCATAGACACGGGTTTTTCT

TTACCATTCTATAAGCGTATCTTGAACAAACCAGTTGGACTCAAGGATTTAGAATCTATT

GATCCAGAATTTTACAATTCTCTCATCTGGGTTAAGGAAAACAATATTGAGGAATGTGAT

TTGGAAATGTACTTCTCCGTTGACAAAGAAATTCTAGGTGAAATTAAGAGTCATGATCTG

AAACCTAATGGTGGCAATATTCTTGTAACAGAAGAAATAAAGAGGAATACATCAGAATG

GTAGCTGAGTGGAGGTTGTCTCGAGGTGTTGAAGAACAGACACAAGCTTTCTTTGAAGGC

TTTAATGAAATTCTTCCCCAGCAATATTTGCAATACTTTGATGCAAAGGAATTAGAGGTC

CTTTTATGTGGAATGCAAGAGATTGATTTGAATGACTGGCAAAGACATGCCATCTACCGT

CATTATGCAAGGACCAGCAAACAAATCATGTGGTTTTGGCAGTTTGTTAAAGAAATTGAT

AATGAGAAGAGAATGAGACTTCTGCAGTTTGTTACTGGAACCTGCCGATTGCCAGTAGGA

GGATTTGCTGATCTCATGGGGAGCAATGGACCACAGAAATTCTGCATTGAAAAAGTTGGG

AAAGAAAATTGGCTACCCAGAAGTCATACCTGTTTTAATCGCCTGGACCTGCCACCATAC

AAGAGCTATGAGCAACTGAAGGAAAAGCTGTTGTTTGCCATAGAAGAAACAGAAGGATTT

GGACAAGAGTAACTTCTGAGAACTTGCACCATGAATGGGCAAGAACTTATTTGCAATGTT

TGTCCTTCTCTGCCTGTTGCACATCTTGTAAAATTGGACAATGGCTCTTTAGAGAGTTAT

CTGAGTGTAAGTAAATTAATGTTCTCATTTAAAAAAAAAAAAAAAAAAA
```

Human NEDL1 nucleic acid sequence (uniprot.org/uniprot/Q76N89).
(SEQ ID NO: 30)

```
GCGCATCAGGCGCTGTTGTTGGAGCCGGAACACCGTGCGACTCTGACCGAACCGGCCCCC

TCCTCGCGCACACACTCGCCGAGCCGCGCGCGCCCCTCCGCCGTGACAGTGGCCGTGGCC

TCCGCTCTCTCGGGGCACCCGGCAGCCAGAGCGCAGCGAGAGCGGGCGGTCGCCAGGGTC

CCCTCCCCAGCCAGTCCCAGGCGCCCGGTGCACTATGCGGGGCACGTGCGCCCCCCAGCT

CTAATCTGCGCGCTGACAGGAGCATGATCTGTGCCCAGGCCAGGGCTGCCAAGGAATTGA

TGCGCGTACACGTGGTGGGTCATTATGCTGCTACACCTGTGTAGTGTGAAGAATCTGTAC

CAGAACAGGTTTTTAGGCCTGGCCGCCATGGCGTCTCCTTCTAGAAACTCCCAGAGCCGA

CGCCGGTGCAAGGAGCCGCTCCGATACAGCTACAACCCCGACCAGTTCCACAACATGGAC

CTCAGGGGCGGCCCCCACGATGGCGTCACCATTCCCCGCTCCACCAGCGACACTGACCTG

GTCACCTCGGACAGCCGCTCCACGCTCATGGTCAGCAGCTCCTACTATTCCATCGGGCAC

TCTCAGGACCTGGTCATCCACTGGGACATAAAGGAGGAAGTGGACGCTGGGGACTGGATT

GGCATGTACCTCATTGATGAGGTCTTGTCCGAAAACTTTCTGGACTATAAAAACCGTGGA
```

-continued

```
GTCAATGGTTCTCATCGGGGCCAGATCATCTGGAAGATCGATGCCAGCTCGTACTTTGTG

GAACCTGAAACTAAGATCTGCTTCAAATACTACCATGGAGTGAGTGGGGCCCTGCGAGCA

ACCACCCCCAGTGTCACGGTCAAAAACTCGGCAGCTCCTATTTTTAAAAGCATTGGTGCT

GATGAGACCGTCCAAGGACAAGGAAGTCGGAGGCTGATCAGCTTCTCTCTCTCAGATTTC

CAAGCCATGGGGTTGAAGAAAGGGATGTTTTTCAACCCAGACCCTTATCTGAAGATTTCC

ATTCAGCCTGGGAAACACAGCATCTTCCCCGCCCTCCCTCACCATGGACAGGAGAGGAGA

TCCAAGATCATAGGCAACACCGTGAACCCCATCTGGCAGGCCGAGCAATTCAGTTTTGTG

TCCTTGCCCACTGACGTGCTGGAAATTGAGGTGAAGGACAAGTTTGCCAAGAGCCGCCCC

ATCATCAAGCGCTTCTTGGGAAAGCTGTCGATGCCCGTTCAAAGACTCCTGGAGAGACAC

GCCATAGGGGATAGGGTGGTCAGCTACACACTTGGCCGCAGGCTTCCAACAGATCATGTG

AGTGGACAGCTGCAATTCCGATTTGAGATCACTTCCTCCATCCACCCAGATGATGAGGAG

ATTTCCCTGAGTACCGAGCCTGAGTCAGCCCAAATTCAGGACAGCCCCATGAACAACCTG

ATGGAAAGCGGCAGTGGGGAACCTCGGTCTGAGGCACCAGAGTCCTCTGAGAGCTGGAAG

CCAGAGCAGCTGGGTGAGGGCAGTGTCCCCGATGGTCCAGGGAACCAAAGCATAGAGCTT

TCCAGACCAGCTGAGGAAGCAGCAGTCATCACGGAGGCAGGAGACCAGGGCATGGTCTCT

GTGGGACCTGAAGGGGCTGGGGAGCTCCTGGCCCAGGTGCAAAAGGACATCCAGCCTGCC

CCCAGTGCAGAAGAGCTGGCCGAGCAGCTGGACCTGGGTGAGGAGGCATCAGCACTGCTG

CTGGAAGACGGTGAAGCCCAGCCAGCACCAAGGAGGAGCCCTTGGAGGAGGAAGCAACG

ACCCAGAGCCGGGCTGGAAGGGAAGAAGAGGAGAAGGAGCAGGAGGAGGAGGGAGATGTG

TCTACCCTGGAGCAGGGAGAGGGCAGGCTGCAGCTGCGGGCCTCGGTGAAGAGAAAAAGC

AGGCCCTGCTCCTTGCCTGTGTCCGAGCTGGAGACGGTGATCGCGTCAGCCTGCGGGGAC

CCCGAGACCCCGCGGACACACTACATCCGCATCCACACCCTGCTGCACAGCATGCCCTCC

GCCCAGGGCGGCAGCGCGGCAGAGGAGGAGGACGGCGCGGAGGAGGAGTCCACCCTCAAG

GACTCCTCGGAGAAGGATGGGCTCAGCGAGGTGGACACGGTGGCCGCTGACCCGTCTGCC

CTGGAAGAGGACAGAGAAGAGCCCGAGGGGGCTACTCCAGGCACGGCGCACCCTGGCCAC

TCCGGGGGCCACTTCCCCAGCCTGGCCAATGGCGCGGCCCAGGATGGCGACACGCACCCC

AGCACCGGGAGCGAGAGCGACTCCAGCCCCAGGCAAGGCGGGGACCACAGTTGCGAGGGC

TGTGACGCGTCCTGCTGCAGCCCCTCGTGCTACAGCTCCTCGTGCTACAGCACGTCCTGC

TACAGCAGCTCGTGCTACAGCGCCTCGTGCTACAGCCCCTCCTGCTACAACGGCAACAGG

TTCGCCAGCCACACGCGCTTCTCCTCCGTGGACAGCGCCAAGATCTCCGAGAGCACGGTC

TTCTCCTCGCAAGACGACGAGGAGGAGGAGAACAGCGCGTTCGAGTCGGTACCCGACTCC

ATGCAGAGCCCTGAGCTGGACCCGGAGTCCACGAACGGCGCTGGGCCGTGGCAAGACGAG

CTGGCCGCCCCTAGCGGGCACGTGGAAAGAAGCCCGGAAGGTCTGGAATCCCCCGTGGCA

GGTCCAAGCAATCGGAGAGAAGACTGGGAAGCTCGAATTGACAGCCACGGGCGGGTCTTT

TATGTGGACCACGTGAACCGCACAACCACCTGGCAGCGTCCGACGGCAGCAGCCACCCCG

GATGGCATGCGGAGATCGGGGTCCATCCAGCAGATGGAGCAACTCAACAGGCGGTATCAA

AACATTCAGCGAACCATTGCAACAGAGAGGTCCGAAGAAGATTCTGGCAGCCAAAGCTGC

GAGCAAGCCCCAGCAGGAGGAGGCGGAGGTGGAGGGAGTGACTCAGAAGCCGAATCTTCC

CAGTCCAGCTTAGATCTAAGGAGAGAGGGGTCACTTTCTCCAGTGAACTCACAAAAAATC

ACCTTGCTGCTGCAGTCCCCAGCGGTCAAGTTCATCACCAACCCCGAGTTCTTCACTGTG
```

-continued

```
CTACACGCCAATTATAGTGCCTACCGAGTCTTCACCAGTAGCACCTGCTTAAAGCACATG

ATTCTGAAAGTCCGACGGGATGCTCGCAATTTTGAACGCTACCAGCACAACCGGGACTTG

GTGAATTTCATCAACATGTTCGCAGACACTCGGCTGGAACTGCCCCGGGGCTGGAGATC

AAAACGGACCAGCAGGGAAAGTCTTTTTTCGTGGACCACAACAGTCGAGCTACCACTTTC

ATTGACCCCCGAATCCCTCTTCAGAACGGTCGTCTTCCCAATCATCTAACTCACCGACAG

CACCTCCAGAGGCTCCGAAGTTACAGCGCCGGAGAGGCCTCAGAAGTTTCTAGAAACAGA

GGAGCCTCTTTACTGGCCAGGCCAGGACACAGCTTAGTAGCTGCTATTCGAAGCCAACAT

CAACATGAGTCATTGCCACTGGCATATAATGACAAGATTGTGGCATTTCTTCGCCAGCCA

AACATTTTTGAAATGCTGCAAGAGCGTCAGCCAAGCTTAGCAAGAAACCACACACTCAGG

GAGAAAATCCATTACATTCGGACTGAGGGTAATCACGGGCTTGAGAAGTTGTCCTGTGAT

GCGGATCTGGTCATTTTGCTGAGTCTCTTTGAAGAAGAGATTATGTCCTACGTCCCCCTG

CAGGCTGCCTTCCACCCTGGGTATAGCTTCTCTCCCCGATGTTCACCCTGTTCTTCACCT

CAGAACTCCCCAGGTTTACAGAGAGCCAGTGCAAGAGCCCCTTCCCCCTACCGAAGAGAC

TTTGAGGCCAAGCTCCGCAATTTCTACAGAAAACTGGAAGCCAAAGGATTTGGTCAGGGT

CCGGGGAAAATTAAGCTCATTATTCGCCGGGATCATTTGTTGGAGGGAACCTTCAATCAG

GTGATGGCCTATTCGCGGAAAGAGCTCCAGCGAAACAAGCTCTACGTCACCTTTGTTGGA

GAGGAGGGCCTGGACTACAGTGGCCCCTCGCGGGAGTTCTTCTTCCTTCTGTCTCAGGAG

CTCTTCAACCCTTACTATGGACTCTTTGAGTACTCGGCAAATGATACTTACACGGTGCAG

ATCAGCCCCATGTCCGCATTTGTAGAAAACCATCTTGAGTGGTTCAGGTTTAGCGGTCGC

ATCCTGGGTCTGGCTCTGATCCATCAGTACCTTCTTGACGCTTTCTTCACGAGGCCCTTC

TACAAGGCACTCCTGAGACTGCCCTGTGATTTGAGTGACCTGGAATATTTGGATGAGGAA

TTCCACCAGAGTTTGCAGTGGATGAAGGACAACAACATCACAGACATCTTAGACCTCACT

TTCACTGTTAATGAAGAGGTTTTTGGACAGGTCACGGAAAGGGAGTTGAAGTCTGGAGGA

GCCAACACACAGGTGACGGAGAAAAACAAGAAGGAGTACATCGAGCGCATGGTGAAGTGG

CGGGTGGAGCGCGGCGTGGTACAGCAGACCGAGGCGCTGGTGCGCGGCTTCTACGAGGTT

GTAGACTCGAGGCTGGTGTCCGTGTTTGATGCCAGGGAGCTGGAGCTGGTGATAGCTGGC

ACCGCGAAATCGACCTAAATGACTGGCGGAATAACACTGAGTACCGGGGAGGTTACCAC

GATGGGCATCTTGTGATCCGCTGGTTCTGGGCTGCGGTGGAGCGCTTCAATAATGAGCAG

AGGCTGAGATTACTGCAGTTTGTCACGGGAACATCCAGCGTGCCCTACGAAGGCTTCGCA

GCCCTCCGTGGGAGCAATGGGCTTCGGCGCTTCTGCATAGAGAAATGGGGGAAAATTACT

TCTCTCCCCAGGGCACACACATGCTTCAACCGACTGGATCTTCCACCGTATCCCTCGTAC

TCCATGTTGTATGAAAAGCTGTTAACAGCAGTAGAGGAAACCAGCACCTTTGGACTTGAG

TGAGGACATGGAACCTCGCCTGACATTTTCCTGGCCAGTGACATCACCCTTCCTGGGATG

ATCCCCTTTTCCCTTTCCCTTAATCAACTCTCCTTTGATTTTGGTATTCCATGATTTTTA

TTTTCAAAC
```

Human NEDL2 nucleic acid sequence (uniprot.org/uniprot/Q9P2P5).

(SEQ ID NO: 31)

```
AGAGTTCCATCAGAGCCTGCAGTGGATGAAAGACAATGATATCCATGACATCCTAGACCT

CACGTTCACTGTGAACGAAGAAGTATTTGGGCAGATAACTGAACGAGAATTAAAGCCAGG

GGGTGCCAATATCCCAGTTACAGAGAAGAACAAGAAGGAGTACATCGAGAGGATGGTGAA

GTGGAGGATTGAGAGGGGTGTTGTACAGCAAACAGAGAGCTTAGTGCGTGGCTTCTATGA

GGTGGTGGATGCCAGGCTGGTATCTGTTTTTGATGCAAGAGAACTGGAATTGGTCATCGC
```

-continued

```
AGGCACAGCTGAAATAGACCTAAGTGATTGGAGAAACAACACAGAATATAGAGGAGGATA

CCATGACAATCATATTGTAATTCGGTGGTTCTGGGCTGCAGTGGAAAGATTCAACAATGA

ACAACGACTAAGGTTGTTACAGTTTGTTACAGGCACATCCAGCATTCCCTATGAAGGATT

TGCTTCACTCCGAGGGAGTAACGGCCCAAGAAGATTCTGTGTGGAGAAATGGGGGAAAAT

CACTGCTCTTCCCAGAGCGCATACATGTTTTAACCGTCTGGATCTGCCTCCCTACCCATC

CTTTTCCATGCTTTATGAAAAACTGTTGACAGCAGTTGAAGAAACCAGTACTTTTGGACT

TGAGTGACCTGGAAGCTGAATGCCCATCTCTGTGGACAGGCAGTTTCAGAAGCTGCCTTC

TAGAAGAATGATTGAACATTGGAAGTTTCAAGAGGATGCTTCCTTTAGGATAAAGCTACG

TGCTGTTGTTTTCCAGGAACAAGTGCTCTGTCACATTTGGGGACTGGAGATGAGTCCTCT

TGGAAGGATTTGGGTGAGCTTGATGCCCAGGGAACAACCCAACCGTCTTTCAATCAACAG

TTCTTGACTGCCAAACTTTTTCCATTTGTTATGTTCCAAGACAAAGATGAACCCATACAT

GATCAGCTCCACGGTAATTTTTAGGGACTCAGGAGAATCTTGAAACTTACCCTTGAACGT

GGTTCAAGCCAAACTGGCAGCATTTGGCCCAATCTCCAAATTAGAGCAAGTTAAATAATA

TAATAAAAGTAAATATATTTCCTGAAAGTACATTCATTTAAGCCCTAAGTTATAACAGAA

TATTCATTTCTTGCTTATGAGTGCCTGCATGGTGTGCACCATAGGTTTCCGCTTTCATGG

GACATGAGTGAAAATGAAACCAAGTCAATATGAGGTACCTTTACAGATTTGCAATAAGAT

GGTCTGTGACAATGTATATGCAAGTGGTATGTGTGTAATTATGGCTAAAGACAAACCATT

ATTCAGTGAATTACTAATGACAGATTTTATGCTTTATAATGCATGAAAACAATTTTAAAA

TAACTAGCAATTAATCACAGCATATCAGGAAAAAGTACACAGTGAGTTCTGTTTATTTTT

TGTAGGCTCATTATGTTTATGTTCTTTAAGATGTATATAAGAACCTACTTATCATGCTGT

ATGTATCACTCATTCCATTTTCATGTTCCATGCATACTCGGGCATCATGCTAATATGTAT

CCTTTTAAGCACTCTCAAGGAAACAAAAGGGCCTTTTATTTTTATAAAGGTAAAAAAAAT

TCCCCAAATATTTTGCACTGAATGTACCAAAGGTGAAGGGACATTACAATATGACTAACA

GCAACTCCATCACTTGAGAAGTATAATAGAAAATAGCTTCTAAATCAAACTTCCTTCACA

GTGCCGTGTCTACCACTACAAGGACTGTGCATCTAAGTAATAATTTTTTAAGATTCACTA

TATGTGATAGTATGATATGCATTTATTTAAAATGCATTAGACTCTCTTCCATCCATCAAA

TACTTTACAGGATGGCATTTAATACAGATATTTCGTATTTCCCCCACTGCTTTTTATTTG

TACAGCATCATTAAACACTAAGCTCAGTTAAGGAGCCATCAGCAACACTGAAGAGATCAG

TAGTAAGAATTCCATTTTCCCTCATCAGTGAAGACACCACAAATTGAAACTCAGAACTAT

ATTTCTAAGCCTGCATTTTCACTGATGCATAATTTTCTTATTAATATTAAGAGACAGTTT

TTCTATGGCATCTCCAAAACTGCATGACATCACTAGTCTTACTTCTGCTTAATTTTATGA

GAAGGTATTCTTCATTTTAATTGCTTTTGGGATTACTCCACATCTTTGTTTATTTCTTGA

CTAATCAGATTTTCAATAGAGTGAAGTTAAATTGGGGGTCATAAAAGCATTGGATTGACA

TATGGTTTGCCAGCCTATGGGTTTACAGGCATTGCCCAAACATTTCTTTGAGATCTATAT

TTATAAGCAGCCATGGAATTCCTATTATGGGATGTTGGCAATCTTACATTTTATAGAGGT

CATATGCATAGTTTTCATAGGTGTTTTGTAAGAACTGATTGCTCTCCTGTGAGTTAAGCT

ATGTTTACTACTGGGACCCTCAAGAGGAATACCACTTATGTTACACTCCTGCACTAAAGG

CACGTACTGCAGTGTGAAGAAATGTTCTGAAAAAGGGTTATAGAAATCTGGAAATAAGAA
```

-continued

```
AGGAAGAGCTCTCTGTATTCTATAATTGGAAGAGAAAAAAAGAAAAACTTTTAACTGGAA

ATGTTAGTTTGTACTTATTGATCATGAATACAAGTATATATTTAATTTTGCAAAAAAAAA

AAAAAAAAAAAAAAG
```

In certain embodiments, the nucleic acids may encode RNA binding proteins having two WW domains or WW domain variants from the human ITCH protein having the nucleic acid sequence:

```
                                              (SEQ ID NO: 32)
CCCTTGCCACCTGGTTGGGAGCAGAGAGTGGACCAGCACGGGCGAGTTTA

CTATGTAGATCATGTTGAGAAAAGAACAACATGGGATAGACCAGAACCTC

TACCTCCTGGCTGGGAACGGCGGGTTGACAACATGGGACGTATTTATTAT

GTTGACCATTTCACAAGAACAACAACGTGGCAGAGGCCAACACTG.
```

In other embodiments, the nucleic acids may encode RNA binding proteins having four WW domains or WW domain variants from the human ITCH protein having the nucleic acid sequence:

```
                                              (SEQ ID NO: 33)
CCCTTGCCACCTGGTTGGGAGCAGAGAGTGGACCAGCACGGGCGAGTTTA

CTATGTAGATCATGTTGAGAAAAGAACAACATGGGATAGACCAGAACCTC

TACCTCCTGGCTGGGAACGGCGGGTTGACAACATGGGACGTATTTATTAT

GTTGACCATTTCACAAGAACAACAACGTGGCAGAGGCCAACACTGGAATC

CGTCCGGAACTATGAACAATGGCAGCTACAGCGTAGTCAGCTTCAAGGAG

CAATGCAGCAGTTTAACCAGAGATTCATTTATGGGAATCAAGATTTATTT

GCTACATCACAAAGTAAAGAATTTGATCCTCTTGGTCCATTGCCACCTGG

ATGGGAGAAGAGAACAGACAGCAATGGCAGAGTATATTTCGTCAACCACA

ACACACGAATTACACAATGGGAAGACCCCAGAAGTCAAGGTCAATTAAAT

GAAAAGCCCTTACCTGAAGGTTGGGAAATGAGATTCACAGTGGATGGAAT

TCCATATTTTGTGGACCACAATAGAAGAACTACCACCTATATAGATCCCC

GCACA.
```

The nucleic acid constructs that encode the RNA binding proteins, described herein, that are fused to at least one WW domain or WW domain variant are non-naturally occurring, that is, they do not exist in nature.

In some embodiments the expression constructs comprise a nucleic acid sequence encoding a WW domain, or variant thereof from the nucleic acid sequence (SEQ ID NO: 23); (SEQ ID NO: 24); (SEQ ID NO: 25); (SEQ ID NO: 26); (SEQ ID NO: 27); (SEQ ID NO: 28); (SEQ ID NO: 29); (SEQ ID NO: 30); (SEQ ID NO: 31); (SEQ ID NO: 32) or (SEQ ID NO: 33). In certain embodiments, the expression constructs encode a fusion protein comprising a WW domain or multiple WW domains, and a Tat protein or variant thereof.

Some aspects of this invention provide expression constructs that encode any of the binding RNAs, cargo RNAs, or fusions of any of the binding RNAs and cargo RNAs described herein. In some embodiments, the expression construct comprises (a) a nucleotide sequence encoding a binding RNA, or variant thereof, operably linked to a heterologous promoter, and (b) a restriction site or a recombination site positioned adjacent to the binding RNA-encoding nucleotide sequence allowing for the insertion of a cargoRNA-encoding nucleotide sequence. In some embodiments, the expression construct comprises (a) a nucleotide sequence encoding a cargo RNA, or variant thereof, operably linked to a heterologous promoter, and (b) a restriction site or a recombination site positioned adjacent to the cargo RNA-encoding nucleotide sequence allowing for the insertion of a binding RNA-encoding nucleotide sequence. In certain embodiments, the expression constructs encode a TAR binding RNA, or variant thereof fused to a cargo RNA. In some embodiments, the cargo RNA is an mRNA.

Nucleic acids encoding any of the fusion proteins, binding RNAs, and/or cargoRNAs, described herein, may be in any number of nucleic acid "vectors" known in the art. As used herein, a "vector" means any nucleic acid or nucleic acid-bearing particle, cell, or organism capable of being used to transfer a nucleic acid into a host cell. The term "vector" includes both viral and nonviral products and means for introducing the nucleic acid into a cell. A "vector" can be used in vitro, ex vivo, or in vivo. Non-viral vectors include plasmids, cosmids, artificial chromosomes (e.g., bacterial artificial chromosomes or yeast artificial chromosomes) and can comprise liposomes, electrically charged lipids (cytofectins), DNA-protein complexes, and biopolymers, for example. Viral vectors include retroviruses, lentiviruses, adeno-associated virus, pox viruses, baculovirus, reoviruses, vaccinia viruses, herpes simplex viruses, Epstein-Barr viruses, and adenovirus vectors, for example. Vectors can also comprise the entire genome sequence or recombinant genome sequence of a virus. A vector can also comprise a portion of the genome that comprises the functional sequences for production of a virus capable of infecting, entering, or being introduced to a cell to deliver nucleic acid therein.

Expression of any of the fusion proteins, binding RNAs, and/or cargoRNAs, described herein, may be controlled by any regulatory sequence (e.g. a promoter sequence) known in the art. Regulatory sequences, as described herein, are nucleic acid sequences that regulate the expression of a nucleic acid sequence. A regulatory or control sequence may include sequences that are responsible for expressing a particular nucleic acid (e.g., a ARRDC1:Tat fusion protein) or may include other sequences, such as heterologous, synthetic, or partially synthetic sequences. The sequences can be of eukaryotic, prokaryotic or viral origin that stimulate or repress transcription of a gene in a specific or non-specific manner and in an inducible or non-inducible manner. Regulatory or control regions may include origins of replication, RNA splice sites, introns, chimeric or hybrid introns, promoters, enhancers, transcriptional termination sequences, poly A sites, locus control regions, signal sequences that direct the polypeptide into the secretory pathways of the target cell, and introns. A heterologous regulatory region is not naturally associated with the expressed nucleic acid it is linked to. Included among the heterologous regulatory regions are regulatory regions from a different species, regulatory regions from a different gene, hybrid regulatory sequences, and regulatory sequences that do not occur in nature, but which are designed by one of ordinary skill in the art.

The term operably linked refers to an arrangement of sequences or regions wherein the components are configured so as to perform their usual or intended function. Thus, a regulatory or control sequence operably linked to a coding sequence is capable of affecting the expression of the coding sequence. The regulatory or control sequences need not be contiguous with the coding sequence, so long as they function to direct the proper expression or polypeptide production. Thus, for example, intervening untranslated but transcribed sequences can be present between a promoter sequence and the coding sequence and the promoter sequence can still be considered operably linked to the coding sequence. A promoter sequence, as described herein, is a DNA regulatory region a short distance from the 5' end of a gene that acts as the binding site for RNA polymerase. The promoter sequence may bind RNA polymerase in a cell and/or initiate transcription of a downstream (3' direction) coding sequence. The promoter sequence may be a promoter capable of initiating transcription in prokaryotes or eukaryotes. Some non-limiting examples of eukaryotic promoters include the cytomegalovirus (CMV) promoter, the chicken β-actin (CBA) promoter, and a hybrid form of the CBA promoter (CBh).

Cells Producing Microvesicles Containing RNA Binding Proteins, Binding RNAs, and Cargo RNAs A microvesicle-producing cell of the present invention may be a cell containing any of the expression constructs, any of the fusion proteins, any of the binding RNAs, any of the cargo RNAs, and/or any of the binding RNAs fused to any of the cargo RNAs described herein. For example, an inventive microvesicle-producing cell may contain one or more recombinant expression constructs encoding (1) an ARRDC1 protein, or PSAP (SEQ ID NO: 1) motif-containing variant thereof and (2) an RNA binding protein (e.g., a Tat protein), that is associated with the ARRDC1 protein, or PSAP (SEQ ID NO: 1) motif-containing variant thereof. In some embodiments, a microvesicle-producing cell may contain one or more recombinant expression constructs encoding (1) an ARRDC1 protein, or PSAP (SEQ ID NO: 1) motif-containing variant thereof, and (2) an RNA binding protein fused to at least one WW domain, or variant thereof, under the control of a heterologous promoter. In certain embodiments, an expression construct in the microvesicle producing cell encodes a binding RNA that associates (e.g., binds specifically) with the RNA binding protein. In some embodiments, an expression construct in the microvesicle producing cell encodes a cargo RNA that associates with the binding RNA. For example, the construct may encode a binding RNA that is fused to a cargo RNA. In some embodiments, the microvesicle-producing cell may express a binding RNA and a cargo RNA from different expression constructs or express a binding RNA and a cargo RNA under the control of different promoters.

Any of the expression constructs, described herein, may be stably inserted into the genome of the cell. In some embodiments, the expression construct is maintained in the cell, but not inserted into the genome of the cell. In some embodiments, the expression construct is in a vector, for example, a plasmid vector, a cosmid vector, a viral vector, or an artificial chromosome. In some embodiments, the expression construct further comprises additional sequences or elements that facilitate the maintenance and/or the replication of the expression construct in the microvesicle-producing cell, or that improve the expression of the fusion protein in the cell. Such additional sequences or elements may include, for example, an origin of replication, an antibiotic resistance cassette, a polyA sequence, and/or a transcriptional isolator. Some expression constructs suitable for the generation of microvesicle producing cells according to aspects of this invention are described elsewhere herein. Methods and reagents for the generation of additional expression constructs suitable for the generation of microvesicle producing cells according to aspects of this invention will be apparent to those of skill in the art based on the present disclosure. In some embodiments, the microvesicle producing cell is a mammalian cell, for example, a mouse cell, a rat cell, a hamster cell, a rodent cell, or a nonhuman primate cell. In some embodiments, the microvesicle producing cell is a human cell.

One skilled in the art may employ conventional techniques, such as molecular or cell biology, virology, microbiology, and recombinant DNA techniques. Exemplary techniques are explained fully in the literature. For example, one may rely on the following general texts to make and use the invention: Sambrook et al., Molecular Cloning: A Laboratory Manual, Second Edition (1989) Cold Spring Harbor Laboratory Press, Cold Spring Harbor, N.Y., and Sambrook et al. Third Edition (2001); DNA Cloning: A Practical Approach, Volumes I and II (D. N. Glover ed. 1985); Oligonucleotide Synthesis (M. J. Gaited. 1984); Nucleic Acid Hybridization (B. D. Hames & S. J. Higgins eds. (1985)); Transcription And Translation Hames & Higgins, eds. (1984); Animal Cell Culture (RI. Freshney, ed. (1986)); Immobilized Cells And Enzymes (IRL Press, (1986)); Gennaro et al. (eds.) Remington's Pharmaceutical Sciences, 18th edition; B. Perbal, A Practical Guide To Molecular Cloning (1984); F. M. Ausubel et al. (eds.), Current Protocols in Molecular Biology, John Wiley & Sons, Inc. (updates through 2001), Coligan et al. (eds.), Current Protocols in Immunology, John Wiley & Sons, Inc. (updates through 2001); W. Paul et al. (eds.) Fundamental Immunology, Raven Press; E. J. Murray et al. (ed.) Methods in Molecular Biology: Gene Transfer and Expression Protocols, The Humana Press Inc. (1991)(especially vol. 7); and J. E. Celis et al., Cell Biology: A Laboratory Handbook, Academic Press (1994).

Delivery of ARMMs Containing RNA Binding Proteins, Binding RNAs and Cargo RNAs.

The inventive microvesicles (e.g., ARMMs) containing any of the expression constructs, any of the fusion proteins, any of the binding RNAs, any of the cargo RNAs, and/or any of the binding RNAs fused to any of the cargo RNAs, described herein, may further have a targeting moiety. The targeting moiety may be used to target the delivery of ARMMs to specific cell types, resulting in the release of the contents of the ARMM into the cytoplasm of the specific targeted cell type. A targeting moiety may selectively bind an antigen of the target cell. For example, the targeting moiety may be a membrane-bound immunoglobulin, an integrin, a receptor, a receptor ligand, an aptamer, a small molecule, or a variant thereof. Any number of cell surface proteins may also be included in an ARMM to facilitate the binding of an ARMM to a target cell and/or to facilitate the uptake of an ARMM into a target cell. Integrins, receptor tyrosine kinases, G-protein coupled receptors, and membrane-bound immunoglobulins suitable for use with embodiments of this invention will be apparent to those of skill in the art and the invention is not limited in this respect. For example, in some embodiments, the integrin is an α1β1, α2β1, α4β1, α5β1, α6β1, αLβ2, αMβ2, αIIbβ3, αVβ3, αVβ5, αVβ6, or a α6β4 integrin. In some embodiments, the receptor tyrosine kinase is a an EGF receptor (ErbB family), insulin receptor, PDGF receptor, FGF receptor, VEGF receptor, HGF receptor, Trk receptor, Eph receptor, AXL receptor, LTK receptor, TIE receptor, ROR receptor, DDR receptor, RET receptor, KLG receptor, RYK receptor, or MuSK receptor. In some embodiments, the G-protein coupled receptor is a rhodopsin-like receptor, the secretin receptor, metabotropic glutamate/pheromone receptor, cyclic AMP receptor, frizzled/smoothened receptor, CXCR4, CCR5, or beta-adrenergic receptor.

Any number of membrane-bound immunoglobulins, known in the art, may be used as targeting moieties to target the delivery of ARMMs containing a cargo protein to any number of target cell types. In certain embodiments, the membrane-bound immunoglobulin targeting moiety binds a tumor associated or tumor specific antigen. Some non-limiting examples of tumor antigens include, CA19-9, c-met, PD-1, CTLA-4, ALK, AFP, EGFR, Estrogen receptor (ER), Progesterone receptor (PR), HER2/neu, KIT, B-RAF, S100, MAGE, Thyroglobulin, MUC-1, and PSMA (Bigbee W., et al. "Tumor markers and immunodiagnosis.", *Cancer Medicine*. 6th ed. Hamilton, Ontario, Canada: BC Decker Inc., 2003; Andriole G, et al. "Mortality results from a randomized prostate-cancer screening trial.", *New England Journal of Medicine*, 360(13):1310-1319, 2009; Schröder F H, et al. "Screening and prostate-cancer mortality in a randomized European study." *New England Journal of Medicine*, 360(13):1320-1328, 2009; Buys S S, et al. "Effect of screening on ovarian cancer mortality: the Prostate, Lung, Colorectal and Ovarian (PLCO) Cancer Screening Randomized Controlled Trial.", *JAMA*, 305(22):2295-2303, 2011; Cramer D W et al. "Ovarian cancer biomarker performance in prostate, lung, colorectal, and ovarian cancer screening trial specimens." *Cancer Prevention Research*, 4(3):365-374, 2011; Roy D M, et al. "Candidate prognostic markers in breast cancer: focus on extracellular proteases and their inhibitors.", *Breast Cancer. July* 3; 6:81-91, 2014; Tykodi S S. et al. "PD-1 as an emerging therapeutic target in renal cell carcinoma: current evidence." *Onco Targets Ther. July* 25; 7:1349-59, 2014; and Weinberg R A. *The Biology of Cancer*, Garland Science, Taylor & Francis Group LLC, New York, N.Y., 2007; the entire contents of each are incorporated herein by reference).

In certain embodiments, the membrane-bound immunoglobulin targeting moiety binds to an antigen of a specific cell type. The cell type may be a stem cell, such as a pluripotent stem cell. Some non-limiting examples of antigens specific to pluripotent stem cells include Oct4 and Nanog, which were the first proteins identified as essential for both early embryo development and pluripotency maintenance in embryonic stem cells (Nichols J, et al. "Formation of pluripotent stem cells in the mammalian embryo depends on the POU transcription factor Oct4.", *Cell*. 95:379-91, 1998; the contents of which are hereby incorporated by reference). In addition to Oct4, Sox2 and Nanog, many other pluripotent stem cell markers have been identified, including Sall4, Dax1, Essrb, Tbx3, Tcl1, Rif1, Nac1 and Zfp281 (Loh Y, et al. "The Oct4 and Nanog transcription network regulates pluripotency in mouse embryonic stem cells.", *Nat Genet*. 38:431-40, 2006). The membrane-bound immunoglobulin targeting moiety may also bind to an antigen of a differentiated cell type. For example, the targeting moiety may bind to an antigen specific for a lung epithelial cell to direct the delivery of an ARMM cargo RNA to lung epithelial cells. As a non-limiting example, a membrane-bound immunoglobulin targeting moiety may bind to the alveolar epithelial type 1 cell specific protein $RTI_{40}$ or $HTI_{56}$ to deliver cargo proteins to alveolar epithelial type 1 cells (McElroy M C et al. "The use of alveolar epithelial type I cell-selective markers to investigate lung injury and repair.", *European Respiratory Journal* 24:4, 664-673, 2004; the entire contents of which are hereby incorporated by reference). As another example, the targeting moiety may bind a mucin, such as muc5ac, or muc5b. It should be appreciated that the examples of antigens provided in this application are not limiting and the targeting moiety may be any moiety capable of binding any cellular antigen known in the art.

Some aspects of this invention relate to the recognition that ARMMs are taken up by target cells, and ARMM uptake results in the release of the contents of the ARMM into the cytoplasm of the target cells. In some embodiments, the cargo RNA is an agent that affects a desired change in the target cell, for example, a change in cell survival, proliferation rate, a change in differentiation stage, a change in a cell identity, a change in chromatin state, a change in the transcription rate of one or more genes, a change in the transcriptional profile, or a post-transcriptional change in gene compression of the target cell. It will be understood by those of skill in the art, that the agent to be delivered (e.g., cargo RNA) will be chosen according to the desired effect in the target cell.

Using any of the cargo RNAs, described herein, or any of the therapeutic RNAs known in the art, expression of one or more genes in a target cell may be modulated In some embodiments, cells from a subject are obtained and a cargo RNA is delivered to the cells by a system or method provided herein ex vivo. In some embodiments, the treated cells are selected for those cells in which a desired gene is expressed or repressed. In some embodiments, treated cells carrying a desired cargo RNA are returned to the subject they were obtained from.

As another example, to augment the differentiation stage of a target cell, for example, to reprogram a differentiated target cell into an embryonic stem cell-like stage, the cell is contacted, in some embodiments, with ARMMs with cargo RNAs that express reprogramming factors, for example, mRNAs that express Oct4, Sox2, c-Myc, and/or KLF4. Similarly, to affect the change in the chromatin state of a target cell, the cell is contacted, in some embodiments, with ARMMs containing a cargo RNA that expresses a chromatin modulator, for example, a DNA methyltransferase, or a histone deacetylase. As another example, if survival of the target cell is to be diminished, the target cell, in some embodiments, is contacted with ARMMs comprising a cytotoxic agent, for example, an mRNA that expresses a cytotoxic protein, or an siRNA that inhibits expression of a protein in a target cell that promotes survival. Additional cargo RNAs suitable for inclusion into ARMMs and for a ARMM-mediated delivery to a target cell or target cell population will be apparent to those skilled in the art, and the invention is not limited in this respect.

In some embodiments, the ARMMs comprising any of the fusion proteins, any of the binding RNAs, any of the cargo RNAs, and/or any of the binding RNAs fused to any of the cargo RNAs, described herein, further include a detectable label. Such ARMMs allow for the labeling of a target cell without genetic manipulation. Detectable labels suitable for direct delivery to target cells are known in the art, and include, but are not limited to, fluorescent proteins, fluorescent dyes, membrane-bound dyes, and enzymes, for example, membrane-bound or cytosolic enzymes, catalyzing the reaction resulting in a detectable reaction product. Detectable labels suitable according to some aspects of this invention further include membrane-bound antigens, for example, membrane-bound ligands that can be detected with commonly available antibodies or antigen binding agents.

In some embodiments, ARMMs are provided that comprise a cargo RNA that encodes a transcription factor, a transcriptional repressor, a fluorescent protein, a kinase, a phosphatase, a protease, a ligase, a chromatin modulator, or a recombinase. In some embodiments, ARMMs are provided that comprise a cargo RNA (e.g., an siRNA) that inhibits expression of a transcription factor, a transcriptional repressor, a fluorescent protein, a kinase, a phosphatase, a protease, a ligase, a chromatin modulator, or a recombinase. In some embodiments, the cargo RNA is a therapeutic RNA. In some embodiments the cargo RNA is an RNA that affects a change in the state or identity of a target cell. For example, in some embodiments, the cargo RNA encodes a reprogramming factor. Suitable transcription factors, transcriptional repressors, fluorescent proteins, kinases, phosphatases, proteases, ligases, chromatin modulators, recombinases, and reprogramming factors may be encoded by a cargo RNA that is associated with a binding RNA to facilitate their incorporation into ARMMs and their function may be tested by any methods that are known to those skilled in the art, and the invention is not limited in this respect.

Methods for isolating the ARMMs described herein are also provided. One exemplary method includes collecting the culture medium, or supernatant, of a cell culture comprising microvesicle-producing cells. In some embodiments, the cell culture comprises cells obtained from a subject, for example, cells suspected to exhibit a pathological phenotype, for example, a hyperproliferative phenotype. In some embodiments, the cell culture comprises genetically engineered cells producing ARMMs, for example, cells expressing a recombinant ARMM protein, for example, a recombinant ARRDC1 or TSG101 protein, such as an ARRDC1 or TSG101 protein fused to an RNA binding protein (e.g., a Tat protein) or variant thereof. In some embodiments, the supernatant is pre-cleared of cellular debris by centrifugation, for example, by two consecutive centrifugations of increasing G value (e.g., 500G and 2000G). In some embodiments, the method comprises passing the supernatant through a 0.2 μm filter, eliminating all large pieces of cell debris and whole cells. In some embodiments, the supernatant is subjected to ultracentrifugation, for example, at 120,000G for 2 hours, depending on the volume of centrifugate. The pellet obtained comprises microvesicles. In some embodiments, exosomes are depleted from the microvesicle pellet by staining and/or sorting (e.g., by FACS or MACS) using an exosome marker as described herein. Isolated or enriched ARMMs can be suspended in culture media or a suitable buffer, as described herein.

Methods of Microvesicle-Mediated Delivery of Cargo RNAs

Some aspects of this invention provide a method of delivering an agent, for example, a cargo RNA associated with a binding RNA (e.g., a P53-expressing RNA associated with a TAR element) to a target cell. In some embodiments, the cargo RNA is loaded into an ARMM by co-expressing in a cell, the cargo RNA associated with a binding RNA (e.g., a TAR element) and an ARRDC1 protein fused to an RNA binding protein (e.g., a Tat protein), or an RNA binding protein (e.g., a Tat protein) fused to a WW domain. The target cell can be contacted with an ARMM in different ways. For example, a target cell may be contacted directly with an ARMM as described herein, or with an isolated ARMM from a microvesicle producing cell. The contacting can be done in vitro by administering the ARMM to the target cell in a culture dish, or in vivo by administering the ARMM to a subject (e.g., parenterally or non-parenterally). In some embodiments, an ARMM is produced from a cell obtained from a subject. In some embodiments, the ARMM that was produced from a cell that was obtained from the subject is administered to the subject from which the ARMM producing cell was obtained. In some embodiments, the ARMM that was produced from a cell that was obtained from the subject is administered to a subject different from the subject from which the ARMM producing cell was obtained. As one example, a cell may be obtained from a subject and engineered to express one or more of the constructs provided herein (e.g., engineered to express a cargo RNA associated with a binding RNA, an ARRDC1 protein, an ARRDC1 protein fused to an RNA binding protein, and/or an RNA binding protein fused to a WW domain). The cell obtained from the subject and engineered to express one or more of the constructs provided herein may be administered to the same subject, or a different subject, from which the cell was obtained. Alternatively, the cell obtained from the subject and engineered to express one or more of the constructs provided herein produces ARMMs, which may be isolated and administered to the same subject form which the cell was obtained or administered to a different subject from which the cell was obtained.

Alternatively, a target cell can be contacted with a microvesicle producing cell as described herein, for example, in vitro by co-culturing the target cell and the microvesicle producing cell, or in vivo by administering a microvesicle producing cell to a subject harboring the target cell. Accordingly, the method may include contacting the target cell with a microvesicle, for example, an ARMM containing any of the cargo RNAs to be delivered, as described herein. The target cell may be contacted with a microvesicle-producing cell, as described herein, or with an isolated microvesicle that has a lipid bilayer, an ARRDC1 protein or variant thereof, a cargo RNA associated with a binding RNA and an RNA binding protein (e.g., a Tat protein) associated with ARRDC1 or a WW domain.

It should be appreciated that the target cell may be of any origin, for example from an organism. In some embodiments, the target cell is a mammalian cell. Some non-limiting examples of a mammalian cell include, without limitation, a mouse cell, a rat cell, hamster cell, a rodent cell, and a nonhuman primate cell. In some embodiments, the target cell is a human cell. It should also be appreciated that the target cell may be of any cell type. For example, the target cell may be a stem cell, which may include embryonic stem cells, induced pluripotent stem cells (iPS cells), fetal stem cells, cord blood stem cells, or adult stem cells (i.e., tissue specific stem cells). In other cases, the target cell may be any differentiated cell type found in a subject. In some embodiments, the target cell is a cell in vitro, and the method includes administering the microvesicle to the cell in vitro, or co-culturing the target cell with the microvesicle-producing cell in vitro. In some embodiments, the target cell is a cell in a subject, and the method comprises administering the microvesicle or the microvesicle-producing cell to the subject. In some embodiments, the subject is a mammalian subject, for example, a rodent, a mouse, a rat, a hamster, or a non-human primate. In some embodiments, the subject is a human subject.

In some embodiments, the target cell is a pathological cell. In some embodiments, the target cell is a cancer cell. In some embodiments, the microvesicle is associated with a binding agent that selectively binds an antigen on the surface of the target cell. In some embodiments, the antigen of the target cell is a cell surface antigen. In some embodiments, the binding agent is a membrane-bound immunoglobulin, an integrin, a receptor, or a receptor ligand. Suitable surface antigens of target cells, for example of specific target cell types, e.g. cancer cells, are known to those of skill in the art, as are suitable binding agents that specifically bind such antigens. Methods for producing membrane-bound binding agents, for example, membrane-bound immunoglobulins, membrane-bound antibodies or antibody fragments that specifically bind a surface antigen expressed on the surface of cancer cells, are also known to those of skill in the art. The choice of the binding agent will depend, of course, on the identity or the type of target cell. Cell surface antigens specifically expressed on various types of cells that can be targeted by ARMMs comprising membrane-bound binding agents will be apparent to those of skill in the art. It will be appreciated that the present invention is not limited in this respect.

Co-Culture Systems

Some aspects of this invention provide in vitro cell culture systems having at least two types of cells: microvesicle producing cells, and target cells that take up the microvesicles produced. Accordingly, in the co-culture systems provided herein, there is a shuffling of the contents of the microvesicles (e.g., ARMMs) to the target cells. Such co-culture systems allow for the expression of a gene product or multiple gene products generated by the microvesicle producing cells in the target cells without genetic manipulation of the target cells.

In some embodiments, a co-culture system is provided that comprises (a) a microvesicle-producing cell population having a recombinant expression construct encoding (i) an ARRDC1 protein, or variant thereof fused to an RNA binding protein (e.g., Tat), under the control of a heterologous promoter, and/or (ii) an RNA binding protein (e.g., Tat) fused to a WW domain, under the control of a heterologous promoter, and/or (iii) an ARRDC1 protein, or variant thereof, under the control of a heterologous promoter, and/or (iv) a binding RNA (e.g., a TAR element) fused to a cargo RNA under the control of a heterologous promoter, and/or (v) a binding RNA (e.g., a TAR element) that associates with a cargo RNA, where the binding RNA and the cargo RNA are under the control of a heterologous promoter; and (b) a target cell population. In some embodiments, the ARRDC1 variant comprises a PSAP (SEQ ID NO: 1) motif. In other embodiments, the microvesicle comprises a TSG101 protein or variant thereof. In some embodiments, the TSG101 protein comprises a UEV domain.

In some embodiments, the microvesicle-producing cell comprises a plurality of expression constructs encoding a plurality of the proteins, fusion proteins and or RNAs provided herein. In some embodiments, the microvesicle-producing cell comprises the following recombinant expression constructs as described in the preceeding paragraph:

In some embodiments, the microvesicle-producing cell comprises one or more expression constructs encoding (i) an ARRDC1 protein, or variant thereof fused to an RNA binding protein (e.g., Tat), under the control of a heterologous promoter, and (iv) a binding RNA (e.g., a TAR element) fused to a cargo RNA under the control of a heterologous promoter.

In some embodiments, the microvesicle-producing cell comprises one or more expression constructs encoding (i) an ARRDC1 protein, or variant thereof fused to an RNA binding protein (e.g., Tat), under the control of a heterologous promoter, and (iv) a binding RNA (e.g., a TAR element) fused to a cargo RNA under the control of a heterologous promoter, and (iii) an ARRDC1 protein, or variant thereof, under the control of a heterologous promoter.

In some embodiments, the microvesicle-producing cell comprises one or more expression constructs encoding (i) an ARRDC1 protein, or variant thereof fused to an RNA binding protein (e.g., Tat), under the control of a heterologous promoter, and (v) a binding RNA (e.g., a TAR element) that associates with a cargo RNA, where the binding RNA and the cargo RNA are under the control of a heterologous promoter.

In some embodiments, the microvesicle-producing cell comprises one or more expression constructs encoding (i) an ARRDC1 protein, or variant thereof fused to an RNA binding protein (e.g., Tat), under the control of a heterologous promoter, and (v) a binding RNA (e.g., a TAR element) that associates with a cargo RNA, where the binding RNA and the cargo RNA are under the control of a heterologous promoter, and (iii) an ARRDC1 protein, or variant thereof, under the control of a heterologous promoter In some embodiments, the microvesicle-producing cell comprises one or more expression constructs encoding (ii) an RNA binding protein (e.g., Tat) fused to a WW domain, under the control of a heterologous promoter, and (iv) a binding RNA (e.g., a TAR element) fused to a cargo RNA under the control of a heterologous promoter.

In some embodiments, the microvesicle-producing cell comprises one or more expression constructs encoding (ii) an RNA binding protein (e.g., Tat) fused to a WW domain, under the control of a heterologous promoter, and (iv) a binding RNA (e.g., a TAR element) fused to a cargo RNA under the control of a heterologous promoter, and (iii) an ARRDC1 protein, or variant thereof, under the control of a heterologous promoter.

In some embodiments, the microvesicle-producing cell comprises one or more expression constructs encoding (ii) an RNA binding protein (e.g., Tat) fused to a WW domain, under the control of a heterologous promoter, and (v) a binding RNA (e.g., a TAR element) that associates with a cargo RNA, where the binding RNA and the cargo RNA are under the control of a heterologous promoter.

In some embodiments, the microvesicle-producing cell comprises one or more expression constructs encoding (ii) an RNA binding protein (e.g., Tat) fused to a WW domain, under the control of a heterologous promoter, and (v) a binding RNA (e.g., a TAR element) that associates with a cargo RNA, where the binding RNA and the cargo RNA are under the control of a heterologous promoter, and (iii) an ARRDC1 protein, or variant thereof, under the control of a heterologous promoter.

One exemplary application of a co-culture system as provided herein is the programming or reprogramming of a target cell without genetic manipulation. For example, in some embodiments, the target cell is a differentiated cell, for example, a fibroblast cell. In some embodiments, the microvesicle producing cells are feeder cells or non-proliferating cells. In some embodiments, the microvesicle-producing cells produce ARMMs comprising one or more cargo RNAs that encode one or more reprogramming factors, (e.g., Oct4, Sox2, Klf4, and c-myc) that are fused to or are associated with a binding RNA. In other embodiments, the microvesicle-producing cells produce ARMMs comprising one or more cargo RNAs that interfere with the expression of one or more genes, for example a gene involved or associated with cell differentiation. In some embodiments, co-culture of the differentiated target cells with the microvesicle producing cells results in the reprogramming of the differentiated target cells to an embryonic state. In some embodiments, co-culture of the differentiated target cells with the microvesicle producing cells results in the programming, or trans-differentiation, of the target cells to a differentiated cell states that is different from the original cell state of the target cells.

Another exemplary application of a co-culture system, as provided herein, is the directed differentiation of embryonic stem cells. In some embodiments, the target cells are undifferentiated embryonic stem cells, and the microvesicle producing cells produce ARMMs comprising one or more cargo RNAs that encode one or more differentiation factors that are fused to or are associated with a binding RNA. Exemplary differentiation factors may include, but are not limited to signaling molecules or transcription factors that trigger or facilitate the differentiation of the embryonic stem cells into differentiated cells of a desired lineage, for example neuronal cells, or mesenchymal cells. In other embodiments, the microvesicle-producing cells produce ARMMs comprising one or more cargo RNAs that interfere with the expression of one or more genes, for example a gene involved or associated with undifferentiated cells.

Yet another exemplary application of a co-culture system, as provided herein, is the maintenance of stem cells, for example, of embryonic stem cells or of adult stem cells in an undifferentiated state. In some such embodiments, the microvesicle producing cells produce ARMMs comprising one or more cargo RNAs that encode one or more signaling molecules and/or transcription factors that are fused to or are associated with a binding RNA. In some embodiments, the one or more signaling molecules and/or transcription factors promote stem cell maintenance and/or inhibit stem cell differentiation. The microvesicle producing cells may create a microenvironment for the stem cells that mimics a naturally occurring stem cell niche. In other embodiments, the microvesicle-producing cells produce ARMMs comprising one or more cargo RNAs that interfere with the expression of one or more genes, for example by inhibiting expression of a gene involved or associated with inhibiting stem cell maintenance or promoting stem cell differentiation.

The microvesicle-producing cell of a culture system may be a cell of any type or origin that is capable of producing any of the ARMMs described herein. For example, the microvesicle-producing cell may be a mammalian cell, examples of which include but are not limited to, a cell from a rodent, a mouse, a rat, a hamster, or a non-human primate. The microvesicle-producing cell may also be from a human. One non-limiting example of a microvesicle-producing cell capable of producing an ARMM is a human embryonic kidney 293T cell. The microvesicle-producing cell may be a proliferating or a non-proliferating cell. In some embodiments, the microvesicle-producing cell is a feeder cell which supports the growth of other cells in the culture. Feeder cells may provide attachment substrates, nutrients, or other factors that are needed for the growth of cells in culture.

The target cell of the culture system can be a cell of any type or origin, which may be contacted with an ARMM from any of the microvesicle-producing cells, described herein. For example, the target cell may be a mammalian cell, examples of which include but are not limited to, a cell from a rodent, a mouse, a rat, a hamster, or a non-human primate. The target cell may also be from a human. The target cell may be from an established cell line (e.g., a 293T cell), or a primary cell cultured ex vivo (e.g., cells obtained from a subject and grown in culture). Target cells may be hematologic cells (e.g., hematopoietic stem cells, leukocytes, thrombocytes or erythrocytes), or cells from solid tissues, such as liver cells, kidney cells, lung cells, heart cells bone cells, skin cells, brain cells, or any other cell found in a subject. Cells obtained from a subject can be contacted with an ARMM from a microvesicle-producing cell and subsequently re-introduced into the same or another subject. In some embodiments, the target cell is a stem cell. The stem cell may be a totipotent stem cell that can differentiate into embryonic and extraembryonic cell types. The stem cell may also be a pluripotent stem cell, a multipotent stem cell, an oligopotent stem cell or a unipotent stem cell. In other embodiments, the target cell is a differentiated cell.

Pharmaceutical Compositions

Other aspects of the present disclosure relate to pharmaceutical compositions comprising any of the ARMMs or microvesicle (e.g., ARMM) producing cells provided herein. The term "pharmaceutical composition", as used herein, refers to a composition formulated for pharmaceutical use. In some embodiments, the pharmaceutical composition further comprises a pharmaceutically acceptable carrier. In some embodiments, the pharmaceutical composition comprises additional agents (e.g. for specific delivery, increasing half-life, or other therapeutic compounds).

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the compound from one site (e.g., the delivery site) of the body, to another site (e.g., organ, tissue or portion of the body). A pharmaceutically acceptable carrier is "acceptable" in the sense of being compatible with the other ingredients of the formulation and not injurious to the tissue of the subject (e.g., physiologically compatible, sterile, physiologic pH, etc.). Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (24) other non-toxic compatible substances employed in pharmaceutical formulations.

Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

In some embodiments, the pharmaceutical composition is formulated for delivery to a subject, e.g., for delivering a cargo RNA (e.g. a cargo RNA that expresses a tumor suppressor) to a cell. Suitable routes of administrating the pharmaceutical composition described herein include, without limitation: topical, subcutaneous, transdermal, intradermal, intralesional, intraarticular, intraperitoneal, intravesical, transmucosal, gingival, intradental, intracochlear, transtympanic, intraorgan, epidural, intrathecal, intramuscular, intravenous, intravascular, intraosseus, periocular, intratumoral, intracerebral, and intracerebroventricular administration.

In some embodiments, the pharmaceutical composition described herein is administered locally to a diseased site (e.g., tumor site). In some embodiments, the pharmaceutical composition described herein is administered to a subject by injection, by means of a catheter, by means of a suppository, or by means of an implant, the implant being of a porous, non-porous, or gelatinous material, including a membrane, such as a sialastic membrane, or a fiber.

In other embodiments, the pharmaceutical composition described herein is delivered in a controlled release system. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105.) Other controlled release systems are discussed, for example, in Langer, supra.

In some embodiments, the pharmaceutical composition is formulated in accordance with routine procedures as a composition adapted for intravenous or subcutaneous administration to a subject, e.g., a human. In some embodiments, pharmaceutical composition for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical composition is administered by injection, an ampoule of sterile water for injection or saline can be provided so that the ingredients can be mixed prior to administration.

A pharmaceutical composition for systemic administration may be a liquid, e.g., sterile saline, lactated Ringer's or Hank's solution. In addition, the pharmaceutical composition can be in solid forms and re-dissolved or suspended immediately prior to use. Lyophilized forms are also contemplated.

The pharmaceutical composition can be contained within a lipid particle or vesicle, such as a liposome or microcrystal, which is also suitable for parenteral administration. The particles can be of any suitable structure, such as unilamellar or plurilamellar, so long as compositions are contained therein. Compounds can be entrapped in "stabilized plasmid-lipid particles" (SPLP) containing the fusogenic lipid dioleoylphosphatidylethanolamine (DOPE), low levels (5-10 mol %) of cationic lipid, and stabilized by a polyethyleneglycol (PEG) coating (Zhang Y. P. et al., Gene Ther. 1999, 6:1438-47). Positively charged lipids such as N-[1-(2,3-dioleoyloxi)propyl]-N,N,N-trimethyl-amoniummethyl-sulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757; each of which is incorporated herein by reference.

The pharmaceutical composition described herein may be administered or packaged as a unit dose, for example. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

Further, the pharmaceutical composition can be provided as a pharmaceutical kit comprising (a) a container containing an ARMM or microvesicle producing cell of the invention and (b) a second container containing a pharmaceutically acceptable diluent (e.g., sterile water) for injection. The pharmaceutically acceptable diluent can be used e.g., for reconstitution or dilution of the ARMM or microvesicle producing cell of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In another aspect, an article of manufacture containing materials useful for the treatment of the diseases described above is included. In some embodiments, the article of manufacture comprises a container and a label. Suitable containers include, for example, bottles, vials, syringes, and test tubes. The containers may be formed from a variety of materials such as glass or plastic. In some embodiments, the container holds a composition that is effective for treating a disease described herein and may have a sterile access port. For example, the container may be an intravenous solution bag or a vial having a stopper pierceable by a hypodermic injection needle. The active agent in the composition is a compound of the invention. In some embodiments, the label on or associated with the container indicates that the composition is used for treating the disease of choice. The article of manufacture may further comprise a second container comprising a pharmaceutically-acceptable buffer, such as phosphate-buffered saline, Ringer's solution, or dextrose solution. It may further include other materials desirable from a commercial and user standpoint, including other buffers, diluents, filters, needles, syringes, and package inserts with instructions for use.

Kits, Vectors, Cells

Some aspects of this disclosure provide kits comprising a nucleic acid construct comprising a nucleotide sequence encoding one or more of any of the proteins (e.g., ARRDC1, and TSG101), fusion proteins (e.g., ARRDC1-Tat, and WW-Tat), and/or RNAs (e.g., TAR, TAR-cargoRNA) provided herein. In some embodiments, the nucleotide sequence encodes any of the proteins, fusion proteins, and/or RNAs provided herein. In some embodiments, the nucleotide sequence comprises a heterologous promoter that drives expression of any of the proteins, fusion proteins, and/or RNAs provided herein.

Some aspects of this disclosure provide kits comprising a nucleic acid construct, comprising (a) a nucleotide sequence encoding an ARRDC1 protein fused to an RNA binding protein (e.g., Tat), or a fusion protein comprising a WW domain fused to an RNA binding protein (e.g., Tat) as provided herein, optionally wherein the nucleotide sequence encodes ARRDC1 and/or TSG101; and (b) a heterologous promoter that drives expression of the sequence of (a). In some embodiments, the kit further comprises an expression construct encoding a binding RNA (e.g., TAR) and/or a cargo RNA. In some embodiments, a further encodes a binding RNA (e.g., TAR) and/or a cargo RNA.

Some aspects of this disclosure provide microveslicle (e.g., ARMM) producing cells comprising any of the proteins, fusion proteins, and/or RNAs provided herein. In some embodiments, the cells comprise a nucleotide that encodes any of the proteins, fusion proteins, and/or RNAs provided herein. In some embodiments, the cells comprise any of the nucleotides or vectors provided herein.

The description of exemplary embodiments of the reporter systems above is provided for illustration purposes only and not meant to be limiting. Additional reporter systems, e.g., variations of the exemplary systems described in detail above, are also embraced by this disclosure.

It should be appreciated however, that additional proteins, fusion proteins, and RNAs would be apparent to the skilled artisan based on the present disclosure and knowledge in the art.

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Figure 5:
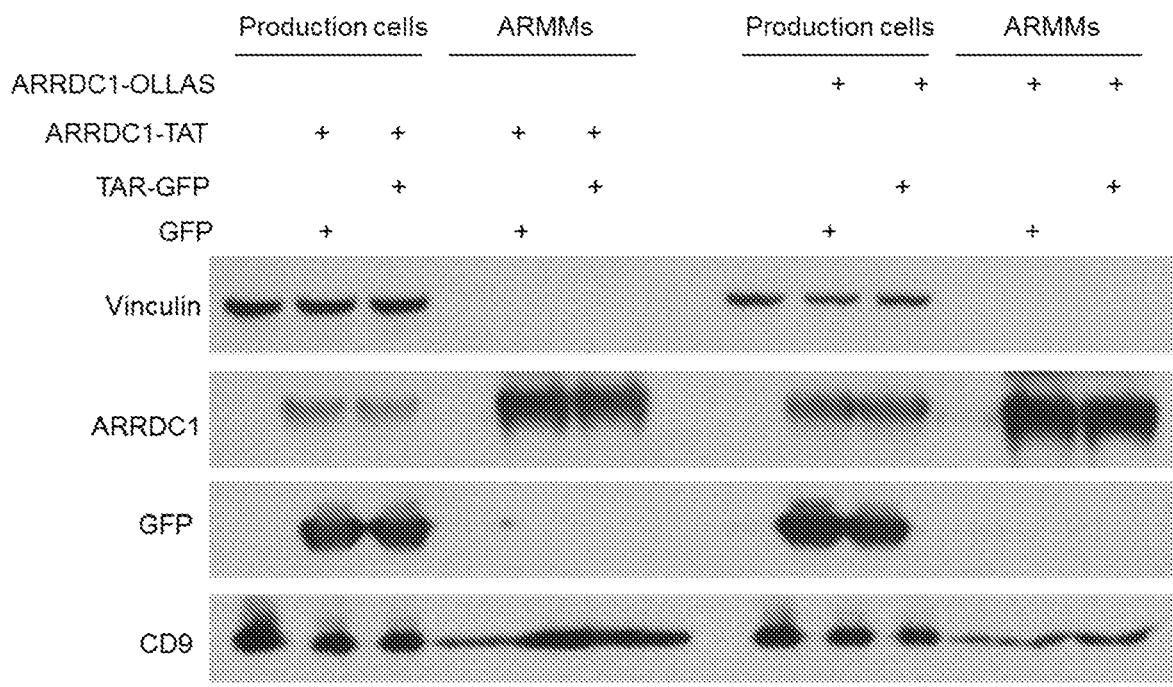
FIG. 5 provides a Western blots showing that an ARRDC1-Tat fusion protein maintains the ability to bud out of cells as ARRDC1-containing ARMMs. For example, cells expressing either the ARRDC1-Tat fusion protein or the ARRDC1 tagged with an OLLAS epitope tag (ARRDC1-OLLAS), which lacks the Tat peptide, produced ARMMs containing ARRDC1-Tat or ARRDC1-OLLAS, respectively. The Western blots further show that plasmid DNA encoding GFP alone or TAR fused to GFP (TAR-GFP) were both capable of expressing GFP protein in cells transfected with the plasmid DNA. The OLLAS epitope tag comprises the amino acid sequence SGFANELGPRLMGH (SEQ ID NO: 108)

Example 1: Packaging Cargo RNAs into ARMMs Via Binding RNAs that Specifically Bind to RNA Binding Proteins An ARRDC1 protein fused to Tat maintained the ability to bud out of cells as ARRDC1-containing ARMMs. For example, cells expressing either the ARRDC1-Tat fusion protein or the ARRDC1 tagged with an OLLAS epitope tag (ARRDC1-OLLAS), which lacks the Tat peptide, produced ARMMS containing ARRDC1-Tat or ARRDC1-OLLAS, respectively. The Western blots (FIG. 5) show that plasmid DNA encoding GFP alone or TAR fused to GFP (TAR-GFP) were both capable of expressing GFP protein in cells transfected with the plasmid DNA.

Figure 6:
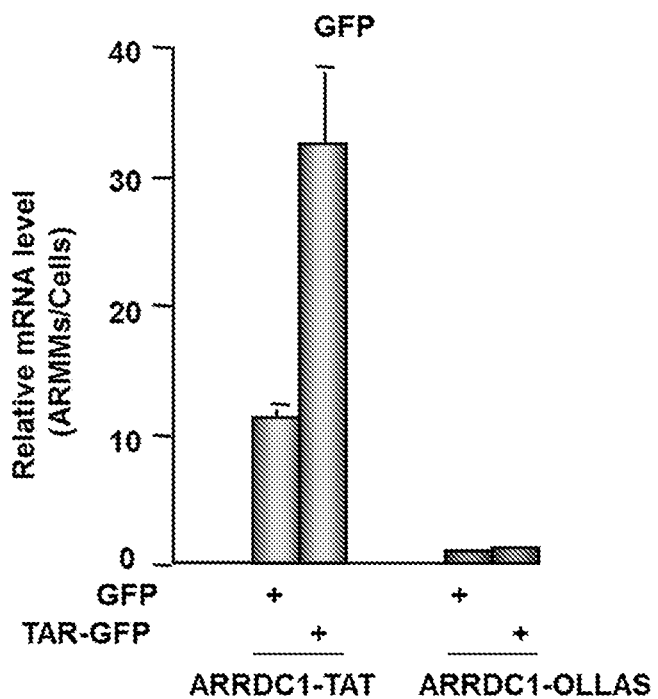
FIG. 6 is a graph showing that TAR-GFP mRNA was more efficiently packaged into ARMMs using the Tat/TAR system. The relative amount of GFP mRNA detected in ARMMs as compared to their respective ARMM producing cells was significantly increased when ARRDC1-Tat and TAR:GFP were co-expressed in cells as compared to cells that co-expressed ARRDC1-OLLAS and GFP; ARRDC1-OLLAS and TAR-GFP; or ARRDC1-Tat and GFP ARRDC1-OLLAS.
Figure 7:
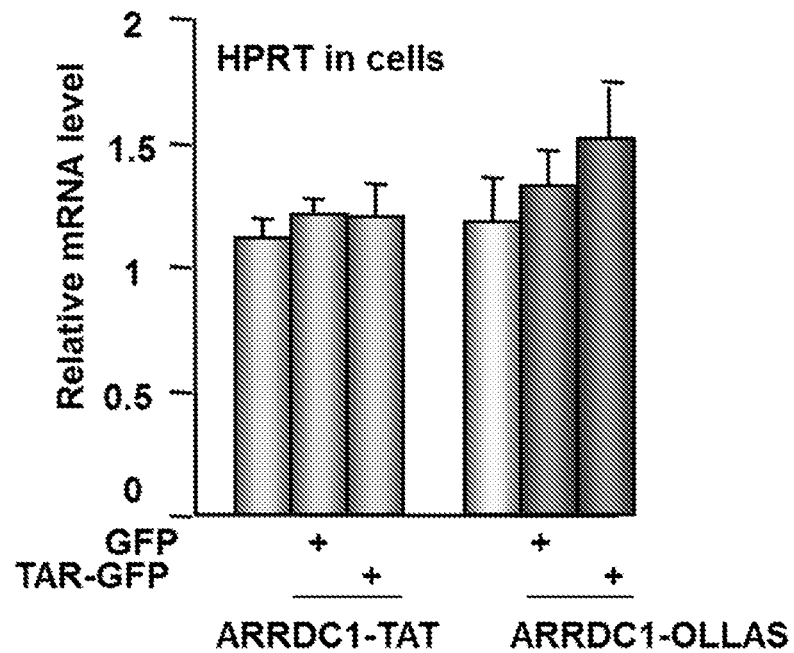
FIG. 7 are graphs showing the relative levels of hypoxanthine-guanine phosphoribosyltransferase (HPRT) control mRNA in (A) ARMM producing cells that express combinations of GFP and ARRDC1-Tat; GFP and ARRDC1-OLLAS; TAR-GFP and ARRDC1-Tat; TAR-GFP and ARRDC1-OLLAS; or a control that does not express any of the constructs, and (B) ARMMs from the ARMM producing cells of (A).
Figure 7:
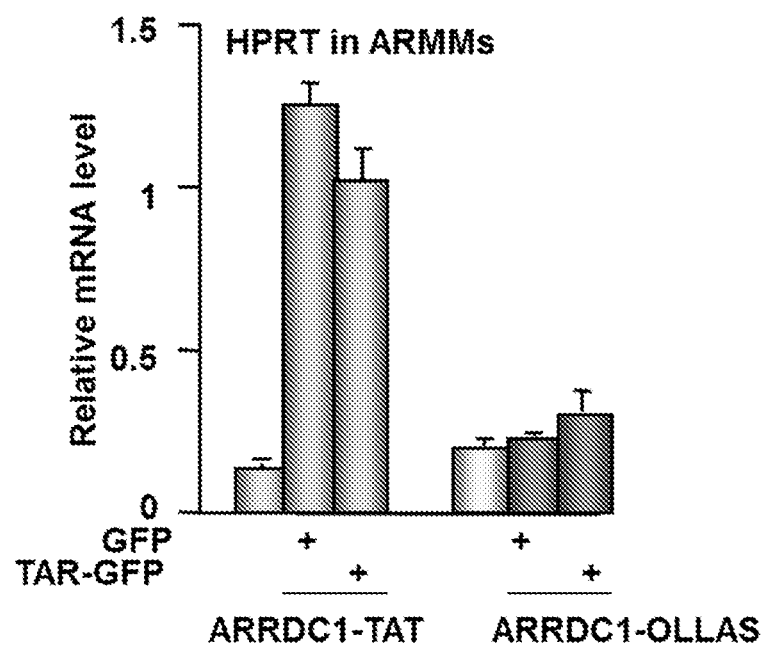

Furthermore, TAR-GFP mRNA was more efficiently packaged into ARMMs using the Tat/TAR system. The relative amount of GFP mRNA detected in ARMMs as compared to their respective ARMM producing cells was significantly increased when ARRDC1-Tat and TAR-GFP were co-expressed in cells as compared to cells that co-expressed ARRDC1-OLLAS and GFP; ARRDC1-OLLAS and TAR-GFP; or ARRDC1-Tat and GFP ARRDC1-OLLAS. See FIG. 6. The relative levels of control, hypoxanthine-guanine phosphoribosyltransferase (HPRT), mRNA in ARMM producing cells that express combinations of GFP and ARRDC1-Tat; GFP and ARRDC1-OLLAS; TAR-GFP and ARRDC1-Tat; TAR-GFP and ARRDC1-OLLAS or a control that does not express any of the constructs, are shown in FIG. 7A. The relative levels of control, (HPRT), mRNA in ARMMs from ARMM producing cells that express combinations of GFP and ARRDC1-Tat; GFP and ARRDC1-OLLAS; TAR-GFP and ARRDC1-Tat; TAR-GFP and ARRDC1-OLLAS or a control that does not express any of the constructs, are shown in FIG. 7B.

Figure 8:
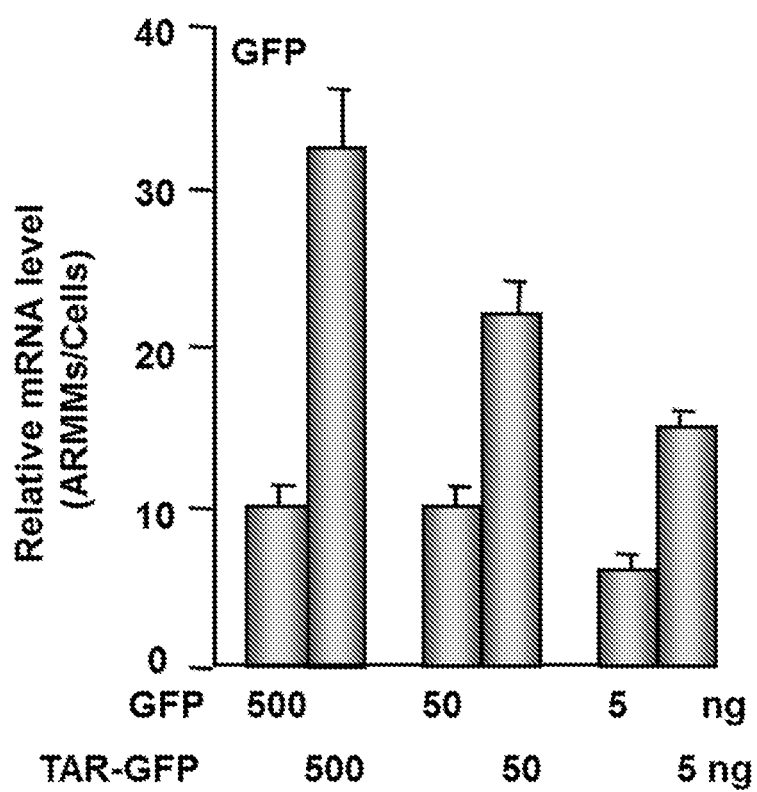
FIG. 8 is a graph showing that TAR-GFP mRNA was efficiently packaged into ARMMs in a dose-dependent manner. The relative amount of GFP mRNA detected in ARMMs as compared to their respective ARMM producing cells increased in a dose-dependent manner for cells co-expressing TAR-GFP and ARRDC1-Tat but not in cells co-expressing GFP and ARRDC1-Tat. The amounts of GFP or TAR-GFP transfected into cells was 500 ng, 50 ng, and 5 ng, respectively.
Figure 9:
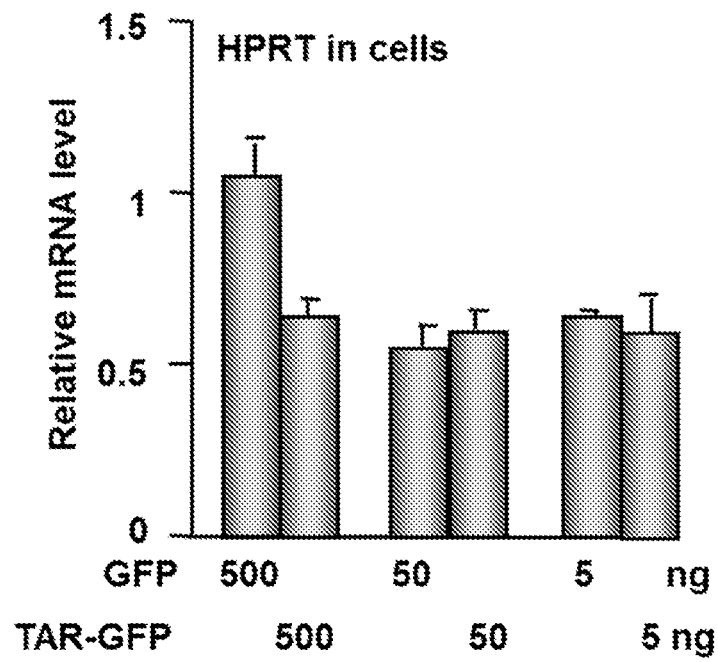
FIG. 9 are graphs showing the relative levels of hypoxanthine-guanine phosphoribosyltransferase (HPRT) control mRNA in (A) ARMM producing cells that were transfected with 500 ng, 50 ng, or 5 ng of either GFP or TAR-GFP, respectively, and (B) ARMMs from the ARMM producing cells of (A).
Figure 9:
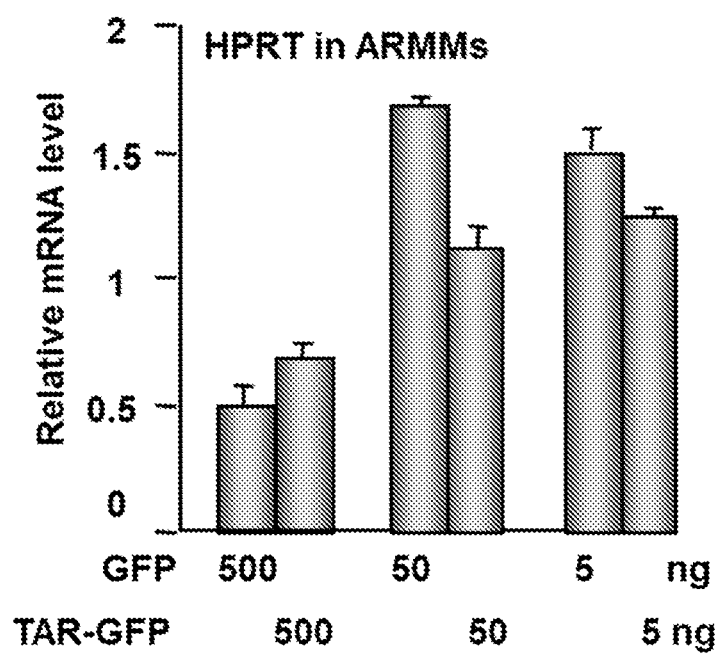

TAR-GFP mRNA was efficiently packaged into ARMMs in a dose-dependent manner. The relative amount of GFP mRNA detected in ARMMs as compared to their respective ARMM producing cells increased in a dose dependent manner for cells co-expressing TAR-GFP and ARRDC1-Tat, but not in cells co-expressing GFP and ARRDC1-Tat (FIG. 8). The amounts of GFP or TAR-GFP transfected into cells was 500 ng, 50 ng and 5 ng, respectively. The relative levels of HPRT control mRNA in ARMM producing cells that were transfected with 500 ng, 50 ng or 5 ng of either GFP or TAR-GFP, respectively, are shown in FIG. 9A. The relative levels of HPRT control mRNA in ARMMs from ARMM producing cells that were transfected with 500 ng, 50 ng or 5 ng of either GFP or TAR-GFP, respectively, are shown in FIG. 9B.

Figure 10:
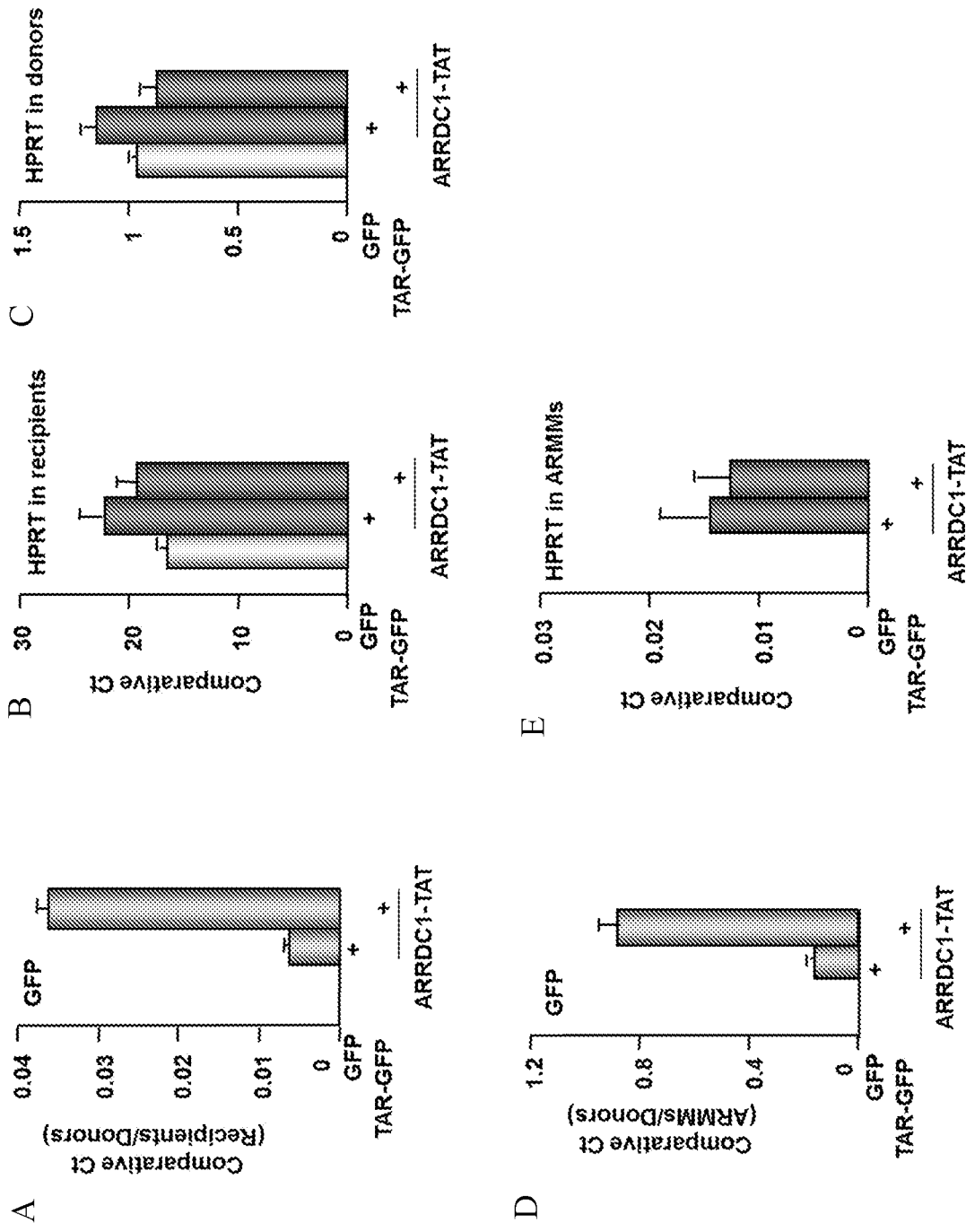
FIG. 10 are graphs showing that ARMMs containing TAR-GFP mRNA were capable of delivering the TAR-GFP mRNA to a target cells in vitro. (A) The relative amount of GFP mRNA delivered to recipient cells was greater when using ARMMs containing ARRDC1-Tat and TAR-GFP as compared to ARMMs containing ARRDC1-Tat and GFP alone. The relative levels of hypoxanthine-guanine phosphoribosyltransferase (HPRT) control mRNA are shown for recipient cells in (B) and for donor ARMM producing cells in (C). The relative amount of GFP mRNA in ARMMs was greater in ARMMs produced from donor cells expressing ARRDC1-Tat and TAR-GFP as compared to ARMMs produced from donor cells expressing ARRDC1-Tat and GFP alone (D). The relative levels of HPRT control mRNA in ARMMs produced from donor cells expressing ARRDC1-Tat and TAR-GFP, or ARRDC1-Tat and GFP are shown in (E).

ARMMs containing TAR-GFP mRNA were capable of delivering the TAR-GFP mRNA to a target cells in vitro. The relative amount of GFP mRNA delivered to recipient cells was greater when using ARMMs containing ARRDC1-Tat and TAR-GFP as compared to ARMMs containing ARRDC1-Tat and GFP alone (FIG. 10A). The relative levels of HPRT control mRNA are shown for recipient cells (FIG. 10B) and for donor ARMM producing cells in (10C). The relative amount of GFP mRNA in ARMMs was greater in ARMMs produced from donor cells expressing ARRDC1-Tat and TAR-GFP as compared to ARMMs produced from donor cells expressing ARRDC1-Tat and GFP alone (FIG. 10D). The relative levels of HPRT control mRNA in ARMMs produced from donor cells expressing ARRDC1-Tat and TAR-GFP, or ARRDC1-Tat and GFP are shown in FIG. 10E.

Example 2: Packaging and Delivery of RNAs (e.g., mRNA Encoding p53) Via ARMMs

Figure 11:
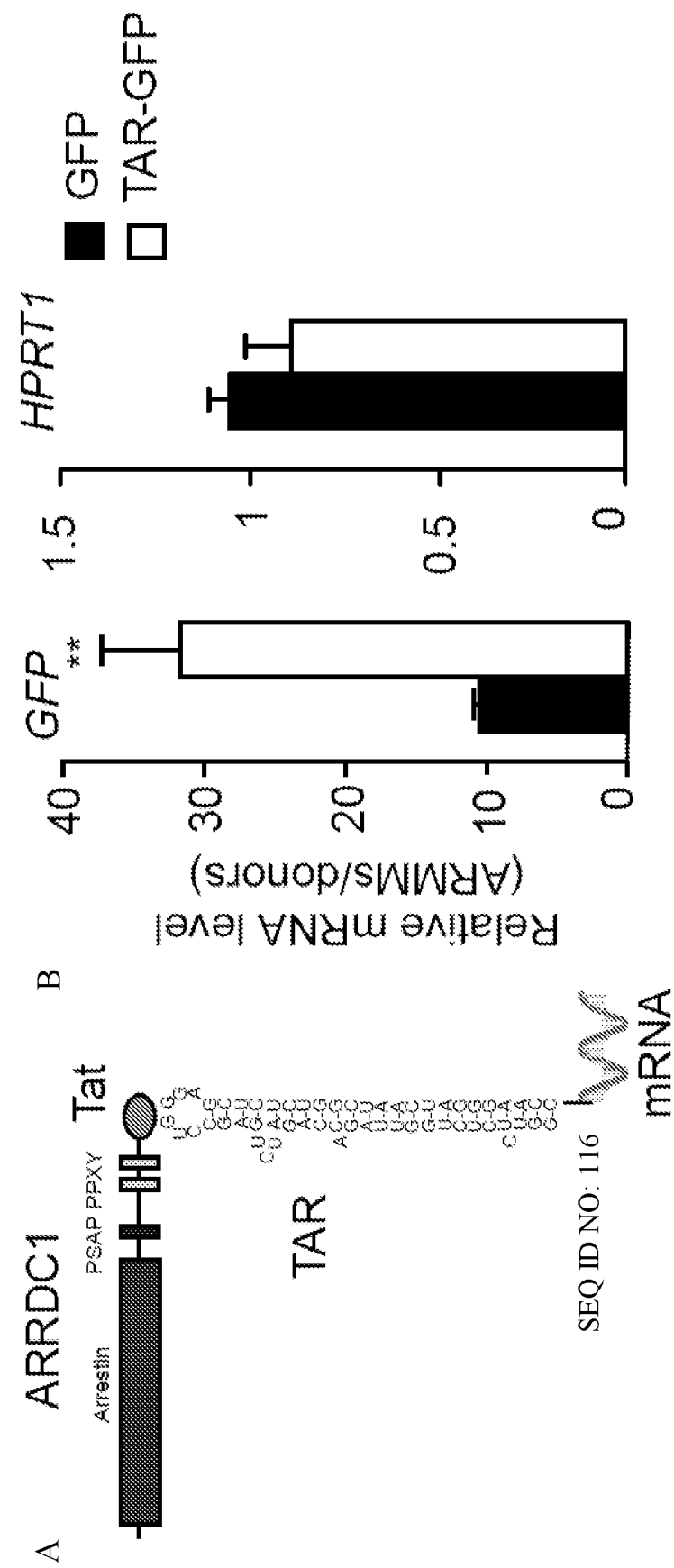
FIG. 11 shows packaging and delivery of RNAs via ARMMs. (A) Shows a schematic of an RNA packaging strategy. Tat peptide, which binds specifically to TAR, is fused to the C-terminus of ARRDC1 to recruit RNA cargo molecules linked to TAR, into ARMMs. (B) Shows packaging of TAR-GFP mRNA in ARMMs. ARRDC1-Tat was co-transfected with TAR-GFP or control GFP construct into HEK293T cells. ARMMs were pelleted via ultracentrifugation. qRT-PCR was done on ARMMs and on the transfected cells for GFP and for a control mRNA (HPRT1). (C) Shows packaging of TAR-p53 mRNA in ARMMs. TAR-p53 was co-transfected with ARRDC1 or ARRDC1-Tat construct into HEK293T cells. ARMMs were pelleted via ultracentrifugation. qRT-PCR was done on ARMMs and on the transfected cells for TAR-p53 and for HPRT1. (D) Shows Transfer of TAR-GFP mRNA into recipient cells. A549 cells were incubated with ARMMs containing TAR-GFP mRNA overnight, washed with PBS extensively and subjected to mRNA analysis by qRT-PCR. (E) Shows transfer of TAR-GFP mRNA into recipient cells. p53-null H1299 cells were incubated with ARMMs containing TAR-p53 mRNA overnight, washed with PBS extensively and subjected to mRNA analysis by qRT-PCR. (F) Shows translation of ARMMs-delivered GFP mRNA in recipient cells. A549 cells were incubated with ARMMs containing TAR-GFP mRNA for 24 h with or without the translational inhibitor cycloheximide (CHX), and subjected to flow cytometry analysis. (G) Shows activation of p53 target genes in recipient cells receiving TAR-p53 ARMMs. P53-null H1299 cells were incubated with ARMMs containing TAR-p53 mRNA for 18 h and subjected to mRNA analysis by qRT-PCR to detect MDM2 and p21 mRNAs. At least 3 independent replicates were done for all assays. *$p<0.05$; **$p<0.01$.
Figure 11:
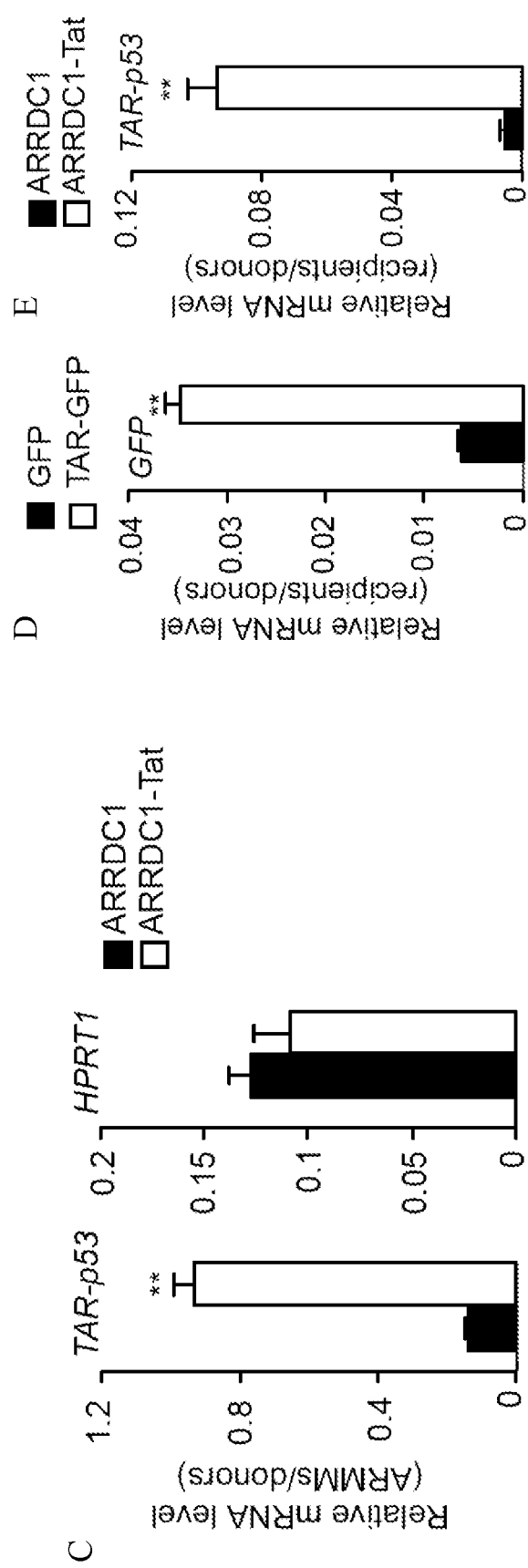
Figure 11:
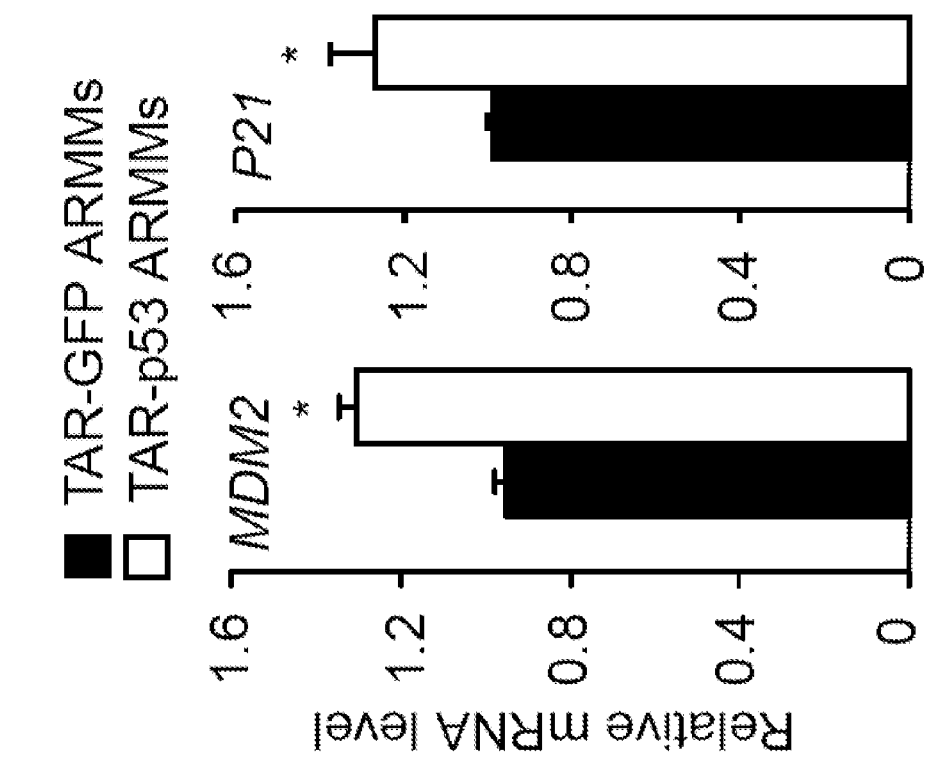
Figure 11:
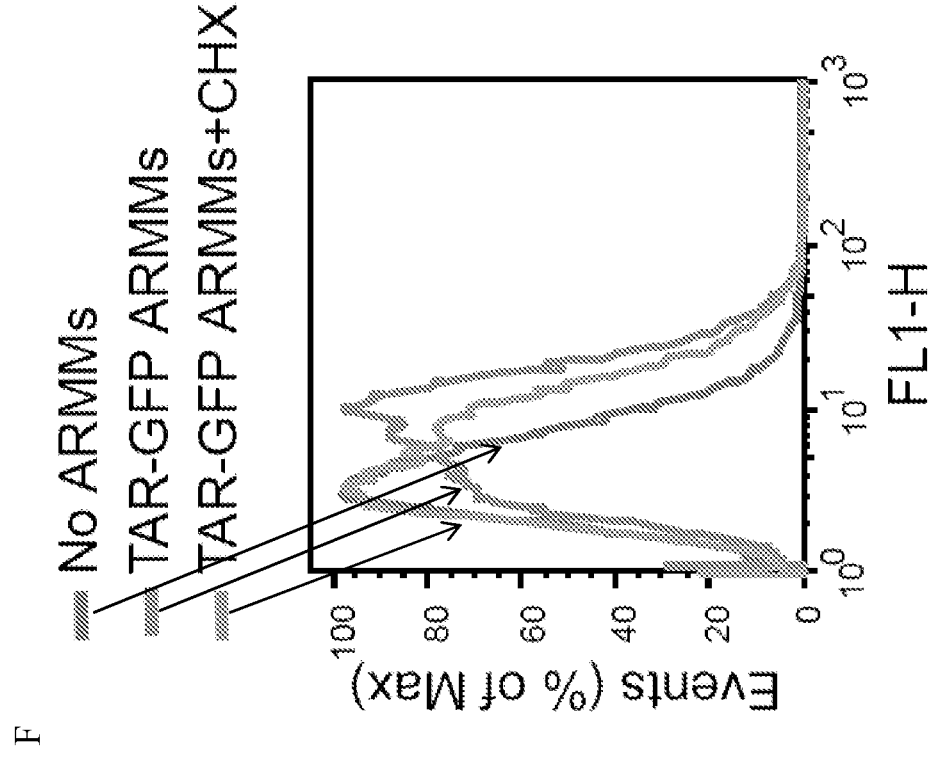
Figure 12:
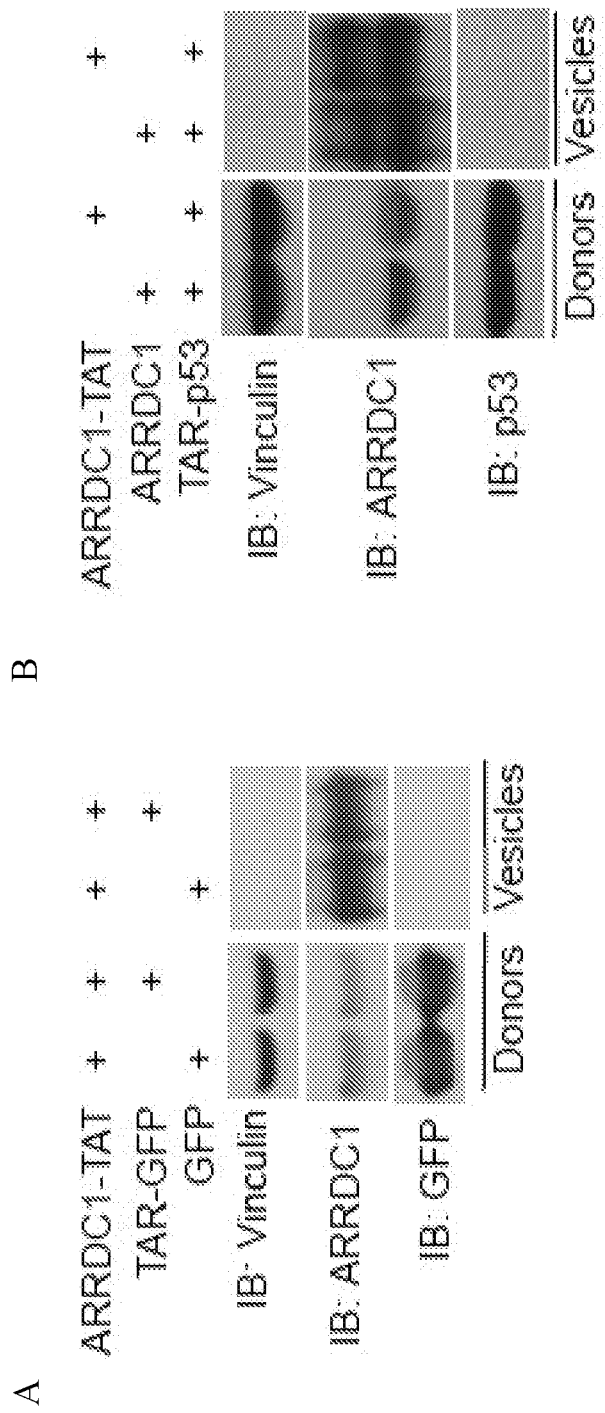
FIG. 12 shows (A) GFP or TAR-GFP was co-transfected with ARRDC1-Tat into HEK293T cells. (B) ARRDC1 or ARRDC1-Tat was co-transfected with TAR-p53 into HEK293T cells. Medium was collected for extracellular vesicles. Cell lysates and vesicles were subjected to Western blot analysis using indicated antibodies.

RNA molecules may be broadly used as therapeutic agents (Kole, R., et al., "RNA therapeutics: beyond RNA interference and antisense oligonucleotides." Nature reviews. Drug discovery 11, 125-140, doi:10.1038/nrd3625 (2012); the contents of which are hereby incorporated by reference in their entirety), but often have to overcome cellular barriers (Dowdy, S. F. "Overcoming cellular barriers for RNA therapeutics." Nature biotechnology 35, 222-229, doi:10.1038/nbt.3802 (2017); the contents of which are hereby incorporated by reference in their entirety). Accordingly, the ability of ARMMs to package and deliver RNAs to recipient cells was tested. To package RNAs into ARMMs, advantage was taken of the Tat (transactivator of transcription) protein, which binds specifically to the stem-loop-containing TAR (Trans-activating Response element) RNA (Roy, S., et al., "A bulge structure in HIV-1 TAR RNA is required for Tat binding and Tat-mediated trans-activation." Genes & development 4, 1365-1373 (1990); and Weeks, K. M. et al., "RNA binding assays for Tat-derived peptides: implications for specificity." Biochemistry 31, 10281-10287 (1992); the contents of each of which are hereby incorporated by reference in their entirety). An expression construct was made with a short Tat peptide fused directly to the C-terminus of ARRDC1 and another construct with TAR fused directly to the 5' end of a cargo mRNA (FIG. 11A). It was reasoned that the high binding affinity between the Tat peptide and TAR will allow the recruitment of the TAR-fused mRNA into ARMMs. The packaging efficiency of both GFP and p53 mRNAs into ARMMs was tested. Either pcDNA3 backbone construct, ARRDC1-Tat with control GFP, or ARRDC1-Tat with TAR-GFP was transfected into production cells, and harvested ARMMs for mRNA and protein analysis. GFP mRNAs were significantly more enriched in ARMMs of ARRDC1-Tat and TAR-GFP co-transfection (FIG. 11B). Similarly p53 mRNA fused to TAR was significantly enriched in ARMMs when co-expressed with ARRDC1-Tat (FIG. 11C). No GFP or p53 proteins were detected by Western blot in either GFP or TAR-GFP-mRNA-containing ARMMs (FIG. 12), indicating that the Tat-TAR system selectively packaged TAR-labeled mRNAs into ARMMs. It was next determined whether the TAR-GFP (or TAR-p53) mRNA in ARMMs can be delivered into and expressed in recipient cells. Incubation of ARMMs containing TAR-fused mRNAs with recipient A549 cells led to detection of GFP or p53 mRNAs in the recipient cells (FIGS. 11D and 11E). Importantly, flow cytometry analysis confirmed that GFP mRNAs in the recipient cells were translated into GFP proteins and this translation was nearly abolished in the presence of translation inhibitor cycloheximide (CHX) (FIG. 11F). Incubation of ARMMs containing TAR-p53 increased transcription of Mdm2 and p21 in the recipient cells (FIG. 11G), indicating that TAR-p53 mRNAs delivered via ARMMs were translated into functional p53 proteins.

Plasmids:

To generate ARRDC1-Tat construct, The DNA sequence of ARRDC1 was PCR amplified followed by insertion into pcDNA3 vector to obtain pcDNA3 ARRDC1 construct. The DNA sequence of Tat (48-65 aa) was synthesized, annealed and inserted at the C-terminus of ARRDC1. The DNA sequence of TAR (1-63 base pairs) was synthesized, annealed, and inserted at the 5' end of EGFP in the pEGFP-N1 vector (Addgene) to obtain the TAR-EGFP construct. Alternatively, the TAR region was inserted at the 5' end of p53 in the pcDNA3 p53 construct to obtain the TAR-p53 construct.

REFERENCES

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. An arrestin domain-containing protein 1 (ARRDC1)-mediated microvesicle (ARMM) comprising:
   a lipid bilayer,
   an ARRDC1 protein or an ARRDC1-protein variant, wherein the ARRDC1-protein variant comprises an amino acid sequence that is at least about 95% identical to the amino acid sequence of any one of SEQ ID NOs: 15-17,
   an RNA binding protein, wherein the ARRDC1 protein or the ARRDC1-protein variant is associated with the RNA binding protein, and
   a binding RNA, wherein the binding RNA is not a guide RNA, and further wherein the binding RNA is associated with the RNA binding protein.

2. The microvesicle of claim 1, wherein the RNA binding protein is fused to at least one WW domain or variant thereof.

3. The microvesicle of claim 2, wherein the at least one WW domain is derived from a WW domain of the ubiquitin ligase WWP1, WWP2, Nedd4-1, Nedd4-2, Smurf1, Smurf2, ITCH, NEDL1, or NEDL2.

4. The microvesicle of claim 1, wherein the ARRDC1 protein or ARRDC1 protein variant comprises at least one PPXY (SEQ ID NO: 2) motif.

5. The microvesicle of claim 1 further comprising a TSG101 protein or TSG101-protein variant, wherein the TSG101-protein variant comprises a fragment of TSG101 and/or an amino acid sequence that is at least about 95% identical to the amino acid sequence of any one of SEQ ID NOs: 20-22.

6. The microvesicle of claim 1, wherein the RNA binding protein comprises a trans-activator of transcription (Tat) protein, or a Tat-protein variant, wherein the Tat-protein variant comprises an amino acid sequence that is at least about 95% identical to the amino acid sequence of any one of SEQ ID NOs: 65-84; a Rev protein, or a Rev-protein variant, wherein the Rev-protein variant comprises an amino acid sequence that is at least about 95% identical to the amino acid sequence of any one of SEQ ID NOs: 93-95; an MS2 phage coat protein, or a MS2 phage coat-protein variant, wherein the MS2 phage coat-protein variant comprises an amino acid sequence that is at least about 95% identical to the amino acid sequence of SEQ ID NO: 99; a P22 N protein, or a P22 N-protein variant, wherein the P22 N-protein variant comprises an amino acid sequence that is at least about 95% identical to the amino acid sequence of SEQ ID NO: 100; a λ N protein, or a λ N-protein variant, wherein the λ N-protein variant comprises an amino acid sequence that is at least about 95% identical to the amino acid sequence of SEQ ID NO: 101; a φ21 protein, or a φ21-protein variant, wherein the φ21-protein variant comprises an amino acid sequence that is at least about 95% identical to the amino acid sequence of SEQ ID NOs: 102; or a HIV-1 nucleocapsid protein, or a HIV-1 nucleocapsid-protein variant wherein the HIV-1 nucleocapsid-protein variant comprises an amino acid sequence that is at least about 95% identical to the amino acid sequence of SEQ ID NO: 103.

7. The microvesicle of claim 1, wherein the binding RNA comprises a trans-activating response element (TAR), a Rev response element (RRE), an MS2 RNA sequence, a P22 boxB RNA sequence, a λ boxB RNA sequence, a φ21 boxB RNA sequence, or a SL3 ψ RNA sequence.

8. The microvesicle of claim 1, wherein the RNA binding protein and the binding RNA are selected from any one of the following pairs:
   (i) a trans-activator of transcription (Tat) protein, or a Tat-protein variant, wherein the Tat-protein variant comprises an amino acid sequence that is at least about 95% identical to the amino acid sequence of any one of SEQ ID NOs: 65-84, and a trans-activating response element (TAR);
   (ii) a Rev protein, or a Rev-protein variant, wherein the Rev-protein variant comprises an amino acid sequence that is at least about 95% identical to the amino acid sequence of any one of SEQ ID NOs: 93-95, and a Rev response element (RRE);

(iii) an MS2 phage coat protein, or a MS2 phage coat-protein variant, wherein the MS2 phage coat-protein variant comprises an amino acid sequence that is at least about 95% identical to the amino acid sequence of SEQ ID NO: 99, and an MS2 RNA sequence;
(iv) a P22 N protein, or a P22 N-protein variant, wherein the P22 N-protein variant comprises an amino acid sequence that is at least about 95% identical to the amino acid sequence of SEQ ID NO: 100, and a P22 boxB RNA sequence;
(v) a λ N protein, or a λ N-protein variant, wherein the λ N-protein variant comprises an amino acid sequence that is at least about 95% identical to the amino acid sequence of SEQ ID NO: 101, and a λ boxB RNA sequence;
(vi) a φ21 protein, or a φ21-protein variant, wherein the φ21-protein variant comprises an amino acid sequence that is at least about 95% identical to the amino acid sequence of SEQ ID NOs: 102, and a φ21 boxB RNA sequence; and
(vii) a HIV-1 nucleocapsid protein, or a HIV-1 nucleocapsid-protein variant, wherein the HIV-1 nucleocapsid-protein variant comprises an amino acid sequence that is at least about 95% identical to the amino acid sequence of SEQ ID NO: 103, and a SL3 ψ RNA sequence.

9. The microvesicle of claim 1, wherein the binding RNA is further associated with a cargo RNA.

10. The microvesicle of claim 9, wherein the cargo RNA comprises a messenger RNA (mRNA), a ribosomal RNA (rRNA), a signal recognition particle RNA (SRP RNA), a transfer RNA (tRNA), a small nuclear RNA (snRNA), a small nucleolar (snoRNA), a SmY RNA (smY), a guide RNA (gRNA), a ribonuclease P (RNase P), a ribonuclease MRP (RNase MRP), a Y RNA, a telomerase RNA component (TERC), a spliced leader RNA (SL RNA), an antisense RNA (asRNA), a cis-natural antisense sequence (cis-NAT), a CRISPR RNA (crRNA), a long noncoding RNA (lncRNA), a microRNA (miRNA), a piwi-interacting RNA (piRNA), a small interfering RNA (siRNA), or a trans-acting siRNA (tasiRNA).

11. An ARRDC1 fusion protein comprising:
an ARRDC1 protein or an ARRDC1-protein variant, wherein the ARRDC1 variant comprises an amino acid sequence that is at least about 95% identical to amino acid sequence of any one of SEQ ID NOs: 15-17, and
an RNA binding protein,
wherein the RNA binding protein is associated with a binding RNA, and further wherein the binding RNA is not a guide RNA.

12. The ARRDC1 fusion protein of claim 11 wherein the RNA binding protein comprises a WW domain or variant thereof.

13. The ARRDC1 fusion protein of claim 11, wherein the RNA binding protein is associated with a recombinant trans-activating response element (TAR) comprising:
a trans-activating response element (TAR) RNA.

14. A microvesicle-producing cell for producing the microvesicle of claim 1 comprising:
a recombinant expression construct encoding the ARRDC1 protein or the ARRDC1-protein variant, the RNA binding protein, and the binding RNA.

15. A method of delivering a cargo RNA to a target cell, the method comprising contacting the target cell with the microvesicle of claim 9.

16. A method of delivering a cargo RNA to a target cell, the method comprising contacting the target cell with the microvesicle-producing cell of claim 14, wherein the microvesicle-producing cell further comprises a cargo RNA associated with the binding RNA.

17. A method of altering the expression of at least one gene in a target cell, the method comprising contacting the target cell with the microvesicle of claim 9, wherein the cargo RNA is capable of altering the expression of a gene.

18. A cell comprising a nucleic acid construct encoding the fusion protein of claim 11.

19. A pharmaceutical composition comprising the microvesicle of claim 1.

20. An ARMM comprising:
a lipid bilayer,
the ARRDC1 fusion protein of claim 11, and
a binding RNA, wherein the binding RNA is associated with the RNA binding protein.

21. A pharmaceutical composition comprising the ARMM of claim 20.

22. A microvesicle-producing cell for producing the ARMM of claim 20 comprising:
a recombinant expression construct encoding the ARRDC1 fusion protein and
the binding RNA.

23. A method of delivering a cargo RNA to a target cell, the method comprising contacting the target cell with the ARMM of claim 20, wherein the ARMM further comprises a cargo RNA associated with the binding RNA.

24. A method of delivering a cargo RNA to a target cell, the method comprising contacting the target cell with the microvesicle-producing cell of claim 22, wherein the microvesicle-producing cell further comprises a cargo RNA associated with the binding RNA.

25. A method of altering the expression of at least one gene in a target cell, the method comprising contacting the target cell with the ARMM of claim 20, wherein the ARMM further comprises an RNA associated with the binding RNA that is capable of altering the expression of a gene.

26. The ARMM of claim 20, wherein the binding RNA is further associated with a cargo RNA.

27. A pharmaceutical composition comprising the microvesicle of claim 9.

28. The microvesicle of claim 9, wherein the binding RNA and the cargo RNA are associated via one or more cleavable linkers.

* * * * *